United States Patent
Rishton et al.

(10) Patent No.: US 11,214,540 B2
(45) Date of Patent: Jan. 4, 2022

(54) COMPOSITIONS FOR TREATING NEURODEGENERATIVE DISEASES

(71) Applicant: COGNITION THERAPEUTICS, INC., Pittsburgh, PA (US)

(72) Inventors: Gilbert M. Rishton, Los Angeles, CA (US); Gary C. Look, Santa Clara, CA (US); Susan M. Catalano, Pittsburgh, PA (US)

(73) Assignee: Cognition Therapeutics, Inc., Pittsburgh, PA (US)

( * ) Notice: Subject to any disclaimer, the term of this patent is extended or adjusted under 35 U.S.C. 154(b) by 0 days.

(21) Appl. No.: 16/613,697

(22) PCT Filed: May 15, 2018

(86) PCT No.: PCT/US2018/032726
§ 371 (c)(1),
(2) Date: Nov. 14, 2019

(87) PCT Pub. No.: WO2018/213281
PCT Pub. Date: Nov. 22, 2018

(65) Prior Publication Data
US 2020/0299234 A1  Sep. 24, 2020

Related U.S. Application Data

(60) Provisional application No. 62/506,226, filed on May 15, 2017.

(51) Int. Cl.
| | | |
|---|---|---|
| C07D 491/107 | (2006.01) |
| C07D 205/04 | (2006.01) |
| C07D 207/08 | (2006.01) |
| C07D 207/16 | (2006.01) |
| C07D 211/22 | (2006.01) |
| C07D 211/46 | (2006.01) |
| C07D 211/48 | (2006.01) |
| C07D 241/04 | (2006.01) |
| C07D 241/08 | (2006.01) |

(Continued)

(52) U.S. Cl.
CPC ......... C07D 205/04 (2013.01); C07D 207/08 (2013.01); C07D 207/16 (2013.01);
(Continued)

(58) Field of Classification Search
CPC .. C07D 403/04; C07D 403/14; C07D 401/04; C07D 491/07; C07D 471/10;
(Continued)

(56) References Cited

U.S. PATENT DOCUMENTS

| | | |
|---|---|---|
| 4,321,386 A | 3/1982 | Lawson |
| 4,582,849 A | 4/1986 | Marzolph et al. |

(Continued)

FOREIGN PATENT DOCUMENTS

| | | |
|---|---|---|
| AU | 2008314922 A1 | 4/2009 |
| CA | 1018188 A | 9/1977 |

(Continued)

OTHER PUBLICATIONS

Martirosyan, et al., Armyanskii Khimicheskii Zhurnal (1971), 24(9), 798-801.*

(Continued)

*Primary Examiner* — Jeffrey H Murray
(74) *Attorney, Agent, or Firm* — Troutman Pepper Hamilton Sanders LLP

(57) ABSTRACT

The present disclosure relates to novel compounds, and pharmaceutical compositions thereof, useful for treating for treating neurodegenerative diseases, including Alzheimer's disease and cognitive decline. Methods for inhibiting synapse number decline or membrane trafficking abnormalities associated with exposure of a neuronal cell to Abeta species are also disclosed. Representative members of these compounds include:

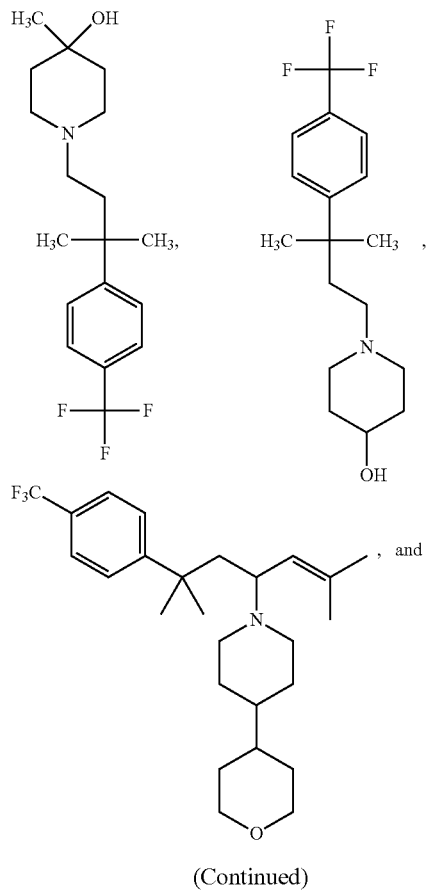

(Continued)

-continued

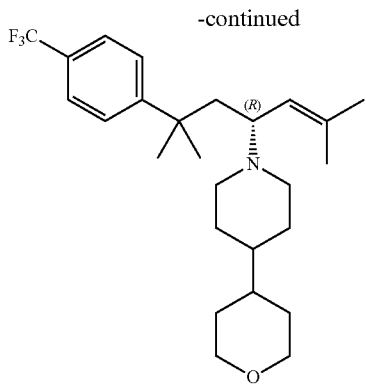

8 Claims, No Drawings

(51) Int. Cl.
C07D 265/30 (2006.01)
C07D 401/04 (2006.01)
C07D 403/06 (2006.01)
C07D 403/14 (2006.01)
C07D 405/04 (2006.01)
C07D 405/12 (2006.01)
C07D 413/14 (2006.01)

(52) U.S. Cl.
CPC .......... C07D 211/22 (2013.01); C07D 211/46 (2013.01); C07D 211/48 (2013.01); C07D 241/04 (2013.01); C07D 241/08 (2013.01); C07D 265/30 (2013.01); C07D 401/04 (2013.01); C07D 403/06 (2013.01); C07D 403/14 (2013.01); C07D 405/04 (2013.01); C07D 405/12 (2013.01); C07D 413/14 (2013.01); C07D 491/107 (2013.01)

(58) Field of Classification Search
CPC .. C07D 413/14; C07D 207/06; C07D 295/02; C07D 405/04; C07D 265/30; C07D 491/107
See application file for complete search history.

(56) References Cited

U.S. PATENT DOCUMENTS

| | | | |
|---|---|---|---|
| 4,697,024 | A | 9/1987 | Donaldson et al. |
| 4,958,029 | A | 9/1990 | Nakagawa et al. |
| 6,011,068 | A | 1/2000 | Nemeth et al. |
| 6,057,371 | A | 5/2000 | Glennon |
| 6,211,244 | B1 | 4/2001 | Van Wagenen et al. |
| 6,235,731 | B1 | 5/2001 | Shibouta et al. |
| 6,518,315 | B1 | 2/2003 | Roufogalis et al. |
| 6,991,814 | B2 | 1/2006 | Ray et al. |
| 7,723,377 | B2 | 5/2010 | Rishton et al. |
| 8,304,547 | B2 | 11/2012 | Sugasawa et al. |
| 8,765,816 | B2 | 7/2014 | Rishton et al. |
| 9,192,585 | B2 | 11/2015 | Rishton et al. |
| 9,365,491 | B2 | 6/2016 | Rishton et al. |
| 9,499,462 | B2 | 11/2016 | Rishton et al. |
| 9,796,672 | B2 | 10/2017 | Rishton et al. |
| 9,815,770 | B2 | 11/2017 | Rishton et al. |
| 10,207,991 | B2 | 2/2019 | Rishton et al. |
| 10,611,728 | B2 | 4/2020 | Rishton et al. |
| 2003/0148392 | A1 | 8/2003 | Citron et al. |
| 2004/0033277 | A1 | 2/2004 | Ray et al. |
| 2006/0153772 | A1 | 7/2006 | Jacobsen |
| 2007/0021413 | A1 | 1/2007 | Herold et al. |
| 2008/0101757 | A1 | 5/2008 | Lin et al. |
| 2008/0103107 | A1 | 5/2008 | Ward et al. |
| 2008/0131233 | A1 | 6/2008 | Yao |
| 2008/0153917 | A1 | 6/2008 | Ellis et al. |
| 2008/0193573 | A1 | 8/2008 | Gow et al. |
| 2008/0312333 | A1 | 12/2008 | Mae et al. |
| 2009/0017038 | A1 | 1/2009 | Colabufo et al. |
| 2009/0022667 | A1 | 1/2009 | Peters et al. |
| 2009/0035295 | A1 | 2/2009 | Hillen et al. |
| 2010/0028333 | A1 | 2/2010 | Getty et al. |
| 2010/0029654 | A1 | 2/2010 | Pasinetti |
| 2010/0093001 | A1 | 4/2010 | Rousseau et al. |
| 2010/0297149 | A1 | 11/2010 | Zhou et al. |
| 2011/0082154 | A1 | 4/2011 | Oksenberg et al. |
| 2011/0092554 | A1 | 4/2011 | Chesworth et al. |
| 2012/0283114 | A1 | 11/2012 | Cohen et al. |
| 2013/0071330 | A1 | 3/2013 | Catalano |
| 2014/0378460 | A1 | 12/2014 | Catalano et al. |
| 2014/0378473 | A1 | 12/2014 | Catalano et al. |
| 2015/0160228 | A1 | 6/2015 | Catalano |
| 2017/0197977 | A9 | 7/2017 | Catalano et al. |
| 2020/0338045 | A1 | 10/2020 | Catalano et al. |

FOREIGN PATENT DOCUMENTS

| | | | |
|---|---|---|---|
| CA | 1275934 | C | 11/1990 |
| CA | 2073841 | A1 | 1/1993 |
| CN | 101121670 | A | 2/2008 |
| DE | 4000610 | A1 | 7/1991 |
| DE | 10320560 | A1 | 1/2004 |
| EP | 0002222 | A1 | 6/1979 |
| EP | 0443606 | A2 | 8/1991 |
| EP | 0613007 | A2 | 8/1994 |
| EP | 0881220 | A1 | 12/1998 |
| EP | 1088550 | A1 | 4/2001 |
| JP | S62283922 | A | 12/1987 |
| JP | H01180822 | A | 7/1989 |
| JP | 01305085 | * | 8/1989 ........... C07D 417/04 |
| JP | H01305085 | A | 12/1989 |
| JP | H02215789 | A | 8/1990 |
| JP | H045266 | A | 1/1992 |
| JP | H06321781 | A | 11/1994 |
| JP | H09157144 | A | 6/1997 |
| JP | 2003113117 | A | 4/2003 |
| JP | 2004002517 | A | 1/2004 |
| WO | 1982002551 | A1 | 8/1982 |
| WO | 1991009594 | A1 | 7/1991 |
| WO | 199511221 | A1 | 4/1995 |
| WO | 1996012697 | A2 | 5/1996 |
| WO | 1999025363 | A1 | 5/1999 |
| WO | 1999029673 | A1 | 6/1999 |
| WO | 2001030335 | A2 | 5/2001 |
| WO | 2001091558 | A1 | 12/2001 |
| WO | 2003016274 | A2 | 2/2003 |
| WO | 2003051380 | A2 | 6/2003 |
| WO | 2005087212 | A1 | 9/2005 |
| WO | 2006020879 | A1 | 2/2006 |
| WO | 2006138349 | A1 | 12/2006 |
| WO | 2007077543 | A2 | 7/2007 |
| WO | 2008042755 | A2 | 4/2008 |
| WO | 2009059214 | A1 | 5/2009 |
| WO | 2010062260 | A1 | 6/2010 |
| WO | 2010088450 | A2 | 8/2010 |
| WO | 2010093704 | A1 | 8/2010 |
| WO | 2012027548 | A1 | 3/2012 |
| WO | 2015020523 | A1 | 2/2015 |

OTHER PUBLICATIONS

International Search Report and Written Opinion dated Jun. 30, 2012 for PCTUS2011026530.
International Search Report and Written Opinion dated May 31, 2012 for PCTUS2012023483.
International Search Report and Written Opinion dated Sep. 21, 2018 for PCT/US2018/032726.
International Search Report and Written Opinion dated Sep. 24, 2010 for PCTUS2010044136.

(56) References Cited

OTHER PUBLICATIONS

Ishikawa et al. "The role of sigma-1 receptors in the pathophysiology of neuropsychiatric diseases" J. Receptor Ligand and Channel Res. 2009 retrieved from http:researchgate.netprofileMasotomo_Ishikawapublication49606718 <http://researchgate.net/profile/Masotomo_Ishikawa/publication/49606718>_the_role_of_signa-1_receptors_in_the_pathophysiology_of_ Neuropsychatric_diseases.

Jacobsen et al. "GSI-953 is a Protein APP-Selective Gamma-Secretase Inhibitor for the Treatment of Alzheimer's Disease" Oral 03-06: Therapeutics and Therapeutic Strategies: Novel Targets 2008 1.

Jiang et al. "Metal-Organic Conjugated Microporous Polymers" Agnew. Chem. Int. Ed. 2011 50:1072-1075.

Jin et al. "Novel tricyclic pyrone compounds prevent intracellular APP C99-induced cell death" J Mol Neurosci Aug.-Oct. 2002 191-2:57-61.

Johansson et al. "Physiochemical characterization of the Alzheimer's disease-related peptides Abeta1-42Arctic and Abeta1-42wt" FEBS J. Jun. 2006 27312:2618-2630.

Kaech et al. "Culturing hippocampal neurons" Nat Protoc 2006 15:2406-2415.

Kamal et al. "Total synthesis of R- and S-turmerone and 7S9R-bisacumol by an efficient chemoenzymatic approach" Tetrahedron: Asymmetry 2009 20:1267-1271.

Kamenetz et al. "APP processing and synaptic function" Neuron. Mar. 27, 2003 376:925-937.

Kholodov et al., Clinical pharmacokinetics, Moscow, Medicine, 1985, pp. 83-98, 134-138, 160, 378-380.

Kimura "Chemical Structural Requirement in Gingerol Derivatives for Potentiation of Prostaglandin F2 alpha-induced Contraction in Isolated Mesenteric Veins of Mice" J. Pharmacobio-Dyn. 1989 12:220-227.

Klyubin et al. "Amyloid beta Protein Dimer-Containing Human CSF Disrupts Synaptic Plasticity: Prevention by Systemic Passive Immunization" J Neurosci. Apr. 16, 2008 2816:4231-4237.

Koffie et al. "Oligomeric amyloid beta associates with postsynaptic densities and correlates with excitatory synapse loss near senile plaques" Proc Natl Acad Sci USA Mar. 10, 2009 10610:4012-4017.

Kornhuber et al. "Cerebrospinal fluid and serum concentrations of the N-methyl-D-aspartate NMDA receptor antagonist memantine in man" Neurosci Lett Aug. 4, 1995 1952:137-139.

Kotilinek et al. "Reversible memory loss in a mouse transgenic model of Alzheimer's disease" J Neurosci. Aug. 1, 2002 2215:6331-6335.

Krafft et al. "ADDLs and the signaling web that leads to Alzheimer's disease" Neuropharmacology 2010 59:230-242.

Lacor et al. "Abeta oligomer-induced aberrations in synapse composition shape and density provide a molecular basis for loss and connectivity in Alzheimer's disease" J Neurosci. Jan. 24, 2007 274:796-807.

Lacor et al. "Synaptic targeting by Alzheimer's-related Amyloid beta oligomers" J Neurosci. Nov. 10, 2004 2445:10191-10200.

Lambert et al. "Monoclonal antibodies that target pathological assemblies of Abeta" J Neurochem Jan. 2007 1001:23-35.

Lambert et al. "Diffusible nonfibrillar ligands derived from Abeta1-42 are potent central nervous system neurotoxins" Proc Natl Acad Sci USA May 26, 1998 9511:6448-6453.

Lannfelt et al. "Safety efficacy and biomarker findings of PBT2 in targeting Abeta as a modifying therapy for Alzheimer's disease: a phase IIa double-blind randomized placebo-controlled trial" Lancet Neurol Sep. 2008 79:779-786.

Laurén et al. "Cellular prion protein mediates impairment of synaptic plasticity by Amyloid-beta oligomers" Nature Feb. 26, 2009 4577233:1128-1132.

Leal P. et al. "Functional Properties of Spice Extracts Obtained via Supercritical Fluid Extraction" J. Agri. Food Chem. 2003 519:2520-2525 Derwent Abstract.

Lecanu et al. "Identification of naturally occurring spirostenols preventing beta-amyloid-induced neurotoxicity" Steroids Jan. 2004 691:1-16.

Lesné et al. "A specific amyloid-beta protein assembly in the brain impairs memory" Nature Mar. 16, 2006 4407082:352-357.

Lesuisse et al. "Long-term culture of mouse cortical neurons as a model for neuronal development aging and death" J. Neurobiol. 2002 51:9-23.

Levine "Alzheimer's beta-peptide oligomer formation at physiologic concentrations" Anal. Biochem. Dec. 1, 2004 3351:81-90.

Levine "Biotin-avidin interaction-based screening assay for Alzheimer's beta-peptide oligomer inhibitors" Analytical Biochemistry 2006 356:265-272.

Li et al. "Soluble oligomers of Amyloid beta protein facilitate hippocampal long-term depression by disrupting neuronal glutamate uptake" Neuron. Jun. 25, 2009 626:788-801.

Li et al. "Total asymmetric synthesis of 7S9R-+-bisacumol" Tetrahedrom: Asymmetry 2003 14:75-78.

Liu et al. "Amyloid ? peptide alters intracellular trafficking and cholesterol homeostasis" Proc. Natl. Acad. Sci 1998 95:13266-3271.

Liu et al. "Cytotoxic Amyloid Peptides Inhibit Cellular 3-45-Dimethyithiazol-2yl-25-Diphenyitetrazolium Bromide MTT Reduction by Enhancing MTT Formazan Exocytosis" J Neurochem. Dec. 1997 696:2285-2293.

Liu et al. "Detecting bioactive Amyloid beta peptide species in Alzheimer's disease" J Neurochem. Nov. 2004 91:648-656.

Liu et al. "Treating Alzheimer's Disease by Inactivating Bioactive Amyloid beta Peptide" Curr Alzheimer Res Apr. 2006 32:129-135.

Lleó et al. "Clinical pathological and biochemical spectrum of Alzheimer disease associated with PS-1 mutations" Am J Geriatr. Psychiatry Mar.-Apr. 2004 122:146-156.

Look et al. "Discovery of ADDL-Targeting Small Molecule Drugs for Alzheimer's disease" Curr Alzheimer Res. Dec. 2007 45:562-567.

Maezawa et al. "A novel tricyclic pyrone compound ameliorates cell death associated with intracellular Amyloid-beta oligomeric complexes" J Neurochem. Jul. 2006 981:57-67.

Maier et al. "Synthesis and SAR Studies of 3-Substituted 1'-Benzylspiro[[2] benzoxepine1 4'-piperidines]" Euro. J. Org. Chem. Feb. 2003 20034:714-720.

Majno "Apoptosis oncosis and necrosis: an overview of cell death" Am J Pathol. Jan. 1995 1461:3-15.

Mann et al. "Amyloid angiopathy and variability in Amyloid beta deposition is determined by mutation position in presenilin-1-linked Alzheimer's disease" Am J Pathol. Jun. 2001 1586:2165-2175

Masaki et al. "A Facile Regio- and Sterio-Specific Allylic Oxidation of Gem-dimethyl Olefins Via Addition of Benzenesulphenyl Chloride. Synthesis of Allylic Oxygenated Terpenes" J. Chem. Soc. Perkin. Trans. I Jul. 4, 1984 4912;1289-1295.

Masuda et al. "Antioxidant properties of gingerol related compounds from ginger" Biofactors 2004 211-4:293-296.

Matsubara et al. Soluble Abeta homeostasis in AD and DS: impairment of anti-amyloidogenic protection by lipoproteins' Neurobiol Aging Aug. 2004 257:833-84.1

Matsuda et al. "Hepatoprotective Constituents from Zedoariae Rhozoma: Absolute Stereostructures of Three New Carabrane-type Sesquiterpenes Curcumenolactones A B and C" Bioorganic & Medicinal Chem. 2001 9:909-916.

Matsuda et al. "Medicinal foodstuffs. XXVIII. Inhibitors of nitric oxide production and new sesquiterpenes zedoarofuran 4-epicurcumenol neocumenol gajutsulactones A and B and zedoaroiides A and B from Sedoariae Rhizoma" Chem. Pharma. Bulletin Pharmaceutical Society of Japan Dec. 1, 2001 4912:1558-1566.

Maurice et al. "The pharmacology of sigma-1 receptors" Pharma. and Thera. Nov. 2009 1242:195-206.

Mayer et al. "Discovery of Begacestat a Notch-1-Sparing ?-Secretase Inhibitor for the Treatment of Alzheimer's Disease" J Med Chem Oct. 3, 2008 51:7348-7351.

Chin et al. "Fyn kinase induces synaptic and cognitive impairments in a transgenic mouse model of Alzheimer's disease" J. Neurosci. Oct. 19, 2005 2542:9694-9703.

Cirrito et al. "Endocytosis is required for synaptic activity-dependent release of Amyloid-beta in vivo" Neuron. Apr. 10, 2008 581:42-51.

(56) References Cited

OTHER PUBLICATIONS

Citron "Strategies for Disease Modification in Alzheimer's Disease" Nat Rev Neurosci. Sep. 2004 59:677-685.
Citron et al. "Evidence that the 42- and 40-amino acid forms of amyloid beta protein are generated from the beta-amyloid precursor protein by different protease activities" Proc. Nat. Acad. Sci. USA Nov. 1996 93:13170-13175.
Cleary et al. "Natural oligomers of the Amyloid-beta protein specifically disrupt cognitive function" Nat Neurosci. Jan. 2005 81:79-84.
Craig et al. "How to build a central synapse: clues from cell culture" Trends Neurosci. Jan. 2006 291:8-20.
Crawford et al. "Methalation of limonene. Novel method for the synthesis of bisabolane sesquiterpenes" J. Amer. Chem. Soc. Jun. 14, 1972 9412:4298-4306.
Dahlgren et al. "Oligomeric and Fibrillar Species of Amyloid-beta Peptides Differentially Affect Neuronal Viability" J Biol Chem. Aug. 30, 2002 27735:32046-32053.
Database CA Chemical Abstracts Service Columbus Ohio Alexander et al. "Terpenoids. XVIII Facile Elaboration of +-ar-turmerone to +-nuciferal via +-ar-curcumene" retrieved from STN Database Accession No. 1971:541008; and Alexander et al. "Terpenoids. XVIII Facile Elaboration of+-ar-turmerone to +-nuciferal via +-ar-curcumene" Indian Journal of Chemistry 1971 98:776-9.
Database CA Chemical Abstracts Service Columbus Ohio Duchene et al. "Improved Syntheses of .+-.-ar-turmerone via organotin reagents" retrieved from STN Database Accession No. 1986:479177; and Duchene et al. "Improved Syntheses of .+-.-ar-turmerone via organotin reagents" Synthetic Communications 1985 1510:873-882.
Database CA Chemical Abstracts Service Columbus Ohio Marterosyan et al. "Synthesis and reactions of .beta gamma-unsaturated amines. X.Condensation of .beta. .gamma-unsaturated amines with aromatichydrocarbons in the presence of aluminum chloride" retrieved from STN Database Accession No. 1744, database accession No. 1972:153257 (abstract) and Marterosyan et al. "Synthesis and reactions of .beta, .gamma-unsaturated amines.X. Condensation of .beta, .gamma-unsaturated amines with aromatichydrocarbons in the presence of aluminum chloride" Martirosyan, et al., Armyanskii Khimicheskii Zhurnal (1971), 24(9), 798-801.
Database CA Chemical Abstracts Service Columbus Ohio MASE, Dec. 8, 1989 "Preparation of pyridylziatholidinecarboxamide derivatives asplatelet-activating factor (PAF) antagonists" retrieved from STN Database Accession No. 1749 (abstract).
Database CA Chemical Abstracts Service Columbus Ohio Park et al. "Allylic Fluorination" retrieved from STN Database Accession No. 1989:8424; and Park et al. "Allylic Fluorination" Archives of Pharmacal Research 1987 104 239-44.
Davigulus et al. 2010, NIH Consensus and State of the Science Statement, 27(4), 1-30 (abstract attached).
De Felice et al. "A Oligomers Induce Neuronal Oxidative Stress through an N-Methyl-D-aspartate Receptor-dependent Mechanism That is Blocked by the Alzheimer Drug Memantine" J. Biol. Chem. 2007 282:11590-11601.
De Felice et al. "Targeting the neurotoxic species in Alzheimer's disease: inhibitors of Abeta oligomerization" FASEB J. Sep. 2004 1812:1366-1372.
Dedov et al. "Gingerols: a novel class of vanilloid receptor VR1 agonists" Br. J. Pharm. Nov. 2002 1376:793-798.
Denniff "Syntheses of the ±-[n]-Gingerois Pungent Principles of Ginger and Related Compounds through Regioselective Aldol Condensations: Relative Pungency Assays" J. Chem. Soc. Perkin 1 1981 82-87.
Dodart et al. "Immunization reverses memory deficits without reducing brain Abeta burden in Alzheimer's disease model" Nat Neurosci May 2002 55:452-457.
Doody et al. "Effect of dimebon on cognition activities of daily living behavior and global function in patients with mild-to-moderate Alzheimer's disease: a randomized double-blind placebo-controlled study" Lancet Jul. 19, 2008 3729634:207-215.

European Search Report and Written Opinion for EP 15743281 dated May 11, 2017.
European Search Report and Written Opinion for EP 18802363 dated Nov. 26, 2020.
Extended European Search Report by the European Patent Office dated Apr. 15, 2015 for European Patent Application No. 12824979.4.
Extended European Search Report for European Patent Application No. 19154222.4 dated Mar. 19, 2019.
Fenili et al. "Properties of scyllo-inositol as a therapeutic treatment of AD-like pathology" J Mol Med. Jun. 2007 856:603-611.
Flood et al. "FAD mutant PS-1 gene-targeted mice: Increased Abeta42 and Abeta deposition without APP overproduction" Neurobiol Aging May-Jun. 2002 233:335-348.
Fujiwara et al. "Acetylcholinesterase Inhibitory Activity of Volatile Oil from Peltophorum dasyrachis Kurz ex Bakar Yellow Batai and Bisabolane-Type Sesquiterpenoids" J. Agri. and Food Chem. Jan. 2010 585:2824-2829.
Fukumoto et al. "Beta-Secretase Activity increases with Aging in Human Monkey and Mouse Brain" Am. J. Path. Feb. 2004 1642:719-725.
Georganopoulou et al. "Nanoparticle-based detection in cerebral spinal fluid of a soluble pathogenic biomarker for Alzheimer's disease" PNAS Feb. 15, 2005 1027:2273-2276.
Golde "Alzheimer disease therapy: can the Amyloid cascade be haltered?" J Clin Invest. Jan. 2003 1111:11-18.
Gopalan et al. "Supercritical Carbon Dioxide Extraction of Tumeric Curcuma longa" J. Agric. Food Chem. 2000 48:2189-2192.
Greene et al. Protective Groups in Organic Synthesis 3rd Ed. Wiley & Sons New York 1999.
Griffith et al., "Elevated brain scyllo-inositol concentrations in patients with Alzheimer's disease" NMR Biomed Dec. 2007 208:709-716.
Grzanna et al. "Ginger—An herbal medicinal product with broad anti-inflammatory actions" J. Medicinal Foods 2005 82:125-132.
Görtz et al. "Neuronal network properties of human teratocarcinoma cell line-derived neurons" Brain Res Aug. 20, 2004 10181:18-25.
Hampel et al., Core candidate neurochemical and imaging biomarkers of Alzheimer's disease, Alzheimers Dement (Jan. 2008), 4(1 ):38-48.
Hansson et al. "Reduced Levels of Amyloid-beta-Binding Proteins in Cerebrospinal Fluid from Alzheimer's Disease Patients" J Alzheimers Dis 2009 162:389-397.
Hisashi et al. "Heptatoproctective Constituents from Zedoariae Rhizoma: Absolute Stereostructures of Three New Carabrane-type Sesquiterpenes Curcumenolactones A B and C" Bioorganic & Med. Chem. 2001 9:909-916.
Hisashi et al. "Medicinal Foodstuffs. XXVIII.1 Inhibitors of Nitric Oxide Production and New Sesquiterpenes Zedoarofuran 4-Epicurcumenol Neocurcumenol Gajutsulactones A and B y and Zedoarolides A and B from Zedoariae Rhizoma" Chem. Pharm. Bull. 2001 4912 13-15:1558-1566.
Ho et al. "Heterogeneity in red wine polyphenolic contents differentially influences Alzheimer's disease-type neuropathology and cognitive deterioration" J Alzheimers Dis. 2009 161:59-72.
Hong et al. "Candidate anti-Abeta fluorine compounds selected from analogs of Amyloid imaging agents" Neurobiol Aging. Oct. 2010 3110:1690-1699.
Hong et al. "Combining the rapid MTT formazan exocytosis assay and the MC65 protection assay led to the discovery of carbazole analogs as small molecule inhibitors of Abeta oligomer-induced cytotoxicity" Brain Res. Jan. 26, 2007 11301:223-234.
Hong et al. "Inhibition of Alzheimer's Amyloid toxicity with a trycyclic pyrone molecule in vitro and in vivo" J Neurochem. Feb. 2009 1084:1097-1108
Hsieh et al. "AMPAR removal underlies Abeta-induced synaptic depression and Dendritic spine loss" Neuron. Dec. 7, 2006 525:831-843.
International Search Report and Written Opinion dated Apr. 30, 2015 for PCTUS2015013754.
International Search Report and Written Opinion dated Feb. 25, 2013 for PCTUS2012052572.

(56) References Cited

OTHER PUBLICATIONS

International Search Report and Written Opinion dated Jan. 16, 2019 for PCT/US2018/058789 .
International Search Report and Written Opinion dated Jan. 18, 2013 for PCTUS2012052578.
International Search Report and Written Opinion dated Jun. 10, 2010 for PCTUS2010030130.
International Search Report and Written Opinion dated Jun. 3, 2008 for PCTUS200779850.
Miklossy et al. "Two novel presenilin-1 mutations Y256S and Q222H are associated with early-onset Alzheimer's disease" Neurobiol. Aging Sep. 2003 245:655-662.
Mori et al. "Synthesis of a Mixture of+-Dehydrojuvabione and its Stereoisomer" Tetrahedron Letters 1967 48:4853-4856.
Morris "Episodic-like memory in animals: psychological criteria neural mechanisms and the value of episodic-like tasks to investigate animal models of neurodegenerative disease" Philos Trans R Soc Lond B Biol Sci. Sep. 29, 2001 3561413:1453-1465.
Morris "The Organization of Behavior" Wiley New York 1949 Brain Research Bulletin May 19 1999 505-6:437-438.
Mucke et al. "High-level neuronal expression of Abeta1-42 in wild-type human Amyloid protein precursor transfenic mice: synaptotoxicity without plaque formation" J Neurochem. Jun. 1, 2000 2011:4050-4058.
Mukaiyama et al., "N-Alkylation of Phthalimide, Carboxamide, and Sulfonamides By Oxidation-Reduction Condensation Using Di-tert-butyl-1 4-benzoquinone and Alkyl Diphenyiphosphinite," Chemistry Letters, vol. 34, No. 2, Apr. 25, 2004, pp. 142-143.
Mustafa et al. "Drug Development Report 9: Pharmacology of Ginger Zingiber Officinale" J. Drug. Dev. 1993 61:25-39.
Negron et al. "Study of the asymmetric induction of the 13-dipolar cycloaddition of chiral azomXethine ylides with unactivated double bonds" CASREACT 1992 117:26230 Accession No. 1992:426230.
Nielsen et al. "Binding and Uptake of Abeta1-42 by Primary Human Astrocytes In Vitro" GLIA 2009 57:978-988.
Nikolaev et al. "APP binds DR6 to trigger axon pruning and neuron death via distrinct caspases" Nature Feb. 19, 2009 4577232:981-989.
Nomura et al. "Mechanism of impairment of long-term potentiation by Amyloid beta is independent of NMDA receptors or voltage-dependent calcium channels in hippocampal CA1 pyramidal neurons" Neurosci Lett. Dec. 31, 2005 3911-2:1-6.
Ono et al. "Effects of grape seed-derived polyphenols on Amyloid beta-protein self-assembly and cytotoxicity" J Biol Chem. Nov. 12, 2008 28347:32176-32187.
Plant et al. "The Production of Amyloid ? Peptide Is a Critical Requirement for the Viability of Central Neurons" The Journal of Neuroscience Jul. 2003 2313:5531-5535.
Poling et al., "Oligomers of the Amyloid-beta protein disrupt working memory: confirmation with two behavioral procedures" Behav Brain Res. Nov. 21, 2008 1932:230-234.
Price et al. "Neuron number in the entorhinal cortex and CA1 in preclinicai Alzheimer disease" Arch Neurol. Sep. 2001 589:1395-1402.
Priller et al. "Mutant presenilin 1 alters synaptic transmission in cultured hippocampal neurons" J Biol Chem. Jan. 12, 2007 2822:1119-1127.
Puzzo et al. "Amyloid-beta Peptide Inhibits Activation of the Nitric OxidecGMPcAMP-Responsive Element-Binding Protein Pathway during Hippocampal Synaptic Plasticity" J Neurosci Jul. 20, 2005 2529:6887-6897.
Puzzo et al. Picomolar Amyloid-beta positively modulates synaptic plasticity and memory in hippocampus J Neurosci. Dec. 31, 2008 2853:14537-14545.
Rana et al. "Syntheses of tricyclic pyrones and pyridinones and protection of Abeta-peptide induced MC65 neuronal cell death" Bioorg Med Chem Lett Feb. 1, 2009 193:670-674.
Remington's Pharmaceutical Sciences Mack Publishing Company Easton Pennsylvania 1985.
Rishton "Nonleadlikeness and leadlikeness in biochemical screening" Drug Discov Today Jan. 15, 2003 82:86-96.
Rishton "Reactive compounds and in vitro false positives in HTS" DDT Sep. 9, 1997 29:382-334.
Rishton et al. "Computational approaches to the prediction of blood-brain barrier permeability: a comparative analysis of central nervous system drugs versus secretase inhibitors for Alzheimer's disease" Curr Opin Drug Discov Devel. May 2006 93:303-313.
Rowan et al. "Mechanisms of the inhibitory effects of Amyloid beta-protein on synaptic plasticity" Exp Gerontol. Nov.-Dec. 2004 3911-12:1661-1667.
Rönicke et al. "Abeta mediated diminution of MTT reduction-an artifact of single cell culture?" PloS One Sep. 18, 2008 39:e3236.
Sampson et al. "Metal protein attenuating compounds for the treatment of Alzheimer's disease review" The Cochrane Collaboration published in The Cochrane Library 2009 Issue 1.
Scheff et al. "Hippocampal synaptic loss in early Alzheimer's disease and mild cognitive impairment" Neurobiol Aging Oct. 2006 2710:1372-1384.
Scheff et al. "Synaptic alternations in CA1 mild Alzheimer's disease and mild cognitive impairment" Neurology 2007 68:1501-1508.
Sejnowski et al. "The Book of Hebb: Minireview" Neuron Dec. 1999 24:773-776.
Sergeev, et al. "Concise course in the molecular pharmacology," Moscow, (1975), 10-11 (In Russian-English translation not available).
Shankar et al. "Amyloid-beta protein dimmers isolated directly from Alzheimer's brains impair synaptic plasticity and memory" Nat Med. Aug. 2008 148:837-842.
Shankar et al. "Natural oligomers of the Alzheimer Amyloid-beta protein induce reversible synapse loss by modulating an NMDA-type glutamate receptor-dependent signaling pathway" J Neurosci. Mar. 14, 2007 2711:2866-2875.
Shin et al. "Zingerone as an Antioxidant against Peroxynitrite" J. of Agric. & Food Chem. 2005 53:7617-7622.
Shrestha et al. Amyloid beta peptide adversely affects spine number and motility in hippocampal neurons Mol Cell Neurosci Nov. 2006 333:274-282.
Snyder et al. "Regulation of NMDA receptor trafficking by Amyloid-beta" Nat Neurosci. Aug. 2005 88:1051-1058.
Song et al. "Memantine protects rat cortical cultured neurons against ?-amyloid-induced toxicity by attenuating tau phosphorylation" European J. Neuro. 2008 28:1989-2002.
Subbarayappa et al."An efficient method for the synthesis of 2, 3-dihydro-1H-isoindoles." Indian Journal of Chemistry 2009 488:545-552.
Supplementary European Search Report by the European Patent Office dated Jun. 19, 2017 for European Patent Application No. 15743281.6.
Supplementary European Search Report from European Patent Office dated Sep. 21, 2015 for European Patent Application No. 12825341.6.
Surh et al. "Enzymic Reduction of [6]-Gingerol a Major Pungent Principle of Ginger in the Cell-Free Preparation of Rat Liver" Life Sci. 1994 5419:321-326.
Terry "Cell death or synaptic loss in Alzheimer's disease" J Neuropathol Exp Neurol. Dec. 2000 5912:1118-1119.
Ting et al. "Amyloid precursor protein overexpression depresses excitatory transmission through both presynaptic and postsynaptic mechanisms" Proc Natl Acad Sci USA Jan. 2, 2007 1041:353-358.
Tomiyama et al. "A New Amyloid beta Variant Favoring oligomerization in Alzheimer's-type dementia" Ann Neurol Mar. 2008 633:377-387.
Tong et al. "beta-amyloid Peptide at Sublethal Concentrations Downregulates Brain-Derived Neurotrophic Factor Functions in Cultured Cortical Neurons" J. Neurosci. Jul. 28, 2004 2430:6799-6809.
Townsend et al. "Orally available compound prevents deficits in memory caused by the Alzheimer Amyloid-beta oligomers" Ann Neurol Dec. 2006 606:668-676.
Turner et al. "Roles of amyloid precursor protein and its fragments in regulating neural activity plasticity and memeory" Prog. in Neurobiol. 2003 70:1-32.

(56) References Cited

OTHER PUBLICATIONS

Uehara et al. "New Bisabolane Sesquiterpenoids from the Rhizomes of Curuma Xanthorrhiza Zinziberaceae" Chem. and Pharma. Bulletin 1989 371:237-240.
Verdile et al. "The role of beta amyloid in Alzheimer's disease: still a cause of everything or the only one who got caught?" Pharmacol Res Oct. 2004 504:397-409.
Walsh et al. "Certain inhibitors of synthetic Amyloid beta-peptide Abeta fibrillogenesis block oligomerization of natural Abeta and thereby rescue long-term potentiation" J Neurosci. Mar. 9, 2005 2510:2455-2462.
Walsh et al. "Naturally secreted oligomers of Amyloid beta protein potently inhibit hippocampal long-term potentiation in vivo" Nature Apr. 4, 2002 4166880:535-539.
Wang et al. "A Versatile Catalyst for Reductive Amination by Transfer Hydogenation" Agnew. Chem. Int. Ed. 2010 49:7548-7552.
Wang et al. "Block of Long-Term Potentiation by Naturally Secreted and Synthetic Amyloid beta-Peptide in Hippocampal Slices is Mediated Via Activation of the Kinases c-Jun N-Terminal Kinase Cyolin-Dependent Kinase 5 and p38 Mitogen-Activated Protein Kinase as well as Metabotropic Glutamate Receptor Type 5" J. Neurosci. Mar. 31, 2004 2413:3370-3378.
Wang et al. "Grape-derived polyphenolics prevent Abeta oligomerization and attenuate cognitive deterioration in a mouse model of Alzheimer's disease" J Neurosci. Jun. 18, 2008 2825:6388-6392.
Wang et al. "Moderate consumption of Cabernet Sauvignon attenuates Abeta neuropathology in a mouse model of Alzheimer's disease" FASEB J. Nov. 2006 2013:2313-2320.
Wang et al. "Soluble oligomers of beta Amyloid 1-42 inhibit long-term potentiation but not long-term depression in rat dentate gyrus" Brain Res. Jan. 11, 2002 9242:133-140.
Weiyan et al. "Research Advances on Chemistry and Pharmacology of Zingiber officinale" Chinese J. of Ethnomedicine and Ethnopharmacology 2008 9.
West et al. "Hippocampal neurons in pre-clinical Alzheimer's disease" Neurobiol Aging Oct. 2004 259:1205-1212.
Whitlock et al. "Learning induces long-term potentiation in the hippocampus" Science Aug. 25, 2006 3135790:1093-1097.
Wolozin "Cholesterol and the Biology of Alzheimer's Disease" Neuron Jan. 8, 2004 41:7-10.
Yang et al. "New ELISAs with high specificity for soluble oligomers of amyloid ?-protein detect natural A? oligomers in human brain but not CSF" Alzheimers Dement. Mar. 2013 92:99-112.
Yao et al. "The Ginkgo biloba extract EGb 761 rescues the PC12 neuronal cells from beta-amyloid-induced cell death by inhibiting the formation of beta-amyloid-derived diffusible neurotoxic ligands" Brain Res. Jan. 19, 2001 8891-2:181-190.
Yu et al. "Per-6-Substituted beta-Cyclodextrin Libraries Inhibit Formation of beta-Amyloid-Peptide Abeta-Derived Soluble Oligomers" J Mol Neurosci Aug.-Oct. 2002 191-2:51-55.
Zhang et al. "A Simple Statistical Parameter for Use in Evaluation and Validation of High Throughput Screening Assays" J Biomol Screen 1999 42:67-73.
Zhang et al. "Chiral Benzyl Centers 1-6 through Asymmetric Catalysis. A Three-Step Synthesis of R-Alpha-Curcumene via Asymmetric Hydrovinylation" Organic Letters American Chemical Society Aug. 3, 2004 618:3159-3161.
Zhao et al. "Amyloid beta oligomers induce impairment of neuronal insulin receptors" FASEB J. 2008 22:246-260.
Zhao et al. "Identification of antihypertensive drugs which inhibit Amyloid-beta protein oligomerization" J Alzheimers Dis. 2009 161:49-57.
Zlokovic "New therapeutic targets in the neurovascular pathway in Alzheimer's disease" Neurotherapeutics Jul. 2008 53:409-414.
Aboul-Enein et al. "Synthesis of certain 1 7 7-trimethylbicyclo 2.2.1 heptane derivatives with anticonfuisant hypoglycemic and anti-inflammatory potential" 2006 CASREACT 147:10056 Accession No. 2006:599283.

Adams et al. "The Leaf Essential Oils and Taxonomy of *Juniperus oxycedrus* L. subsp. *oxycedrus* subsp. *badia* H. Gay Debeaux and subsp. *macrocarpa* Sibth. & Sm. Ball." J. Essent. Oil Res. Mar.Apr. 1999 11:167-172.
Albright "Diverse Approaches to Alzheimer's Therapies Continue to Show Progress at ICAD" International Conference on Alzheimer's Disease 2008 Jul. 26-31, 2008 Chicago Illinois.
Arai et al. "Chemically conditioned extracts of ginger oil: leadlike 'alkaloidal' compounds derived from natural extracts via reductive amination" Gen. Biochem. Biotech. and Pharma.—Poster Wednesday Jan. 25, 2006 Laguna DoubleTree Hotel.
Balaji et al. "Toxicity Prediction of Compounds from Turmeric" Food and Chemical Toxicology 2010 vol. 48 2951-2959.
Banerjee et al. "Chemical Modification of Turmeric Oil to More Value Added Products" Indian Perfumer 1981 vol. 25 25-30.
Barghorn et al. "Globular amyloid beta-peptide1-42 oligomer—a homogenous and stable neuropathological protein in Alzheimer's disease" J. Neurochem. Nov. 2005 953:834-847.
Batra et al. "Hydrogenolysis of 3-methyl-4-phenylmethyl-52H-isoxazolone derivatives: A reinvestigation" Indian J. Chem. Jan. 1992 31B:60-62.
Beckurts et al. Archiv der Pharmazie und Berichte der Deutschen Phamazeutischen Gessellschaft 1927 265:15-26.
Begum et al., "Curcumin Structure-Function Bioavailability and Efficacy in Models of Neuroinflammation and Alzheimer's Disease" J. Pharma. Experimental Thera. Feb. 4, 2008 3261:196-208.
Belikov et al. V.G., "Pharmaceutical Chemistry," Moscow, Vyshaya Shkola Publishing House, (1993), 43-46.
Blossom et al. "Beyond mild cognitive impairmentl vascular cognitive impairment, no dementia" Alzheimers Res Ther. 2009; 1(1): 16 pages.
Bornholdt et al. "Ring Opening of Pymisyl-Protected Aziridines with Organocuprates" Chem. A European J. 2010 16:12474-12480.
Brody et al., "Amyloid-beta Dynamics Correlate with Neurological Status in the Injured Human Brain" Science Aug. 29, 2008 3215893:1221-1224.
Bu "Apolipoprotein E and its receptors in Alzheimer's disease: pathways pathogenesis and therapy" Nat Rev Neurosci. May 2009 105:333-344.
Calabrese et al. "Rapid concurrent alternations in pre- and postsynaptic structure induced by naturally-secreted Amyloid-beta protein" Mol. Cell. Neurosci. Feb. 2, 2007 1-11.
Campbell Med. Hypotheses 2001 563:388-391.
Casagrande et al. "Systhesis of Some Isoindolines and 1234-Tetrahydroisoquinolines and heir Evaluation as ?-Adrenergic and Adrenergic Neuron Blocking Agents" II Farmaco Edizion Scientifica 1972 276:445-470.
Catalano et al. "The role of Amyloid-beta derived diffusible ligands ADDLs in Alzheimer's disease" Curr Top Med Chem. 2006 66:597-608.
Chang et al. "AMPA receptor downscaling at the onset of Alzheimer's disease pathology in double knockin mice" PNAS Feb. 28, 2006 1039:3410-3415.
Chang et al. "Supercritical carbon dioxide extraction of turmeric oil from Curcuma longa Linn and purification of turmerones" Separation and Purification Technology 2006 47:119-125.
Chemical Abstracts Registry No. 1099652-84-2.
Chemical Abstracts Registry No. 1099652-96-6.
Chemical Abstracts Registry No. 1179275-25-2.
Chemical Abstracts Registry No. 1179710-89-4.
Chemical Abstracts Registry No. 1181691-78-0.
Chemical Abstracts Registry No. 1181707-36-7.
Chemical Abstracts Registry No. 1181721-34-5.
Chemical Abstracts Registry No. 1181772-10-0.
Chemical Abstracts Registry No. 1181779-90-7.
Chemical Abstracts Registry No. 1181977-85-4.
Chemical Abstracts Registry No. 1181984-40-6.
Chemical Abstracts Registry No. 1182269-99-3.
Chemical Abstracts Registry No. 1184509-73-6.
Chemical Abstracts Registry No. 1216315-24-0.
Chemical Abstracts Registry No. 1291982-54-1.
Chemical Abstracts Registry No. 1292175-79-1.
Chemical Abstracts Registry No. 1307058-18-9.

(56) References Cited

OTHER PUBLICATIONS

Chemical Abstracts Registry No. 1307880-18-7.
Chemical Abstracts Registry No. 415960-77-9.
Chemical Abstracts Registry No. 415970-72-8.
Chemical Abstracts Registry No. 415971-26-5.
Chemical Abstracts Registry No. 416863-98-4.
Chemical Abstracts Registry No. 416864-44-3.
Chemical Abstracts Registry No. 416865-91-3.
Chemical Abstracts Registry No. 416866-75-6.
Chemical Abstracts Registry No. 416867-24-8.
Chemical Abstracts Registry No. 416870-18-3.
Chemical Abstracts Registry No. 416870-75-2.
Chemical Abstracts Registry No. 864420-46-2.

* cited by examiner

COMPOSITIONS FOR TREATING NEURODEGENERATIVE DISEASES

CROSS-REFERENCE TO RELATED APPLICATIONS

This application is a U.S. national stage filing under 35 U.S.C. § 371 of International Application No. PCT/US2018/032726 filed May 15, 2018 entitled "COMPOSITIONS FOR TREATING NEURODEGENERATIVE DISEASES", which claims priority under 35 U.S.C. § 119(e) to U.S. Provisional Application No. 62/506,226, filed May 15, 2017, the contents of which is hereby incorporated by reference in its entirety.

GOVERNMENT INTEREST

This invention was made with support from the U. S. government under a grant from the National Institute On Aging of the National Institute of Health, grant number U01AG047059. The U. S. government has certain rights in this invention.

SUMMARY

Various embodiments provide novel compounds, pharmaceutical compositions comprising such compounds, and methods for inhibiting or restoring synapse loss in neuronal cells, modulating a membrane trafficking change in neuronal cells, and treating cognitive decline and neurodegenerative diseases and disorders.

Some embodiments of the present disclosure are directed to a compound of Formula I or pharmaceutically acceptable salt thereof:

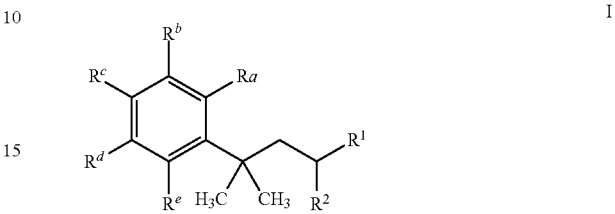

wherein:
each of $R^a$, $R^b$, $R^c$, $R^d$ and $R^e$ is independently selected from the group consisting of H, hydroxyl, halo, alkyl, alkoxy, $CF_3$, $SO_2CH_3$, and morpholino;
$R^1$ is selected from the group consisting of hydrogen, alkyl, phenyl, or $-CH=C(CH_3)_2$; and
$R^2$ is an optionally substituted cyclic amino group.

Some embodiments of the present disclosure are directed to a compound selected from the group consisting of

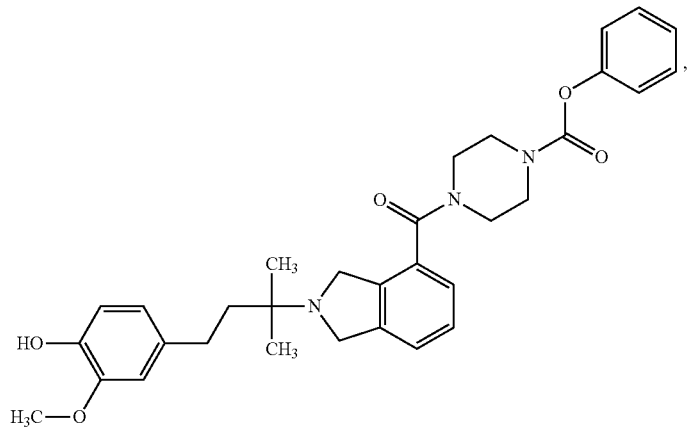

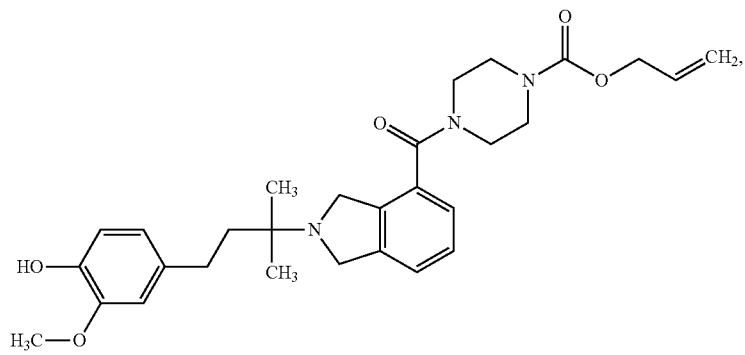

-continued
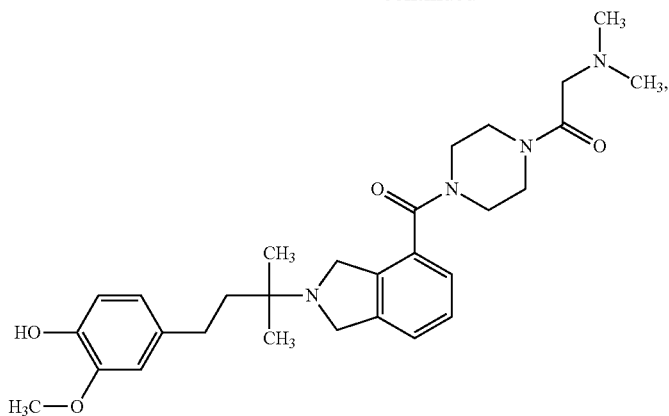
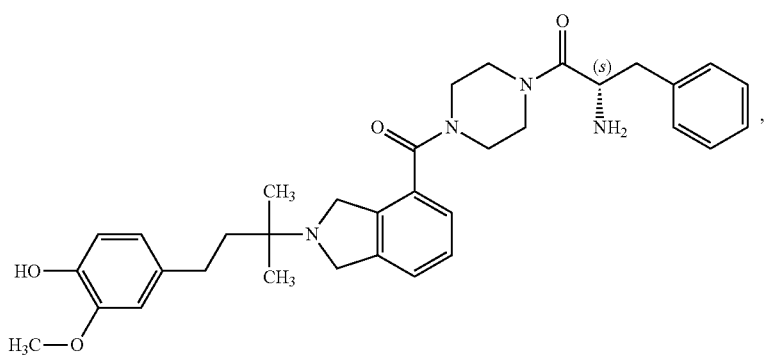
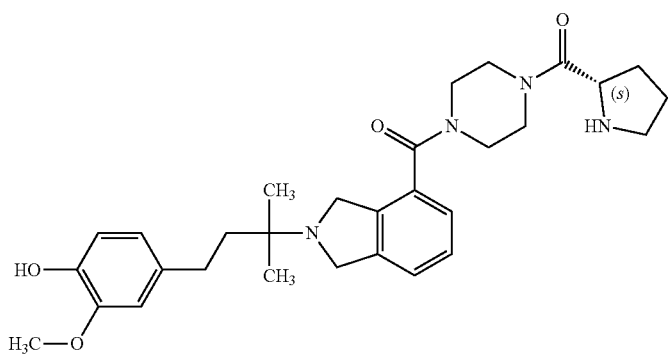
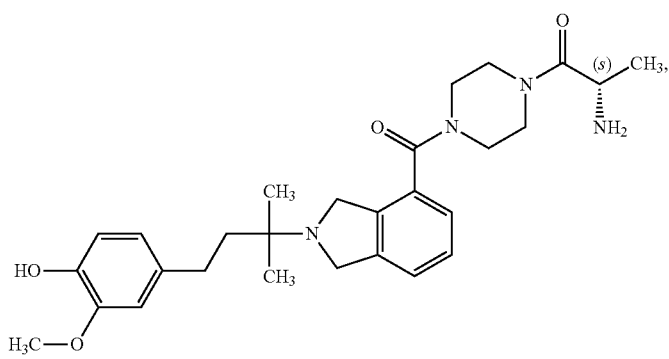

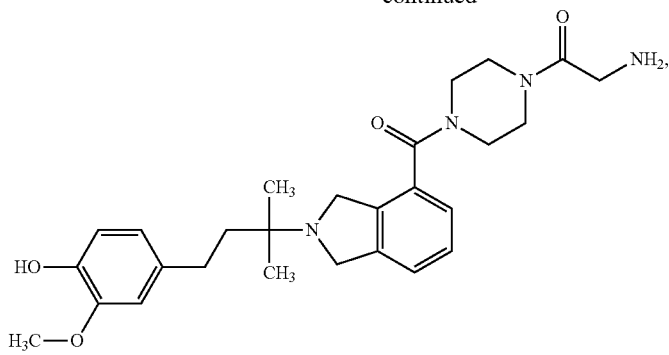
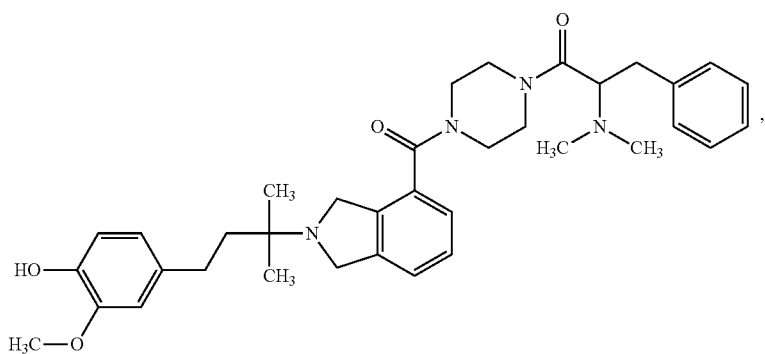
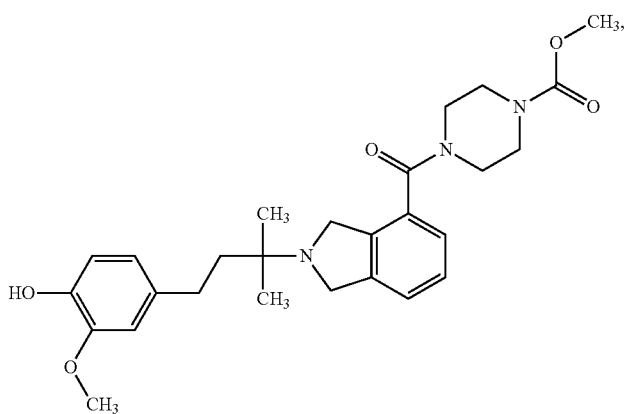
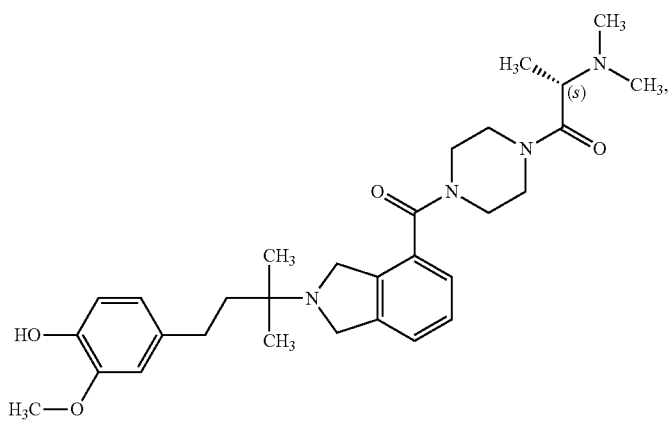

-continued
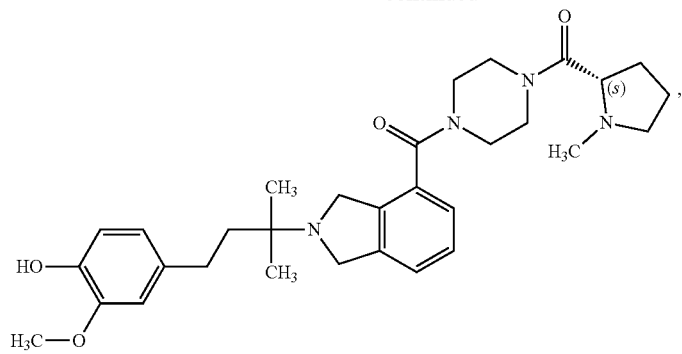
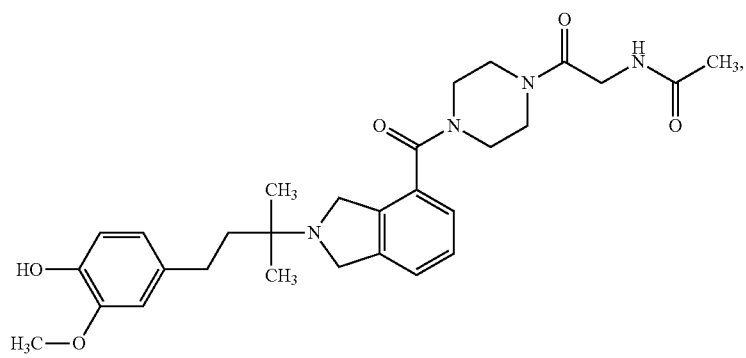
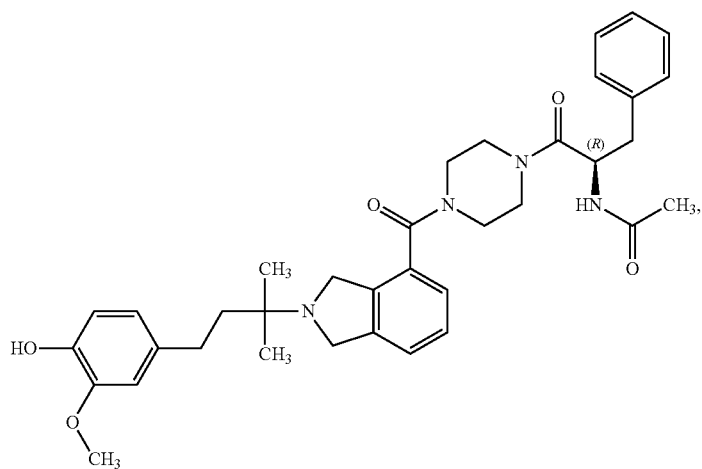
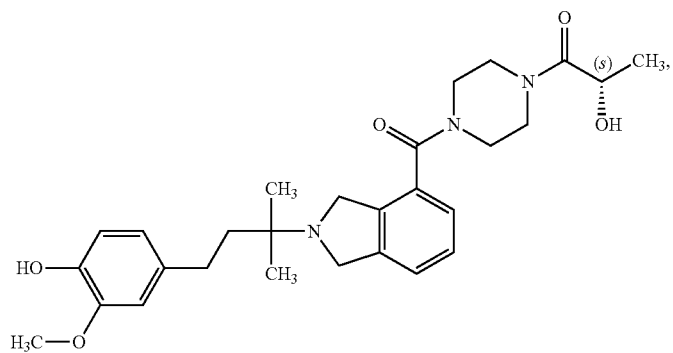

-continued

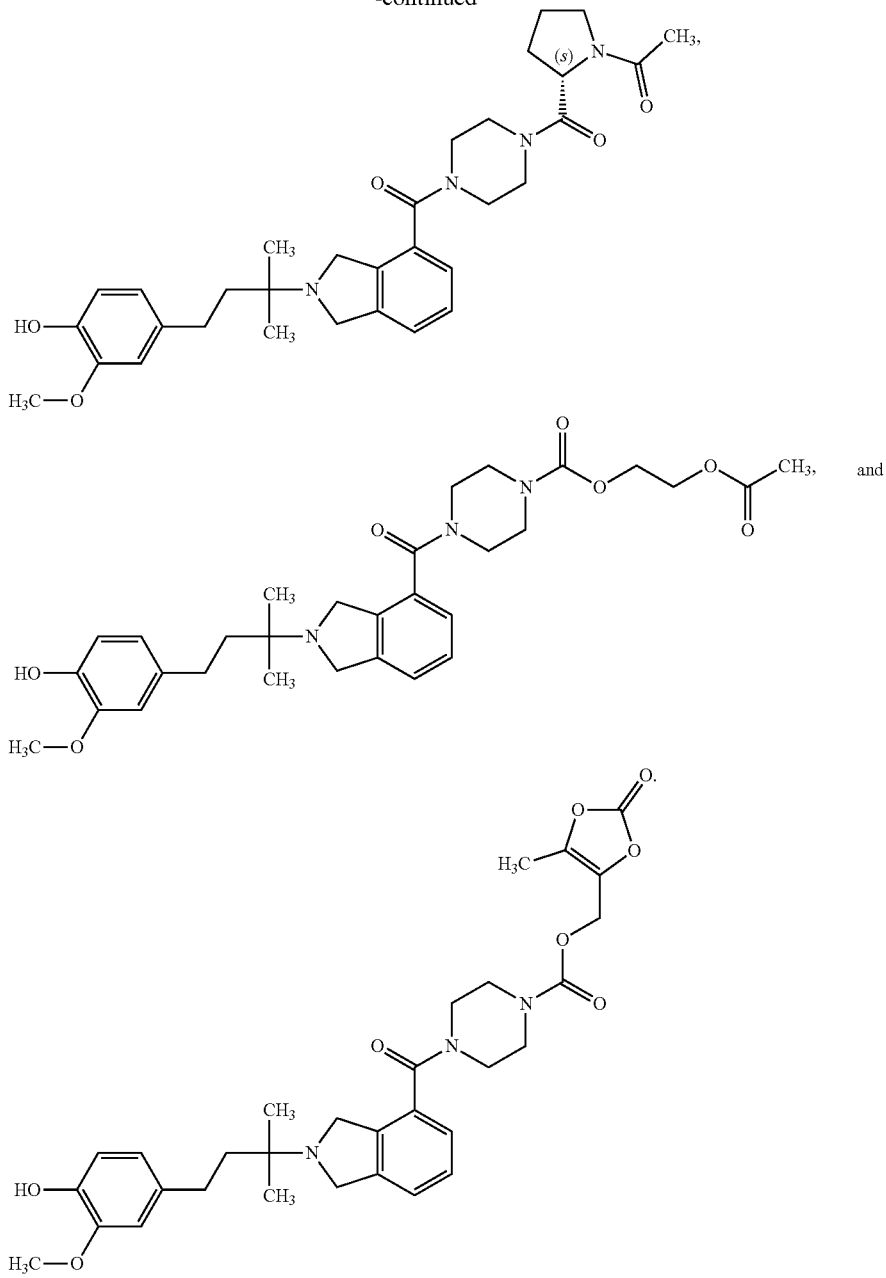

and

Embodiments herein describe a pharmaceutical composition comprising: a compound according to any embodiment described herein, or a pharmaceutically acceptable salt thereof; and a pharmaceutically acceptable carrier or diluent Some embodiments describe a method of treating Alzheimer's disease (AD) comprising administering to the subject a therapeutically effective amount of a compound or a pharmaceutical composition according to any embodiment described herein.

Some embodiments describe a method of inhibiting cognitive decline in a subject exhibiting, or at risk of exhibiting, cognitive decline, comprising administering a therapeutically effective amount of a compound or a pharmaceutical composition according to any embodiment described herein.

Some embodiments describe a method of inhibiting amyloid beta effect on a neuronal cell comprising administering to a subject in need thereof, a therapeutically effective amount of a pharmaceutical composition according to any embodiment described herein.

Some embodiments describe a method of treating mild cognitive impairment in Alzheimer's disease in a subject in need thereof, comprising administering to the subject a therapeutically effective amount of a pharmaceutical composition according to any embodiment described herein.

Some embodiments describe use of a compound according to according to any embodiment described herein, in the manufacture of a medicament for the treatment of Alzheimer's disease.

Some embodiments describe a compound according to any embodiment described herein, for use in the treatment of Alzheimer's disease.

Some embodiments describe a compound according to any embodiment described herein, for use in medical therapy.

Some embodiments describe a pharmaceutical composition comprising a therapeutically effective amount of a compound according to any embodiment described herein, and pharmaceutically acceptable salt thereof, and a pharmaceutically acceptable carrier or diluent.

DETAILED DESCRIPTION

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein, are incorporated by reference in their entirety. Nothing herein is to be construed as an admission that the invention is not entitled to antedate such disclosure by virtue of prior invention.

Definitions

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed.

At various places in the present specification, substituents of compounds of the disclosure are disclosed in groups or in ranges. It is specifically intended that embodiments of the disclosure include each and every individual subcombination of the members of such groups and ranges. For example, the term "$C_{1-6}$ alkyl" is specifically intended to individually disclose, e.g. methyl ($C_1$ alkyl), ethyl ($C_2$ alkyl), propyl ($C_3$ alkyl), butyl ($C_4$ alkyl), pentyl ($C_5$ alkyl), and hexyl ($C_6$ alkyl) as well as, e.g. $C_1$-$C_2$ alkyl, $C_1$-$C_3$ alkyl, $C_1$-$C_4$ alkyl, $C_2$-$C_3$ alkyl, $C_2$-$C_4$ alkyl, $C_3$-$C_6$ alkyl, $C_4$-$C_5$ alkyl, and $C_5$-$C_6$ alkyl.

The articles "a" and "an" as used herein, mean "one or more" or "at least one," unless otherwise indicated. That is, reference to any element of the present invention by the indefinite article "a" or "an" does not exclude the possibility that more than one of the element is present.

As used herein, the term "about" means plus or minus 10% of the numerical value of the number with which it is being used. Therefore, about 50 mL means in the range of 45 mL-55 mL.

"Abeta species" or "Aβ" shall include compositions comprising soluble amyloid peptide-containing components such as Abeta monomers, Abeta oligomers, or complexes of Abeta peptide (in monomeric, dimeric or polymeric form) with other soluble peptides or proteins as well as other soluble Abeta assemblies, including any processed product of amyloid precursor protein. Soluble Aβ oligomers are known to be neurotoxic. Even Aβ1-42 dimers are known to impair synaptic plasticity in mouse hippocampal slices. In one theory known in the art, native Aβ1-42 monomers are considered neuroprotective, and self-association of Aβ monomers into soluble Abeta oligomers is required for neurotoxicity. However, certain Aβ mutant monomers (arctic mutation (E22G) are reported to be associated with familial Alzheimer's Disease.

Unless specifically indicated, the term "active ingredient" is to be understood as referring to a compound according to any embodiment describe herein.

"Administering," or "administration" and the like, when used in conjunction with the compounds of the disclosure refers to providing the compounds or pharmaceutical compositions according to any of the embodiments described herein, to a subject in need of treatment. Preferably the subject is a mammal, more preferably a human. The present invention comprises administering the pharmaceutical composition of the invention alone or in conjunction with another therapeutic agent. When a pharmaceutical composition of the invention is administered in conjunction with another therapeutic agent, the pharmaceutical composition of the invention and the other therapeutic agent. can be administered at the same time or different times.

The term "agonist" refers to a compound, the presence of which results in a biological activity of a receptor that is the same as the biological activity resulting from the presence of a naturally occurring ligand for the receptor.

The term "alkanoyl" or "alkylcarbonyl" as used herein, is meant to refer to an alkyl group attached to a carbonyl radical. An example of an alkanoyl is

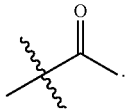

As used herein, the term "alkyl" is meant to refer to a saturated hydrocarbon group which is straight-chained or branched. Example alkyl groups include, but are not limited to, methyl (Me), ethyl (Et), propyl (e.g. n-propyl and isopropyl), butyl (e.g. n-butyl, isobutyl, t-butyl), pentyl (e.g. n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. "$C_1$-$C_{10}$ alkyl" or "$C_{1-10}$alkyl", is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" or "$C_{1-6}$ alkyl" denotes alkyl having 1 to 6 carbon atoms. The term "alkylene" refers to a divalent alkyl linking group. An example of alkylene is methylene ($CH_2$).

As used herein, "alkenyl" is intended to include hydrocarbon chains of either straight or branched configuration with one or more, preferably one to three, carbon-carbon double bonds that may occur in any stable point along the chain. For example, "$C_2$-$C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

The term "alkoxy" or "alkyloxy" refers to an —O-alkyl group. "$C_1$-$C_6$ alkoxy" or "$C_{1-6}$ alkoxy" (or alkyloxy), is intended to include $C_1$, $C_2$, $C_3$, $C_4$, $C_5$, and $C_6$, alkoxy groups. Examples of alkoxy groups include, but are not limited to, methoxy, ethoxy, propoxy (e.g., n-propoxy and isopropoxy), and t-butoxy.

The term "alkoxyxlkoxy" refers to an alkoxy group attached to an alkoxy group. An example of an alkoxy group includes —O—$(CH_2)_2$—$OCH_3$.

As used herein, "alkynyl" is intended to include hydrocarbon chains of either straight or branched configuration having one or more, preferably one to three, carbon-carbon triple bonds that may occur in any stable point along the chain. For example, "$C_2$-$C_6$ alkynyl" is intended to include $C_2$, $C_3$, $C_4$, $C_5$, and $C_6$ alkynyl groups; such as ethynyl, propynyl, butynyl, pentynyl, and hexynyl.

As used herein, an "amyloid beta effect," for example, a "nonlethal amyloid beta effect," or "Abeta oligomer effect," refers to an effect, particularly a nonlethal effect, on a cell that is contacted with an Abeta species. For example, it has been found that when a neuronal cell is contacted with a soluble Amyloid-beta ("Abeta") oligomer, the oligomers bind to a subset of synapses on a subset of neuronal cells in vitro. This binding can be quantified in an assay measuring Abeta oligomer binding in vitro for example. Another documented effect of Abeta species is a reduction in synapse number, which has been reported to be about 18% in the human hippocampus (Scheff et al, 2007) and can be quantified (for example, in an assay measuring synapse number). As another example, it has been found that, when a neuronal cell is contacted with an Amyloid-beta ("Abeta") oligomer, membrane trafficking is modulated and alteration of membrane trafficking ensues. This abnormality can be visualized with many assays, including but not limited to, an MTT assay. For example, yellow tetrazolium salts are endocytosed by cells and the salts are reduced to insoluble purple formazan by enzymes located within vesicles in the endosomal pathway. The level of purple formazan is a reflection of the number of actively metabolizing cells in culture, and reduction in the amount of formazan is taken as a measure of cell death or metabolic toxicity in culture. When cells that are contacted with a yellow tetrazolium salt are observed through a microscope, the purple formazan is first visible in intracellular vesicles that fill the cell. Over time, the vesicles are exocytosed and the formazan precipitates as needle-shaped crystals on the outer surface of the plasma membrane as the insoluble formazan is exposed to the aqueous media environment. Still other effects of Abeta species include cognitive decline, such as a decline in the ability to form new memories and memory loss which can be measured in assays using animal models in vivo. In some embodiments, an Abeta effect is selected from Abeta oligomer-induced synaptic dysfunction, for example, as seen in an in vitro assay, such as a membrane trafficking assay, or a synapse loss assay, or Abeta oligomer mediated sigma-2 receptor activation of caspase-3, or Abeta induced neuronal dysfunction, Abeta mediated decrease in long term potentiation (LTP), or in cognitive decline in a behavioral assay, or in a patient in need thereof.

In some embodiments, a test compound is said to be effective to treat cognitive decline or a disease associated therewith when it can inhibit an effect associated with soluble Abeta oligomer species on a neuronal cell more than about 10%, preferably more than 15%, and preferably more than 20% as compared to a negative control. In some embodiments, a test agent is said to be effective when it can inhibit a processed product of amyloid precursor protein-mediated effect more than about 10%, preferably more than 15%, and preferably more than 20% as compared to a positive control. Although the present specification focuses on inhibition of nonlethal effects of Abeta species, such as abnormalities in neuronal metabolism and synapse number reduction, these are shown to correlate with cognitive function and are furthermore expected, over time, to result in reduction (compared to untreated subjects) of downstream measurable symptoms of amyloid pathology, notably clinical symptoms such as 1) fibril or plaque accumulation measured by amyloid imaging agents such as fluorbetapir, PittB or any other imaging agent, 2) synapse loss or cell death as measured by glucose hypometabolism detected with FDG-PET, 3) changes in protein expression or metabolite amount in the brain or body detectable by imaging or protein/metabolite detection in cerebrospinal fluid, brain biopsies or plasma obtained from patients by ELISA, (such as changes in levels and or ratios of Abeta 42, phosphorylated tau, total tau measured by ELISA, or patterns of protein expression changes detectable in an ELISA panel), 4) cerebral vascular abnormalities as measured by the presence of vascular edema or microhemorrhage detectable by MRI and any other symptoms detectable by imaging techniques, and 5) cognitive loss as measured by any administered cognitive test such as ADAS-Cog, MMSE, CBIC or any other cognitive testing instrument.

The term "animal" as used herein, includes, but is not limited to, humans and non-human vertebrates such as wild, experimental, domestic and farm animals and pets.

The term "antagonist" refers to an entity, e.g. a compound, antibody or fragment, the presence of which results in a decrease in the magnitude of a biological activity of a receptor. In certain embodiments, the presence of an antagonist results in complete inhibition of a biological activity of a receptor. As used herein, the term "sigma-2 receptor antagonist" is used to describe a compound that acts as a "functional antagonist" at the sigma-2 receptor in that it blocks Abeta effects, for example, Abeta oligomer-induced synaptic dysfunction, for example, as seen in an in vitro assay, such as a membrane trafficking assay, or a synapse loss assay, or Abeta oligomer mediated sigma-2 receptor activation of caspase-3, or in a behavioral assay, or in a patient in need thereof. The functional antagonist may act directly by inhibiting binding of, for example, an Abeta oligomer to a sigma-2 receptor, or indirectly, by interfering with downstream signaling resultant from Abeta oligomer binding the sigma-2 receptor.

As used herein, "aryl" refers to monocyclic or polycyclic (e.g. having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms. In some embodiments, aryl groups have from 5 to about 10 carbon atoms.

As used herein, "arylalkyl" refers to an aryl group attached to an alkyl radical. In preferred embodiments the alkyl is a $C_{1-6}$ alkyl.

The term "aroyl" or "arylcarbonyl" as used herein, refers to an aryl group attached to a carbonyl radical. Examples of aroyl include but are not limited to benzoyl.

As used herein the term "brain penetrability" refers to the ability of a drug, antibody or fragment, to cross the blood-brain barrier. In some embodiments, an animal pharmacokinetic (pK) study, for example, a mouse pharmacokinetic/blood-brain barrier study can be used to determine or predict brain penetrability. In some embodiments various concentrations of a compound or pharmaceutical composition according to any embodiment described herein, can be administered, for example at 3, 10 and 30 mg/kg, for example p.o. for 5 days and various pK properties are measured, e.g., in an animal model. In some embodiments, dose related plasma and brain levels are determined. In some embodiments, brain Cmax>100, 300, 600, 1000, 1300, 1600, or 1900 ng/mL. In some embodiments good brain penetrability is defined as a brain/plasma ratio of >0.1, >0.3, >0.5, >0.7, >0.8, >0.9, preferably >1, and more preferably >2, >5, or >10. In other embodiments, good brain penetrability is defined as greater than about 0.1%, 1%, 5%, greater than about 10%, and preferably greater than about 15% of an administered dose crossing the BBB after a predetermined period of time. In certain embodiments, the dose is administered orally (p.o.). In other embodiments, the dose is administered intravenously (i.v.), prior to measuring pK properties. Pharmacokinetic assays and brain penetrability are described in Example 7.

As used herein, "cognitive decline" can be any negative change in an animal's cognitive function. For example cognitive decline, includes but is not limited to, memory loss (e.g. behavioral memory loss), failure to acquire new memories, confusion, impaired judgment, personality changes, disorientation, or any combination thereof. A compound that is effective to treat cognitive decline can be thus effective by restoring long term neuronal potentiation (LTP) or long term neuronal depression (LTD) or a balance of synaptic plasticity measured electrophysiologically; inhibiting, treating, and/or abatement of neurodegeneration; inhibiting, treating, and/or abatement of general amyloidosis; inhibiting, treating, abatement of one or more of amyloid production, amyloid assembly, amyloid aggregation, and amyloid oligomer binding; inhibiting, treating, and/or abatement of a nonlethal effect of one or more of Abeta species on a neuron cell (such as synapse loss or dysfunction and abnormal membrane trafficking); and any combination thereof. Additionally, that compound can also be effective in treating Abeta related neurodegenerative diseases and disorders including, but not limited to dementia, including but not limited to Alzheimer's Disease (AD) including mild Alzheimer's disease, Down's syndrome, vascular dementia (cerebral amyloid angiopathy and stroke), dementia with Lewy bodies, HIV dementia, Mild Cognitive Impairment (MCI); Age-Associated Memory Impairment (AAMI); Age-Related Cognitive Decline (ARCD), preclinical Alzheimer's Disease (PCAD); and Cognitive Impairment No Dementia (CIND).

As used herein, the term "contacting" refers to the bringing together or combining of molecules (or of a molecule with a higher order structure such as a cell or cell membrane) such that they are within a distance that allows for intermolecular interactions such as the non-covalent interaction between two peptides or one protein and another protein or other molecule, such as a small molecule. In some embodiments, contacting occurs in a solution in which the combined or contacted molecules are mixed in a common solvent and are allowed to freely associate. In some embodiments, the contacting can occur at or otherwise within a cell or in a cell-free environment. In some embodiments, the cell-free environment is the lysate produced from a cell. In some embodiments, a cell lysate may be a whole-cell lysate, nuclear lysate, cytoplasm lysate, and combinations thereof. In some embodiments, the cell-free lysate is lysate obtained from a nuclear extraction and isolation wherein the nuclei of a cell population are removed from the cells and then lysed. In some embodiments, the nuclei are not lysed, but are still considered to be a cell-free environment. The molecules can be brought together by mixing such as vortexing, shaking, and the like.

The term "cyclic amino" or "cyclic amino group" as used herein, is a heterocycloalkyl or heteroaryl group containing a nitrogen radical, thus allowing bonding through the nitrogen atom. The group can be represented by the formula:

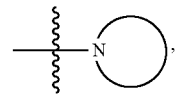

wherein

is any heterocyclic or heteroaromatic ring containing 0-3 additional heteroatoms selected from nitrogen, sulfur and oxygen.

The term "cycloalkanoyl" or "cycloalkylcarbonyl" as used herein, is meant to describe a cycloalkyl group attached to a carbonyl radical. Examples of cycloalkanoyl include but are not limited to,

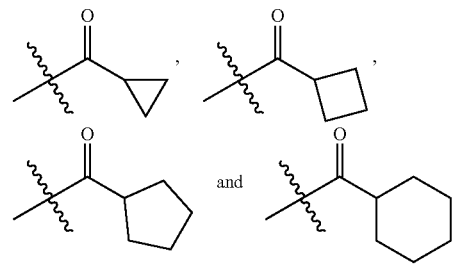

As used herein, "cycloalkyl" refers to non-aromatic cyclic hydrocarbons including cyclized alkyl, alkenyl, and alkynyl groups that contain up to 20 ring-forming carbon atoms. Cycloalkyl groups can include mono- or polycyclic (e.g. having 2, 3 or 4 fused rings) ring systems as well as spiro ring systems. A cycloalkyl group can contain from 3 to about 15, from 3 to about 10, from 3 to about 8, from 3 to about 6, from 4 to about 6, from 3 to about 5, or from 5 to about 6 ring-forming carbon atoms. Ring-forming carbon atoms of a cycloalkyl group can be optionally substituted by oxo or sulfido. Example of cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e. having a bond in common with) to the cycloalkyl ring, for example, benzo or thienyl derivatives of cyclopentane, cyclopentene, cyclohexane, and the like (e.g. 2,3-dihydro-1H-indene-1-yl, or 1H-inden-2(3H)-one-1-yl). Preferably, "cycloalkyl" refers to cyclized alkyl groups that contain up to 20 ring-forming carbon atoms. Examples of cycloalkyl preferably include cyclopropyl, cyclobutyl, cyclopentyl, cyclohexyl, cycloheptyl, adamantyl, and the like The term "cycloalkylalkyl" refers to a cycloalkyl group attached to an alkyl radical. In preferred embodiments the alkyl is a $C_{1-6}$ alkyl.

The term "drug-like properties" is used herein, to describe the pharmacokinetic and stability characteristics of a compound upon administration; including brain penetrability, metabolic stability and/or plasma stability.

As used herein, the term "effective amount" refers to an amount that results in measurable inhibition of at least one symptom or parameter of a specific disorder or pathological process. For example, an amount of a disclosure compound according to any embodiment described herein, that provides a measurably lower synapse reduction in the presence of Abeta oligomer qualifies as an effective amount because it reduces a pathological process even if no clinical symptoms of amyloid pathology are altered, at least immediately.

As used herein, "halo" or "halogen" includes fluorine, chlorine, bromine, and iodine.

As used herein, "haloalkoxy" represents a haloalkyl group as defined herein, with the indicated number of carbon atoms, attached through an oxygen bridge. For example, "$C_1$-$C_6$ haloalkoxy" or "$C_{1-6}$ haloalkoxy", is intended to include $C_1$, $C_2$, $C_3$, $C_4$, $C_5$, and $C_6$ haloalkoxy groups. An example haloalkoxy group is $OCF_3$. As used herein, "trihalomethoxy" refers to a methoxy group having three halogen substituents. Examples of trihalomethoxy groups include, but are not limited to, —$OCF_3$, —$OCClF_2$, —$OCCl_3$, and the like.

As used herein, "haloalkyl" is intended to include both branched and straight-chain saturated aliphatic hydrocarbon groups having the specified number of carbon atoms, substituted with one or more halogens. Example haloalkyl groups include, but are not limited to, $CF_3$, $C_2F_5$, $CHF_2$, $CCl_3$, $CHCl_2$, $C_2Cl_5$, $CH_2CF_3$, and the like.

As used herein, "heteroaryl" groups refer to an aromatic heterocycle having up to 20 ring-forming atoms and having at least one heteroatom ring member (ring-forming atom) such as sulfur, oxygen, or nitrogen. In some embodiments, the heteroaryl group has at least one or more heteroatom ring-forming atoms each independently selected from sulfur, oxygen, and nitrogen. Heteroaryl groups include monocyclic and polycyclic (e.g. having 2, 3 or 4 fused rings) systems. Examples of heteroaryl groups include without limitation, pyridyl (a.k.a. pyridinyl), pyrimidinyl, pyrazinyl, pyridazinyl, triazinyl, furyl, quinolyl, isoquinolyl, thienyl, imidazolyl, thiazolyl, indolyl, pyrryl (a.k.a. pyrrolyl), oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 1 to about 5, from about 1 to about 4, from about 1 to about 3, from about 1 to about 2, carbon atoms as ring-forming atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

The term "heterocycloalkoxy" as used herein, refers to an —O-heterocycloalkyl group. An example of a heterocycloalkoxy group is

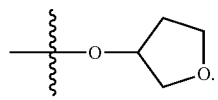

As used herein, "heterocycloalkyl" or "heterocyclyl" refers to a non-aromatic heterocyclyl group having up to 20 ring-forming atoms including cyclized alkyl, alkenyl, and alkynyl groups where one or more of the ring-forming carbon atoms is replaced by a heteroatom such as an O, N, or S atom. Heterocycloalkyl groups can be mono- or polycyclic (e.g. both fused and spiro systems). For example, "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, pyrrolidin-2-one-3-yl, and the like. Ring-forming carbon atoms and heteroatoms of a heterocycloalkyl group can be optionally substituted by oxo or sulfido. For example, a ring-forming S atom can be substituted by 1 or 2 oxo (i.e. form a S(O) or S(O)$_2$). For example, a ring-forming C atom can be substituted by oxo (i.e. form carbonyl). Also included in the definition of heterocycloalkyl are moieties that have one or more aromatic rings fused (i.e. having a bond in common with) to the nonaromatic heterocyclic ring, for example pyridinyl, thiophenyl, phthalimidyl, naphthalimidyl, and benzo derivatives of heterocycles such as indoline, isoindoline, isoindolin-1-one-3-yl, 4,5,6,7-tetrahydrothieno[2,3-c]pyridine-5-yl, 5,6-dihydrothieno[2,3-c]pyridin-7(4H)-one-5-yl, and 3,4-dihydroisoquinolin-1(2H)-one-3yl groups. Ring-forming carbon atoms and heteroatoms of the heterocycloalkyl group can be optionally substituted by oxo or sulfido. In some embodiments, the heterocycloalkyl group has from 2 to about 20 carbon atoms or 3 to 20 carbon atoms. In some embodiments, the heterocycloalkyl group contains 3 to about 14, 3 to about 7, or 5 to 6 ring-forming atoms. In some embodiments, the heterocycloalkyl group has 1 to 4 heteroatoms. In some embodiments, the heterocycloalkyl group contains 0 to 3 double bonds. In some embodiments, the heterocycloalkyl group contains 0 to 2 triple bonds.

In the present application, the term "high affinity" is intended to mean a compound which exhibits a $K_i$ value of less than 600 nM, 500 nM, 400 nM, 300 nM, 200 nM, less than 150 nM, less than 100 nM, less than 80 nM, less than 60 nM, or preferably less than 50 nM in a sigma receptor binding assay, for example against [3H]-DTG, as disclosed by Weber et al., Proc. Natl. Acad. Sci (USA) 83: 8784-8788 (1986), incorporated herein by reference, which measures the binding affinity of compounds toward both the sigma-1 and sigma-2 receptor sites. Especially preferred compounds exhibit $K_i$ values of less than about 150 nM, preferably less than 100 nM, less than about 60 nM, less than about 10 nM, or less than about 1 nM against [3H]-DTG.

The terms "hydroxyl" and "hydroxy" are used interchangeably to mean an OH group.

The term "improves" is used to convey that the disclosure changes either the characteristics and/or the physical attributes of the tissue to which it is being provided, applied or administered. The term "improves" may also be used in conjunction with a disease state such that when a disease state is "improved" the symptoms or physical characteristics associated with the disease state. are diminished, reduced, eliminated, delayed or averted.

The term "inhibiting" includes the blockade, aversion of a certain result or process, or the restoration of the converse result or process. In terms of prophylaxis or treatment by administration of a compound of the disclosure, "inhibiting" includes protecting against (partially or wholly) or delaying the onset of symptoms, alleviating symptoms, or protecting against, diminishing or eliminating a disease, condition or disorder.

The term "inhibiting trafficking deficits" refers to the ability to block soluble Aβ oligomer-induced membrane trafficking deficits in a cell, preferably a neuronal cell. A compound capable of inhibiting trafficking deficits has an $EC_{50}$<20 μM, less than 15 μM, less than 10 μM, less than 5 μM, and preferably less than 1 μM in the membrane trafficking assay, and further is capable of at least 50%, preferably at least 60%, and more preferably at least 70% maximum inhibition of the Abeta oligomer effects of soluble Abeta oligomer-induced membrane trafficking deficits, for example, as described in Example 6.

The term "log P" refers to the partition coefficient of a compound. The partition coefficient is the ratio of concentrations of un-ionized compound in each of two solution phases, for example, octanol and water. To measure the partition coefficient of ionizable solute compounds, the pH of the aqueous phase is adjusted such that the predominant form of the compound is un-ionized. The logarithm of the ratio of concentrations of the un-ionized solute compound in the solvents is called log P. The log P is a measure of lipophilicity. For example, $$\log P_{oct/wat} = \log([\text{solute}]_{octanol}/[\text{solute}]_{un\text{-}ionized,water}).$$

As used herein the term "metabolic stability" refers to the ability of a compound to survive first-pass metabolism (intestinal and hepatic degradation or conjugation of a drug administered orally). This can be assessed, for example, in vitro by exposure of the compounds to mouse or human hepatic microsomes. In some embodiments, good metabolic stability refers to a $t_{1/2}$ >5 min, >10 min, >15 minutes, >20 minutes, and preferably >30 min upon exposure of a compound to mouse or human hepatic microsomes. In some embodiments, good metabolic stability refers to an Intrinsic Clearance Rate ($Cl_{int}$) of <300 uL/min/mg, preferably ≤200 uL/min/mg, and more preferably ≤100 uL/min/mg.

The term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl group.

As used herein, the term "natural ligand" refers to a ligand present in a subject that can bind to a protein, receptor, membrane lipid or other binding partner in vivo or that is replicated in vitro. The natural ligand can be synthetic in origin, but must also be present naturally and without human intervention in the subject. For example, Abeta oligomers are known to exist in human subjects. Therefore the Abeta oligomers found in a subject would be considered natural ligands. The binding of Abeta oligomers to a binding partner can be replicated in vitro using recombinant or synthetic techniques, but the Abeta oligomer would still be considered a natural ligand regardless of how the Abeta oligomer is prepared or manufactured. A synthetic small molecule that can also bind to the same binding partner is not a natural ligand if it does not exist in a subject. For example, compounds which are described herein, are not normally present in a subject, and, therefore, would not be considered natural ligands.

As used herein, the term "a neuronal cell" can be used to refer to a single cell or to a population of cells. In some embodiments, the neuronal cell is a primary neuronal cell. In some embodiments, the neuronal cell is an immortalized or transformed neuronal cell or a stem cell. A primary neuronal cell is a neuronal cell that cannot differentiate into other types of neuronal cells, such as glia cells. A stem cell is one that can differentiate into neurons and other types of neuronal cells such as glia. In some embodiments, assays utilize a composition comprising at least one neuronal cell is free of glia cells. In some embodiments, the composition comprises less than about 30%, 25%, 20%, 15%, 10%, 5%, or 1% of glia cells, which are known to internalize and accumulate Abeta. The primary neuronal cell can be derived from any area of the brain of an animal. In some embodiments, the neuronal cell is a hippocampal or cortical cell. The presence of glia cells can be determined by any method. In some embodiments, glia cells are detected by the presence of GFAP and neurons can be detected by staining positively with antibodies directed against MAP2.

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valence of the designated atom or moiety is not exceeded, and that the substitution results in a stable compound. For example, if a methyl group (i.e. $CH_3$) is optionally substituted, then up to 3 hydrogen atoms on the carbon atom can be replaced with substituent groups. Substituent groups include, but are not limited to, alkanoyl, alkoxy, alkoxyalkyl, (alkoxy)alkoxyalkyl, alkoxycarbonyl, alkyl, aryloxy, aryloyl, cycloalkanoyl, substituted or unsubstituted $C_3$-$C_{10}$ cycloalkyl, —OC(O)NCH($CH_3$)$_2$, (N,N-dimethylamino)pyridinyl, (N,N-dimethylamino)sulfonyl, halo, heterocyclyl, (heterocyclyl)alkoxyalkyl, heterocycloalkyl, hydroxyl, hydroxyalkyl, methylpiperidinyl, methylsulfonyl, methylsulfonylphenyl, morpholinylpyridinyl, optionally substituted $C_1$-$C_{10}$ alkyl, optionally substituted $C_5$-$C_{10}$ aryl, optionally substituted $C_3$-$C_{10}$ heteroaryl, perfluoroalkyl, phenyl, piperidinyl, pyrrolidinylpyridinyl, tetrahydropyranyl, $CF_3$. A substituted alkyl group for example indicates that one or more hydrogen atoms on the alkyl group is replaced with a substituent group, selected from but not limited to, halo, hydroxyl, alkoxy, heterocycloalkoxy, alkoxyalkoxy, C(O)OMe, and C(O)OEt. A substituted aryl group for example, indicates that one or more hydrogen atoms on the aryl group is replaced with a substituent group, selected from but not limited to, —SO$_2$Me or phenyl group. A substituted heteroaryl group for example, indicates that one or more hydrogen atoms on the heteroaryl group is replaced with a substituent group, selected from, but not limited to, heterocycloalkyl, heteroaryl, N,N-dimethylamino. A substituted heterocycloalkyl group for example, indicates that one or more hydrogen atoms on the heterocycloalkyl group is replaced with a substituent group, selected from, but not limited to, heterocyclalkyl, heteroaryl, N,N-dimethylamino, hydroxyl, alkoxy, alkoxycarbonyl, alkyl, aryl, sulfonyl, dimethylaminosulfonyl, aroyl, cycloalkanoyl, alkanoyl and —OC(O)NCH(CH$_3$)$_2$. In some instances two hydrogen atoms on the same carbon of, for example, a heterocyclyl or alkyl group are replaced with a group to form a spiro compound selected from but not limited to, for example,

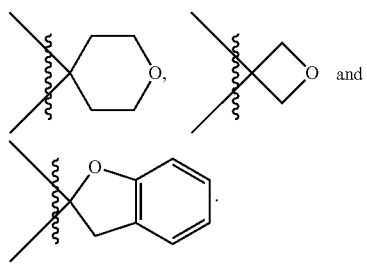

The term "partial agonist" refers to a compound the presence of which results in a biological activity of a receptor that is of the same type as that resulting from the presence of a naturally occurring ligand for the receptor, but of a lower magnitude.

The phrase "pharmaceutically acceptable" refers to molecular entities and compositions that are generally regarded as safe and nontoxic. In particular, pharmaceutically acceptable carriers, diluents or other excipients used in the pharmaceutical compositions of this disclosure are physiologically tolerable, compatible with other ingredients, and do not typically produce an allergic or similar untoward reaction (for example, gastric upset, dizziness and the like) when administered to a patient. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The phrase "pharmaceutically acceptable salt(s)", as used herein, includes those salts of compounds of the disclosure that are safe and effective for use in mammals and that possess the desired biological activity. Pharmaceutically acceptable salts include salts of acidic or basic groups present in compounds of the disclosure or in compounds identified pursuant to the methods of the disclosure. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the disclosure can form pharmaceutically acceptable salts with various amino acids. Suitable base salts include, but are not limited to, aluminum, calcium, lithium, magnesium, potassium, sodium, zinc, iron and diethanolamine salts. Pharmaceutically acceptable base addition salts are also formed with amines, such as organic amines. Examples of suitable amines are N,N'-dibenzylethylenediamine, chloroprocaine, choline, diethanolamine, dicyclohexylamine, ethylenediamine, N-methylglucamine, and procaine.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "selectivity" or "selective" refers to a difference in the binding affinity of a compound ($K_i$) for a sigma receptor, for example, a sigma-2 receptor, compared to a non-sigma receptor. The compound possess high selectivity for a sigma receptor in synaptic neurons. The $K_i$ for a sigma-2 receptor or both a sigma-2 and a sigma-1 receptor is compared to the $K_i$ for a non-sigma receptor. In some embodiments, the compound is a selective sigma-2 receptor antagonist, or sigma-1 receptor ligand, and has at least 10-fold, 20-fold, 30-fold, 50-fold, 70-fold, 100-fold, or 500-fold higher affinity, or more, for binding to a sigma receptor compared to a non-sigma receptor as assessed by a comparison of binding dissociation constant $K_i$ values, or $IC_{50}$ values, or binding constant, at different receptors. Any known assay protocol can be used to assess the $K_i$ or $IC_{50}$ values at different receptors, for example, by monitoring the competitive displacement from receptors of a radiolabeled compound with a known dissociation constant, for example, by the method of Cheng and Prusoff (1973) (Biochem. Pharmacol. 22, 3099-3108), or specifically as provided herein.

As used herein the term "plasma stability" refers to the degradation of compounds in plasma, for example, by enzymes such as hydrolases and esterases. Any of a variety of in vitro assays can be employed. Test compounds are incubated in plasma over various time periods. The percent parent compound (analyte) remaining at each time point reflects plasma stability. Poor stability characteristics can tend to have low bioavailability. Good plasma stability can be defined as greater than 50% analyte remaining after 30 min, greater than 50% analyte remaining after 45 minutes, and preferably greater than 50% analyte remaining after 60 minutes.

"Sigma-2 ligand" refers to a compound that binds to a sigma-2 receptor and includes agonists, antagonists, partial agonists, inverse agonists and simply competitors for other ligands of this receptor or protein.

The term "sigma-2 receptor antagonist compound" refers to a compound that binds to a sigma-2 receptor in a measurable amount and acts as a functional antagonist with respect to Abeta effects oligomer induced synaptic dysfunction resultant from sigma-2 receptor binding.

The terms "subject," "individual" or "patient" are used interchangeably and as used herein, are intended to include human and non-human animals. Non-human animals includes all vertebrates, e.g. mammals and non-mammals, such as non-human primates, sheep, dogs, cats, cows, horses, chickens, amphibians, and reptiles, although mammals are preferred, such as non-human primates, sheep, dogs, cats, cows and horses. Preferred subjects include human patients. The methods are particularly suitable for treating human patients having a disease or disorder described herein.

A "test compound" is a compound according to any embodiment described herein that is being tested in any test. Tests include any in vivo or in vitro test, computer model or simulation, virtual drug trial, stem cell and genetic testing methods, non-invasive imaging techniques and the like.

As used herein, the term "therapeutic" means an agent utilized to treat, combat, ameliorate, protect against or improve an unwanted condition or disease of a subject.

A "therapeutically effective amount" of a compound, pharmaceutically acceptable salt thereof or pharmaceutical composition according to any embodiment described herein, is an amount sufficient to produce a selected effect on at least one symptom or parameter of a specific disease or disorder. The therapeutic effect may be objective (i.e., measurable by some test or marker) or subjective (i.e., subject gives an indication of or feels an effect or physician observes a change). A therapeutically effective amount of a compound, according to any embodiment described herein, may broadly range from 0.01 mg/kg to about 500 mg/kg, about 0.01 to about 250 mg/kg, about 0.01 to about 25 mg/kg, about 0.05 mg/kg to about 20 mg/kg, about 0.1 mg/kg to about 400 mg/kg, about 0.1 mg/kg to about 200 mg/kg, about 0.1 mg/kg to about 25 mg/kg, about 0.1 to about 10 mg/kg, about 0.2 to about 5 mg/kg, about 1 mg/kg to about 300 mg/kg, about 10 mg/kg to about 100 mg/kg, body weight. The effect contemplated herein, includes both medical therapeutic and/or prophylactic treatment, as appropriate. The specific dose of a compound administered according to this disclosure to obtain therapeutic and/or prophylactic effects is determined by the particular circumstances surrounding the case, including, for example, the compound administered, the route of administration, the co-administration of other active ingredients, the condition being treated, the activity of the specific compound employed, the specific composition employed, the age, body weight, general health, sex and diet of the patient; the time of administration, route of administration, and rate of excretion of the specific compound employed and the duration of the treatment. The therapeutically effective amount administered will be determined by the physician in the light of the foregoing relevant circumstances and the exercise of sound medical judgment. A therapeutically effective amount of a compound, according to any embodiment described herein, is typically an amount such that when it is administered in a physiologically tolerable excipient composition, it is sufficient to achieve an effective systemic concentration or local concentration in the tissue. The total daily dose of the compounds according to any embodiment described herein administered to a human or other animal in single or in divided doses can be in amounts, for example, from about 0.01 mg/kg to about 500 mg/kg, about 0.01 to about 250 mg/kg, about 0.01 to about 25 mg/kg, about 0.05 mg/kg to about 20 mg/kg, about 0.1 mg/kg to about 400 mg/kg, about 0.1 mg/kg to about 200 mg/kg, about 0.1 mg/kg to about 25 mg/kg, about 0.1 to about 10 mg/kg, about 0.2 to about 5 mg/kg, about 1 mg/kg to about 300 mg/kg, about 10 mg/kg to about 100 mg/kg, body weight per day. Single dose pharmaceutical compositions of any embodiment described herein, may contain such amounts or submultiples thereof to make up the daily dose. For example, the compounds according to any embodiment described herein, may be administered on a regimen of 1 to 4 times per day, such as once, twice, three times or four times per day. In some embodiments, the therapeutically effective amount of a compound according to any embodiment disclosed herein, can range between about 0.01 and about 25 mg/kg/day. In some embodiments the therapeutically effective amount is between a lower limit of about 0.01 mg/kg of body weight, about 0.1 mg/kg of body weight, about 0.2 mg/kg of body weight, about 0.3 mg/kg of body weight, about 0.4 mg/kg of body weight, about 0.5 mg/kg of body weight, about 0.60 mg/kg of body weight, about 0.70 mg/kg of body weight, about 0.80 mg/kg of body weight, about 0.90 mg/kg of body weight, about 1 mg/kg of body weight, about 2.5 mg/kg of body weight, about 5 mg/kg of body weight, about 7.5 mg/kg of body weight, about 10 mg/kg of body weight, about 12.5 mg/kg of body weight, about 15 mg/kg of body weight, about 17.5 mg/kg of body weight, about 20 mg/kg of body weight, about 22.5 mg/kg of body weight, and about 25 mg/kg of body weight; and an upper limit of 25 mg/kg of body weight, about 22.5 mg/kg of body weight, about 20 mg/kg of body weight, about 17.5 mg/kg of body weight, about 15 mg/kg of body weight, about 12.5 mg/kg of body weight, about 10 mg/kg of body weight, about 7.5 mg/kg of body weight, about 5 mg/kg of body weight, about 2.5 mg/kg of body weight, about 1 mg/kg of body weight, about 0.9 mg/kg of body weight, about 0.8 mg/kg of body weight, about 0.7 mg/kg of body weight, about 0.6 mg/kg of body weight, about 0.5 mg/kg of body weight, about 0.4 mg/kg of body weight, about 0.3 mg/kg of body weight, about 0.2 mg/kg of body weight, about 0.1 mg/kg of body weight, and about 0.01 mg/kg of body weight. In some embodiments, the therapeutically effective amount is about 0.1 mg/kg/day to about 10 mg/kg/day; in some embodiments the therapeutically effective amount is about 0.2 and about 5 mg/kg/day. In some embodiments, treatment regimens according to the disclosure comprise administration to a patient in need of such treatment will usually include from about 1 mg to about 5000 mg, about 10 mg to about 2000 mg, about 10 mg to about 200 mg, about 20 to about 1000 mg, about 20 to about 500 mg, about 20 to about 400 mg, about 40 to about 800 mg, about 50 mg to about 500 mg, about 80 to about 1600 mg and about 50 mg, of a compound according to any embodiment disclosed herein, or a pharmaceutically acceptable salt thereof, per day in single or multiple doses. In some embodiments the therapeutically effective amount is a total daily dose of 50 mg to 500 mg. In some embodiments, the daily dose is between a lower limit of about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg; about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg; about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, 300 mg, about 305 mg, about 310 mg, about 315 mg; about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395, about 400 mg, about 405 mg, about 410 mg, about 415 mg; about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, and about 500 mg and an upper limit of about 500 mg, about 495 mg, about 490 mg, about 485 mg, about 480 mg, about 475 mg, about 470 mg, about 465 mg, about 460 mg, about 455 mg, about 450 mg, about 445 mg, about 440 mg, about 435 mg, about 430 mg, about 425 mg, about 420 mg, about 415 mg, about 410 mg, about 405 mg, about 400 mg, about 395 mg, about 390 mg, about 385 mg, about 380 mg, about 375 mg, about 370 mg, about 365 mg, about 360 mg, about 355 mg, about 350 mg, about 345 mg, about 340 mg, about 335 mg, about 330 mg, about 325 mg, about 320 mg, about 315 mg, about 310 mg, about 305 mg about 300 mg, about 295 mg, about 290 mg, about 285 mg, about 280 mg, about 275 mg, about 270 mg, about 265 mg, about 260 mg, about 255 mg, about 250 mg, about 245 mg, about 240 mg, about 235 mg, about 230 mg, about 225 mg, about 220 mg, about 215 mg, about 210 mg, about 205 mg 200 mg, about 195 mg, about 190 mg, about 185 mg, about 180 mg, about 175 mg, about 170 mg, about 165 mg, about 160 mg, about 155 mg, about 150 mg, about 145 mg, about 140 mg, about 135 mg, about 130 mg, about 125 mg, about 120 mg, about 115 mg, about 110 mg, about 105 mg, about 100 mg, about 95 mg, about 90 mg; about 85 mg, about 80 mg, about 75 mg, about 70 mg, about 65 mg, about 60 mg, about 55 mg, and about 50 mg of a compound according to any embodiment herein. In some embodiments, the total daily dose is about 50 mg to 150 mg. In some embodiments, the total daily dose is about 50 mg to 250 mg. In some embodiments, the total daily dose is about 50 mg to 350 mg. In some embodiments, the total daily dose is about 50 mg to 450 mg. In some embodiments, the total daily dose is about 50 mg. It will be understood that the pharmaceutical formulations of the disclosure need not necessarily contain the entire amount of the compound that is effective in treating the disorder, as such effective amounts can be reached by administration of a plurality of divided doses of such pharmaceutical formulations. The compounds may be administered on a regimen of 1 to 4 times per day, such as once, twice, three times or four times per day.

The term "therapeutic phenotype" is used to describe a pattern of activity for compounds in the in vitro assays that is predictive of behavioral efficacy. A compound that (1) selectively binds with high affinity to a sigma-2 receptor, and (2) acts as a functional antagonist with respect to Abeta oligomer-induced effects in a neuron, is said to have the "therapeutic phenotype" if (i) it blocks or reduces Aβ-induced membrane trafficking deficits; (ii) it blocks or reduces Aβ-induced synapse loss and (iii) it does not affect trafficking or synapse number in the absence of Abeta oligomer. This pattern of activity in the in vitro assays is termed the "therapeutic phenotype" and is predictive of behavioral efficacy.

The term "therapeutic profile" is used to describe a compound that meets the therapeutic phenotype, and also has good brain penetrability (the ability to cross the blood brain barrier), good plasma stability and good metabolic stability.

The term "tissue" refers to any aggregation of similarly specialized cells which are united in the performance of a particular function.

The terms "treat," "treated," or "treating" as used herein, refers to both therapeutic treatment and prophylactic or preventative measures, wherein the object is to protect against (partially or wholly) or slow down (e.g., lessen or postpone the onset of) an undesired physiological condition, disorder or disease, or to obtain beneficial or desired clinical results such as partial or total restoration or inhibition in decline of a parameter, value, function or result that had or would become abnormal. For the purposes of this disclosure, beneficial or desired clinical results include, but are not limited to, alleviation of symptoms; diminishment of the extent or vigor or rate of development of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether or not it translates to immediate lessening of actual clinical symptoms, or enhancement or improvement of the condition, disorder or disease. Treatment seeks to elicit a clinically significant response without excessive levels of side effects. Treatment also includes prolonging survival as compared to expected survival if not receiving treatment.

Human Amyloid Beta and Sigma-2 Antagonists

Overproduction and accumulation of amyloid beta is a pathologic feature of Alzheimer's disease. Human amyloid beta (Abeta) is the main component of insoluble amyloid plaques-deposits found in the brain of patients with Alzheimer's disease. The plaques are composed of fibrillar aggregates of Abeta. Amyloid beta fibrils have been associated with the advanced stages of Alzheimer's disease.

The cognitive hallmark of early Alzheimer's disease is an extraordinary inability to form new memories. Early memory loss is considered a synapse failure caused by soluble Aβ oligomers. These oligomers block long-term potentiation, a classic experimental paradigm for synaptic plasticity, and they are strikingly elevated in AD brain tissue and transgenic AD models. It has been hypothesized that early memory loss stems from synapse failure before neuron death and that synapse failure derives from actions of soluble Aβ oligomers rather than fibrils. Lacor et al., *Synaptic targeting by Alzheimer's-related amyloid β oligomers*, J. Neurosci. 2004, 24(45):10191-10200.

Abeta is a cleavage product of an integral membrane protein, amyloid precursor protein (APP), found concentrated in the synapses of neurons. Soluble forms of Abeta are present in the brains and tissues of Alzheimer's patients, and their presence correlates with disease progression. Yu et al., 2009, *Structural characterization of a soluble amyloid beta-peptide oligomer*, Biochemistry, 48(9):1870-1877. Soluble amyloid β oligomers have been demonstrated to induce changes in neuronal synapses that block learning and memory.

Smaller, soluble Aβ oligomers interfere with a number of signaling pathways critical for normal synaptic plasticity, ultimately resulting in spine and synapse loss. Selkoe et al., 2008, *Soluble oligomers of the amyloid beta-protein impair synaptic plasticity and behavior*, Behav Brain Res 192(1): 106-113. Alzheimer's begins and persists as a synaptic plasticity disease.

The presence of soluble Aβ oligomers is believed to be to be responsible for early cognitive decline in the pre-Alzheimer's diseased brain. It is known that amyloid beta oligomers bind at neuronal synapses and that sigma-2 receptors are present in significant amounts in neurons and glia.

Sigma receptors are multifunctional adapter/chaperone proteins that participate in several distinct protein signaling complexes in a tissue and state-related manner. The sigma-2 receptor is expressed in brain and various peripheral tissues at low levels. (Walker et al., 1990 *Sigma receptors: biology and function*. Pharmacol. Rev. 42:355-402). Sigma-2 receptors are present in human hippocampus and cortex. The sigma-2 receptor was also previously validated as a biomarker for tumor cell proliferation. (Mach et al., *Sigma-2 receptors as potential biomarkers of proliferation in breast cancer*. Cancer Res. 57:156-161, 1997).

Sigma-2 receptors are implicated in many signaling pathways such as heme binding, Cytochrome P450 metabolism, cholesterol synthesis, progesterone signaling, apoptosis and membrane trafficking. Only a subset of sigma receptor binding sites/signaling pathways are relevant to oligomer signaling in AD. No sigma-2 receptor knock-outs are currently available and human mutations in sigma-2 sequence have not been studied in a neurodegeneration context.

A sigma-2 receptor was recently identified as the progesterone receptor membrane component 1 (PGRMC1) in rat liver by use of a photoaffinity probe WC-21, which irreversibly labels sigma-2 receptors in rat liver. Xu et al. *Identification of the PGRMC1 protein complex as the putative sigma-2 receptor binding site*. Nature Communications 2, article number 380, Jul. 5, 2011, incorporated herein by reference. PGRMC1 (progesterone receptor membrane component 1) was identified as the critical 25 kDa component of sigma-2 receptor activity in August 2011 by Xu et al. PGRMC1 is a single transmembrane protein with no homology to sigma-1 protein; family members include PGRMC2 and neudesin. PGRMC1 contains a cytochrome b5 heme-binding domain. PGRMC1 is a single transmembrane protein with no homology to S1 protein; family members include PGRMC2 and neudesin. PGRMC1 contains a cytochrome b5 heme-binding domain. Endogenous PGRMC ligands include progesterone/steroids, cholesterol metabolites, glucocorticoids, and heme. PGRMC1 functions as chaperone/adapter associated with different protein complexes in different subcellular locations (Cahill 2007. *Progesterone receptor membrane component 1: an integrative review*. J. Steroid Biochem. Mol. Biol. 105:16-36). PGRMC1 binds heme with reducing activity, complexes with CYP450 proteins (regulated redox reactions), associates with PAIRBP1 and mediates progesterone block of apoptosis, and associates with Insig-1 and SCAP to induce SRE-related gene transcription in response to low cholesterol. The *C. elegans* homolog VEM1 associates with UNC-40/DCC to mediate axon guidance. PGRMC1 contains two SH2 target sequences, an SH3 target sequence, a tyrosine kinase site, two acidophilic kinase sites (CK2), and consensus binding sites for ERK1 and PDK1. PGRMC1 contains several ITAM sequences involved in membrane trafficking (vesicle transport, clathrin-dependent endocytosis of calveolin-containing pits).

While not being bound by theory, it is proposed that the sigma-2 receptor is a receptor for Abeta oligomer in neurons. Various receptors have been proposed in the literature for soluble Abeta oligomers including prion protein, insulin receptor, beta adrenergic receptor and RAGE (receptor for advanced glycation end products). Lauren, J. et al, 2009, Nature, 457(7233): 1128-1132; Townsend, M. et al, J. Biol. Chem. 2007, 282:33305-33312; Sturchler, E. et al, 2008, J. Neurosci. 28(20):5149-5158. Indeed many investigators believe that Abeta oligomer may bind to more than one receptor protein. Without being bound by theory, the present inventors postulate an additional receptor for Abeta oligomer located (not necessarily exclusively) in neurons.

Without being bound by theory, Abeta oligomers are sigma receptor agonists that bind to sigma protein complexes and cause aberrant trafficking and synapse loss. It is demonstrated herein, that compounds described herein that antagonize this interaction and/or sigma receptor function in neurons will compete or otherwise interfere with Abeta oligomers and return neuronal responses to normal. Such compounds are considered functional sigma-2 receptor antagonists.

In some embodiments, a compound of any embodiment described herein, may act as a functional antagonist in a neuronal cell with respect to inhibiting soluble Aβ oligomer induced synapse loss, and inhibiting soluble Aβ oligomer induced deficits in a membrane trafficking assay; exhibiting high affinity at a sigma-2 receptor; as well as having high selectivity for one or more sigma receptors compared to any other non-sigma receptor; and exhibiting good drug-like properties.

In some embodiments, a compound according to any embodiment described herein, that acts as functional antagonist meeting certain in vitro assay criteria detailed herein, will exhibit behavioral efficacy, or be predicted to have behavioral efficacy, in one or more relevant animal behavioral models. In some embodiments, behavioral efficacy is determined at 10 mg/kg p.o., or less.

In vitro assay platforms predictive of behavioral efficacy useful in the invention described herein, are known in the art, in particular, in U.S. Pat. No. 9,796,672, herein incorporated by reference in its entirety. In accordance with the in vitro assay platform, a compounds of any embodiment described herein, may bind with high affinity to a sigma-2 receptor; acts as a functional antagonist with respect to Abeta oligomer-induced effects in a neuron; inhibits Abeta oligomer-induced synapse loss in a central neuron or reduces Abeta oligomer binding to neurons to inhibit synapse loss; and does not affect trafficking or synapse number in the absence of Abeta oligomer. This pattern of activity in the in vitro assays is termed the "therapeutic phenotype". The ability of a compound according to any embodiment described herein, to block Abeta oligomer effects in mature neurons without affecting normal function in the absence of Abeta oligomers meets the criteria for the therapeutic phenotype. A compounds of any embodiment described herein, having a therapeutic phenotype, can block Abeta oligomer-induced synaptic dysfunction.

In some embodiments, a compound according to any embodiment described herein, exhibits sigma-2 antagonist activity, high affinity for the sigma-2 receptor, and the ability to block soluble Abeta oligomer binding or Abeta oligomer-induced synaptic dysfunction.

In some embodiments, a compound according to any embodiment described herein, is designed to enhance the ability to cross the blood-brain barrier.

In some embodiments, a compound according to any embodiment described herein, blocks binding between soluble Abeta oligomers and a sigma-2 receptor.

In some embodiments, a compound according to any embodiment described herein, exhibits high affinity for the sigma-2 receptor.

Embodiments of the invention are directed to compounds according to any embodiment described herein, useful for treating neurodegenerative disease and cognitive decline, pharmaceutical compositions containing such compounds and pharmaceutically acceptable carries, excipients, or diluents, and methods for treating neurodegenerative disease and cognitive decline by administering such compounds and pharmaceutical compositions in a pharmaceutically acceptable amount.

Compounds of the Invention

Various embodiments are directed to a compound of Formula I:

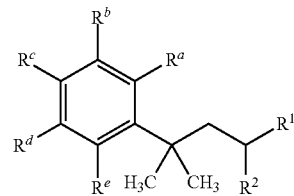

I or a pharmaceutically acceptable salt thereof.

Each of substituents $R^a$, $R^b$, $R^c$, $R^d$ and $R^e$ of Formula I is independently selected from the group consisting of, H, hydroxyl, halo, alkyl, alkoxy, $CF_3$, $SO_2CH_3$, and morpholino.

Substituent $R^1$ of Formula I is selected from the group consisting of hydrogen, alkyl, phenyl, or —CH=C(CH$_3$)$_2$.

Substituent $R^2$ of Formula I is an optionally substituted cyclic amino group.

In some embodiments, each of substituents $R^a$, $R^b$, $R^c$, $R^d$ and $R^e$ of Formula I is independently selected from the group consisting of, H, hydroxyl, $C_1$, F, methyl, —OCH$_3$, —OC(CH$_3$)$_3$, O—CH(CH$_3$)$_2$, $CF_3$, $SO_2CH_3$, and morpholino.

In some embodiments, each of substituents $R^a$, $R^b$, $R^c$, $R^d$ and $R^e$ of Formula I is independently selected from the group consisting of, H, Cl, F, and $CF_3$.

In some embodiments, each of substituents $R^a$, $R^b$, $R^d$ and $R^e$ of Formula I is independently H and $R^c$, is selected from the group consisting of H, hydroxyl, halo, alkyl, alkoxy, $CF_3$, $SO_2CH_3$, and morpholino.

In some embodiments, each of substituents $R^a$, $R^b$, $R^d$ and $R^e$ of Formula I is independently H and $R^c$, is selected from the group consisting of H, hydroxyl, Cl, F, methyl, —OCH$_3$, —OC(CH$_3$)$_3$, O—CH(CH$_3$)$_2$, $CF_3$, $SO_2CH_3$, and morpholino.

In some embodiments, each of substituents $R^a$, $R^b$, $R^d$ and $R^e$ of Formula I is independently H and $R^c$, is selected from the group consisting of H, Cl, F, and $CF_3$.

In various embodiments, $R^2$ is any heterocycloalkyl or heteroaryl containing a nitrogen in the ring that is bound to the aliphatic chain of Formula I through the nitrogen atom. In some embodiments, for example, $R^2$ is an optionally substituted cyclic amino group selected from:

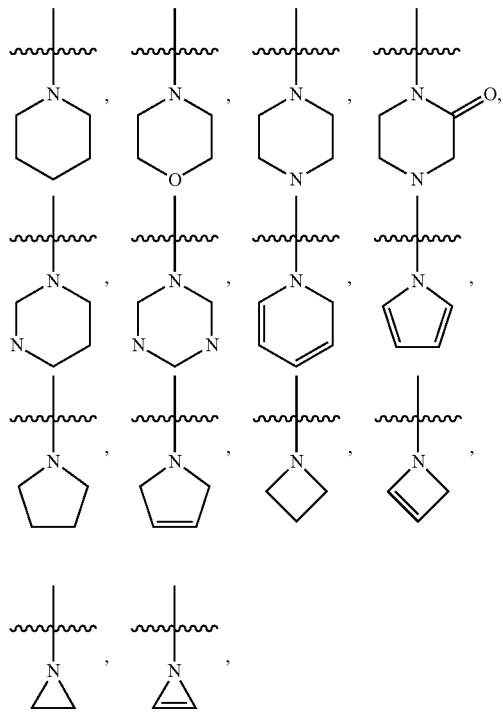

and the like, wherein each nitrogen containing heterocycloalkyl or heteroaryl can be optionally substituted with one or more substituents selected from, hydroxyl, halo, $CF_3$, alkoxy, aryloxy, optionally substituted $C_1$-$C_{10}$ alkyl, optionally substituted $C_5$-$C_{10}$ aryl, optionally substituted $C_3$-$C_{10}$ heteroaryl, substituted or unsubstituted $C_3$-$C_{10}$ cycloalkyl or heterocycloalkyl.

In various embodiments, $R^2$ is selected from the group consisting of optionally substituted aziridinyl, optionally substituted pyrrolidinyl, optionally substituted imidizolidinyl, optionally substituted piperidinyl, optionally substituted piperazinyl, optionally substituted oxopiperazinyl, and optionally substituted morpholinyl.

In some embodiments, when $R^2$ is a substituted cyclic amino, one or more of the hydrogen atoms in the cyclic amino group is replaced with a group selected from alkanoyl, alkoxy, alkoxyalkyl, (alkoxy)alkoxyalkyl, alkoxycarbonyl, alkyl, aryloxy, aryloyl, cycloalkanoyl, —OC(O)NCH(CH$_3$)$_2$, (N,N-dimethylamino)pyridinyl, (N,N-dimethylamino)sulfonyl, halo, heterocyclyl, (heterocyclyl)alkoxyalkyl, hydroxyl, hydroxyalkyl, methylpiperidinyl, methylsulfonyl, methylsulfonylphenyl, morpholinylpyridinyl, perfluoroalkyl, phenyl, piperidinyl, pyrrolidinylpyridinyl, tetrahydropyranyl, and $CF_3$. In some embodiments two hydrogen atoms on the same carbon of the cyclic amino group are replaced with a compound selected from

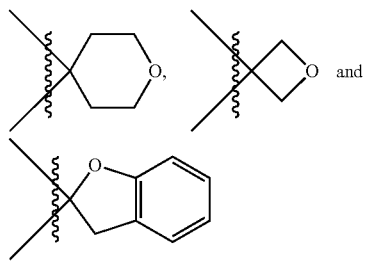

and to form a spiro compound.

In some embodiments, $R^2$ is a pyrrolidinyl or a substituted pyrrolidinyl substituted with one or more substituents selected from the group consisting of alkoxyalkyl, alkoxycarbonyl, alkyl, hydroxyl, and hydroxyalkyl. In some embodiments $R^2$ is a substituted pyrrolidinyl substituted with a single substituent selected from the group consisting of alkoxyalkyl, alkoxycarbonyl, alkyl, hydroxyl, and hydroxyalkyl. In some embodiments $R^2$ is a substituted pyrrolidinyl substituted with a single substituent selected from the group consisting of hydroxyl, hydroxymethyl, methoxymethyl, methoxycarbonyl and methyl.

In some embodiments, $R^2$ is a piperidinyl or a substituted piperidinyl substituted with one or more substituents selected from the group consisting of alkoxy, alkoxyalkyl, (alkoxy)alkoxyalkyl, alkoxycarbonyl, alkyl, aryloxy, —OC(O)NCH(CH$_3$)$_2$, (N,N-dimethylamino)pyridinyl, halo, heterocyclyl, (heterocyclyl)alkoxyalkyl, hydroxy, hydroxyalkyl, methylpiperidinyl, methylsulfonylphenyl, morpholinylpyridinyl, perfluoroalkyl, phenyl, piperidinyl, pyrrolidinylpyridinyl, tetrahydropyranyl, and $CF_3$. In some embodiments, $R^2$ is a piperidinyl or a substituted piperidinyl substituted with a single substituent selected from the group consisting of alkoxy, alkoxyalkyl, (alkoxy)alkoxyalkyl, alkoxycarbonyl, alkyl, aryloxy, —OC(O)NCH(CH$_3$)$_2$, (N,N-dimethylamino)pyridinyl, halo, heterocyclyl, (heterocyclyl)alkoxyalkyl, hydroxyl, hydroxyalkyl, methylpiperidinyl, methylsulfonylphenyl, morpholinylpyridinyl, perfluoroalkyl, phenyl, piperidinyl, pyrrolidinylpyridinyl, tetrahydropyranyl, and $CF_3$. In some embodiments, $R^2$ is a piperidinyl or a substituted piperidinyl substituted with a single substituent selected from the group consisting of alkoxy, alkoxyalkyl, (alkoxy)alkoxyalkyl, alkoxycarbonyl, alkyl, aryloxy, —OC(O)NCH(CH$_3$)$_2$, (N,N-dimethylamino)pyridinyl, halo, heterocyclyl, (heterocyclyl)alkoxyalkyl, hydroxyl, hydroxyalkyl, methylpiperidinyl, methylsulfonylphenyl, morpholinylpyridinyl, perfluoroalkyl, phenyl, piperidinyl, pyrrolidinylpyridinyl, tetrahydropyranyl, and $CF_3$. In some embodiments, $R^2$ is a piperidinyl or a substituted piperidinyl substituted with a single substituent selected from the group consisting of methyl, isopropyl, isobutyl, $CF_3$, hydroxymethyl, hydroxyethyl, (isopropyloxy)ethyl, —(CH$_2$)$_2$O(CH$_2$)$_2$OCH$_3$, —(CH$_2$)$_3$OCH$_3$, —C(O)OMe, —C(O)OEt, hydroxyl, methoxy, isopropyloxy, phenyloxy, F, ethoxy, phenyl,

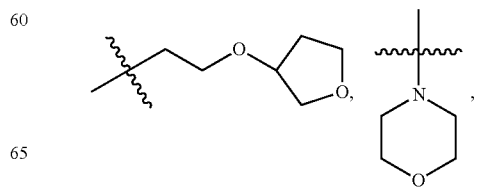

-continued

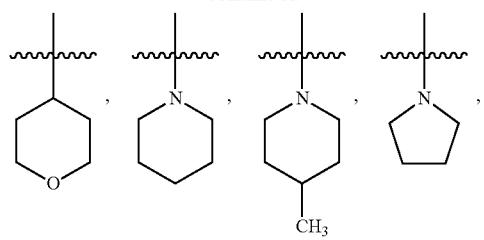

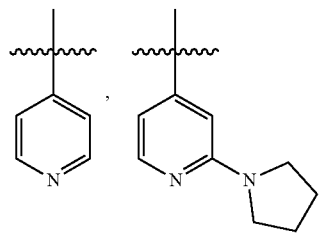

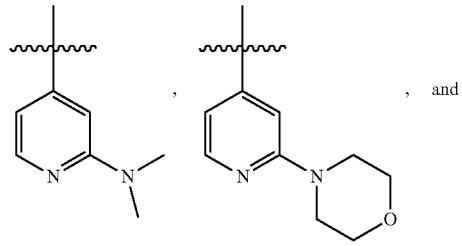, and

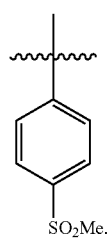
SO₂Me.

-continued

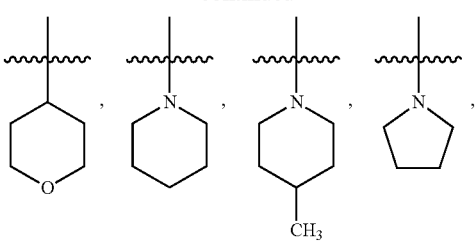

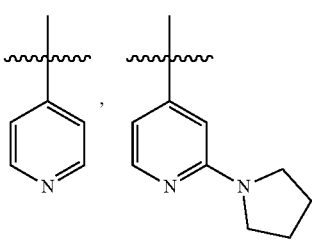

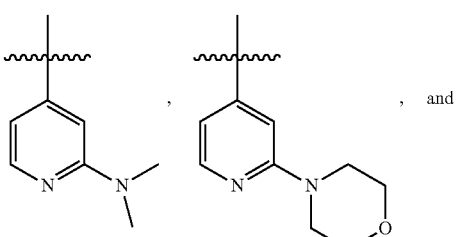, and

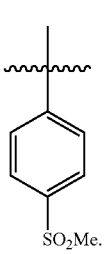
SO₂Me.

In some embodiments, $R^2$ is a piperidinyl or a substituted piperidinyl substituted at the 4 position of the piperidinyl with a single substituent selected from the group consisting of alkoxy, alkoxyalkyl, (alkoxy)alkoxyalkyl, alkoxycarbonyl, alkyl, aryloxy, —OC(O)NCH(CH₃)₂, (N,N-dimethylamino)pyridinyl, halo, heterocyclyl, (heterocyclyl)alkoxyalkyl, hydroxyl, hydroxyalkyl, methylpiperidinyl, methylsulfonylphenyl, morpholinylpyridinyl, perfluoroalkyl, phenyl, piperidinyl, pyrrolidinylpyridinyl, tetrahydropyranyl, and CF₃. In some embodiments, $R^2$ is a piperidinyl or a substituted piperidinyl substituted at the 4 position of the piperidinyl with a single substituent selected from the group consisting of methyl, isopropyl, isobutyl, CF₃, hydroxymethyl, hydroxyethyl, (isopropyloxy)ethyl, —(CH₂)₂O(CH₂)₂OCH₃, —(CH₂)₃OCH₃, —C(O)OMe, —C(O)OEt, hydroxyl, methoxy, isopropyloxy, phenyloxy, F, ethoxy, phenyl,

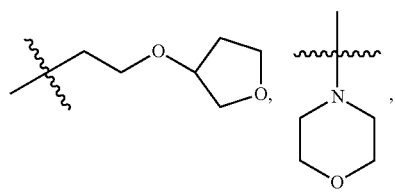

In some embodiments, $R^2$ is a piperidinyl or a substituted piperidinyl substituted with two substituent groups on the same carbon of the piperidinyl independently selected from the group consisting of alkoxyalkyl, alkyl, —OC(O)NCH(CH₃)₂, hydroxyl, and phenyl. In some embodiments, $R^2$ is a piperidinyl or a substituted piperidinyl substituted with two substituent groups at the 4 position of the piperidinyl independently selected from the group consisting of alkoxyalkyl, alkyl, —OC(O)NCH(CH₃)₂, hydroxyl, and phenyl. In some embodiments $R^2$ is a piperidinyl or a substituted piperidinyl substituted with two substituent groups at the 4 position selected from the group consisting of hydroxyl and methyl; hydroxyl and ethyl; hydroxyl and —(CH₂)₂OCH₃; hydroxyl and phenyl; methyl and phenyl; methyl and —OC(O)NCH(CH₃)₂; and butyl and —OC(O)NCH(CH₃)₂. In some embodiments two hydrogen atoms on the same carbon of the piperidinyl are replaced with a compound selected from

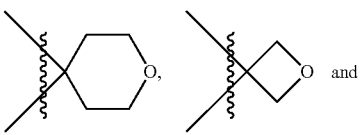 and

-continued

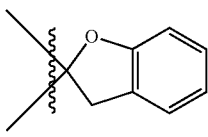

to form a spiro compound. In some embodiments two hydrogen atoms at the 4 position of the piperidinyl are replaced with a compound selected from

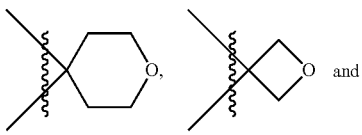 and to form a spiro compound.

In some embodiments, $R^2$ is a piperazinyl or a substituted piperazinyl substituted with one or more substituents selected from the group consisting of alkanoyl, alkoxycarbonyl, aryloyl, cycloalkanoyl, (N,N-dimethylamino)sulfonyl, heterocyclyl, methylsulfonyl, and phenyl. In some embodiments, $R^2$ is a substituted piperazinyl substituted with a single substituent selected from the group consisting of alkanoyl, alkoxycarbonyl, aryloyl, cycloalkanoyl, (N,N-dimethylamino)sulfonyl, heterocyclyl, methylsulfonyl, and phenyl. In some embodiments, $R^2$ is a substituted piperazinyl substituted with a single substituent selected from the group consisting of —C(O)OC(CH$_3$)$_3$, —C(O)OCH$_2$CH(CH$_3$)$_2$, —C(O)OCH$_2$CH$_3$, —C(O)OCH$_3$, phenyl, —C(O)CH$_3$, —C(O)Ph, —SO$_2$Me, —SO$_2$N(CH$_3$)$_2$,

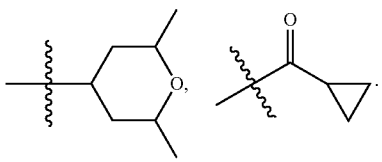

In some embodiments, $R^2$ is a substituted piperazinyl substituted with a single substituent at the 4 position selected from the group consisting of —C(O)OC(CH$_3$)$_3$, —C(O)OCH$_2$CH(CH$_3$)$_2$, —C(O)OCH$_2$CH$_3$, —C(O)OCH$_3$, phenyl, —C(O)CH$_3$, —C(O)Ph, —SO$_2$Me, —SO$_2$N(CH$_3$)$_2$,

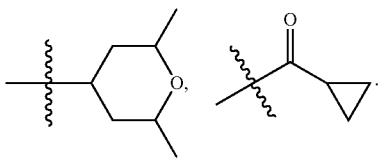

In certain embodiments, $R^2$ is a substituted piperdinyl of formula:

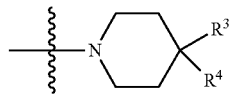

wherein, $R^3$ is hydrogen or $C_1$-$C_8$ alkyl, and $R^4$ is hydrogen, hydroxyl, halogen, $CF_3$, alkoxy, aryloxy, optionally substituted $C_1$-$C_{10}$ alkyl, optionally substituted $C_5$-$C_{10}$ aryl, optionally substituted $C_3$-$C_{10}$ heteroaryl, optionally substituted $C_3$-$C_{10}$ cycloalkyl or optionally substituted $C_3$-$C_{10}$ heterocycloalkyl.

In some embodiments, $R^2$ is

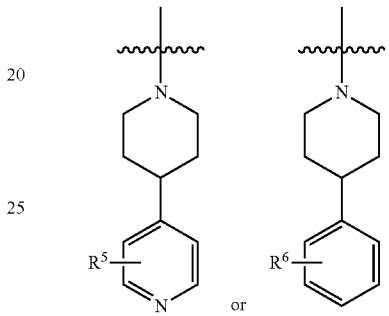

wherein each of $R^5$ and $R^6$ is independently, hydrogen, hydroxyl, sulfonyl, dialkylamino, optionally substituted $C_1$-$C_{10}$ alkyl, optionally substituted $C_5$-$C_{10}$ aryl optionally substituted $C_3$-$C_{10}$ heteroaryl, optionally substituted $C_3$-$C_{10}$ cycloalkyl or optionally substituted $C_3$-$C_{10}$ heterocycloalkyl. In some embodiments $R^5$ is hydrogen, dialkylamino, or $C_3$-$C_{10}$ heterocycloalkyl. In some embodiments $R^5$ is hydrogen, dialkylamino, pyrrolidinyl or morpholinyl. In some embodiments, $R^6$ is sulfonyl. In some embodiments, $R^6$ is methylsulfonyl.

In some embodiments, $R^2$ is:

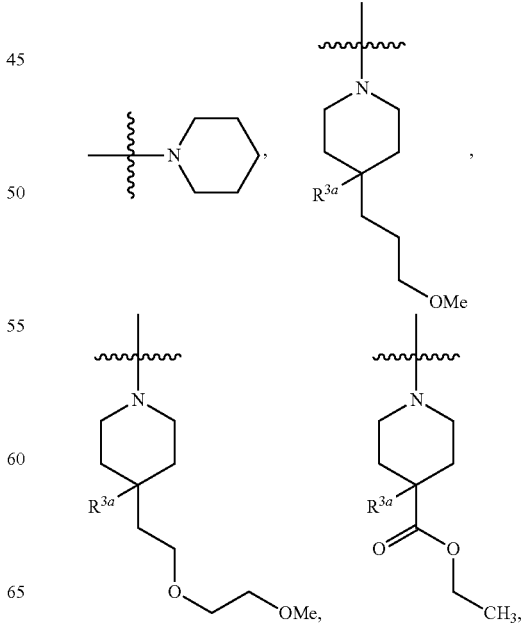

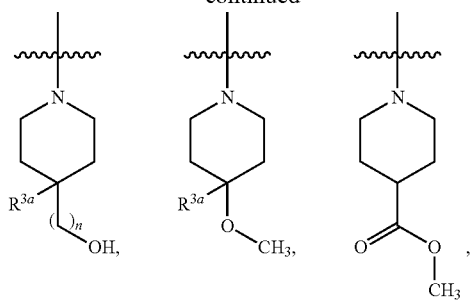
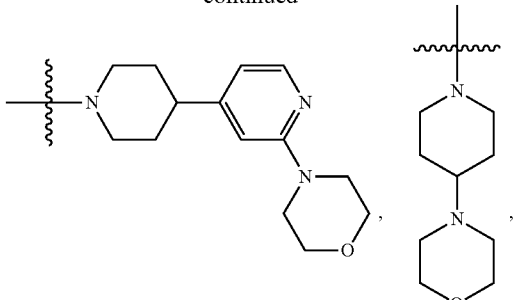
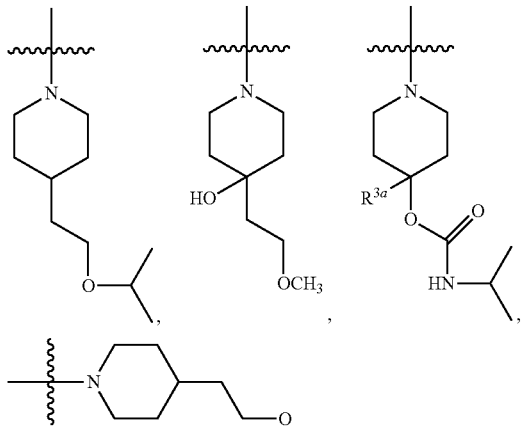
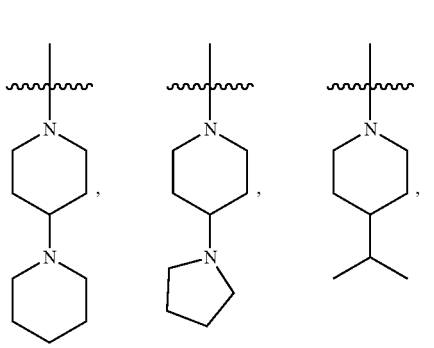
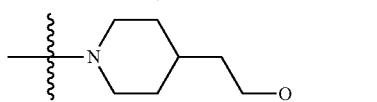
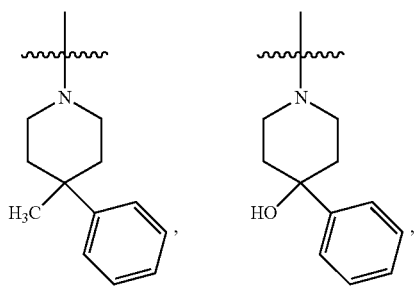
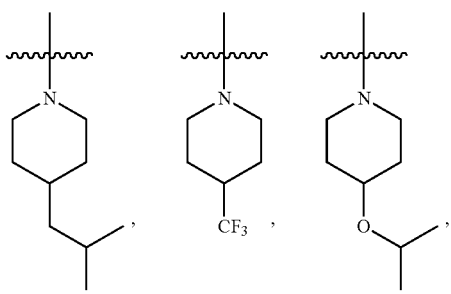
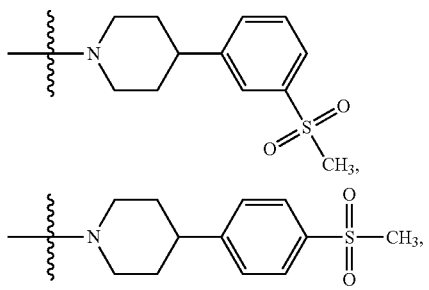
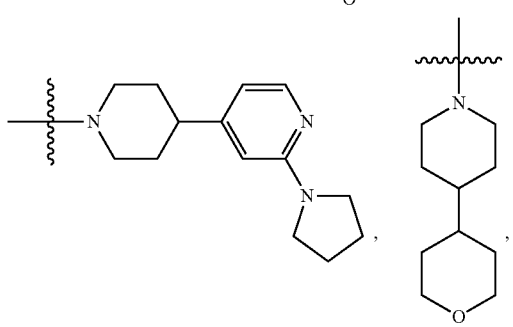
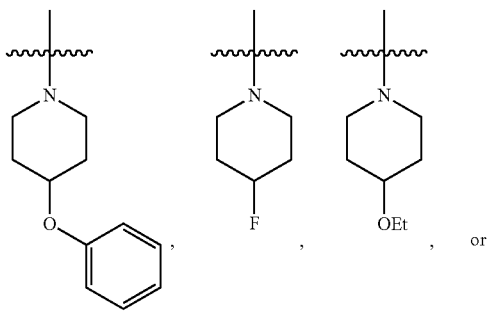
wherein $R^{3a}$ selected from the group consisting of hydrogen and $C_1$-$C_8$ alkyl; and n is an integer selected from 0, 1 and 2.

In some embodiments $R^2$ is

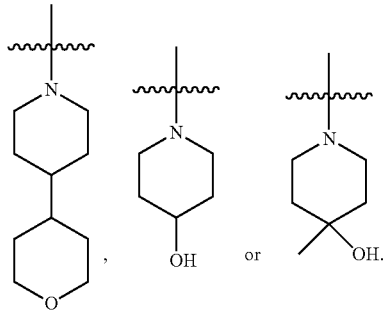

In some embodiments, $R^2$ is optionally substituted morpholinyl. In some embodiments, $R^2$ is morpholinyl.

In some embodiments $R^2$ or is optionally substituted piperazinyl of the formula

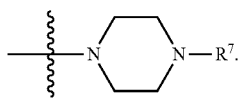

wherein $R^7$ is hydrogen, hydroxyl, sulfonyl, dialkylaminosulfonyl, alkoxycarbonyl, acyl, benzoyl, cycloalkylcarbonyl, optionally substituted $C_1$-$C_{10}$ alkyl, optionally substituted $C_5$-$C_{10}$ aryl optionally substituted $C_3$-$C_{10}$ heteroaryl, optionally substituted $C_3$-$C_{10}$ cycloalkyl or optionally substituted $C_3$-$C_{10}$ heterocycloalkyl. In some embodiments $R^7$ is sulfonyl, dialkylaminosulfonyl, alkoxycarbonyl, acyl, benzoyl, cycloalkylcarbonyl, $C_5$-$C_{10}$ aryl or optionally substituted $C_3$-$C_{10}$ heterocycloalkyl.

In some embodiments $R^2$ is

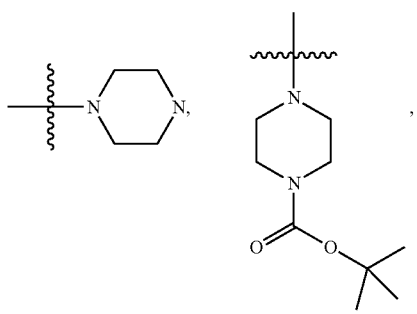

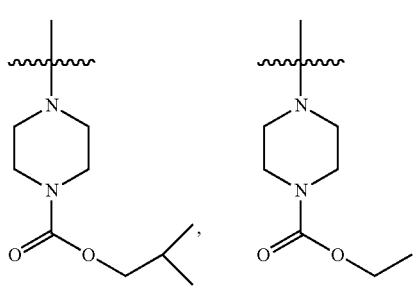

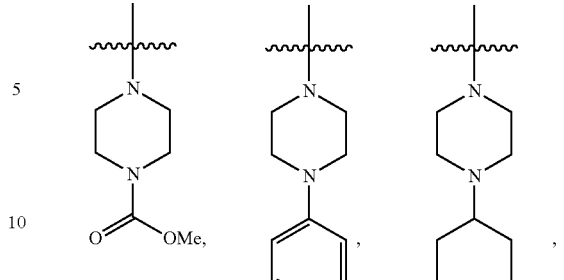

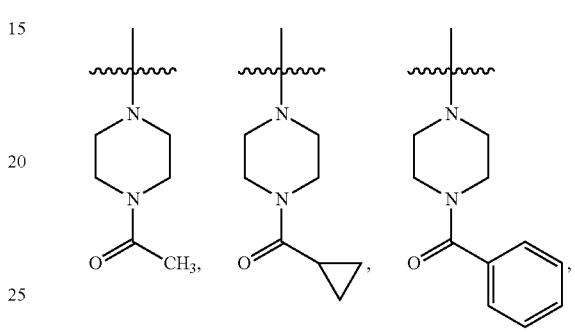

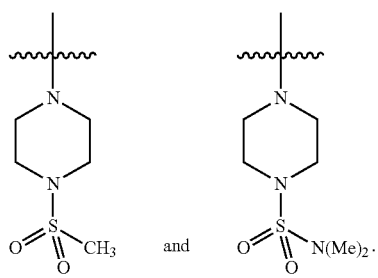

In various embodiments, $R^2$ is optionally substituted pyrrolidinyl:

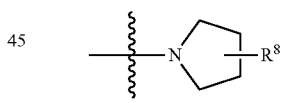

where $R^8$ is hydrogen, hydroxyl, sulfonyl, optionally substituted $C_1$-$C_{10}$ alkyl, optionally substituted $C_5$-$C_{10}$ aryl, optionally substituted $C_3$-$C_{10}$ heteroaryl, optionally substituted $C_3$-$C_{10}$ cycloalkyl or optionally substituted $C_3$-$C_{10}$ heterocycloalkyl. In some embodiments, $R^8$ is hydrogen, hydroxyl or optionally substituted $C_1$-$C_{10}$ alkyl.

In some embodiments, $R^2$ is:

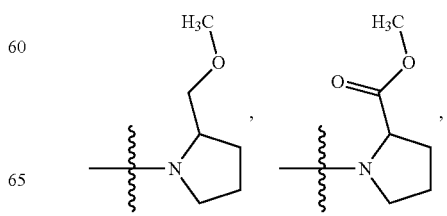

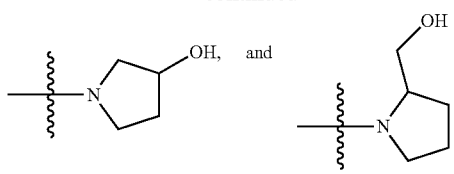

In some embodiments, R² is an optionally substituted bicyclic ring or an optionally substituted fused ring. For example, in some embodiments, R² is selected from the group consisting of:

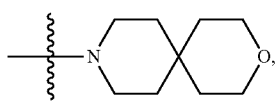

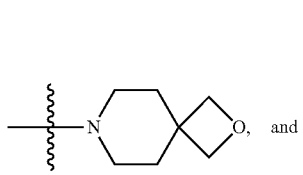 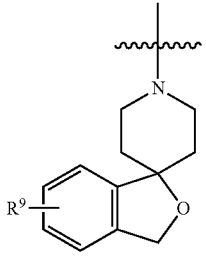

where R⁹ is hydrogen, hydroxyl, sulfonyl, optionally substituted $C_1$-$C_{10}$ alkyl, optionally substituted $C_5$-$C_{10}$ aryl, optionally substituted $C_3$-$C_{10}$ heteroaryl, optionally substituted $C_3$-$C_{10}$ cycloalkyl or optionally substituted $C_3$-$C_{10}$ heterocycloalkyl.

In some embodiments, R² is

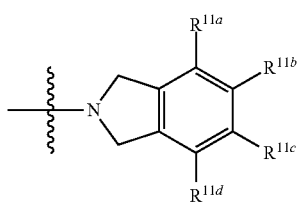

wherein each of $R^{11a}$, $R^{11b}$, $R^{11c}$, and $R^{11d}$, is, independently selected from, hydrogen, hydroxy, sulfonyl, optionally substituted $C_1$-$C_{10}$ alkyl, optionally substituted $C_5$-$C_{10}$ aryl, optionally substituted $C_3$-$C_{10}$ heteroaryl, optionally substituted $C_3$-$C_{10}$ cycloalkyl or optionally substituted $C_3$-$C_{10}$ heterocycloalkyl. In particular embodiments, R² is

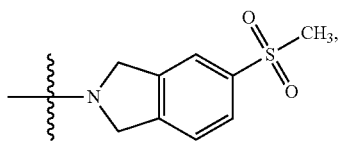

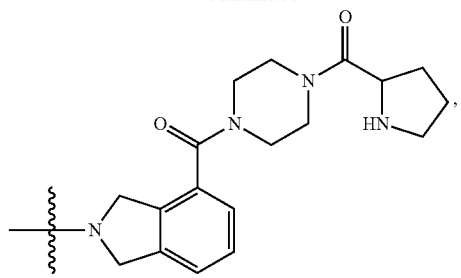

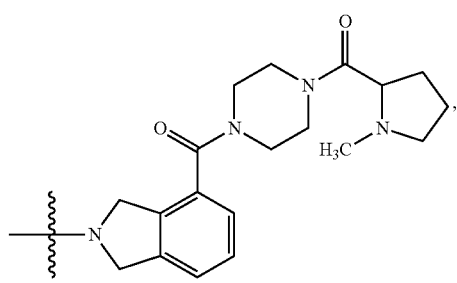

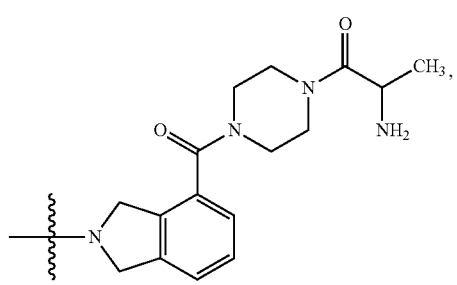

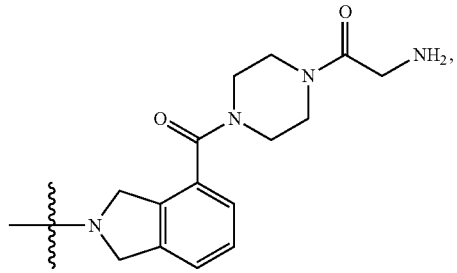

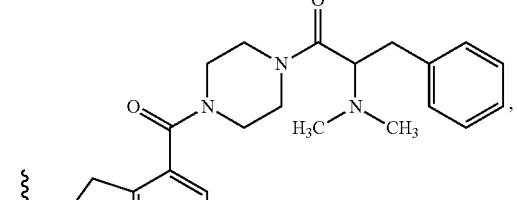

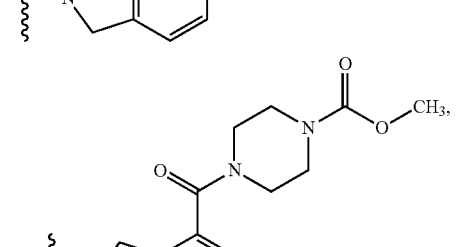

-continued

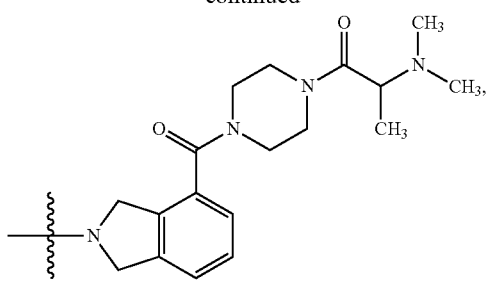

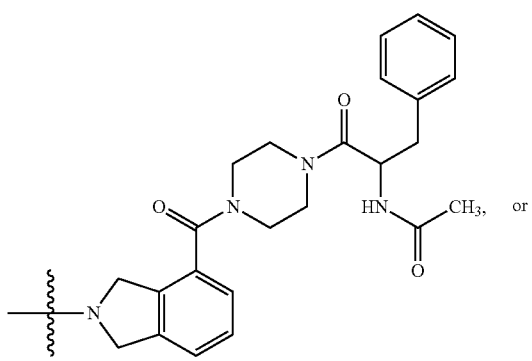

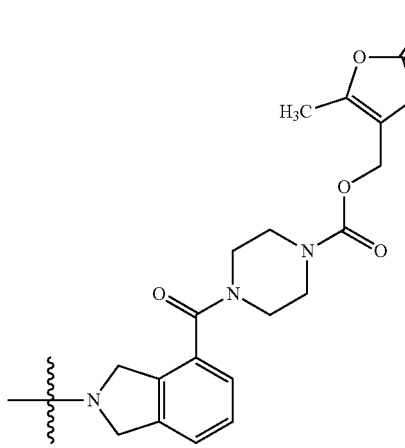

Some embodiments disclosed herein describe a compound wherein each $R^a$, $R^b$, $R^c$, $R^d$ and $R^e$ is selected from any embodiment disclosed herein for each of $R^a$, $R^b$, $R^c$, $R^d$ and $R^e$; $R^1$ is selected from any embodiment disclosed herein for $R^1$; and $R^2$ is selected from any embodiment disclosed herein for $R^2$.

Some embodiments are directed to a compound selected from

Example 1

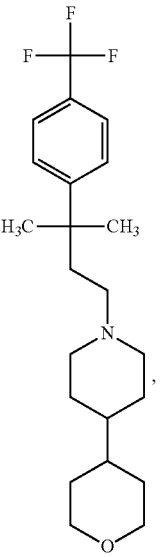

Example 2

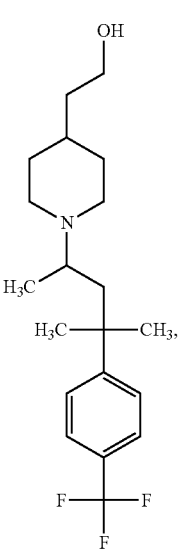

-continued
Example 3
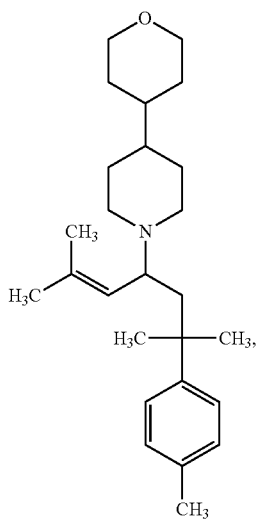
Example 4
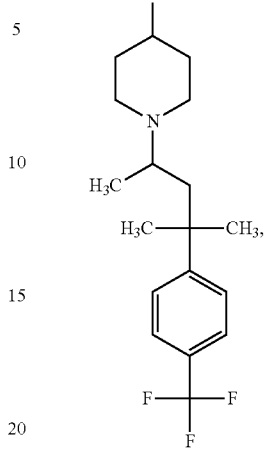
Example 5
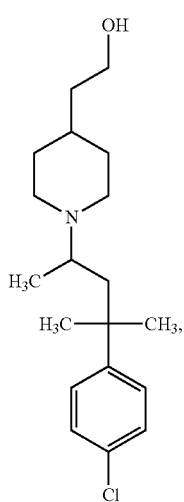
-continued
Example 6
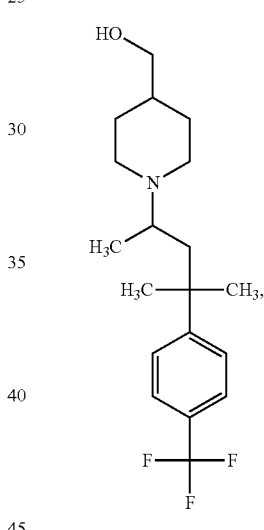
Example 7
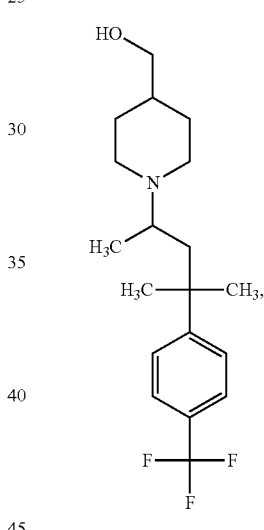
Example 8

Example 9
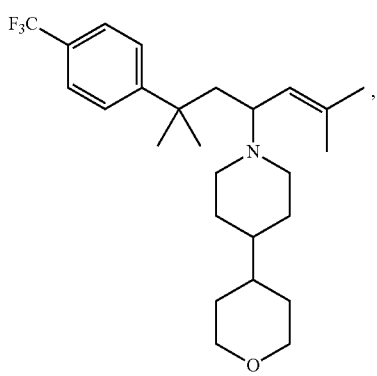
Example 10
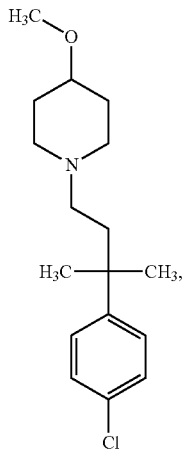
Example 11
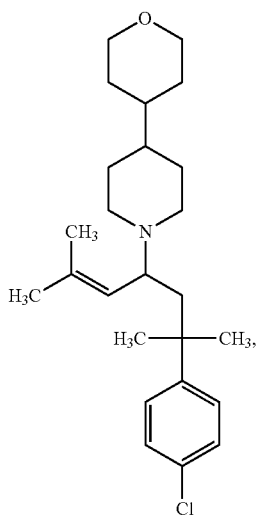
Example 12
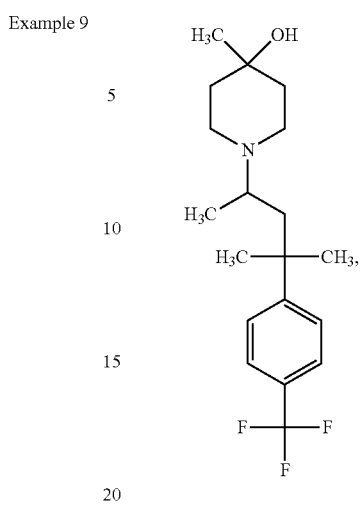
Example 13
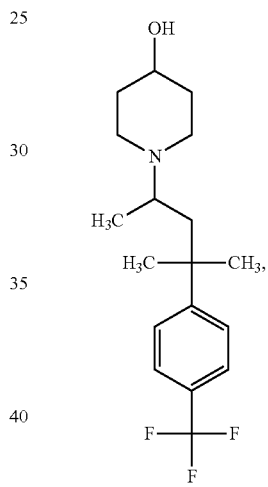
Example 14
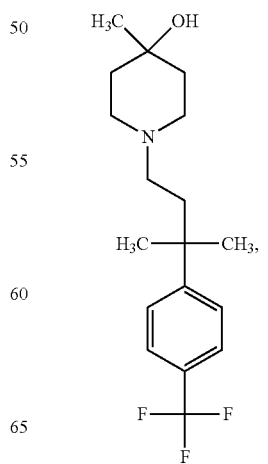

Example 15
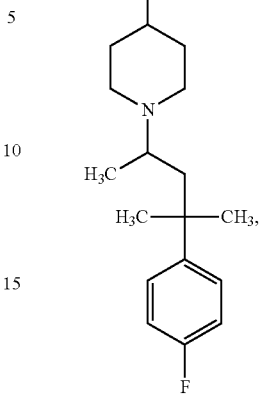
Example 16
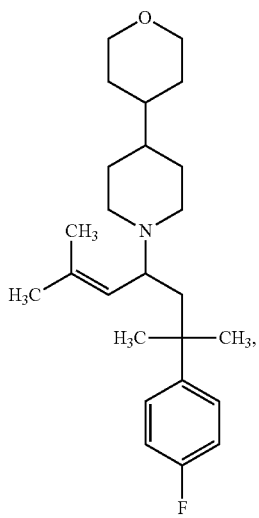
Example 17
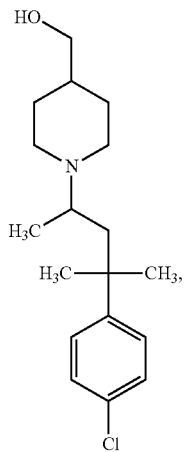
Example 19
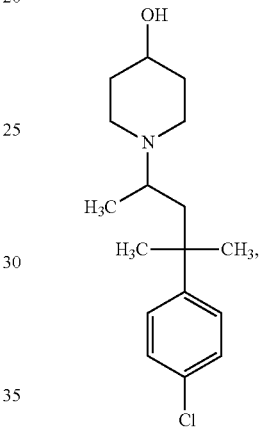
Example 20
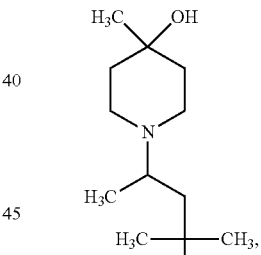
Example 22
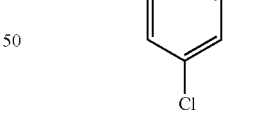
Example 23
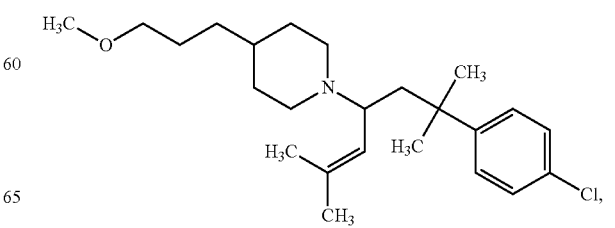

Example 24
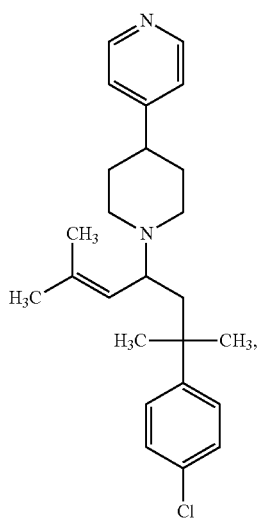
Example 25
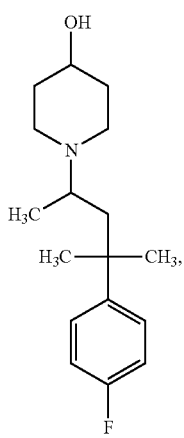
Example 27
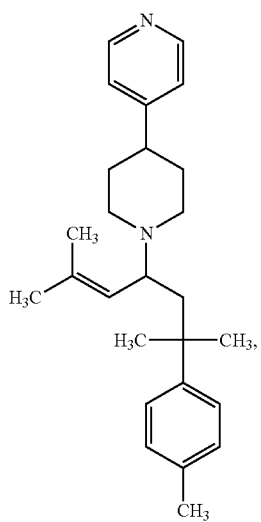
Example 28
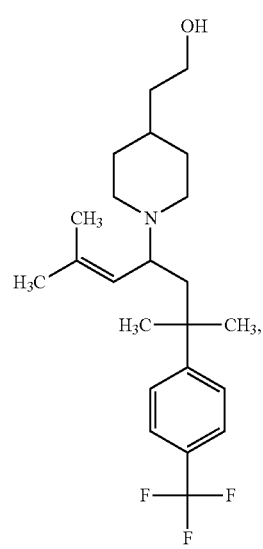
Example 29
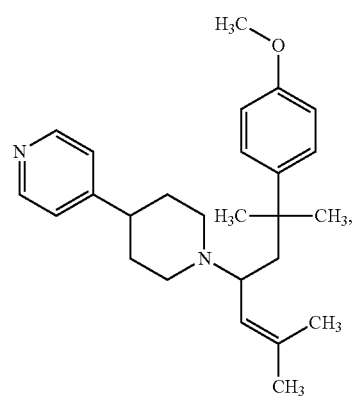
Example 30
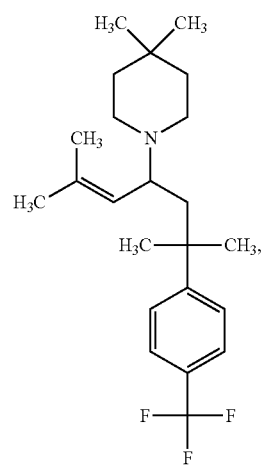

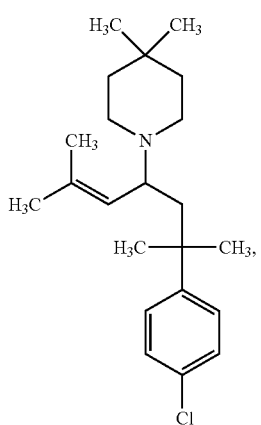
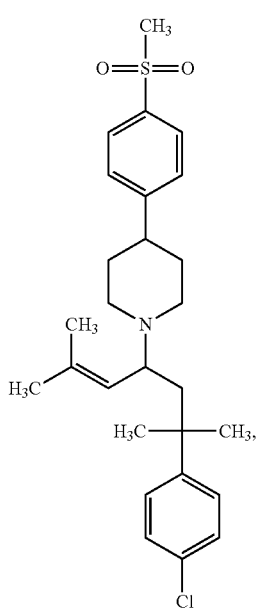
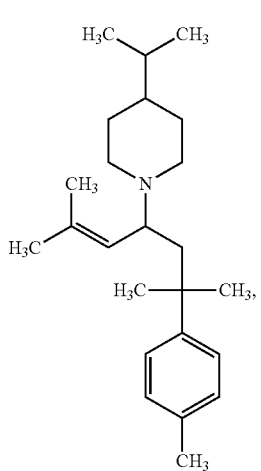
Example 31
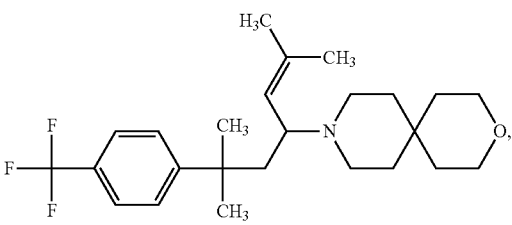
Example 34
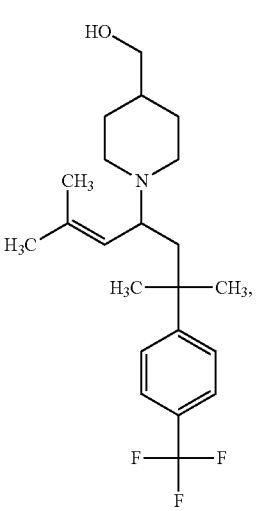
Example 35
Example 32
Example 33
Example 36
Example 37

Example 38
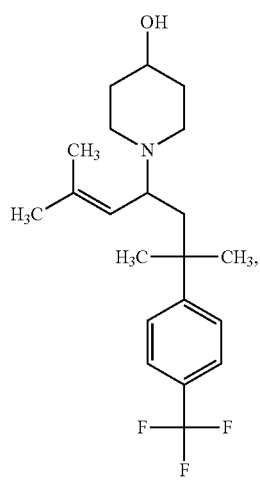
Example 39
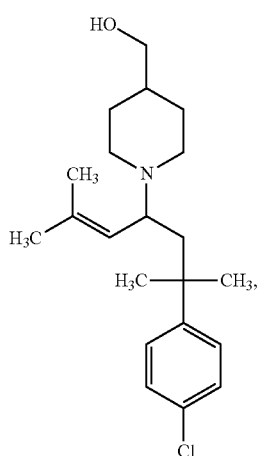
Example 40
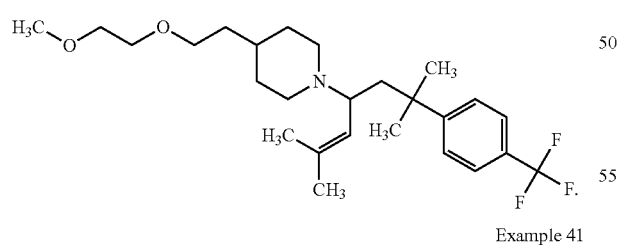
Example 41
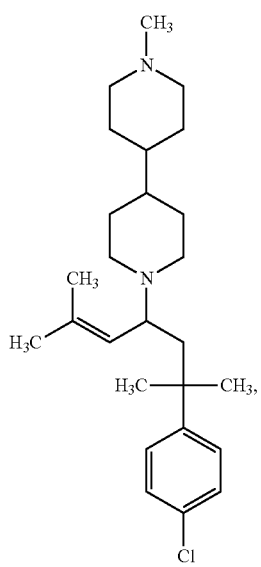
Example 42
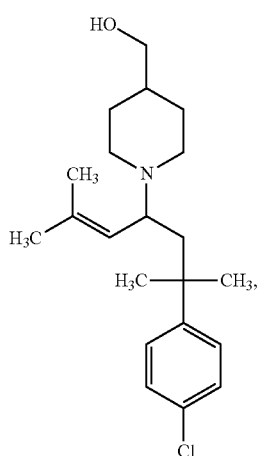
Example 43
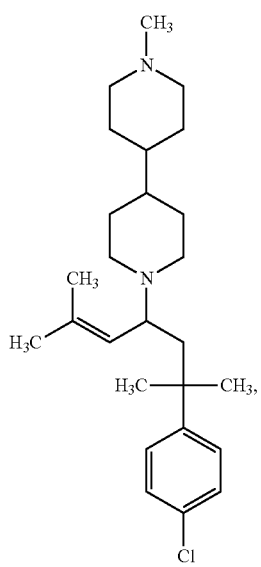
Example 44
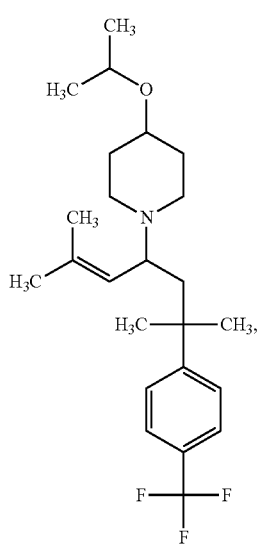

Example 45
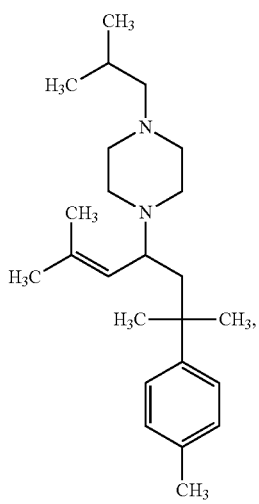
Example 46
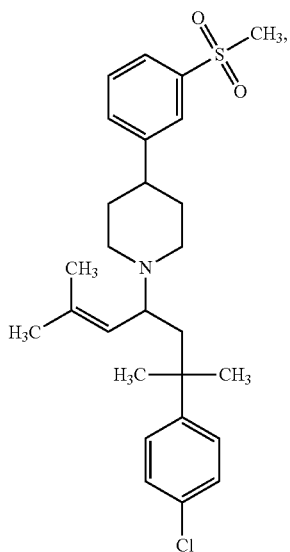
Example 47
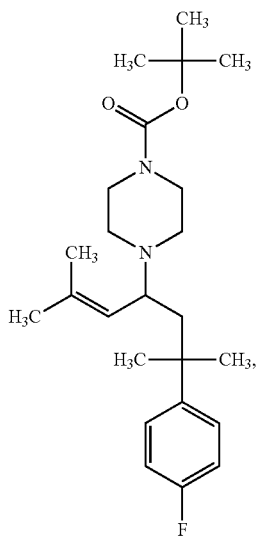
Example 49
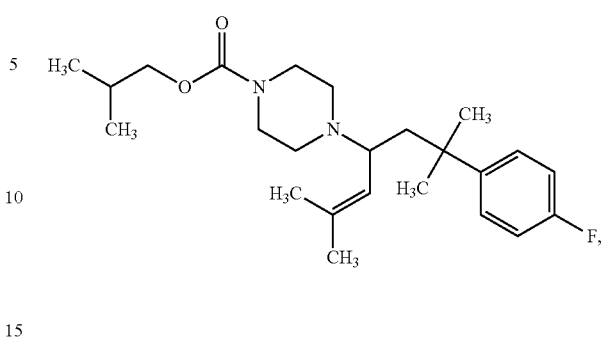
Example 50
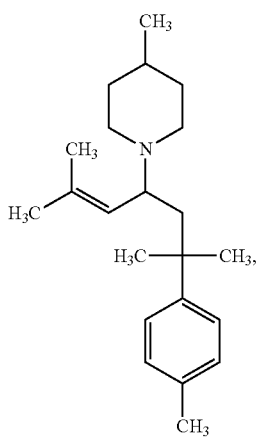
Example 51
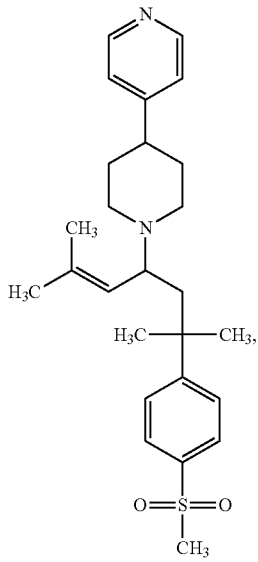

Example 53
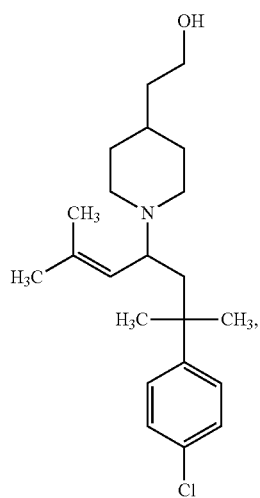
Example 55
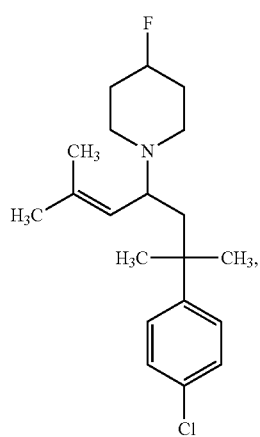
Example 56
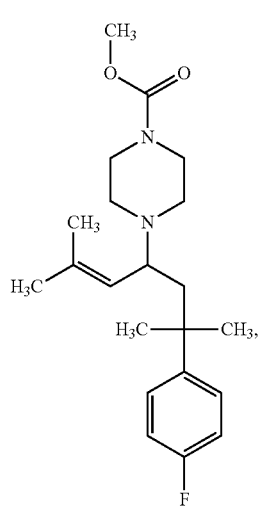
Example 58
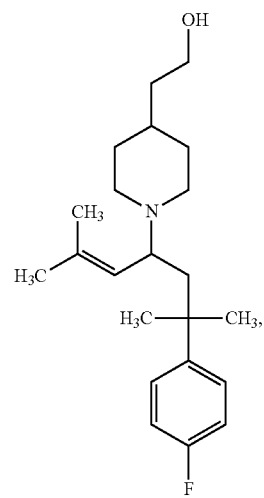
Example 59
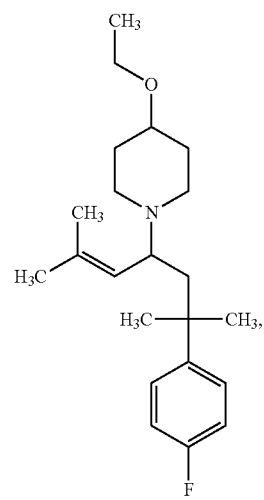
Example 60
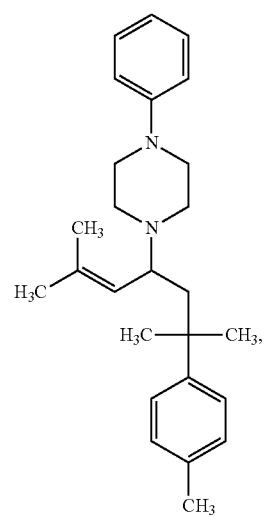

Example 61

Example 62

Example 63

Example 67

Example 68

Example 70

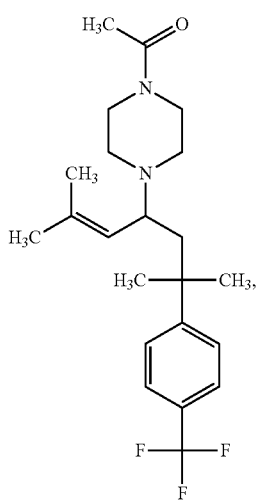
Example 71
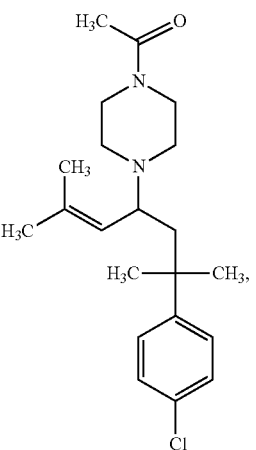
Example 75
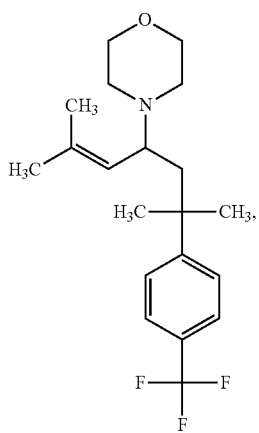
Example 72
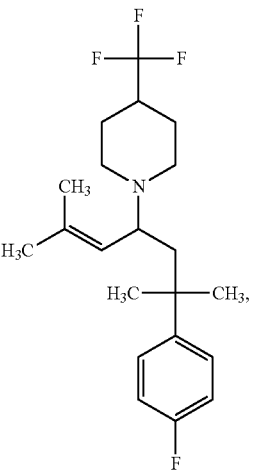
Example 76
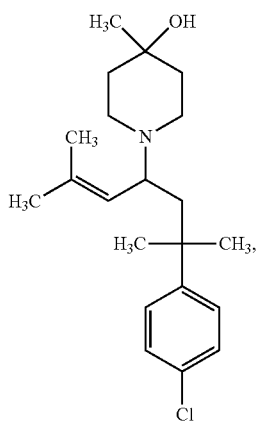
Example 73
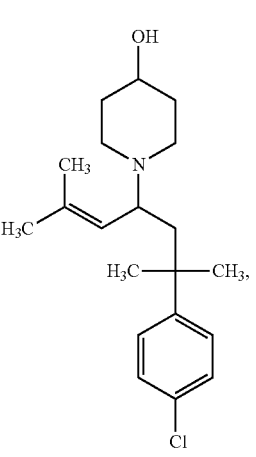
Example 77

Example 79
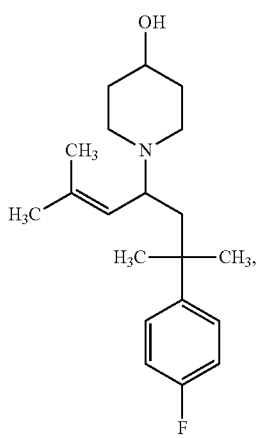
Example 81
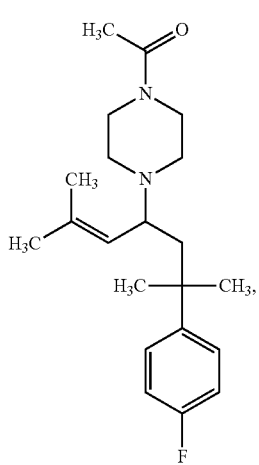
Example 82
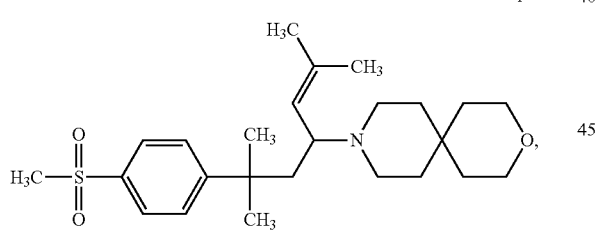
Example 83
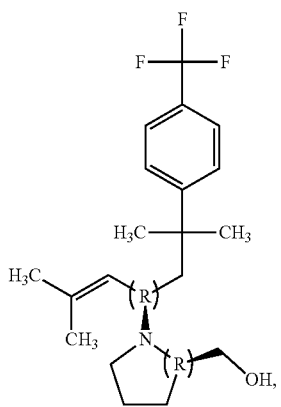
Example 84
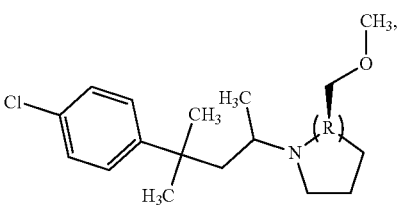
Example 85
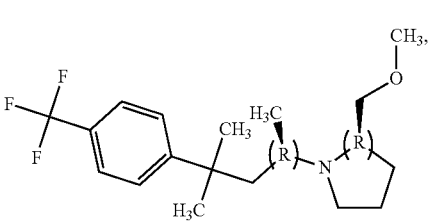
Example 86
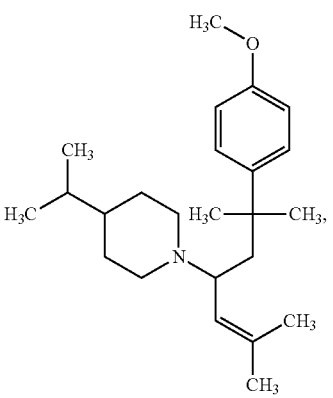
Example 87
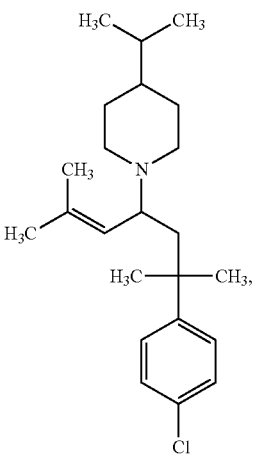

Example 89
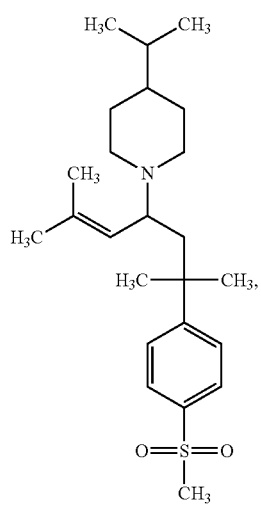
Example 90
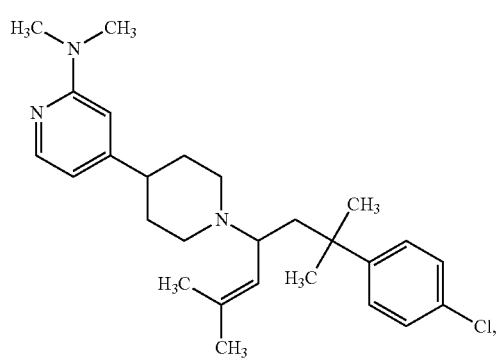
Example 97
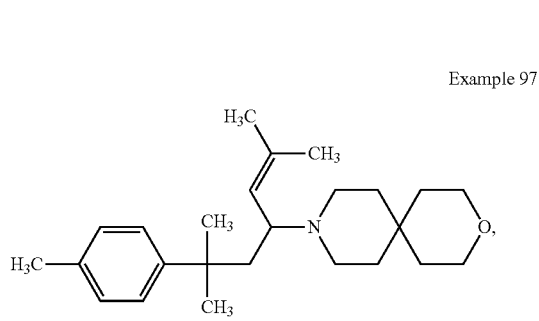
Example 98
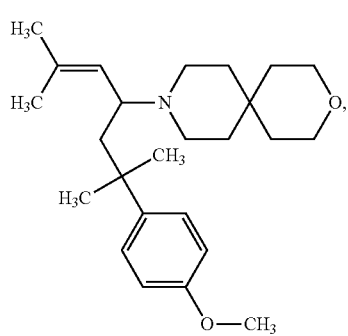
Example 107
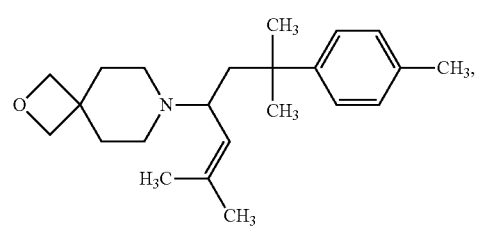
Example 116
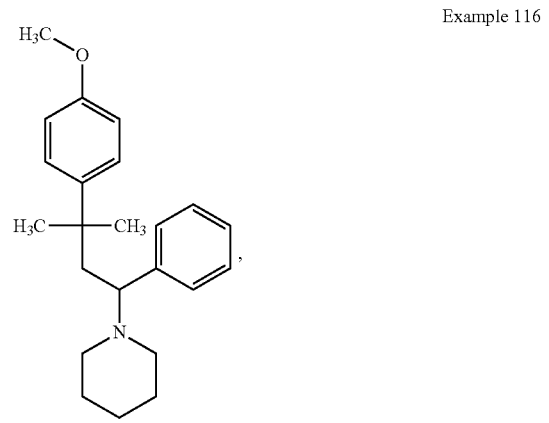
Example 117
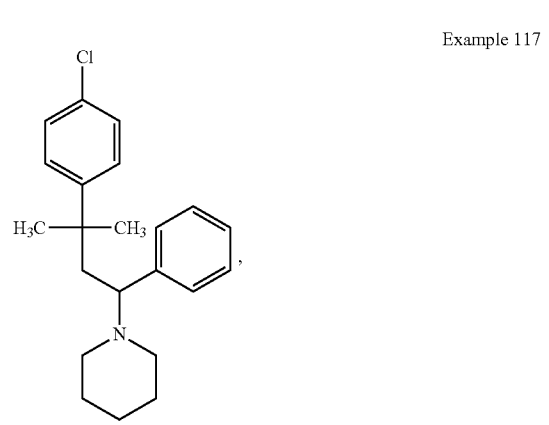
Example 118
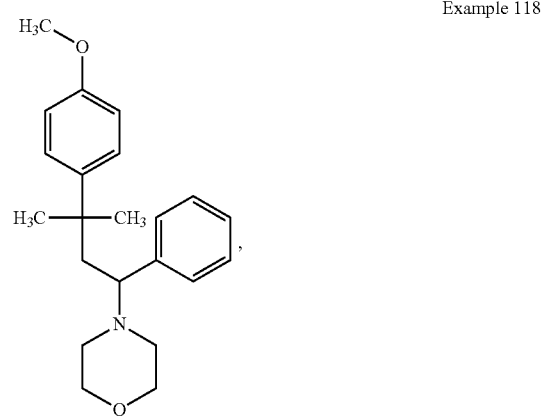

Example 119
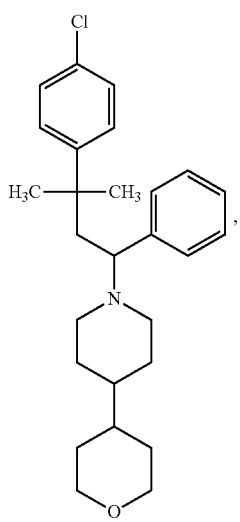
Example 120
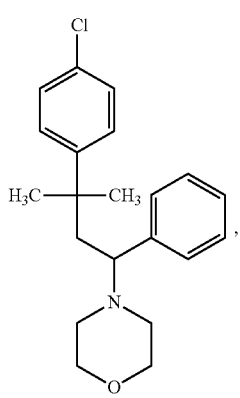
Example 122
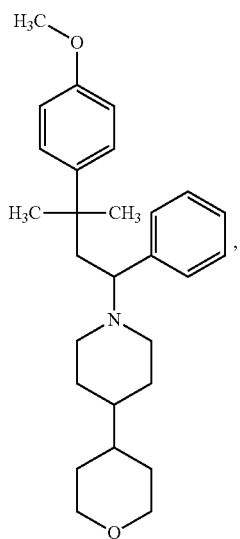
Example 123
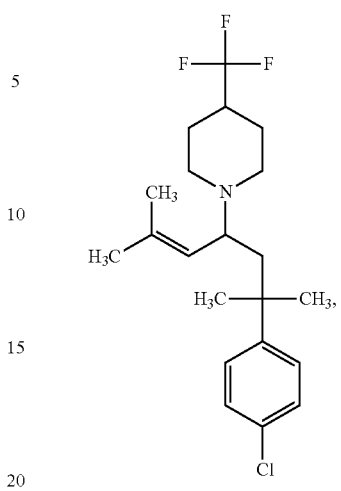
Example 124
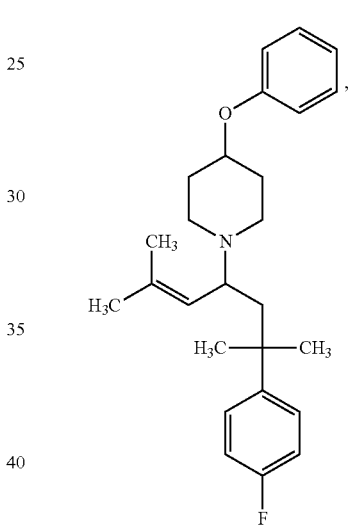
Example 125
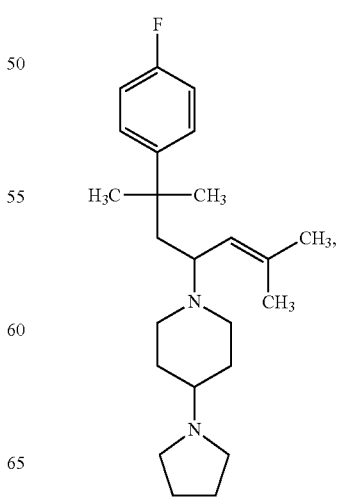

Example 126
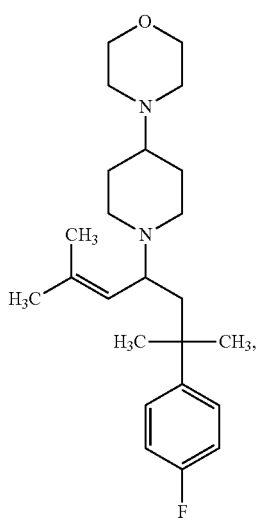
Example 127
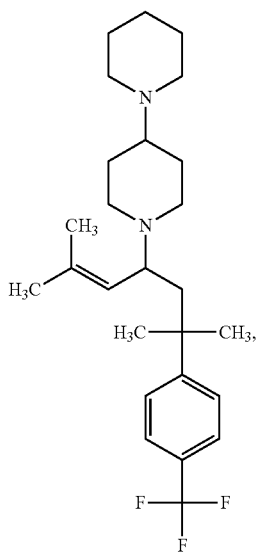
Example 128
Example 129
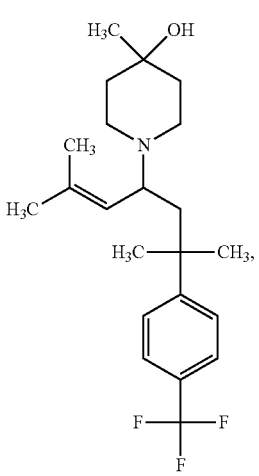
Example 130
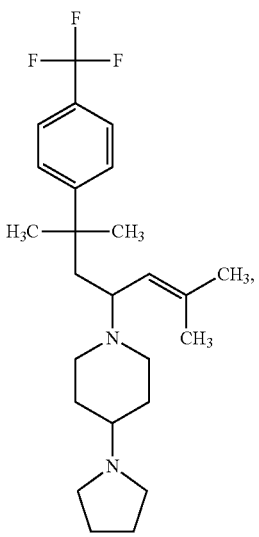
Example 131
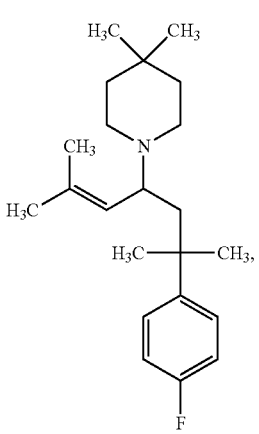

Example 132
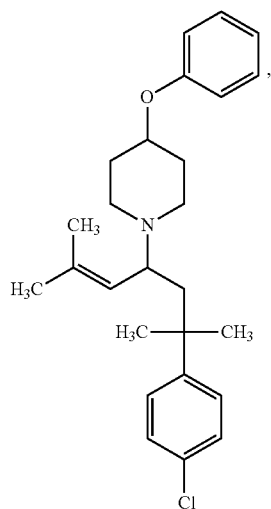
Example 133
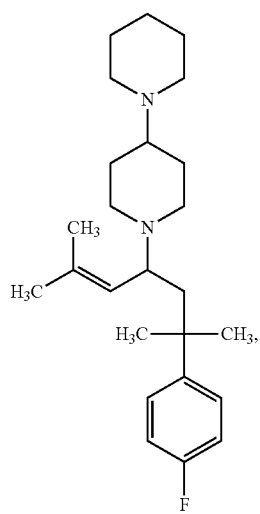
Example 134
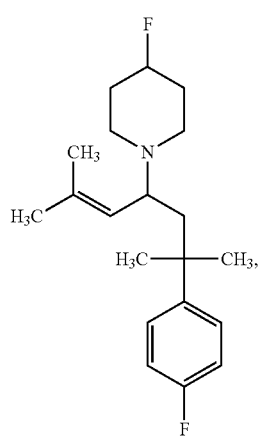
Example 135
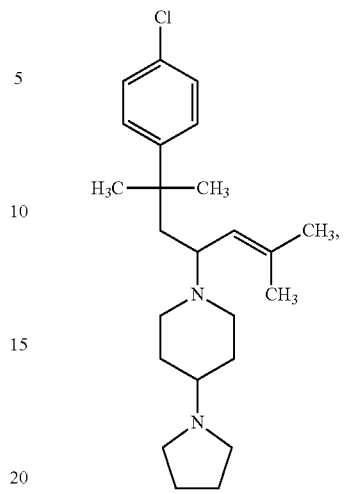
Example 136
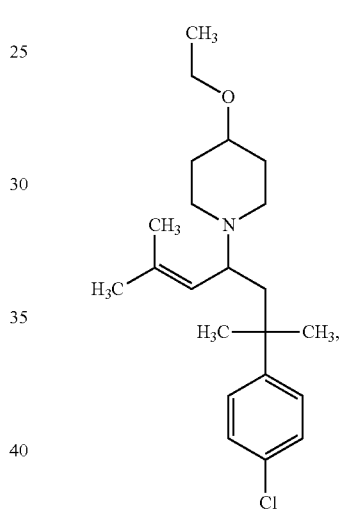
Example 137
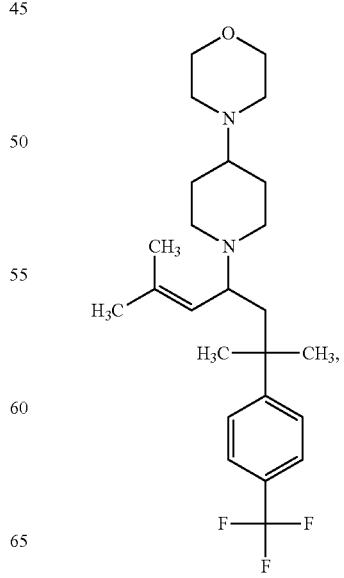

Example 138
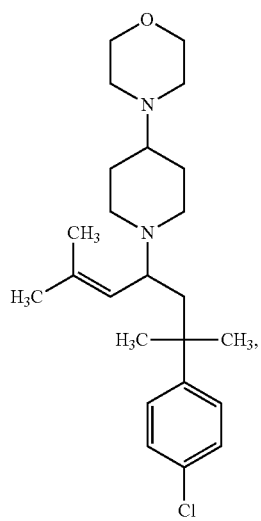
Example 139
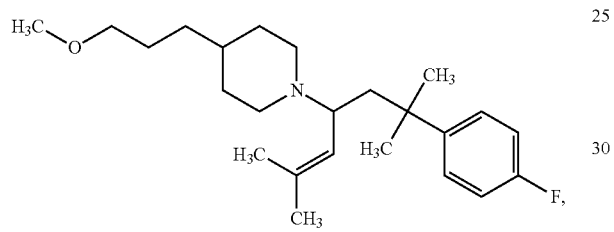
Example 140
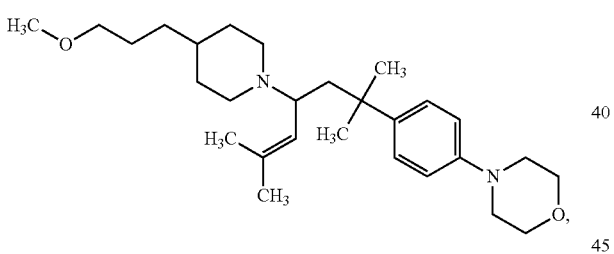
Example 141
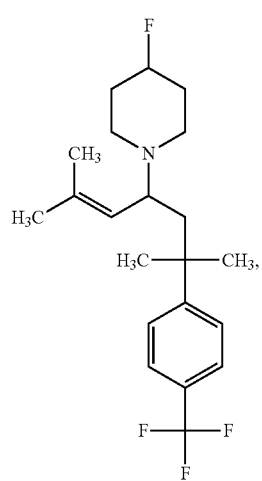
Example 142
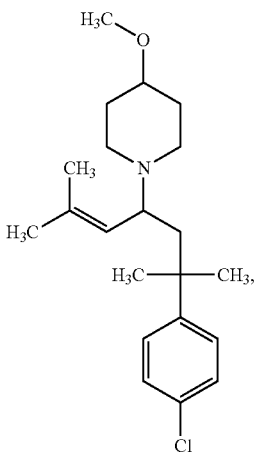
Example 143
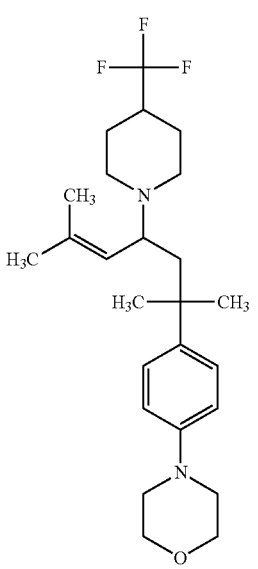
Example 144
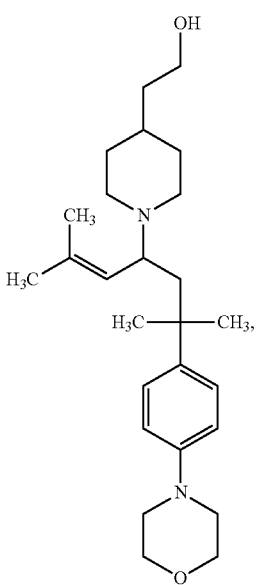

Example 145
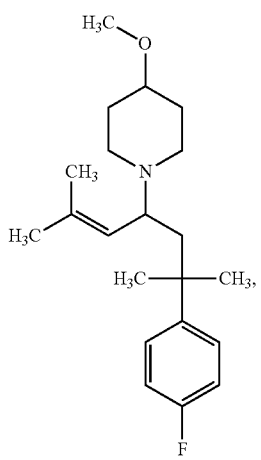
Example 146
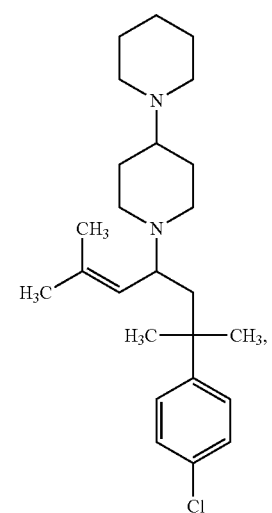
Example 147
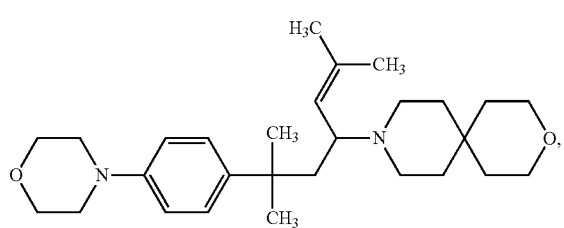
Example 148
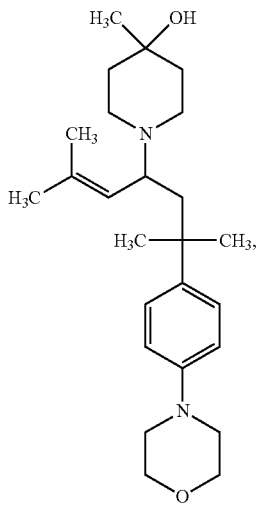
Example 149
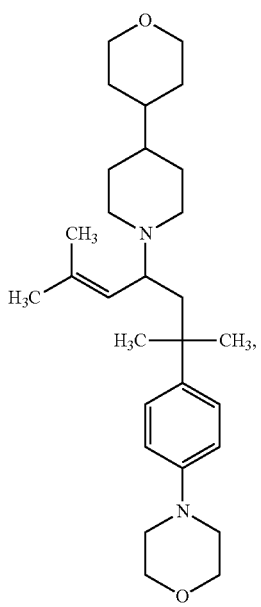
Example 150

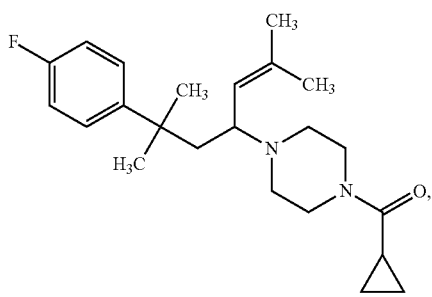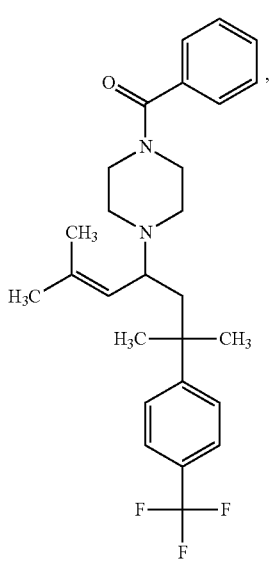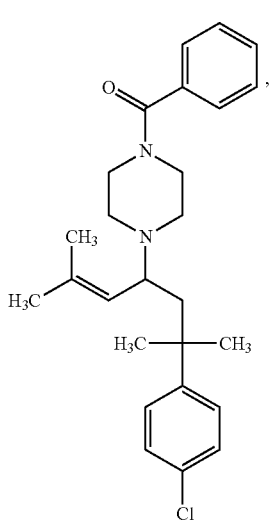

Example 158
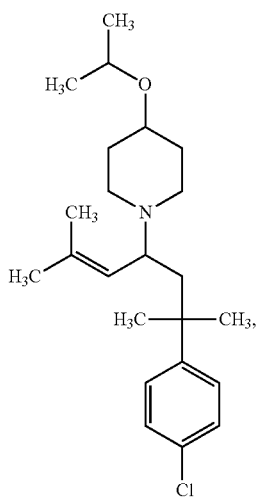
Example 159
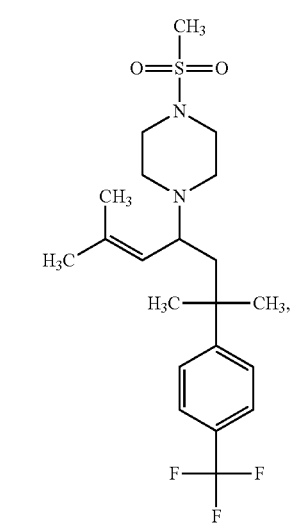
Example 160
Example 161
Example 162
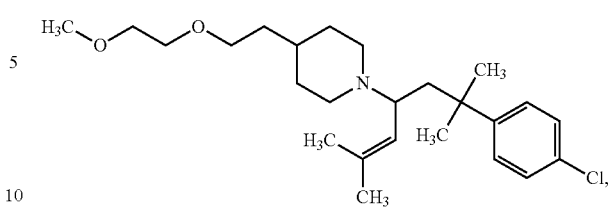
Example 163
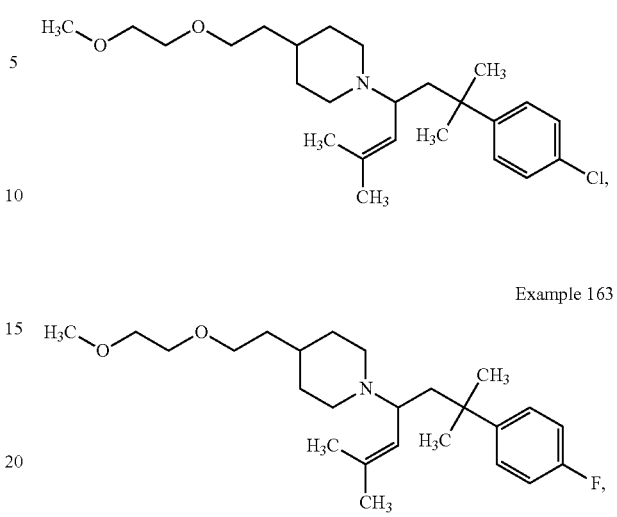
Example 164
Example 167
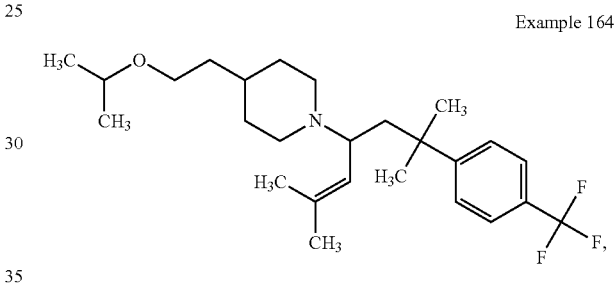
Example 168
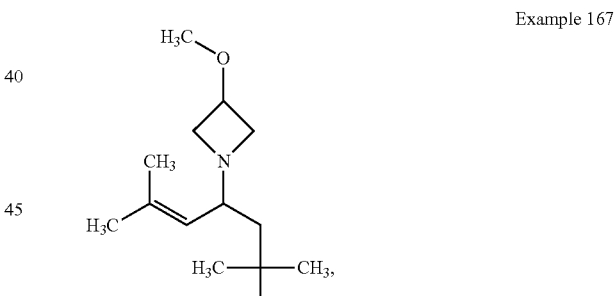
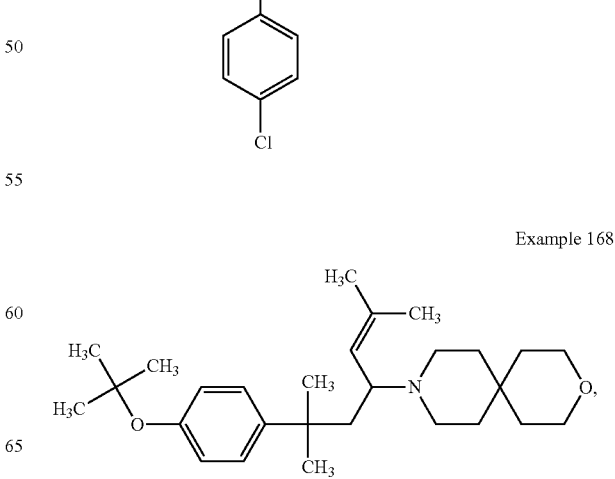

Example 169
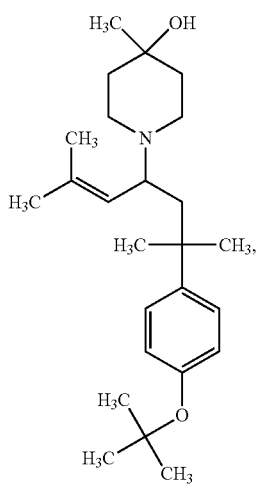
Example 170
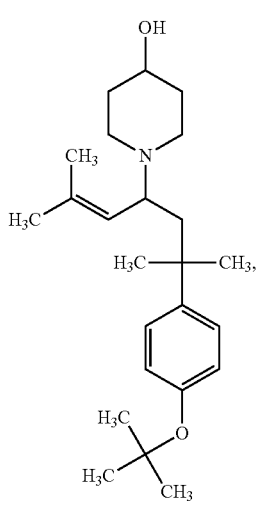
Example 171
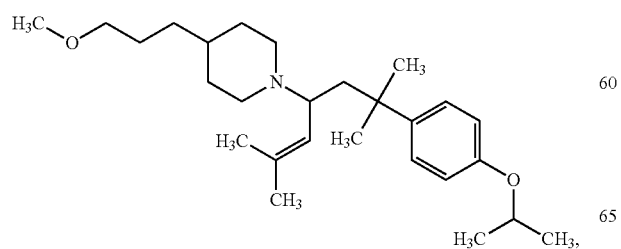
Example 178
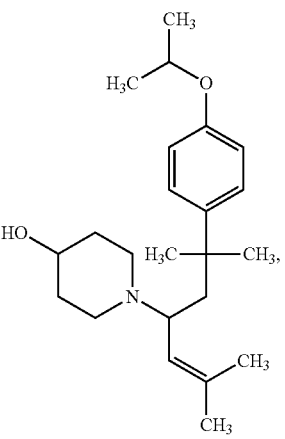
Example 179
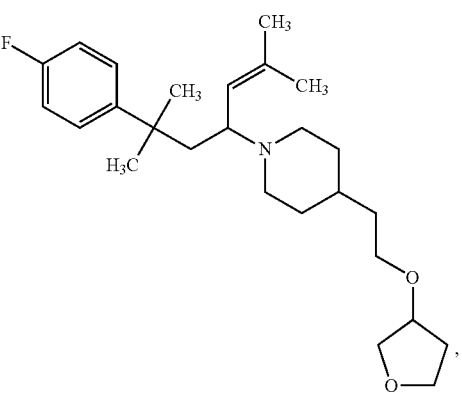
Example 180
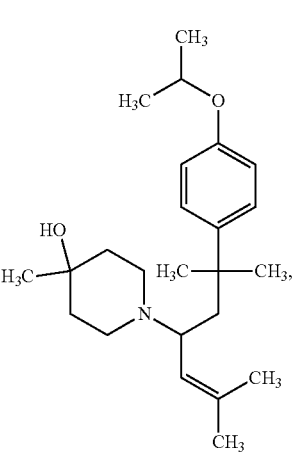

Example 181
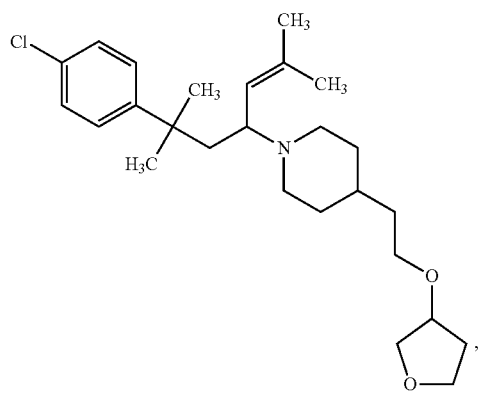
Example 182
Example 183
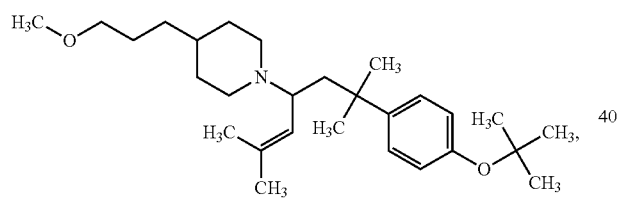
Example 185
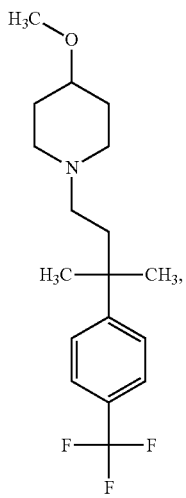
Example 187
Example 189
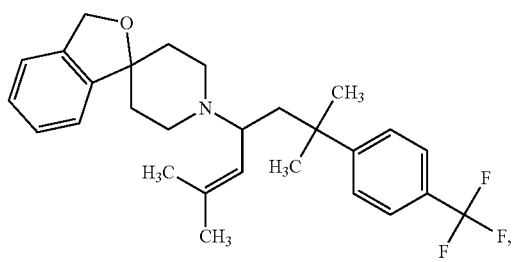
Example 191
Example 192
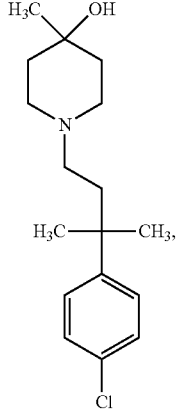

Example 193
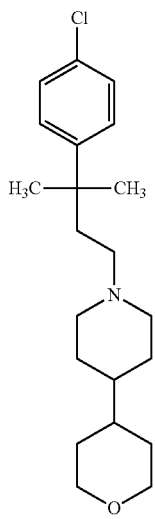
Example 194
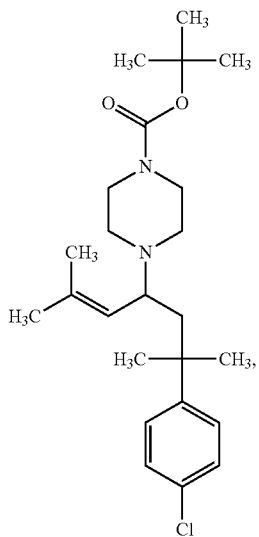
Example 195
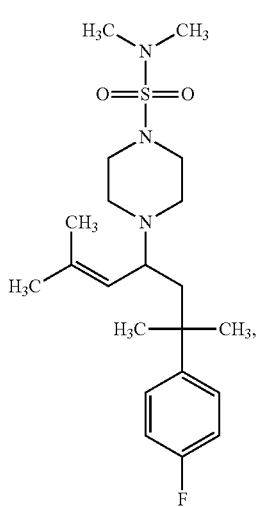
Example 196
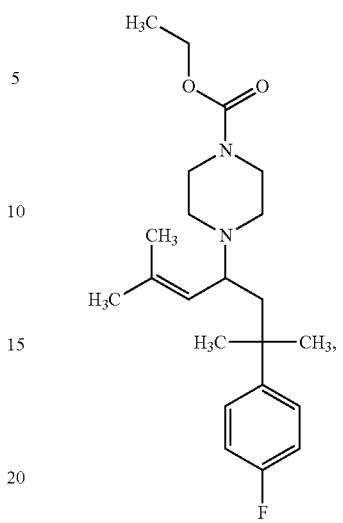
Example 197
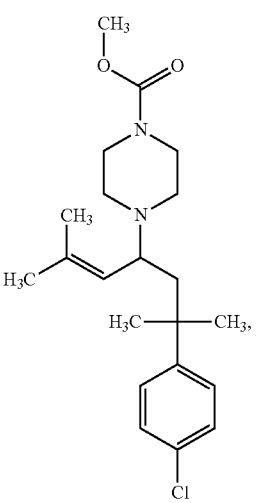
Example 198
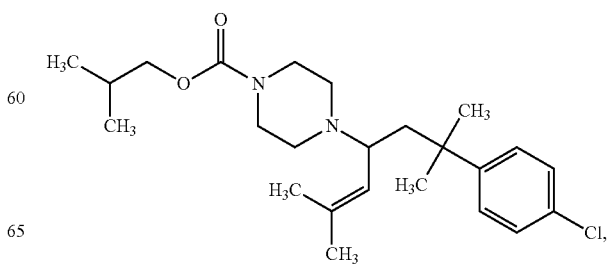

Example 199
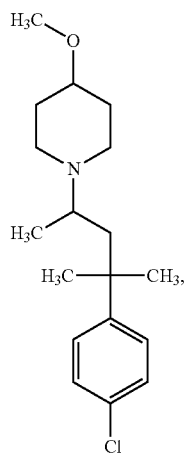
Example 200
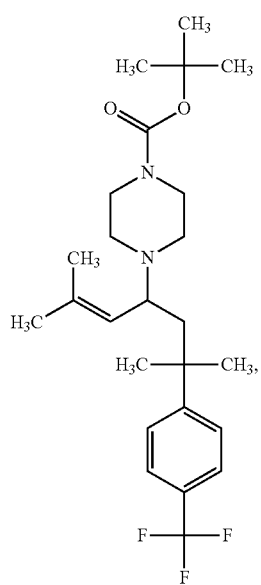
Example 201
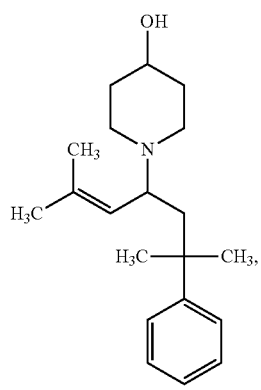
Example 202
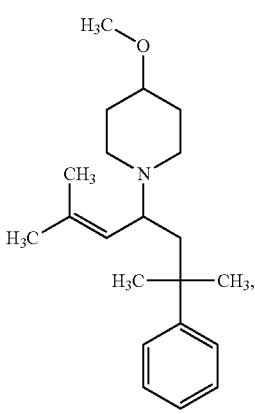
Example 203
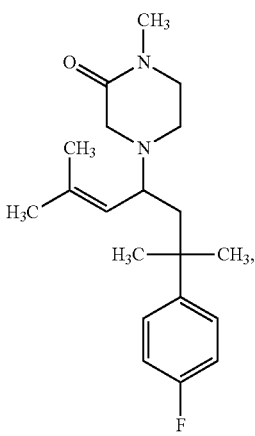
Example 204
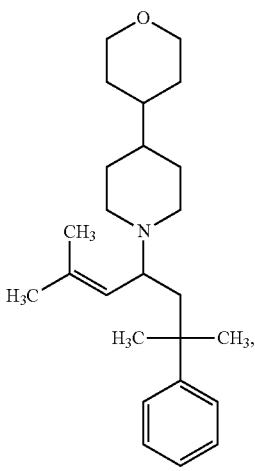

Example 205
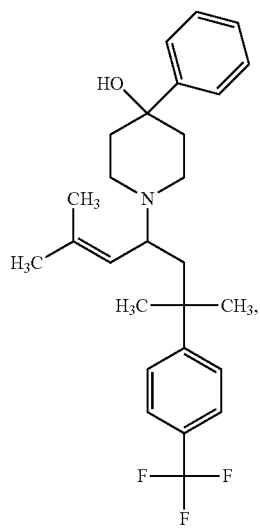
Example 206
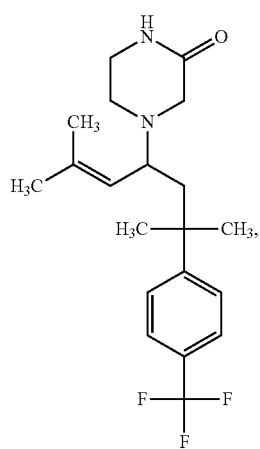
Example 207
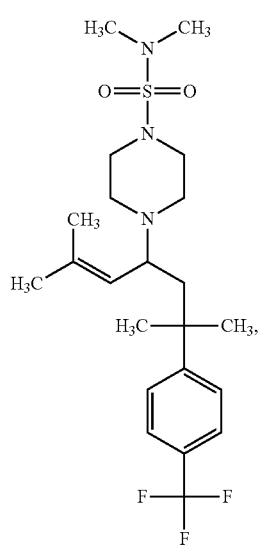
Example 208
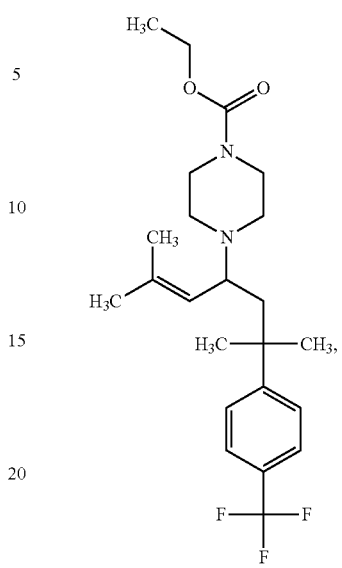
Example 209
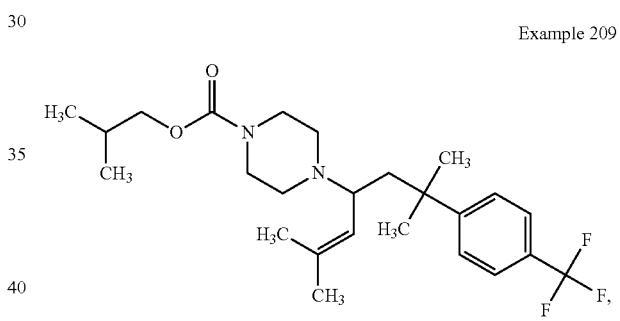
Example 210
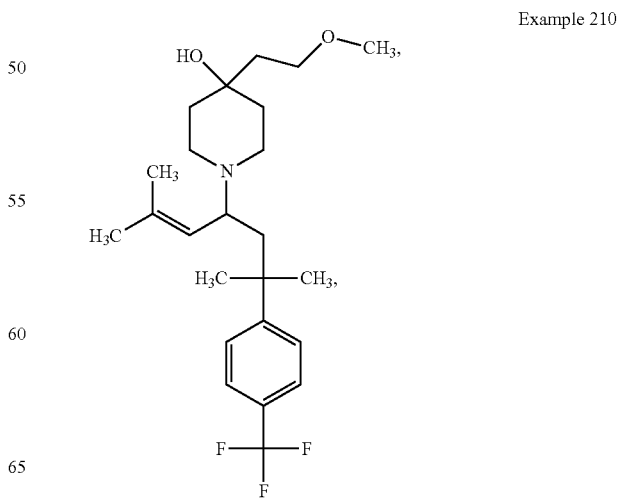

Example 211
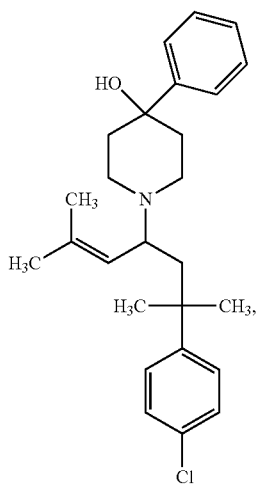
Example 212
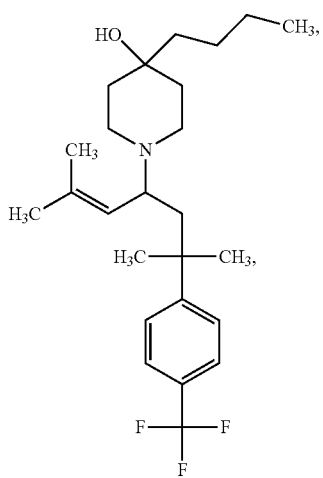
Example 213
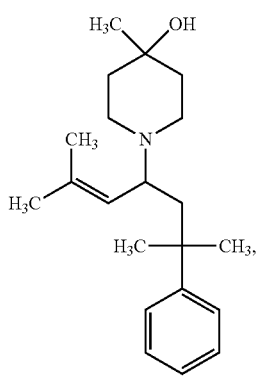
Example 214
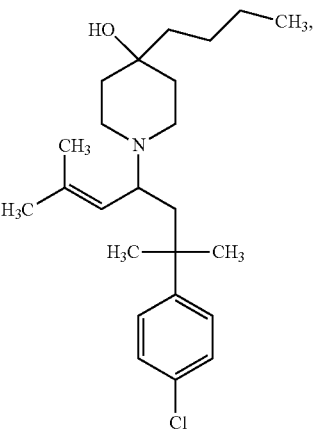
Example 215
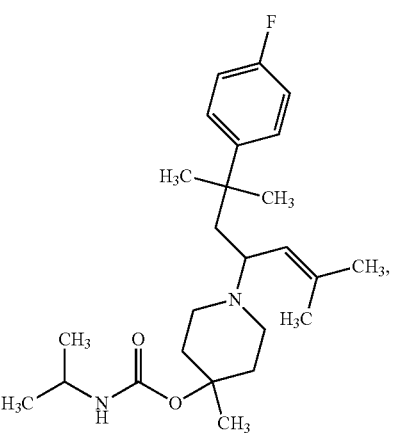
Example 216
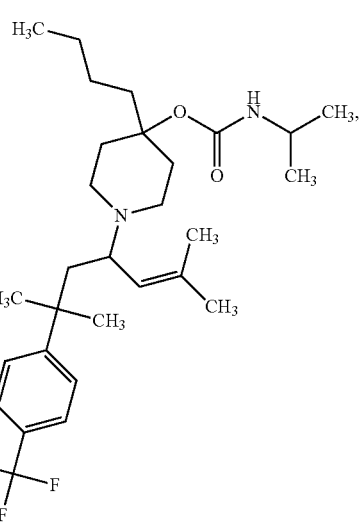

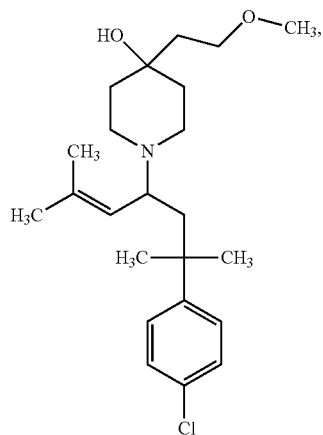
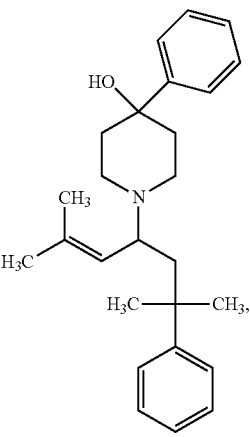
Example 217
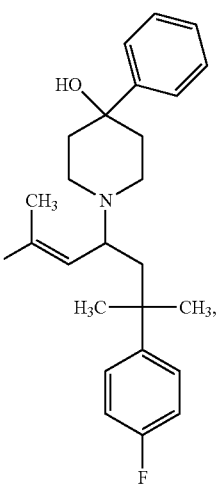
Example 218
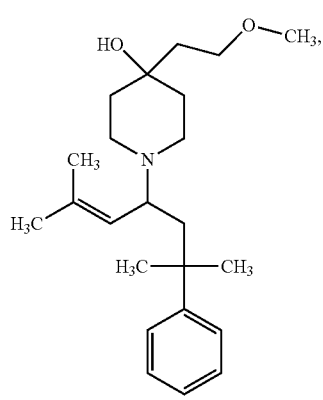
Example 219
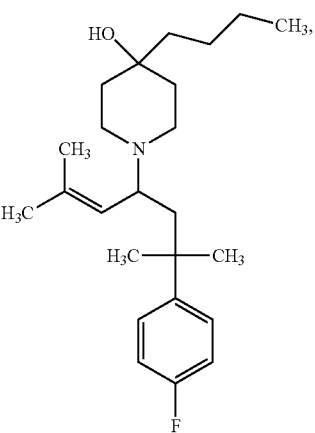
Example 220
Example 221
Example 222

Example 223
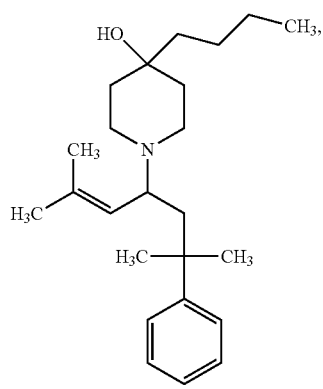
Example 224
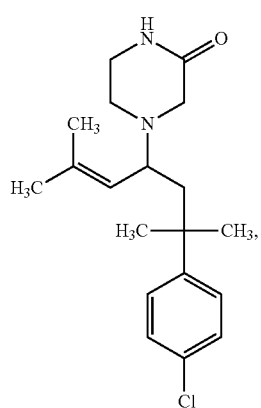
Example 225
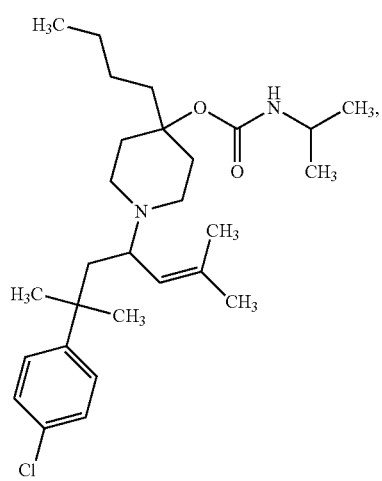
Example 226
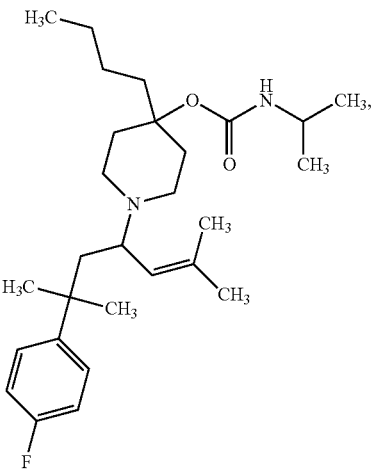
Example 227
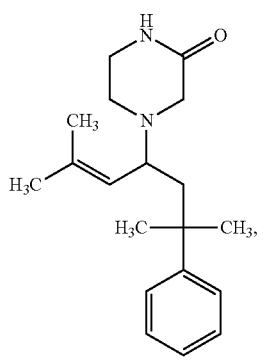
Example 228
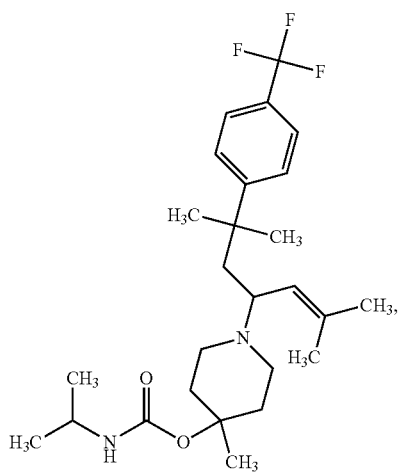
Example 229
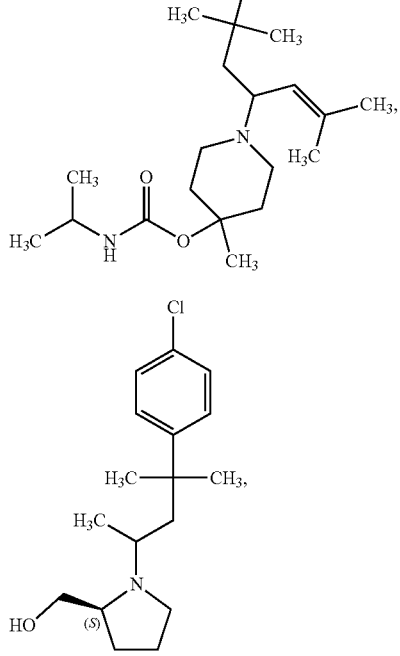

| | |
|---|---|
| 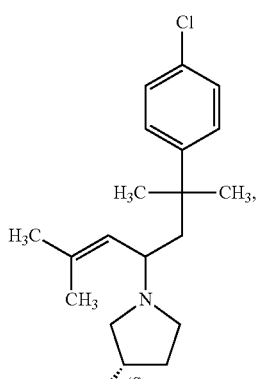 | Example 230 |
| 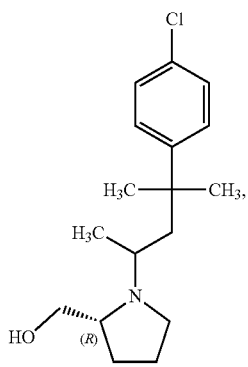 | Example 231 |
| 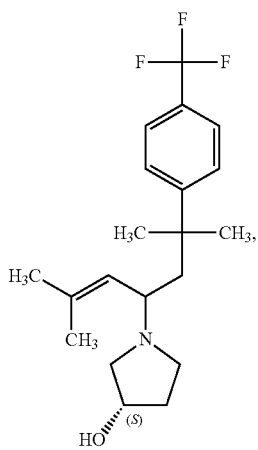 | Example 232 |
| 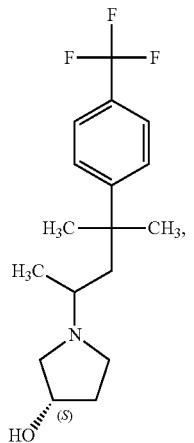 | Example 233 |
| 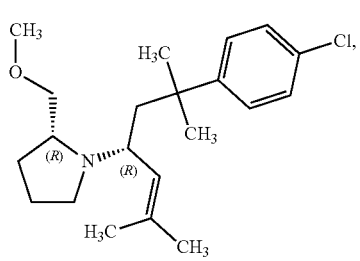 | Example 234 |
| 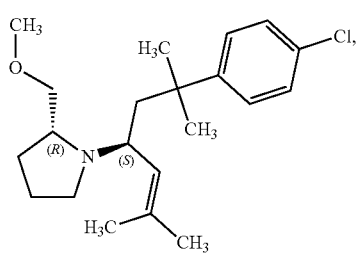 | Example 235 |
| 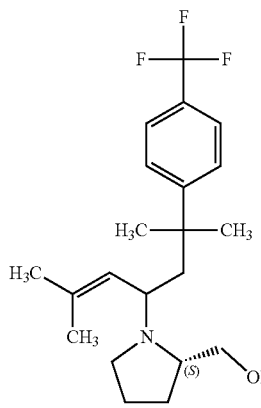 | Example 236 |
| 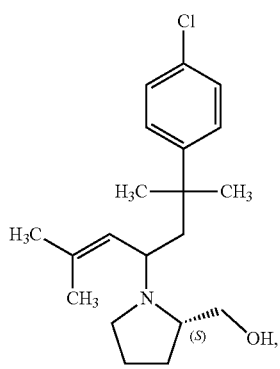 | Example 237 |
| 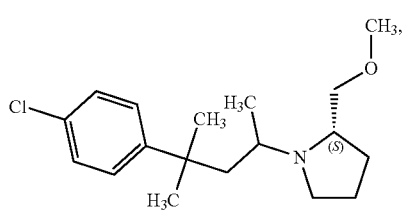 | Example 238 |

Example 239
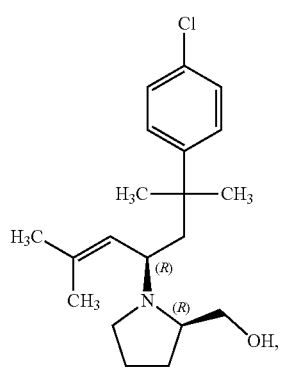
Example 240
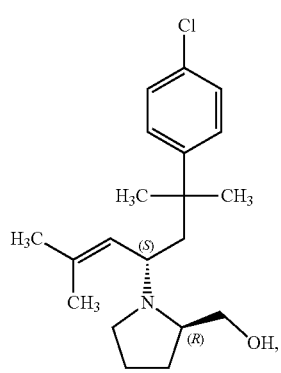
Example 241
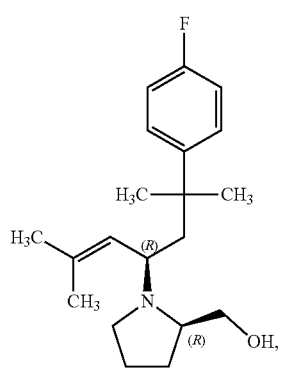
Example 242
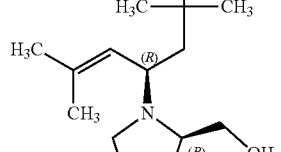
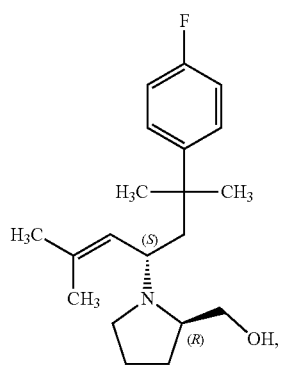
Example 243
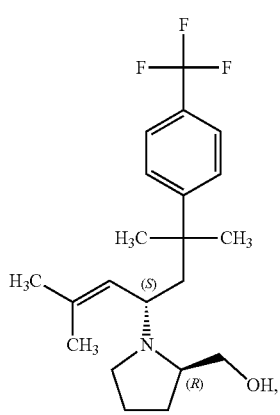
Example 244
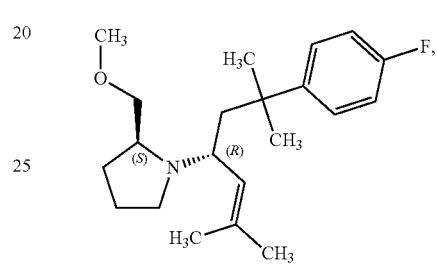
Example 245
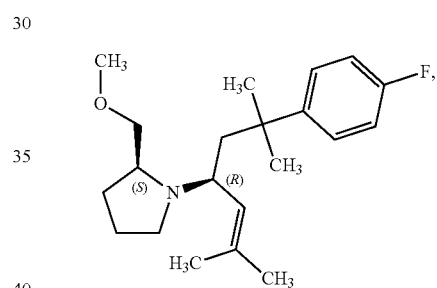
Example 246
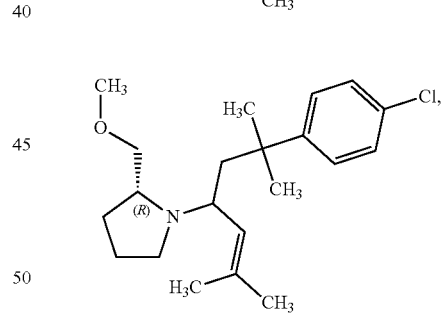
Example 247
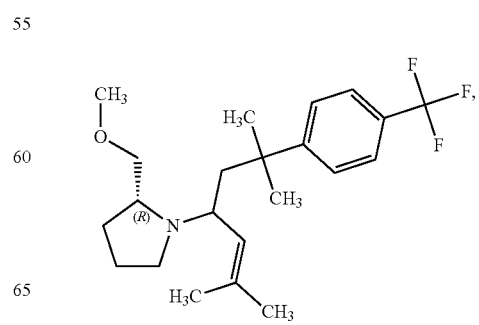

101
-continued
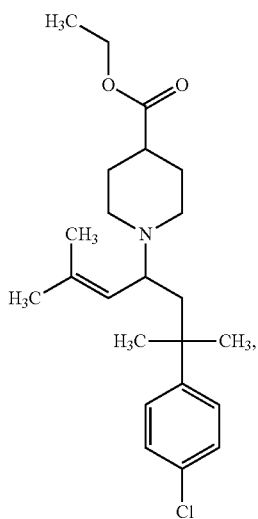
Example 248
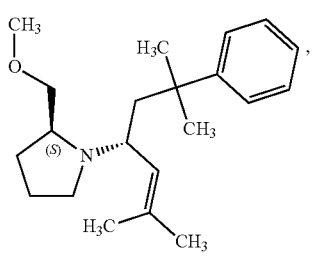
Example 249
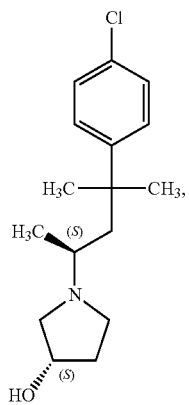
Example 250
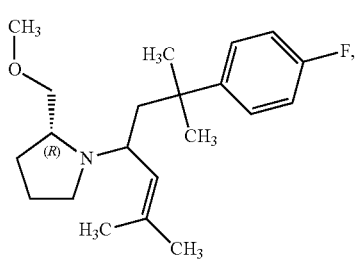
Example 251
102
-continued
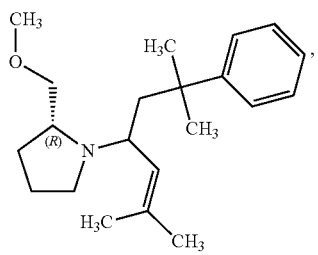
Example 252
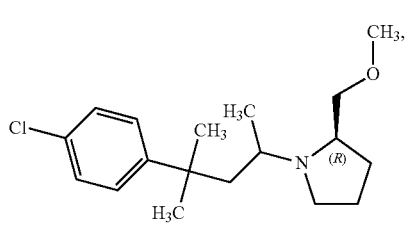
Example 253
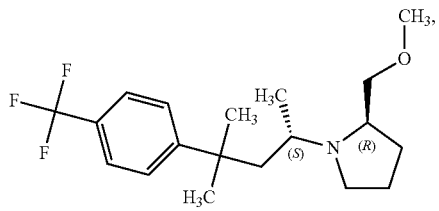
Example 254
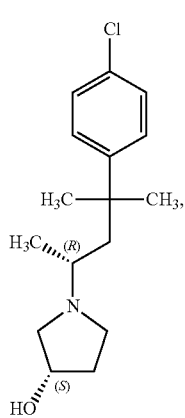
Example 255

Example 261
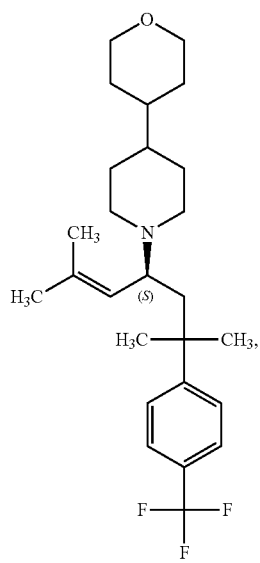
Example 262
Example 263
Example 264
Example 265
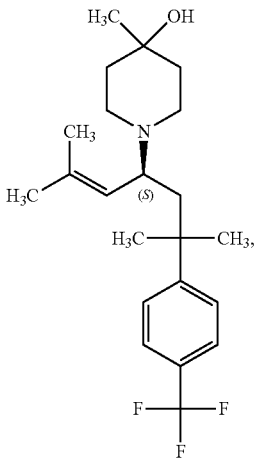
Example 266
Example 267
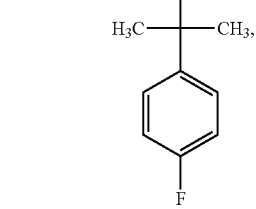

Example 268
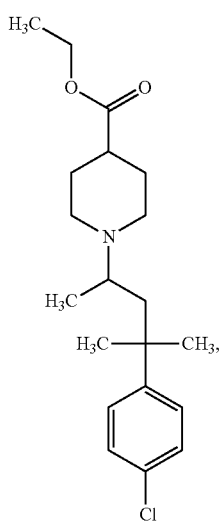
Example 278
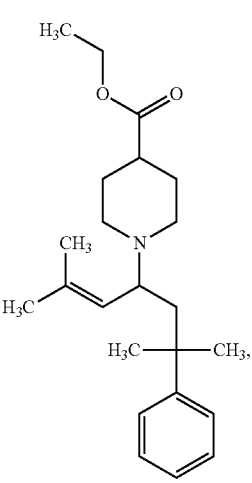
Example 275
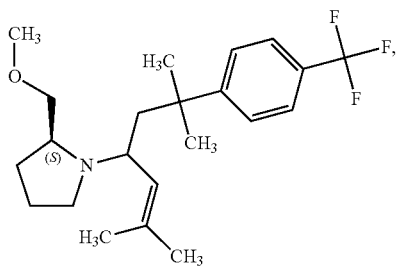
Example 276
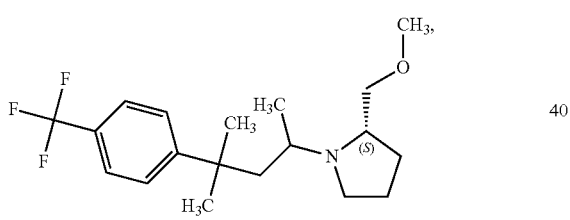
Example 283
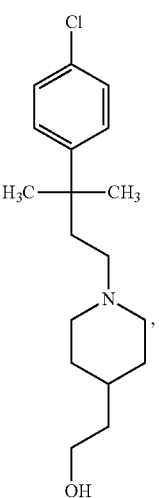
Example 277
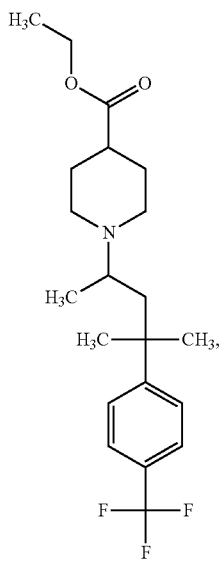
Example 284

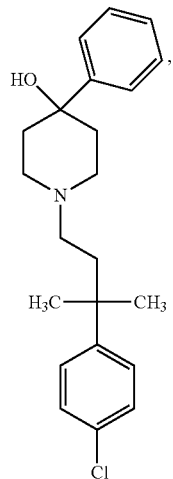
Example 285
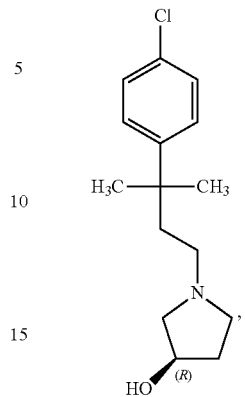
Example 288
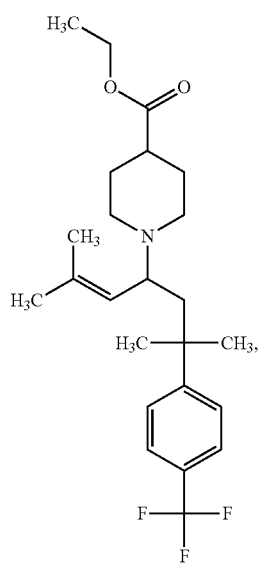
Example 286
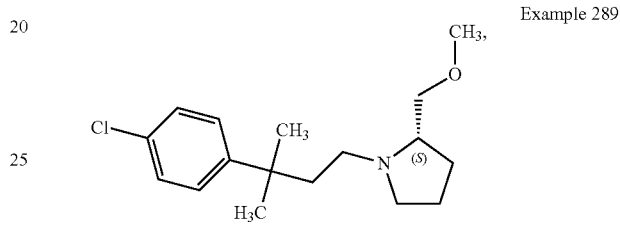
Example 289
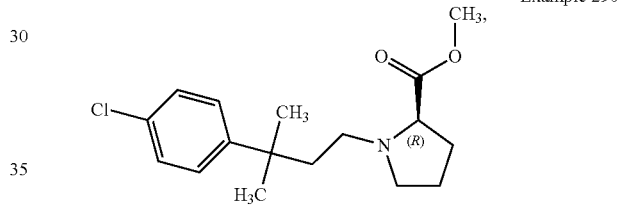
Example 290
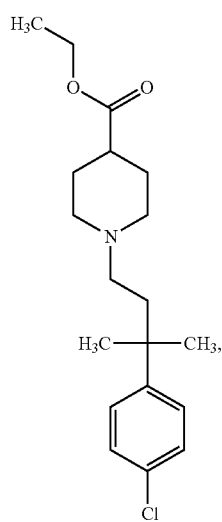
Example 287
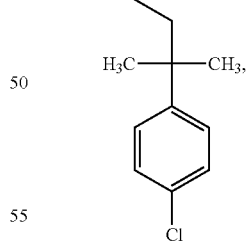
Example 291
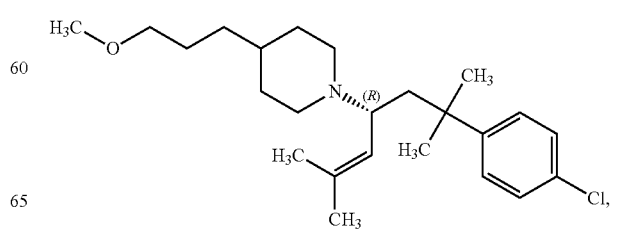
Example 292

Example 293
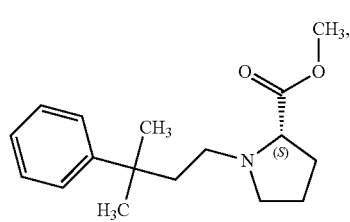
Example 294
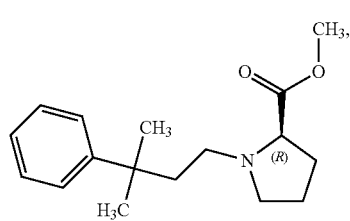
Example 295
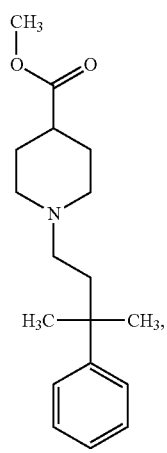
Example 296
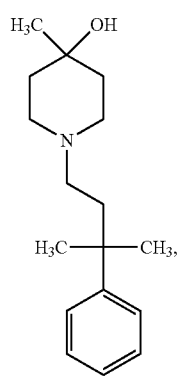
Example 297
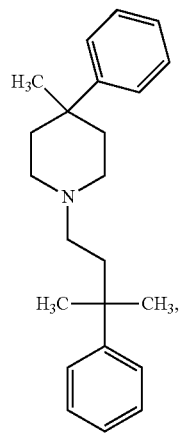
Example 298
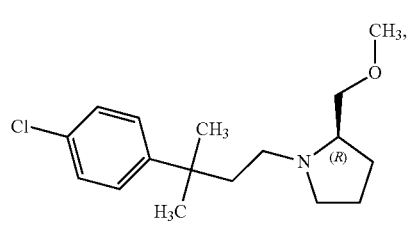
Example 299
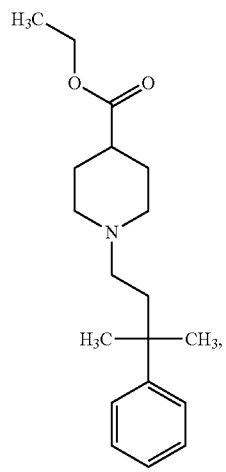
Example 300
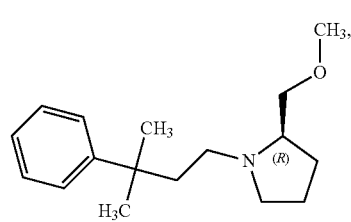

Example 301
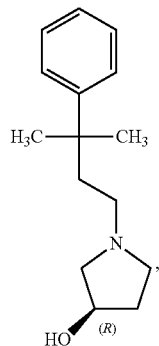
Example 302
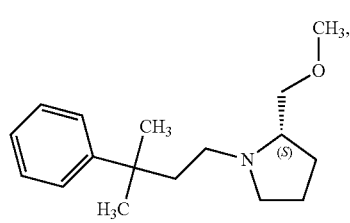
Example 303
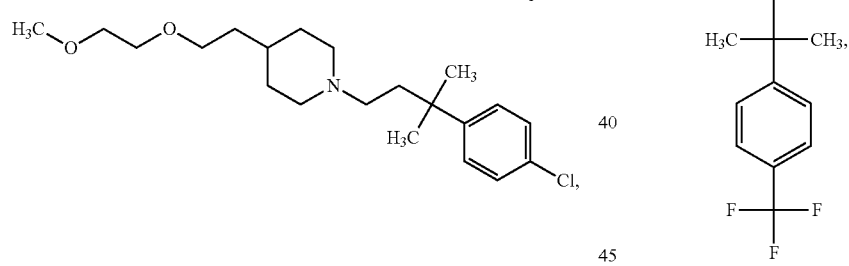
Example 304
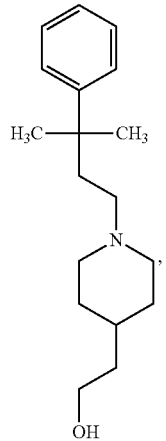
Example 306
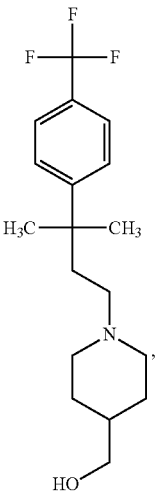
Example 307
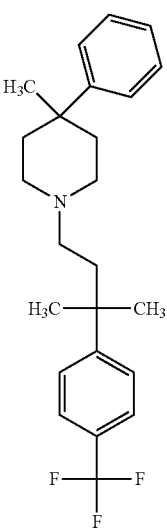
Example 308
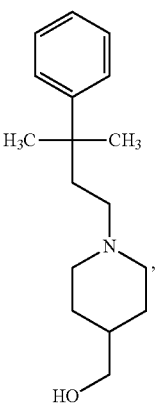

Example 310
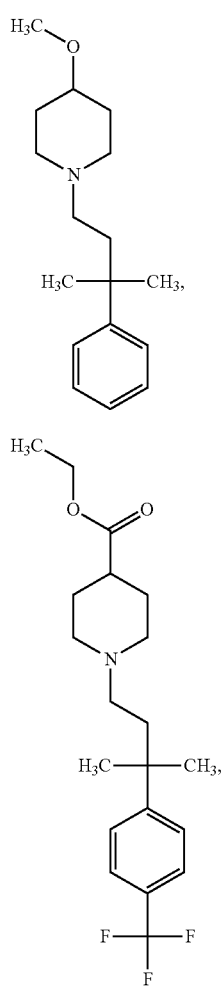
Example 311
Example 312
Example 313
Example 314
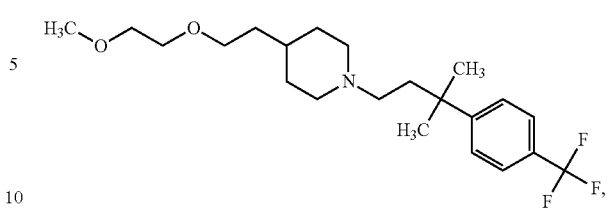
Example 315
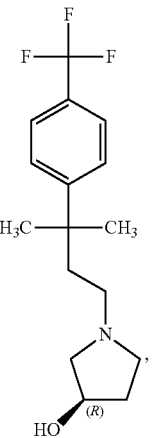
Example 316
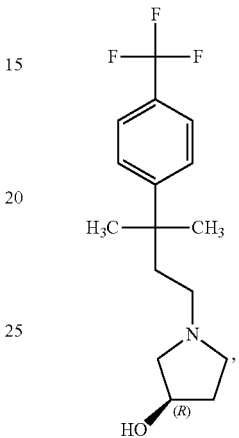
Example 317
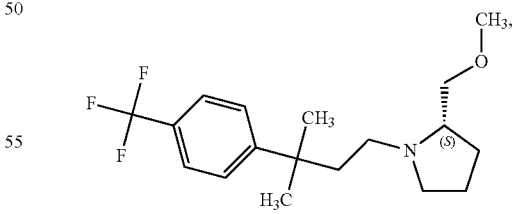
Example 318
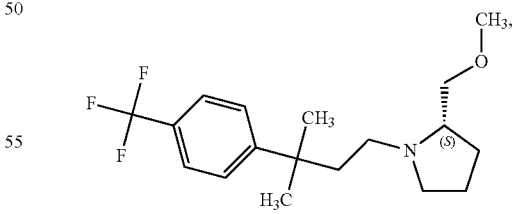

Example 319
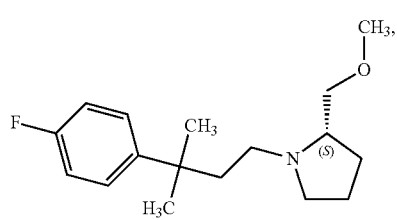
Example 320
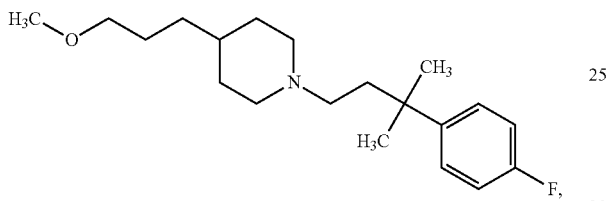
Example 321
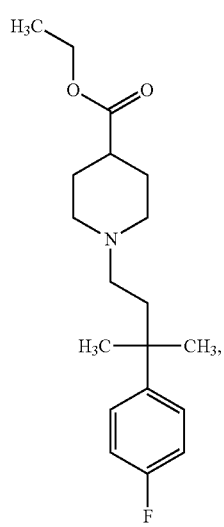
Example 322
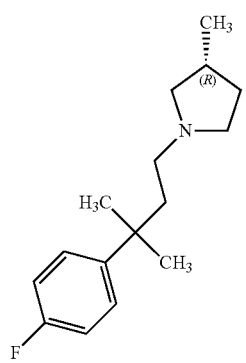
Example 323
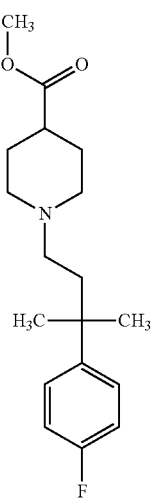
Example 324
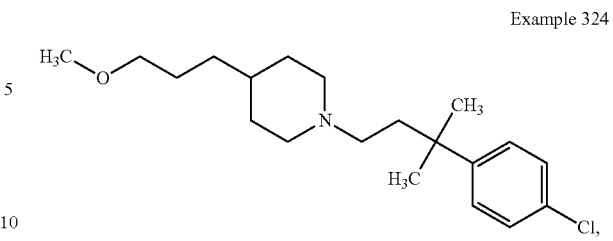
Example 325
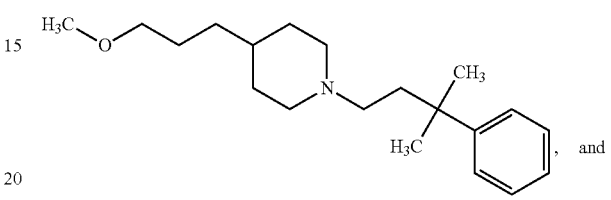
Example 326
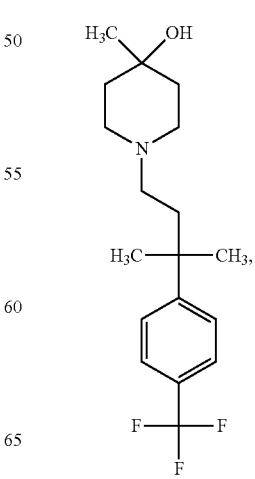
Some embodiments are directed to a compound selected from the group consisting of
Example 14

-continued

Example 17

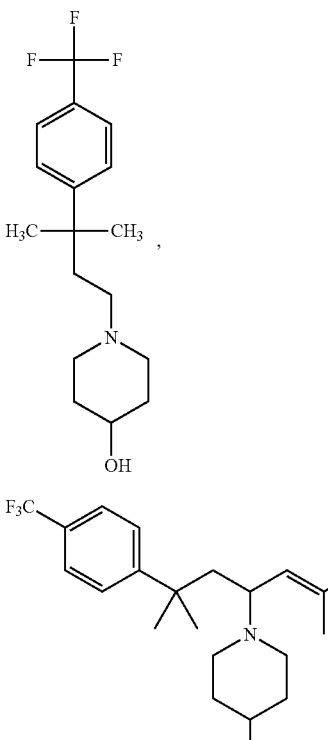

Example 9

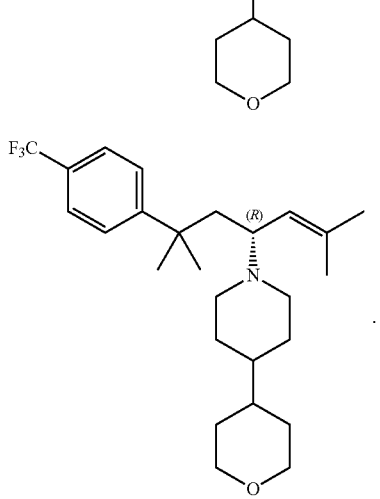

and

Example 262

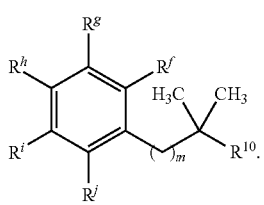

Further embodiments are directed to compounds of Formula II or pharmaceutically acceptable salt thereof:

II

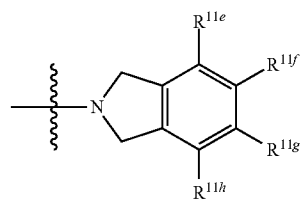

Each of substituents $R^f$, $R^g$, $R^h$, $R^i$ and $R^j$ of Formula II is independently selected from the group consisting of, H, hydroxyl, halo, alkyl, alkoxy, $CF_3$, $SO_2CH_3$, and morpholino.

Substituent $R^{10}$ of Formula II is an optionally substituted cyclic amino group and m is an integer from 0 to 3.

In some embodiments each of substituents $R^f$, $R^g$, $R^h$, $R^i$ and $R^j$ of Formula II is independently selected from the group consisting of, H, hydroxyl, and alkoxy. In some embodiments each of substituents $R^f$, $R^g$, $R^h$, $R^i$ and $R^j$ of Formula II is independently selected from the group consisting of, H, hydroxyl, and methoxy. In some embodiments each of substituents $R^f$, $R^g$, and $R^j$ is H and each of $R^g$, and $R^h$ is independently selected from the hydroxyl, or methoxy.

In some embodiments, $R^{10}$ is an optionally substituted aziridinyl, optionally substituted pyrolidinyl, optionally substituted imidizolidinyl, optionally substituted piperidinyl, optionally substituted piperazinyl, optionally substituted oxopiperazinyl, or optionally substituted morpholinyl, and any of the individual substituted or unsubstituted piperdinyl, substituted or unsubstituted morpholinyl, substituted or unsubstituted piperazinyl, substituted or unsubstituted pyrrolidinyl, substituted or unsubstituted bicyclic, or substituted or unsubstituted fused rings described above in relation to Formula I.

In some embodiments, $R^{10}$ is an optionally substituted fused ring, such as:

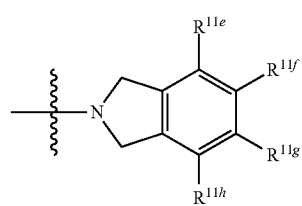

wherein each of $R^{11e}$, $R^{11f}$, $R^{11g}$, and $R^{11h}$ is independently selected from, hydrogen, hydroxy, sulfonyl, optionally substituted $C_1$-$C_{10}$ alkyl, optionally substituted $C_5$-$C_{10}$ aryl optionally substituted $C_3$-$C_{10}$ heteroaryl, optionally substituted $C_3$-$C_{10}$ cycloalkyl or optionally substituted $C_3$-$C_{10}$ heterocycloalkyl. In certain embodiments $R^{10}$ is not

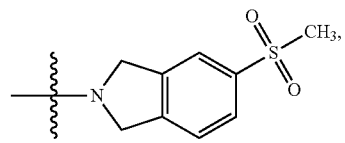

when m is 2.

In some embodiments, $R^{10}$ is

119
-continued
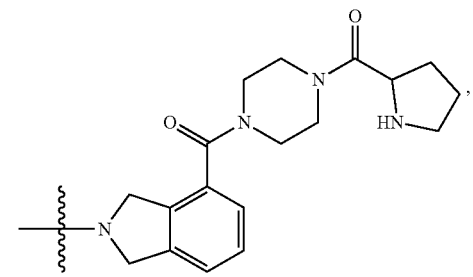
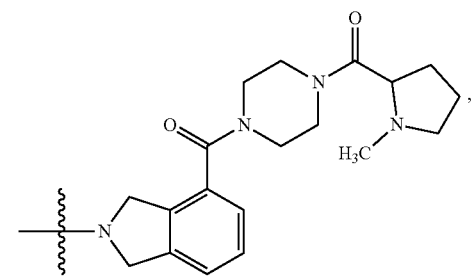
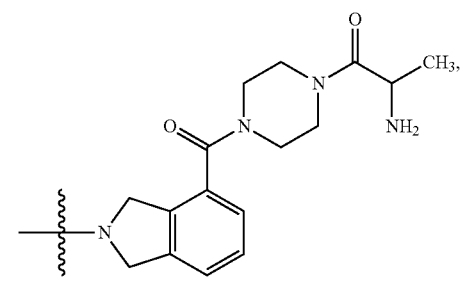
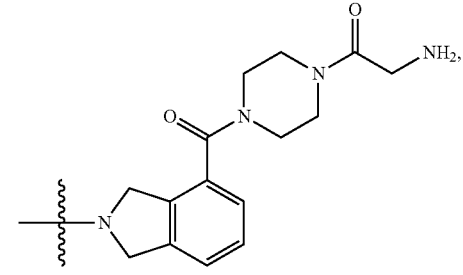
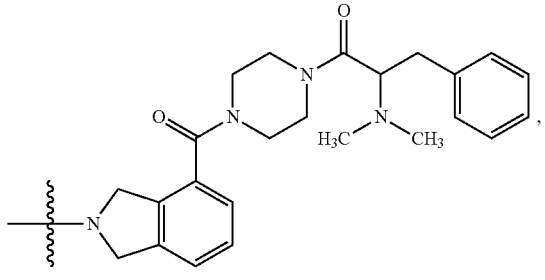
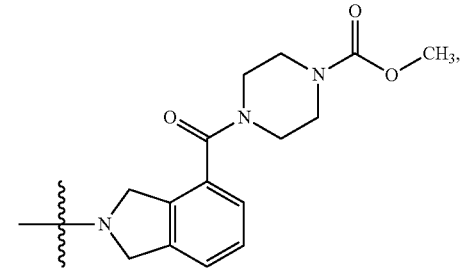
120
-continued
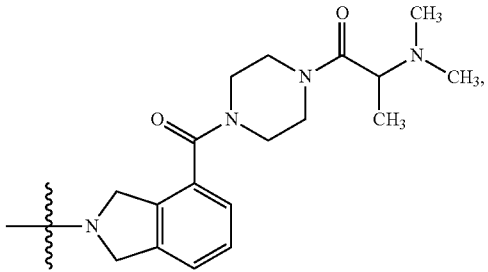
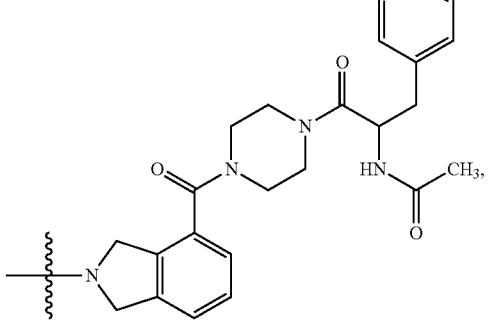
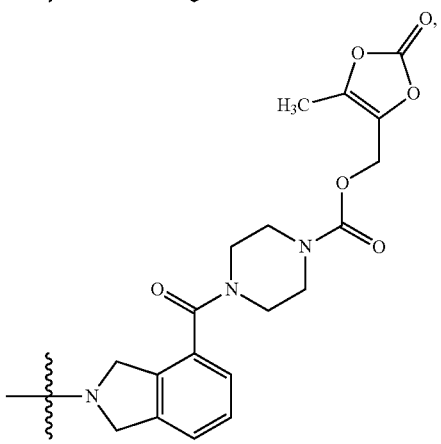
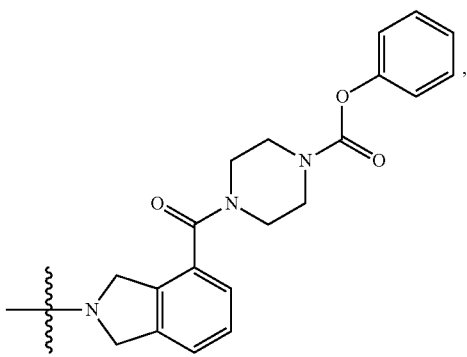
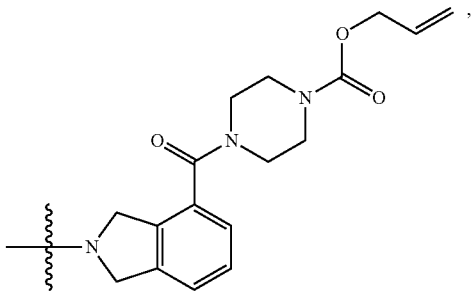

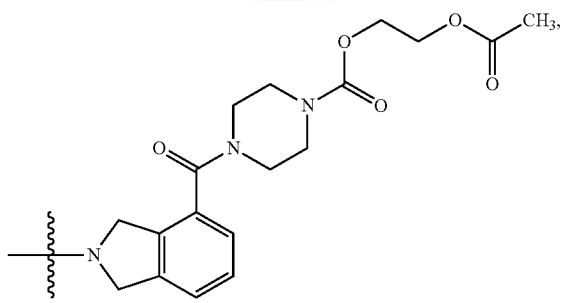

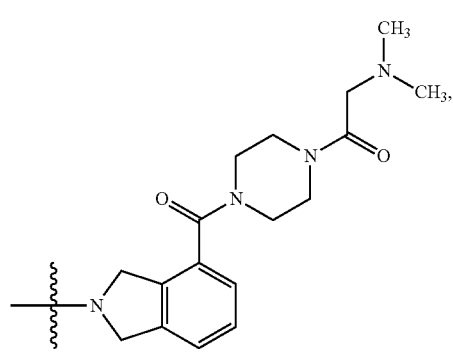

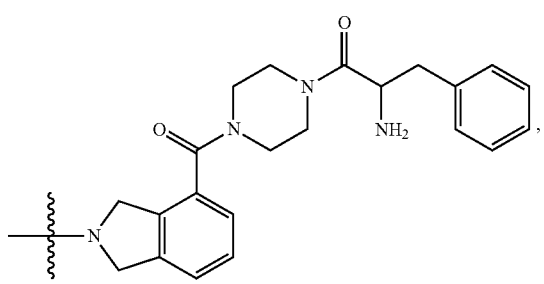

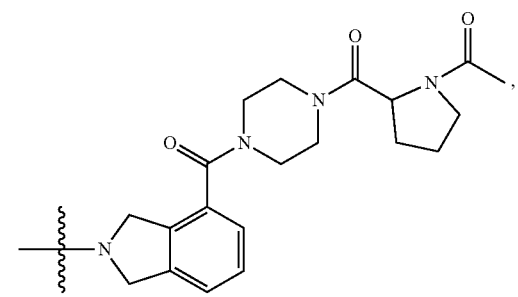

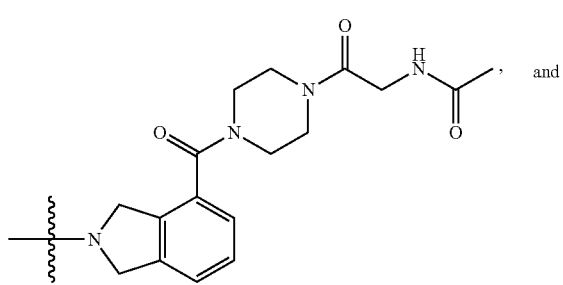

and

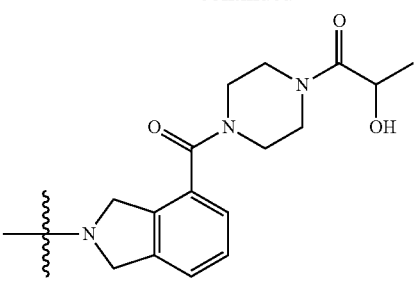

Some embodiments describe a compound of Formula IIa:

IIa

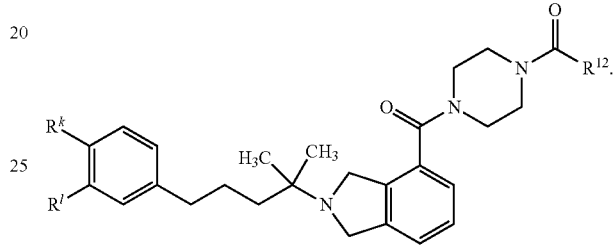

Each of substituents $R^k$ and $R^l$ is independently selected from the group consisting of H, hydroxyl, halo, alkyl, alkoxy, $CF_3$, $SO_2CH_3$, and morpholino.

Substituent $R^{12}$ is selected from the group consisting of aryloxy, alkenyloxy, alkoxy, aminoalkyl, N,N-dimethylaminoalkyl, pyrrolidinyl, n-methylpyrrolidinyl, N-acylpyrrolidinyl, carboxyaminoalkyl, hydroxyalkyl, $-O(CH_2)_2OC(O)CH_3$,

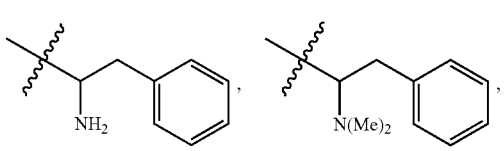

, and

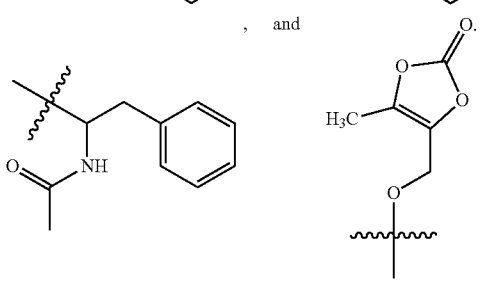

In some embodiments each of substituents $R^k$ and $R^l$ is independently selected from the group consisting of H, hydroxyl and methoxy. In some embodiments $R^l$ is methoxy and $R^k$ is hydroxyl.

In some embodiments substituent $R^{12}$ is selected from the group consisting of phenyloxy, $-OCH_2CH=CH_2$, methoxy, $-CH_2NH_2$, $-CH(NH_2)CH_3$, $-CH_2N(Me)_2$, $-CH(CH_3)N(Me)_2$, $-CH_2NHC(O)CH_3$, $-CH(OH)CH_3$, $-O(CH_2)_2OC(O)CH_3$,

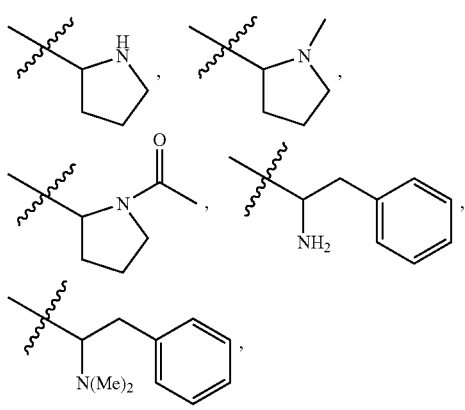
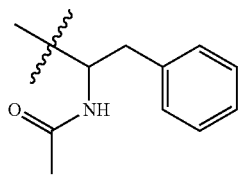
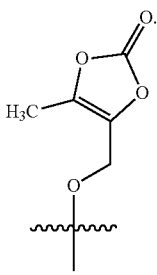
Some embodiments describe a compound selected from the group consisting of
Example 26
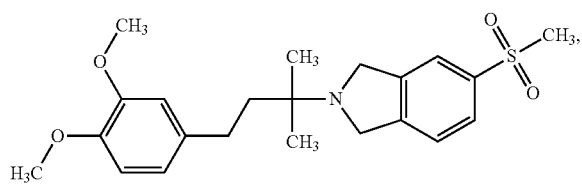
Example 256
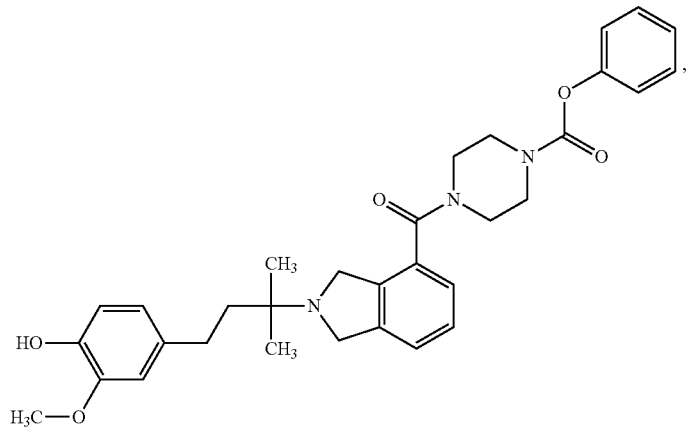
Example 257
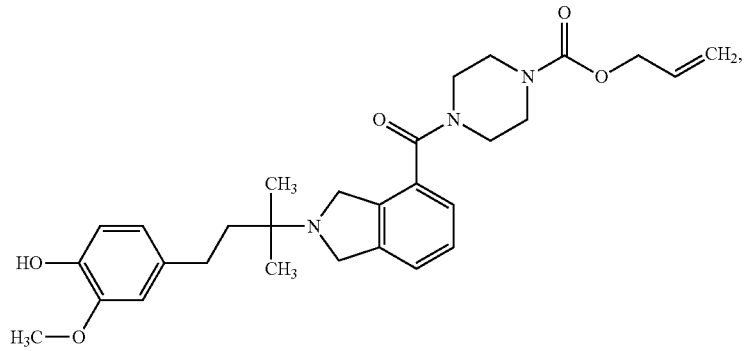

-continued
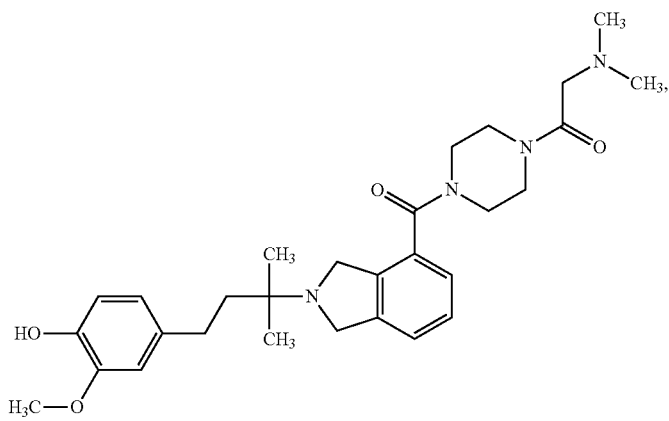
Example 258
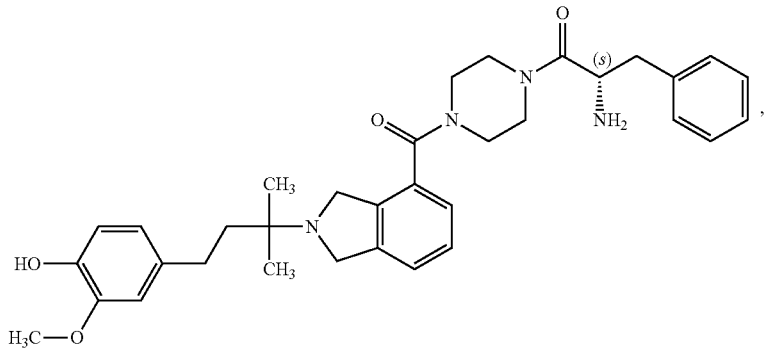
Example 259
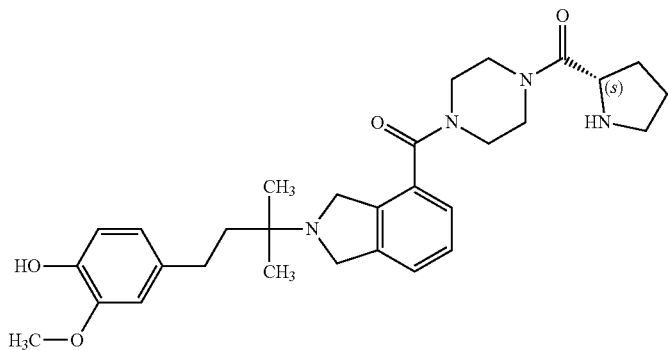
Example 260
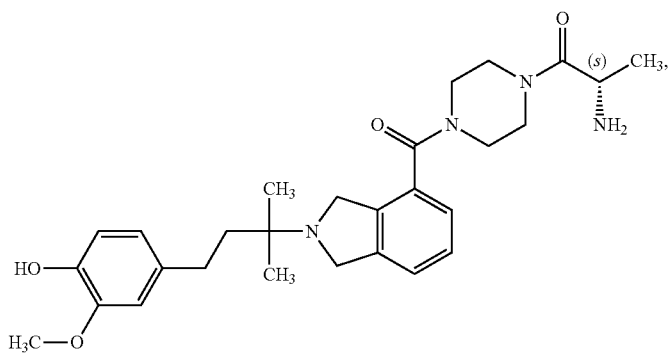
Example 269

-continued
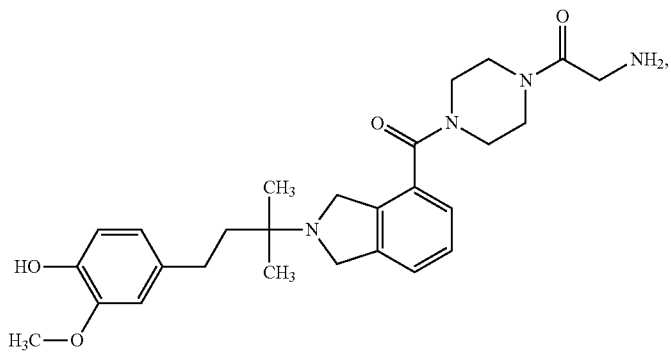
Example 270
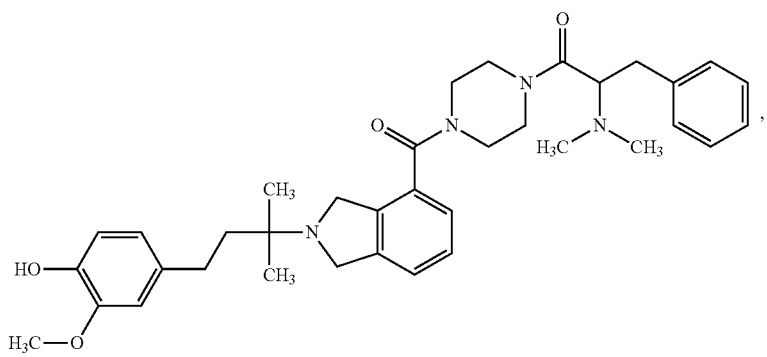
Example 271
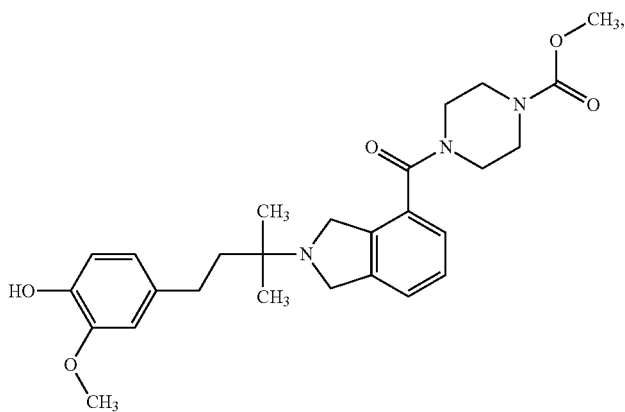
Example 272
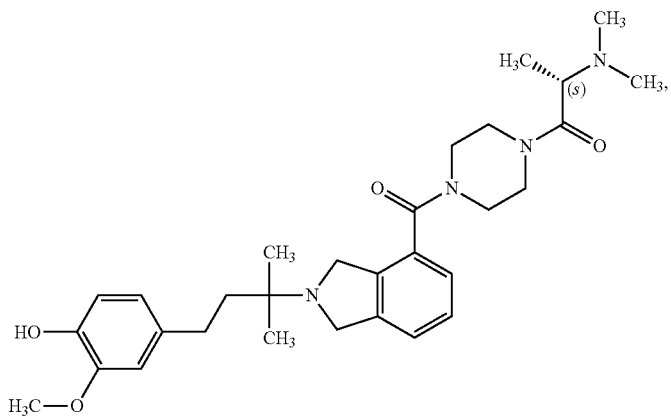
Example 273

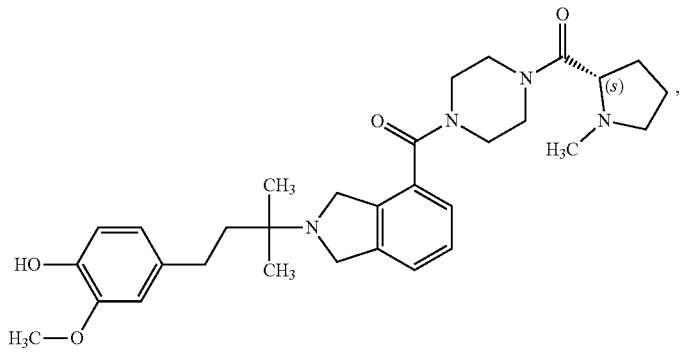
Example 274
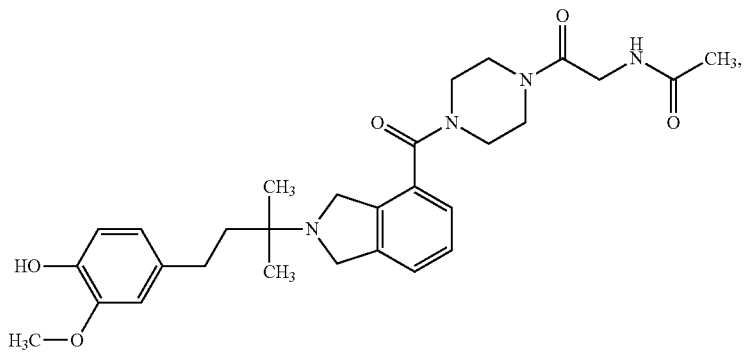
Example 279
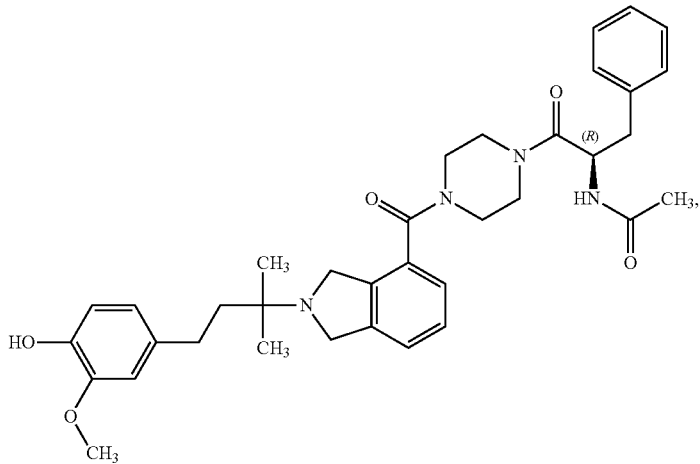
Example 280
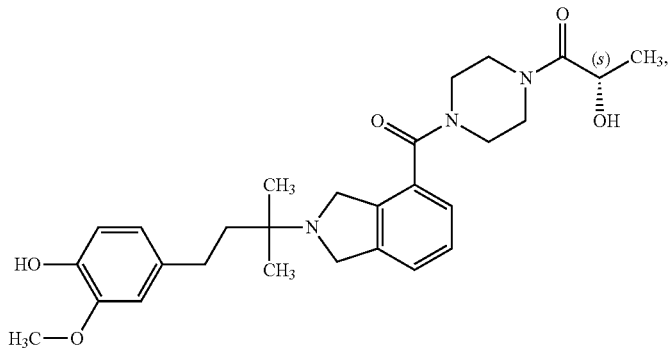
Example 281

-continued
Example 282
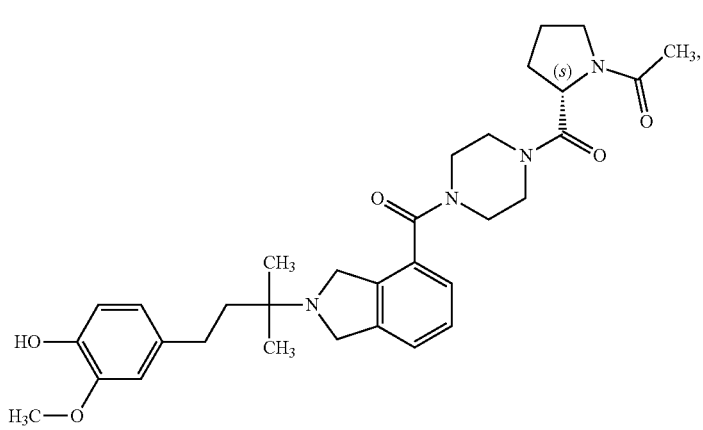
Example 305
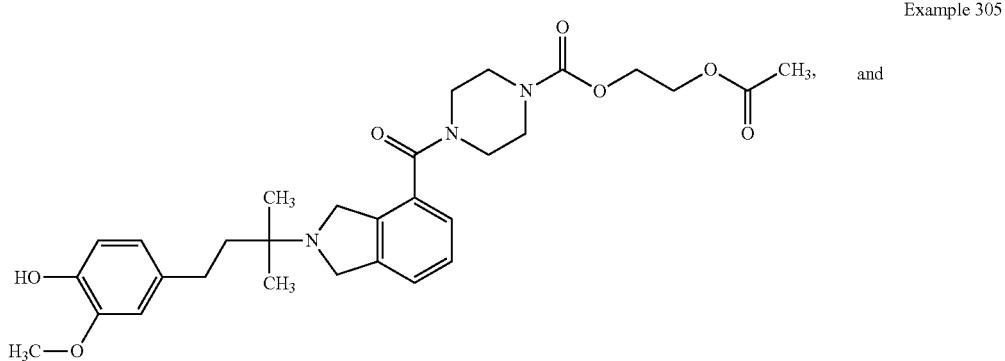
and
Example 309
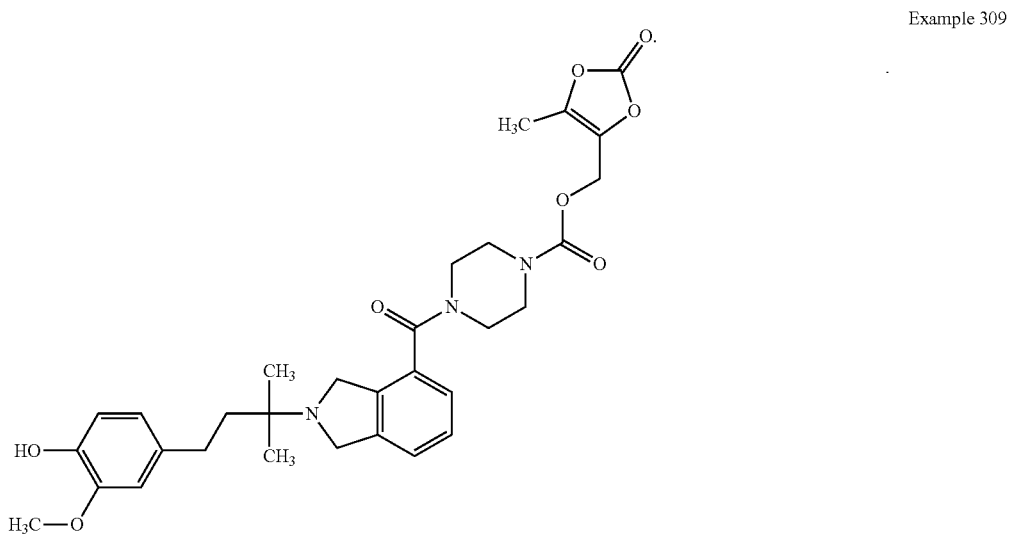 [SMILES: COc1cc(CCC(C)(C)N2Cc3cccc(C(=O)N4CCN(C(=O)OCc5oc(=O)oc5C)CC4)c3C2)ccc1O]

Some embodiments describe a compound selected from the group consisting of
Example 18
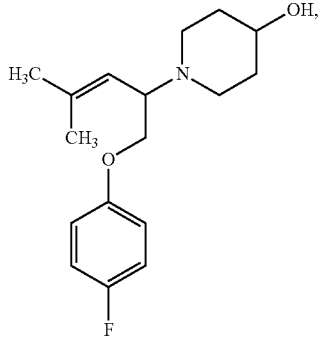
Example 21
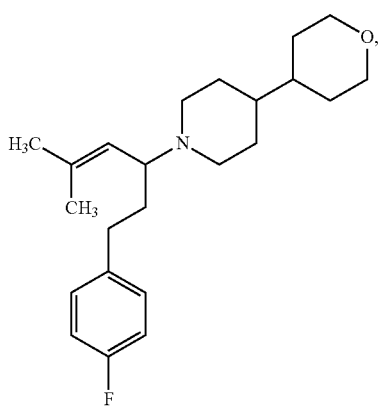
Example 48
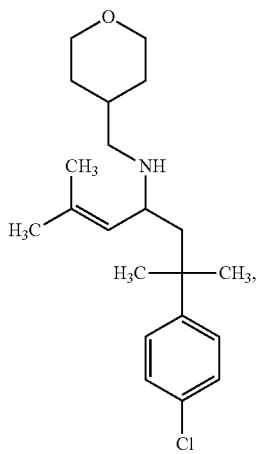
-continued
Example 52
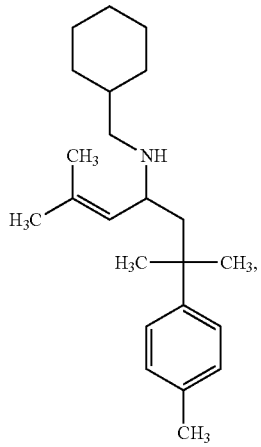
Example 54
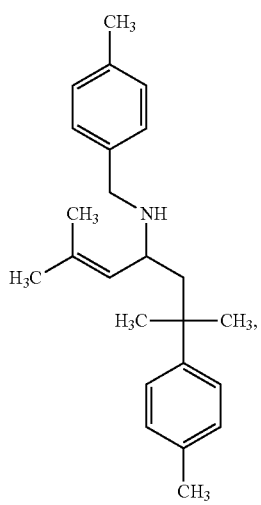
Example 57
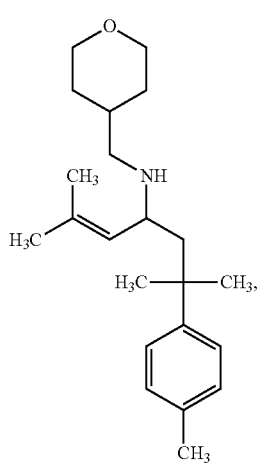

Example 64
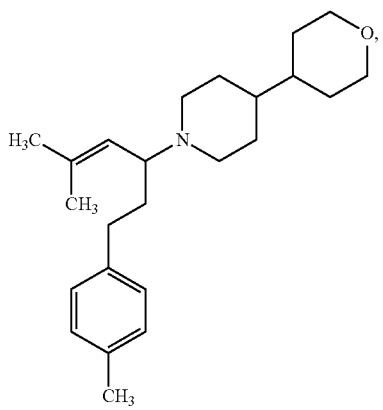
Example 65
Example 66
Example 69
Example 74
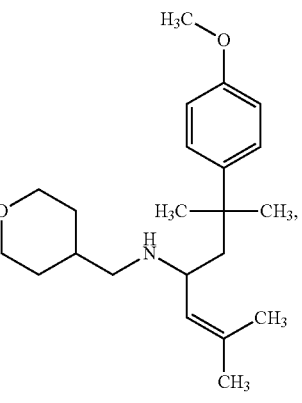
Example 78
Example 80
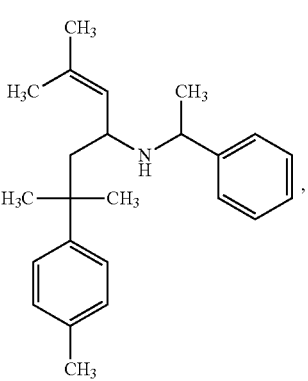
Example 88
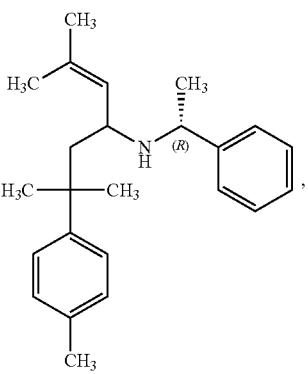
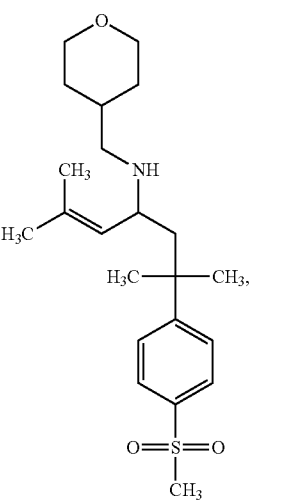

-continued
Example 91
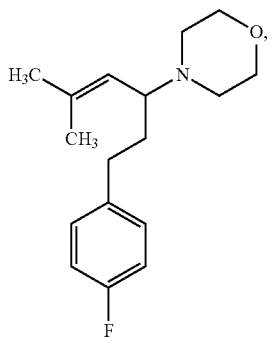
Example 92
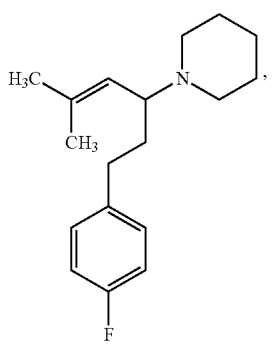
Example 93
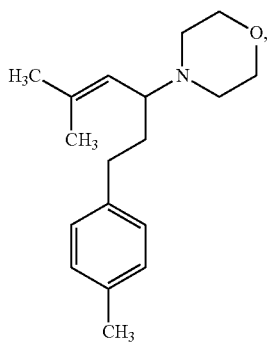
Example 94
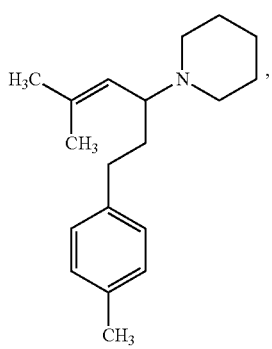
-continued
Example 95
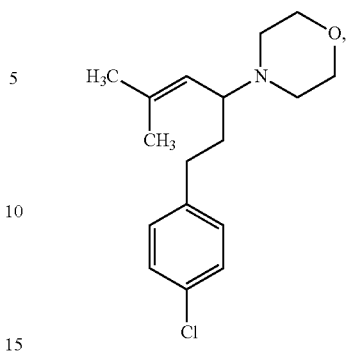
Example 96
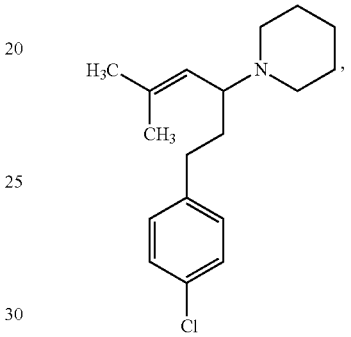
Example 99
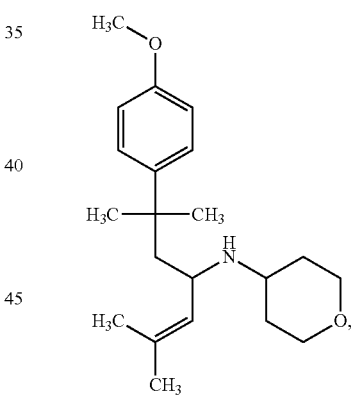
Example 100
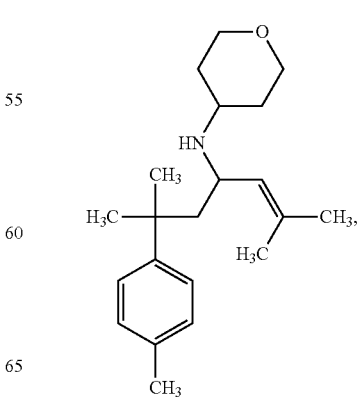

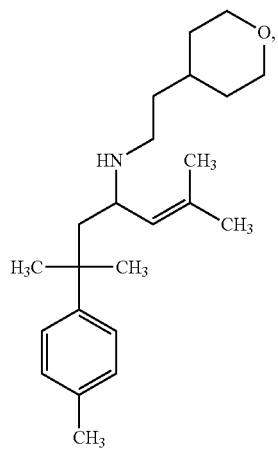
Example 101
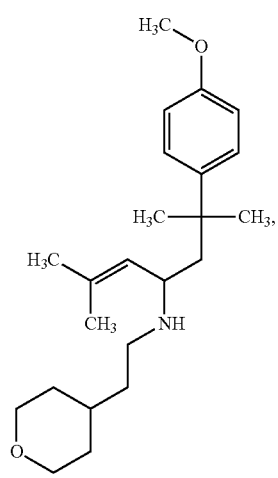
Example 102
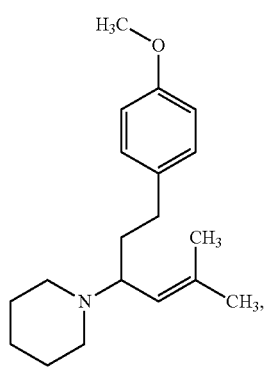
Example 103
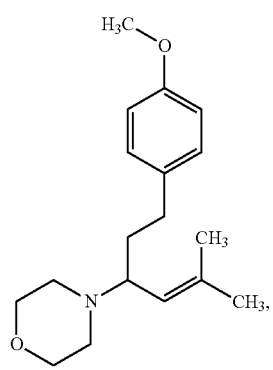
Example 104
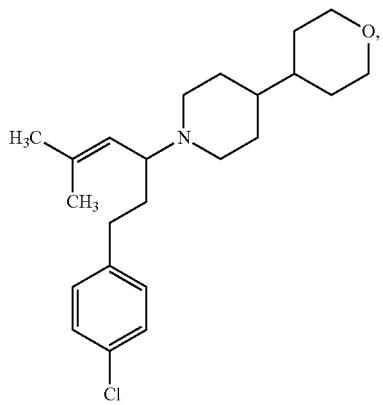
Example 105
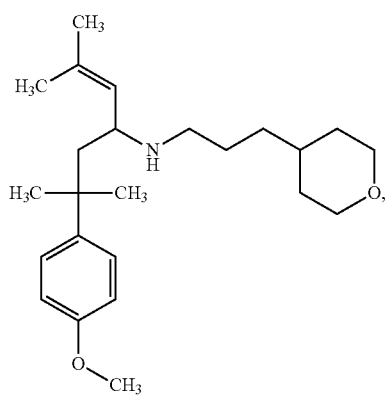
Example 106
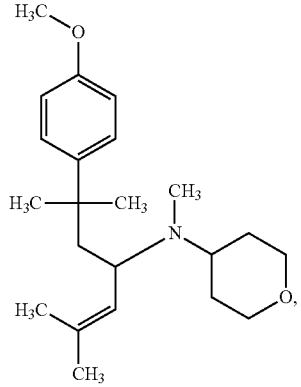
Example 108
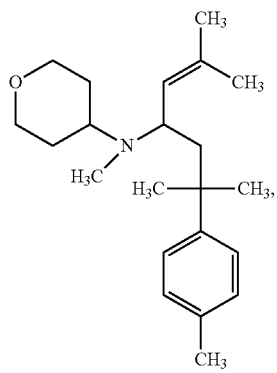
Example 109

Example 110
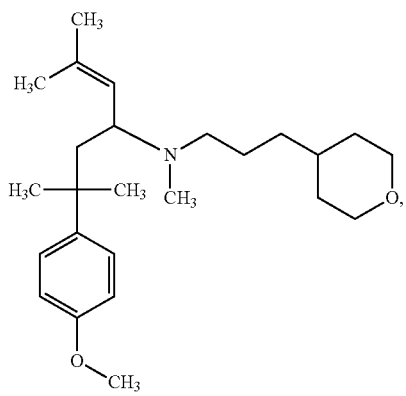
Example 111
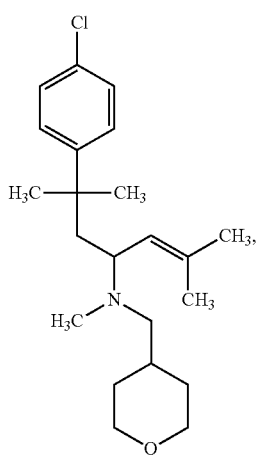
Example 112
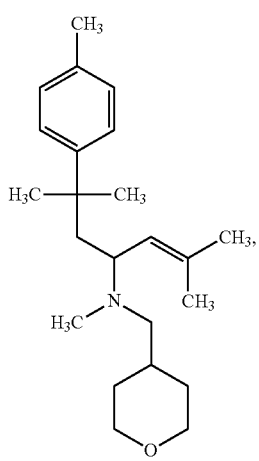
Example 113
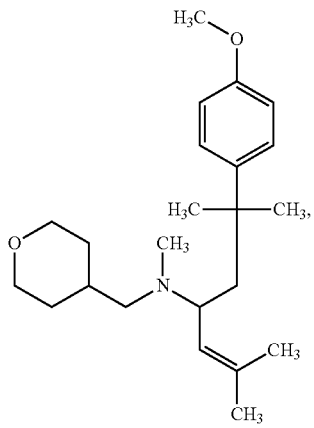
Example 114
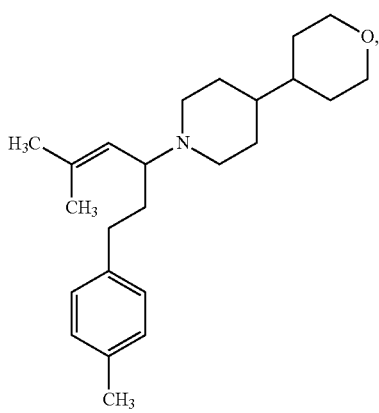
Example 115
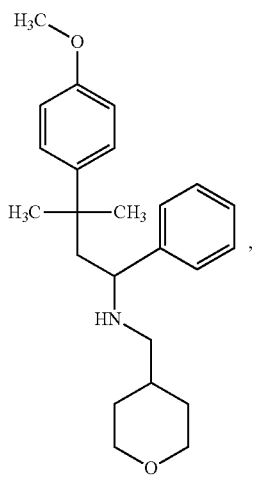

-continued
Example 121
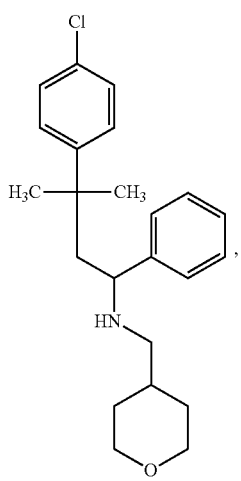
Example 165
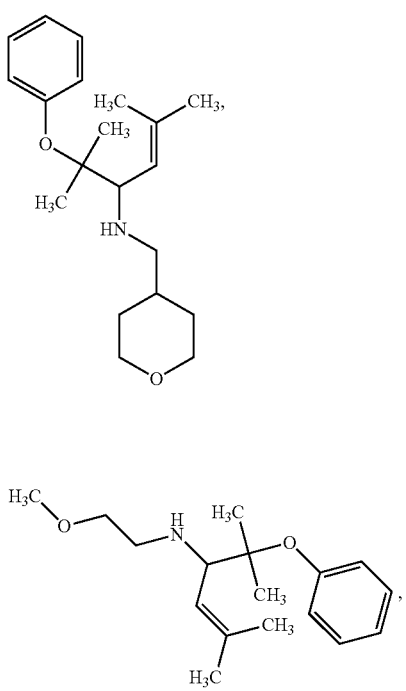
Example 166
Example 172
-continued
Example 173
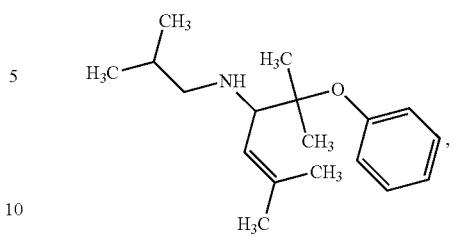
Example 174
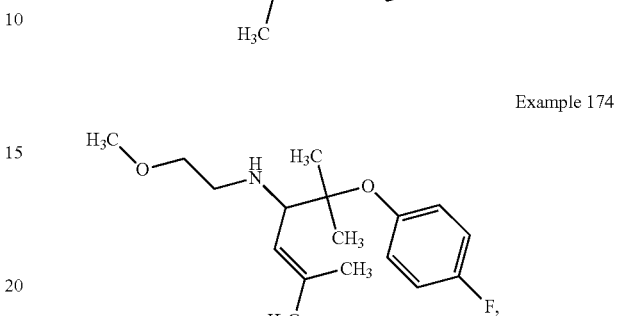
Example 175
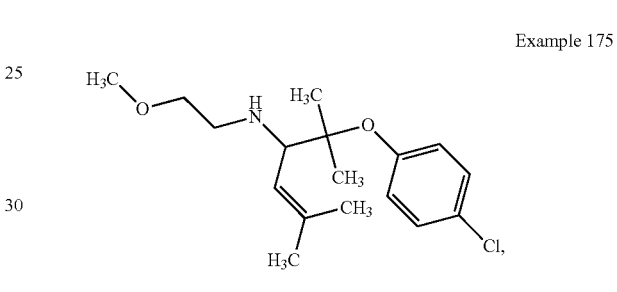
Example 176
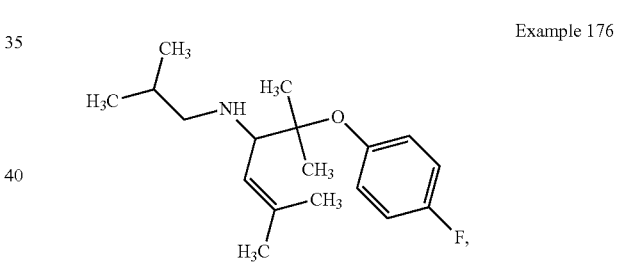
Example 177
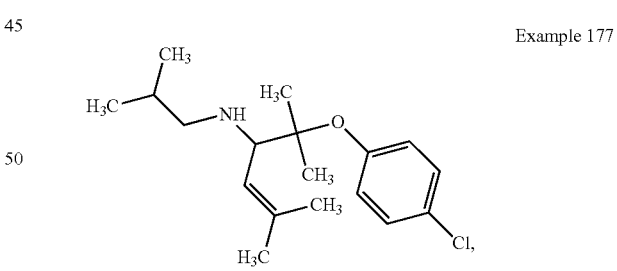
Example 184
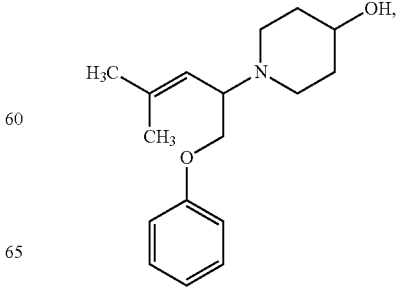

-continued

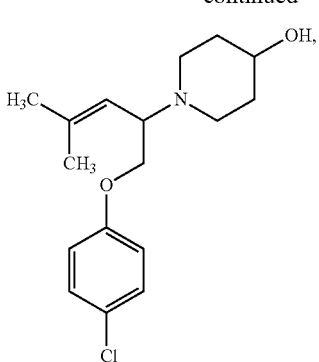

Example 186

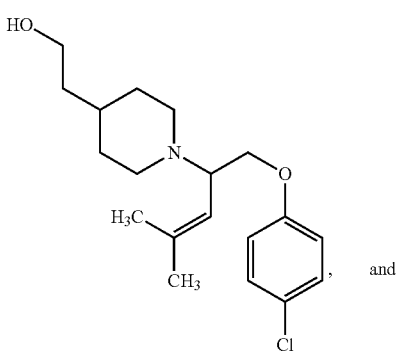

Example 188 and

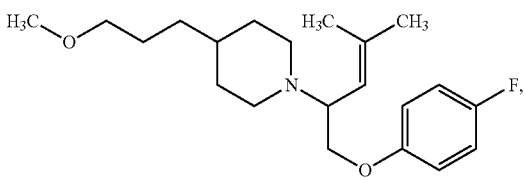

Example 190

Additional embodiments include salts, solvates, stereoisomers, prodrugs, and active metabolites of the compounds according to any embodiment described herein.

Some embodiments are directed to free base forms of the compounds according to any embodiment described herein. Other embodiments include salts of such compounds including, for example, pharmaceutically acceptable acid addition salts or pharmaceutically acceptable addition salts of free bases. Examples of pharmaceutically acceptable acid addition salts include, but are not limited to, salts derived from nitric, phosphoric, sulfuric, or hydrobromic, hydroiodic, hydrofluoric, phosphorous, as well as salts derived from nontoxic organic acids such as aliphatic mono- and dicarboxylic acids, phenyl-substituted alkanoic acids, hydroxyl alkanoic acids, alkanedioic acids, aromatic acids, aliphatic and aromatic sulfonic acids, and acetic, maleic, succinic, or citric acids. Non-limiting examples of such salts include napadisylate, besylate, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Additional salt forms of the compounds described above include salts of amino acids such as arginate and the like and gluconate, galacturonate (see e.g., Berge, et al. "Pharmaceutical Salts," J. Pharma. Sci. 1977; 66:1).

Pharmaceutically acceptable base addition salts are formed with metals or amines, such as alkali and alkaline earth metals or organic amines. Examples of metals used as cations are sodium, potassium, magnesium, calcium, and the like. Examples of suitable amines include N,N'-dibenzylethylenediamine, chloroprocaine, choline, diethanolamine, dicyclohexylamine, ethylenediamine, N-methylglucamine, and procaine. The base addition salts of said acidic compounds are prepared by contacting the free acid form with a sufficient amount of the desired base to produce the salt in the conventional manner. The free acid form may be regenerated by contacting the salt form with an acid and isolating the free acid.

Various embodiments include total and partial salts, i.e. salts with 1, 2 or 3, preferably 2, equivalents of base per mole of acid of a compound or salt described above, with 1, 2 or 3 equivalents, preferably 1 equivalent, of acid per mole of base of a compound of according to any embodiment described herein. Typically, a pharmaceutically acceptable salt of a compound according to any embodiment described herein, may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound according to any embodiment described herein, and the resulting mixture evaporated to dryness (lyophilized) to obtain the acid addition salt as a solid. Alternatively, a compound according to any embodiment described herein, may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Many organic compounds can form complexes with solvents in which they are reacted or from which they are precipitated or crystallized. These complexes are known as "solvates." For example, a complex with water is known as a "hydrate." Various embodiments include solvates of a compound according to any embodiment described herein. In some embodiments, salts of these compounds can form solvates.

Further embodiments include N-oxides of the compounds according to any embodiment described herein. N-oxides include heterocycles containing an otherwise unsubstituted $sp^2$ N atom. Examples of such N-oxides include pyridyl N-oxides, pyrimidyl N-oxides, pyrazinyl N-oxides and pyrazolyl N-oxides.

Compounds according to any embodiment described herein, may have one or more chiral centers and, depending on the nature of individual substituents, they can also have geometrical isomers. Thus, embodiments include stereoisomers, diastereomers, and enantiomers of the compounds according to any embodiment described herein. A chiral compound can exist as either an individual enantiomer or as a mixture of enantiomers. A mixture containing equal proportions of the enantiomers is called a "racemic mixture." A mixture containing unequal portions of the enantiomers is described as having an "enantiomeric excess" (ee) of either the R or S compound. The excess of one enantiomer in a mixture is often described with a % enantiomeric excess. The ratio of enantiomers can also be defined by "optical purity" wherein the degree at which the mixture of enantiomers rotates plane polarized light is compared to the individual optically pure R and S compounds. The compounds can also be a substantially pure (+) or (−) enantiomer of the compounds described herein. In some embodiments, a composition can include a substantially pure enantiomer that is at least 90%, 91%, 92%, 93%, 94%, 95%, 96%, 97%, 98%, or 99% of one enantiomer. In certain embodiments, a composition may include a substantially pure enantiomer that is at least 99.5% one enantiomer.

The description above encompasses all individual isomers of the compounds according to any embodiment described herein, and the description or naming of a particular compound in the specification and claims is intended to include both individual enantiomers and mixtures thereof. Methods for the determination of stereochemistry and the resolution or stereotactic synthesis of stereoisomers are well-known in the art. Diastereomers differ in both physical properties and chemical reactivity. A mixture of diastereomers can be separated into enantiomeric pairs based on solubility, fractional crystallization or chromatographic properties, e.g., thin layer chromatography, column chromatography or HPLC. Purification of complex mixtures of diastereomers into enantiomers typically requires two steps. In a first step, the mixture of diastereomers is resolved into enantiomeric pairs, as described above. In a second step, enantiomeric pairs are further purified into compositions enriched for one or the other enantiomer or, more preferably resolved into compositions comprising pure enantiomers. Resolution of enantiomers typically requires reaction or molecular interaction with a chiral agent, e.g. solvent or column matrix. Resolution may be achieved, for example, by converting the mixture of enantiomers, e.g., a racemic mixture, into a mixture of diastereomers by reaction with a pure enantiomer of a second agent, i.e., a resolving agent. The two resulting diastereomeric products can then be separated. The separated diastereomers are then reconverted to the pure enantiomers by reversing the initial chemical transformation.

Resolution of enantiomers can also be accomplished by differences in their non-covalent binding to a chiral substance, e.g., by chromatography on homochiral adsorbants. The noncovalent binding between enantiomers and the chromatographic adsorbant establishes diastereomeric complexes, leading to differential partitioning in the mobile and bound states in the chromatographic system. The two enantiomers therefore move through the chromatographic system, e.g. column, at different rates, allowing for their separation Further embodiments include prodrugs of the compounds according to any embodiment described herein, i.e. compounds which release an active compound according to any of the embodiments described herein, in vivo when administered to a mammalian subject. A prodrug is a pharmacologically active or more typically an inactive compound that is converted into a pharmacologically active agent by a metabolic transformation. Prodrugs of a compound according to any embodiment described herein, are prepared by modifying functional groups present in the compound according to any embodiment described herein, in such a way that the modifications may be cleaved in vivo to release the parent compound. In vivo, a prodrug readily undergoes chemical changes under physiological conditions (e.g. are hydrolyzed or acted on by naturally occurring enzyme(s)) resulting in liberation of the pharmacologically active agent. Prodrugs include compounds according to any embodiment described herein, wherein a hydroxyl, amino, or carboxy group is bonded to any group that may be cleaved in vivo to regenerate the free hydroxyl, amino or carboxy group, respectively. Examples of prodrugs include, but are not limited to esters (e.g., acetate, formate, and benzoate derivatives) of compounds according to any embodiment described herein, or any other derivative which upon being brought to the physiological pH or through enzyme action is converted to the active parent drug. Conventional procedures for the selection and preparation of suitable prodrug derivatives are described in the art (see, for example, Bundgaard. Design of Prodrugs. Elsevier, 1985).

The invention also embraces isolated compounds. An isolated compound refers to a compound which represents at least 10%, preferably at least 20%, more preferably at least 50% and most preferably at least 80% of the compound present in a mixture.

In some embodiments, one or more hydrogen atoms of a compound according to any embodiment described herein, is replaced by a deuterium. It is well established that deuteration of physiologically active compounds offer the advantage of retaining the pharmacological profile of their hydrogen counterparts while positively impacting their metabolic outcome. Selective replacement of one or more hydrogen with deuterium, in a compound according to any embodiment described herein, could improve the safety, tolerability and efficacy of the compound when compared to its all hydrogen counterpart.

Methods for incorporation of deuterium into compounds is well established. Using metabolic studies establish in the art, a compound according to any embodiment described herein, can be tested to identify sites for selective placement of a deuterium isotope, wherein the isotope will not be metabolized. Moreover these studies identify sites of metabolism as the location where a deuterium atom would be placed.

Pharmaceutical Compositions

Some embodiments describe a pharmaceutical composition comprising: a compound according to any embodiment described herein, a pharmaceutically acceptable salt thereof, a solvate thereof, a stereoisomer thereof, a prodrug thereof, or an active metabolites thereof; and a pharmaceutically acceptable carrier or diluent. The pharmaceutical compositions can be prepared in a manner well known in the pharmaceutical art, and can be administered by a variety of routes, depending upon whether local or systemic treatment is desired and upon the area to be treated.

While it is possible that a compound as described in any embodiment herein, may be administered as the bulk substance, it is preferable to present the compound in a pharmaceutical formulation, e.g., wherein the active agent is in an admixture with a pharmaceutically acceptable carrier selected with regard to the intended route of administration and standard pharmaceutical practice.

In particular, the disclosure provides a pharmaceutical composition comprising a therapeutically effective amount of at least one compound according to any embodiment described herein, and optionally, a pharmaceutically acceptable carrier.

Combinations

For the pharmaceutical compositions and methods of the disclosure, a compound according to any embodiment described herein, may be used in combination with other therapies and/or active agents.

In some embodiments, the compound according to any embodiment described herein, can be combined with one or more of a cholinesterase inhibitor, an N-methyl-D-aspartate (NMDA) glutamate receptor antagonist, a beta-amyloid specific antibody, a beta-secretase 1 (BACE1, beta-site amyloid precursor protein cleaving enzyme 1) inhibitor, a tumor necrosis factor alpha (TNF alpha) modulator, an intravenous immunoglobulin (IVIG), or a prion protein antagonist. In some embodiments the compound is combined with a cholinesterase inhibitor selected from tacrine (COGNEX®; Sciele), donepezil (ARICEPT®; Pfizer), rivastigmine (EXELON®; Novartis), or galantamine (RAZADYNE®; Ortho-McNeil-Janssen). In some embodiments, the compound is combined with a TNFalpha modulator that is perispinal etanercept (ENBREL®, Amgen/Pfizer). In some embodiments, the compound is combined with a beta-amyloid specific antibody selected from bapineuzumab (Pfizer), solanezumab (Lilly), PF-04360365 (Pfizer), GSK933776(GlaxoSmithKline), Gammagard (Baxter) or Octagam (Octapharma). In some embodiments, the compound is combined with an NMDA receptor antagonist that is memantine (NAMENDA®; Forest). In some embodiments, the BACE1 inhibitor is MK-8931 (Merck). In some embodiments, the compound is combined with IVIG as described in Magga et al., J Neuroinflam 2010, 7:90, Human intravenous immunoglobulin provides protection against Ab toxicity by multiple mechanisms in a mouse model of Alzheimer's disease, and Whaley et al., 2011, Human Vaccines 7:3, 349-356, Emerging antibody products and Nicotiana manufacturing; each of which is incorporated herein by reference. In some embodiments, the compound is combined with a prion protein antagonist as disclosed in Strittmatter et al., US 2010/0291090, which is incorporated herein by reference.

Accordingly, the disclosure provides, in a further aspect, a pharmaceutical composition comprising at least one compound according to any embodiment described herein, or pharmaceutically acceptable derivative thereof; a second active agent; and, optionally a pharmaceutically acceptable carrier.

When combined in the same formulation it will be appreciated that the two or more compounds must be stable and compatible with each other and the other components of the formulation. When formulated separately they may be provided in any convenient formulation, in such manner as are known for such compounds in the art.

Preservatives, stabilizers, dyes and flavoring agents may be provided in any pharmaceutical composition described herein. Examples of preservatives include sodium benzoate, ascorbic acid and esters of p-hydroxybenzoic acid. Antioxidants and suspending agents may be also used.

With respect to combinations including biologics such as monoclonal antibodies or fragments, suitable excipients will be employed to prevent aggregation and stabilize the antibody or fragment in solution with low endotoxin, generally for parenteral administration, for example, intravenous, administration. For example, see Formulation and Delivery Issues for Monoclonal Antibody Therapeutics, Daugherty et al., in Current Trends in Monoclonal Antibody Development and Manufacturing, Part 4, 2010, Springer, New York pp 103-129.

The compounds according to any embodiment described herein, may be milled using known milling procedures such as wet milling to obtain a particle size appropriate for tablet formation and for other formulation types. Finely divided (nanoparticulate) preparations of the compounds may be prepared by processes known in the art, for example see WO 02/00196 (SmithKline Beecham).

Compounds according to any embodiment described herein, or pharmaceutically acceptable salts thereof, a solvate thereof, a stereoisomer thereof, a prodrug thereof, or an active metabolites thereof, can be formulated for any route of administration.

Routes of Administration and Unit Dosage Forms

The routes for administration (delivery) include, but are not limited to, one or more of: oral (e.g., as a tablet, capsule, or as an ingestible solution), topical, mucosal (e.g., as a nasal spray or aerosol for inhalation), parenteral (e.g., by an injectable form), gastrointestinal, intraspinal, intraperitoneal, intramuscular, intravenous, intracerebroventricular, or other depot administration etc.

Therefore, the pharmaceutical compositions according to any embodiment described herein, include those in a form especially formulated for the mode of administration. In certain embodiments, the pharmaceutical compositions of the disclosure are formulated in a form that is suitable for oral delivery. In some embodiments, the compound is an orally bioavailable compound, suitable for oral delivery. In other embodiments, the pharmaceutical compositions of the disclosure are formulated in a form that is suitable for parenteral delivery.

The compounds according to any embodiment described herein, may be formulated for administration in any convenient way for use in human or veterinary medicine and the disclosure therefore includes within its scope pharmaceutical compositions comprising a compound according to any embodiment described herein, adapted for use in human or veterinary medicine. Such pharmaceutical compositions may be presented for use in a conventional manner with the aid of one or more suitable carriers. Acceptable carriers for therapeutic use are well-known in the pharmaceutical art, and are described, for example, in Remington's Pharmaceutical Sciences, Mack Publishing Co. (A. R. Gennaro edit. 1985). The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

There may be different pharmaceutical composition/formulation requirements depending on the different delivery systems. It is to be understood that not all of the compounds need to be administered by the same route. Likewise, if the pharmaceutical composition comprises more than one active component, then those components may be administered by different routes. By way of example, the pharmaceutical composition of the disclosure may be formulated to be delivered using a mini-pump or by a mucosal route, for example, as a nasal spray or aerosol for inhalation or ingestible solution, or parenterally in which the pharmaceutical composition is formulated by an injectable form, for delivery by, for example, an intravenous, intramuscular or subcutaneous route. Alternatively, the formulation may be designed to be delivered by multiple routes.

The combination of a compound according to any embodiment described herein, and an antibody or antibody fragment molecule can be formulated and administered by any of a number of routes and are administered at a concentration that is therapeutically effective in the indication or for the purpose sought. To accomplish this goal, the antibodies may be formulated using a variety of acceptable excipients known in the art. Typically, the antibodies are administered by injection, for example, intravenous injection. Methods to accomplish this administration are known to those of ordinary skill in the art. For example, Gokarn et al., 2008, J Pharm Sci 97(8):3051-3066, incorporated herein by reference, describe various high concentration antibody self buffered formulations. For example, monoclonal antibodies in self buffered formulation at e.g., 50 mg/mL mAb in 5.25% sorbitol, pH 5.0; or 60 mg/mL mAb in 5% sorbitol, 0.01% polysorbate 20, pH 5.2; or conventional buffered formulations, for example, 50 mg/mL mAb1 in 5.25% sorbitol, 25 or 50 mM acetate, glutamate or succinate, at pH 5.0; or 60 mg/mL in 10 mM acetate or glutamate, 5.25% sorbitol, 0.01% polysorbate 20, pH 5.2; other lower concentration formulations can be employed as known in the art.

Because some compounds of the disclosure cross the blood brain barrier they can be administered by a variety of methods including for example systemic (e.g., by iv, SC, oral, mucosal, transdermal route) or localized methods (e.g., intracranially). Where the compound according to any embodiment described herein, is to be delivered mucosally through the gastrointestinal mucosa, it should be able to remain stable during transit though the gastrointestinal tract; for example, it should be resistant to proteolytic degradation, stable at acid pH and resistant to the detergent effects of bile. For example, compounds according to any embodiment described herein, prepared for oral administration may be coated with an enteric coating layer. The enteric coating layer material may be dispersed or dissolved in either water or in a suitable organic solvent. As enteric coating layer polymers, one or more, separately or in combination, of the following can be used; e.g., solutions or dispersions of methacrylic acid copolymers, cellulose acetate phthalate, cellulose acetate butyrate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s). In some embodiments, the aqueous enteric coating layer is a methacrylic acid copolymer.

Where appropriate, the pharmaceutical compositions according to any embodiment described herein, can be administered by inhalation, by use of a skin patch, orally in the form of tablets containing excipients such as starch or lactose, or in capsules or ovules either alone or in admixture with excipients, or in the form of elixirs, solutions or suspensions containing flavoring or coloring agents, or they can be injected parenterally, for example intravenously, intramuscularly or subcutaneously. For buccal or sublingual administration the pharmaceutical compositions according to any embodiment described herein, may be administered in the form of tablets or lozenges, which can be formulated in a conventional manner.

Where the pharmaceutical composition according to any embodiment described herein, is to be administered parenterally, such administration includes without limitation: intravenously, intraarterially, intrathecally, intraventricularly, intracranially, intramuscularly or subcutaneously administering the compound of the disclosure; and/or by using infusion techniques. Antibodies or fragments are typically administered parenterally, for example, intravenously.

Pharmaceutical compositions according to any embodiment described herein, suitable for injection or infusion may be in the form of a sterile aqueous solution, a dispersion or a sterile powder that contains the active ingredient, adjusted, if necessary, for preparation of such a sterile solution or dispersion suitable for infusion or injection. This preparation may optionally be encapsulated into liposomes. In all cases, the final preparation must be sterile, liquid, and stable under production and storage conditions. To improve storage stability, such preparations may also contain a preservative to prevent the growth of microorganisms. Prevention of the action of micro-organisms can be achieved by the addition of various antibacterial and antifungal agents, e.g., paraben, chlorobutanol, or acsorbic acid. In many cases isotonic substances are recommended, e.g., sugars, buffers and sodium chloride to assure osmotic pressure similar to those of body fluids, particularly blood. Prolonged absorption of such injectable mixtures can be achieved by introduction of absorption-delaying agents, such as aluminum monostearate or gelatin.

Dispersions can be prepared in a liquid carrier or intermediate, such as glycerin, liquid polyethylene glycols, triacetin oils, and mixtures thereof. The liquid carrier or intermediate can be a solvent or liquid dispersive medium that contains, for example, water, ethanol, a polyol (e.g., glycerol, propylene glycol or the like), vegetable oils, non-toxic glycerine esters and suitable mixtures thereof. Suitable flowability may be maintained, by generation of liposomes, administration of a suitable particle size in the case of dispersions, or by the addition of surfactants.

For parenteral administration, the compound according to any embodiment described herein, is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Sterile injectable solutions can be prepared by mixing a compound according to any embodiment described herein, with an appropriate solvent and one or more of the aforementioned carriers, followed by sterile filtering. In the case of sterile powders suitable for use in the preparation of sterile injectable solutions, preferable preparation methods include drying in vacuum and lyophilization, which provide powdery mixtures of the compounds and desired excipients for subsequent preparation of sterile solutions.

The compounds according to any embodiment described herein, may be formulated for use in human or veterinary medicine by injection (e.g., by intravenous bolus injection or infusion or via intramuscular, subcutaneous or intrathecal routes) and may be presented in unit dose form, in ampoules, or other unit-dose containers, or in multi-dose containers, if necessary with an added preservative. The pharmaceutical compositions for injection may be in the form of suspensions, solutions, or emulsions, in oily or aqueous vehicles, and may contain formulatory agents such as suspending, stabilizing, solubilizing and/or dispersing agents. Alternatively the active ingredient may be in sterile powder form for reconstitution with a suitable vehicle, e.g., sterile, pyrogen-free water, before use.

The compounds according to any embodiment described herein, can be administered in the form of tablets, capsules, troches, ovules, elixirs, solutions or suspensions, for immediate-, delayed-, modified-, sustained-, pulsed- or controlled-release applications.

The compounds according to any embodiment described herein, may also be presented for human or veterinary use in a form suitable for oral or buccal administration, for example in the form of solutions, gels, syrups, or suspensions, or a dry powder for reconstitution with water or other suitable vehicle before use. Solid pharmaceutical compositions such as tablets, capsules, lozenges, troches, pastilles, pills, boluses, powder, pastes, granules, bullets or premix preparations may also be used. Solid and liquid pharmaceutical compositions for oral use may be prepared according to methods well-known in the art. Such pharmaceutical compositions may also contain one or more pharmaceutically acceptable carriers and excipients which may be in solid or liquid form.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

The pharmaceutical compositions according to any embodiment described herein, may be administered orally, in the form of rapid or controlled release tablets, microparticles, mini tablets, capsules, sachets, and oral solutions or suspensions, or powders for the preparation thereof. Oral preparations may optionally include various standard pharmaceutical carriers and excipients, such as binders, fillers, buffers, lubricants, glidants, dyes, disintegrants, odorants, sweeteners, surfactants, mold release agents, antiadhesive agents and coatings. Some excipients may have multiple roles in the pharmaceutical compositions, e.g., act as both binders and disintegrants.

Examples of pharmaceutically acceptable disintegrants for oral pharmaceutical compositions according to any embodiment described herein, include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and cross-linked polyvinylpyrrolidone.

Examples of pharmaceutically acceptable binders for oral pharmaceutical compositions according to any embodiment described herein, include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthine resin, alginates, magnesium☐aluminum silicate, polyethylene glycol or bentonite.

Examples of pharmaceutically acceptable fillers for oral pharmaceutical compositions according to any embodiment described herein, include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulphate.

Examples of pharmaceutically acceptable lubricants useful in the pharmaceutical compositions according to any embodiment described herein, include, but are not limited to, magnesium stearate, talc, polyethylene glycol, polymers of ethylene oxide, sodium lauryl sulphate, magnesium lauryl sulphate, sodium oleate, sodium stearyl fumarate, and colloidal silicon dioxide.

Examples of suitable pharmaceutically acceptable odorants for the oral pharmaceutical compositions according to any embodiment described herein, include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral pharmaceutical compositions according to any embodiment described herein, include, but are not limited to, synthetic and natural dyes such as titanium dioxide, beta-carotene and extracts of grapefruit peel.

Examples of useful pharmaceutically acceptable coatings for the oral pharmaceutical compositions according to any embodiment described herein, typically used to facilitate swallowing, modify the release properties, improve the appearance, and/or mask the taste of the pharmaceutical compositions include, but are not limited to, hydroxypropylmethylcellulose, hydroxypropylcellulose and acrylate-methacrylate copolymers.

Suitable examples of pharmaceutically acceptable sweeteners for the oral pharmaceutical compositions according to any embodiment described herein, include, but are not limited to, aspartame, saccharin, saccharin sodium, sodium cyclamate, xylitol, mannitol, sorbitol, lactose and sucrose.

Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulphate and polysorbates.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

As indicated, a compounds according to any embodiment described herein, can be administered intranasally or by inhalation and is conveniently delivered in the form of a dry powder inhaler or an aerosol spray presentation from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of a compound according to any embodiment described herein, and a suitable powder base such as lactose or starch.

For topical administration by inhalation a compounds according to any embodiment described herein, may be delivered for use in human or veterinary medicine via a nebulizer.

The pharmaceutical compositions of the disclosure may contain from 0.01 to 99% weight per volume of the active material. For topical administration, for example, the pharmaceutical composition will generally contain from 0.01-10%, more preferably 0.01-1% of the active material.

A compound according to any embodiment described herein, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The pharmaceutical composition or unit dosage form, according to any embodiment described herein, may be administered according to a dosage and administration regimen defined by routine testing in the light of the guidelines given above in order to obtain optimal activity while minimizing toxicity or side effects for a particular patient. The dosage of the compounds or unit dosage form may vary according to a variety of factors such as underlying disease conditions, the individual's condition, weight, sex and age, and the mode of administration. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter is within the scope of the disclosure. Clinically significant attenuation or amelioration means perceptible to the patient and/or to the physician.

In some embodiments, the amount of the compound to be administered can range between about 0.01 and about 25 mg/kg/day. Generally, dosage levels of between 0.01 to 25 mg/kg of body weight daily are administered to the patient, e.g., humans. In some embodiments the therapeutically effective amount is between a lower limit of about 0.01 mg/kg of body weight, about 0.1 mg/kg of body weight, about 0.2 mg/kg of body weight, about 0.3 mg/kg of body weight, about 0.4 mg/kg of body weight, about 0.5 mg/kg of body weight, about 0.60 mg/kg of body weight, about 0.70 mg/kg of body weight, about 0.80 mg/kg of body weight, about 0.90 mg/kg of body weight, about 1 mg/kg of body weight, about 2.5 mg/kg of body weight, about 5 mg/kg of body weight, about 7.5 mg/kg of body weight, about 10 mg/kg of body weight, about 12.5 mg/kg of body weight, about 15 mg/kg of body weight, about 17.5 mg/kg of body weight, about 20 mg/kg of body weight, about 22.5 mg/kg of body weight, and about 25 mg/kg of body weight; and an upper limit of 25 mg/kg of body weight, about 22.5 mg/kg of body weight, about 20 mg/kg of body weight, about 17.5 mg/kg of body weight, about 15 mg/kg of body weight, about 12.5 mg/kg of body weight, about 10 mg/kg of body weight, about 7.5 mg/kg of body weight, about 5 mg/kg of body weight, about 2.5 mg/kg of body weight, about 1 mg/kg of body weight, about 0.9 mg/kg of body weight, about 0.8 mg/kg of body weight, about 0.7 mg/kg of body weight, about 0.6 mg/kg of body weight, about 0.5 mg/kg of body weight, about 0.4 mg/kg of body weight, about 0.3 mg/kg of body weight, about 0.2 mg/kg of body weight, about 0.1 mg/kg of body weight, and about 0.01 mg/kg of body weight. In some embodiments, the therapeutically effective amount is about 0.1 mg/kg/day to about 10 mg/kg/day; in some embodiments the therapeutically effective amount is about 0.2 and about 5 mg/kg/day. It will be understood that the pharmaceutical formulations of the disclosure need not necessarily contain the entire amount of the compound that is effective in treating the disorder, as such effective amounts can be reached by administration of a plurality of divided doses of such pharmaceutical formulations. The compounds may be administered on a regimen of 1 to 4 times per day, such as once, twice, three times or four times per day.

In some embodiments of the disclosure, a compound according to any embodiment described herein, is formulated in capsules or tablets, usually containing about 10 to about 200 mg of the compounds. In some embodiments the capsule or tablet contains between a lower limit of about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg; about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, and about 200 mg, and an upper limit of about 200 mg, about 195 mg, about 190 mg, about 185 mg, about 180 mg, about 175 mg, about 170 mg, about 165 mg, about 160 mg, about 155 mg, about 150 mg, about 145 mg, about 140 mg, about 135 mg, about 130 mg, about 125 mg, about 120 mg, about 115 mg, about 110 mg, about 105 mg, about 100 mg, about 95 mg, about 90 mg; about 85 mg, about 80 mg, about 75 mg, about 70 mg, about 65 mg, about 60 mg, about 55 mg, about 50 mg, about 45 mg, about 40 mg, about 35 mg, about 30 mg, about 25 mg, about 20 mg, about 15 mg, and about 10 mg of a compound according to any embodiment herein.

In some embodiments, a compound according to any embodiment herein is administered to a patient at a total daily dose of 50 mg to 500 mg. In some embodiments, the daily dose is between a lower limit of about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg; about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg; about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, 300 mg, about 305 mg, about 310 mg, about 315 mg; about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395, about 400 mg, about 405 mg, about 410 mg, about 415 mg; about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, and about 500 mg and an upper limit of about 500 mg, about 495 mg, about 490 mg, about 485 mg, about 480 mg, about 475 mg, about 470 mg, about 465 mg, about 460 mg, about 455 mg, about 450 mg, about 445 mg, about 440 mg, about 435 mg, about 430 mg, about 425 mg, about 420 mg, about 415 mg, about 410 mg, about 405 mg, about 400 mg, about 395 mg, about 390 mg, about 385 mg, about 380 mg, about 375 mg, about 370 mg, about 365 mg, about 360 mg, about 355 mg, about 350 mg, about 345 mg, about 340 mg, about 335 mg, about 330 mg, about 325 mg, about 320 mg, about 315 mg, about 310 mg, about 305 mg about 300 mg, about 295 mg, about 290 mg, about 285 mg, about 280 mg, about 275 mg, about 270 mg, about 265 mg, about 260 mg, about 255 mg, about 250 mg, about 245 mg, about 240 mg, about 235 mg, about 230 mg, about 225 mg, about 220 mg, about 215 mg, about 210 mg, about 205 mg 200 mg, about 195 mg, about 190 mg, about 185 mg, about 180 mg, about 175 mg, about 170 mg, about 165 mg, about 160 mg, about 155 mg, about 150 mg, about 145 mg, about 140 mg, about 135 mg, about 130 mg, about 125 mg, about 120 mg, about 115 mg, about 110 mg, about 105 mg, about 100 mg, about 95 mg, about 90 mg; about 85 mg, about 80 mg, about 75 mg, about 70 mg, about 65 mg, about 60 mg, about 55 mg, and about 50 mg of a compound according to any embodiment herein. In some embodiments, the total daily dose is about 50 mg to 150 mg. In some embodiments, the total daily dose is about 50 mg to 250 mg. In some embodiments, the total daily dose is about 50 mg to 350 mg. In some embodiments, the total daily dose is about 50 mg to 450 mg. In some embodiments, the total daily dose is about 50 mg.

A pharmaceutical composition for parenteral administration contains from about 0.01% to about 100% by weight of the active compound according to any embodiment described herein, based upon 100% weight of total pharmaceutical composition.

Generally, transdermal dosage forms contain from about 0.01% to about 100% by weight of the active compound according to any embodiment described herein, versus 100% total weight of the dosage form.

The pharmaceutical composition or unit dosage form may be administered in a single daily dose, or the total daily dosage may be administered in divided doses. In addition, co administration or sequential administration of another compound for the treatment of the disorder may be desirable. To this purpose, the combined active principles are formulated into a simple dosage unit.

Compounds according to any embodiment described herein, may be prepared by the general methods outlined in, for example, WO2013/029057, incorporated herein by reference, or as described hereinafter, said methods constituting a further aspect of the disclosure.

Compounds according to any embodiment disclosed herein can be synthesized in accordance with general methods provided herein and specific synthetic examples.

It will be appreciated by those skilled in the art that it may be desirable to use protected derivatives of intermediates used in the preparation of the compounds according to any embodiment described herein. Protection and deprotection of functional groups may be performed by methods known in the art (see, for example, Green and Wuts Protective Groups in Organic Synthesis. John Wiley and Sons, New York, 1999.). Hydroxy or amino groups may be protected with any hydroxy or amino protecting group. The amino protecting groups may be removed by conventional techniques. For example, acyl groups, such as alkanoyl, alkoxycarbonyl and aroyl groups, may be removed by solvolysis, e.g., by hydrolysis under acidic or basic conditions. Arylmethoxycarbonyl groups (e.g., benzyloxycarbonyl) may be cleaved by hydrogenolysis in the presence of a catalyst such as palladium-on-charcoal.

The synthesis of the target compounds is completed by removing any protecting groups which may be present in the penultimate intermediates using standard techniques, which are well-known to those skilled in the art. The deprotected final products are then purified, as necessary, using standard techniques such as silica gel chromatography, HPLC on silica gel and the like, or by recrystallization.

Methods of Use

In some embodiments, the disclosure provides methods of inhibiting synapse number decline or membrane trafficking abnormalities associated with exposure of a neuronal cell to Abeta species by administration of a compound according to any embodiment described herein.

In some embodiments the disclosure also provides methods for treating cognitive decline and/or a neurodegenerative disease, e.g. Alzheimer's disease or mild cognitive impairment (MCI) in a patient comprising administering to the patient a compound according to any embodiment described herein.

In some embodiments, the neurodegenerative disease is selected from Age-Associated Memory Impairment (AAMI), Age-Related Cognitive Decline (ARCD), agitation synucleinopathies, Alzheimer's disease (AD), Amyotrophic lateral sclerosis (ALS) dementia, autosomal-dominant Parkinson's disease, Cognitive Impairment No Dementia (CIND), dementia, Diffuse Lewy Body Disease (DLBD) also known as Dementia with Lewy Bodies (DLB), disorders or conditions characterized by the presence of Lewy bodies, Down syndrome, dyskinesia, HIV dementia, Huntington's disease, Incidental LBD, Inherited LBD, Lewy body dysphagia, Mild Cognitive Impairment (MCI), multiple sclerosis, multiple system atrophy (MSA), Olivopontocerebellar Atrophy, Parkinson's disease (PD), preclinical Alzheimer's Disease (PCAD), Psychosis, Pure Autonomic Failure, Shy-Drager Syndrome, Striatonigral Degeneration, synucleinopathies, combined Alzheimer's and Parkinson disease and/or MSA, vascular dementia, diseases, disorders or conditions associated with abnormal expression, stability, activities and/or cellular processing of α-synuclein, diseases, disorders or conditions characterized by the presence of Lewy bodies, and combinations thereof.

In some embodiments, the method of inhibiting, or treating, cognitive decline and/or a neurodegenerative disease, e.g. Alzheimer's disease, comprises inhibiting, or treating one or more symptoms of cognitive decline selected from the group consisting of memory loss, confusion, impaired judgment, personality changes, disorientation, and loss of language skills. In some embodiments, the method comprises inhibiting, or treating, diseases or disorders or conditions mediated by or associated with Abeta oligomers.

In some embodiments, the method of inhibiting, or treating, cognitive decline and/or a neurodegenerative disease, e.g. Alzheimer's disease, comprises one or more of: (i) restoration of long term potentiation (LTP), long term depression (LTD) or synaptic plasticity detectable by electrophysiological measurements or any of the other negative changes in cognitive function as mentioned in the definition of the term above; and/or (ii) inhibiting, or treating, neurodegeneration; and/or (iii) inhibiting, or treating, general amyloidosis; and/or (iv) inhibiting, or treating, one or more of amyloid production, amyloid assembly, amyloid aggregation, and amyloid oligomer binding, and amyloid deposition; and/or (v) inhibiting, treating, and/or abating an effect, notably a nonlethal effect, of one or more of Abeta oligomers on a neuron cell.

In some embodiments, the method of inhibiting, treating, and/or abating cognitive decline and/or a neurodegenerative disease, e.g. Alzheimer's disease, comprises inhibiting, treating, and/or abating one or more of amyloid production, amyloid assembly, the activity/effect of one or more of Abeta oligomers on a neuron cell, amyloid aggregation, amyloid binding, and amyloid deposition.

In some embodiments, the method of inhibiting, treating, and/or abating cognitive decline and/or a neurodegenerative disease, e.g. Alzheimer's disease, comprises inhibiting, treating, and/or abating one or more of the activity/effect of one or more of Abeta oligomers on a neuron cell.

In some embodiments, the activity/effect of one or more of Abeta oligomers on a neuron cell, amyloid aggregation and amyloid binding is the effect of Abeta oligomers on membrane trafficking or synapse number. In some embodiments, a compound according to any embodiment described herein, inhibits the Abeta oligomer effect on membrane trafficking or synapse number or Abeta oligomer binding.

In some embodiments, the disclosure provides methods of treating a proteopathic disease associated with Abeta oligomer toxicity, specifically nonlethal Abeta oligomer effects. In some embodiments, the method comprises contacting a subject with such a proteopathic disease with a compound according to any embodiment described herein, or a pharmaceutical composition containing the same that binds the sigma-2 receptor.

In some embodiments, the proteopathic disease is a CNS proteopathy, characterized by an increase in Abeta protein, such as MCI, Down's Syndrome, macular degeneration or Alzheimer's disease, and the like.

In some embodiments, the disclosure provides methods of treating one or more mild cognitive impairment (MCI), or dementia by administering a compound according to any embodiment described herein. In some embodiments, the disclosure provides methods of treating MCI, and dementia.

In some embodiments, the disclosure provides methods of treating Alzheimer's Disease by administering a compound according to any embodiment described herein.

In some embodiments, the disclosure provides methods of treating an individual with a compound according to any embodiment described herein, to restore, partially or totally, the subject's cells to a normal phenotype in terms of functions affected adversely by Abeta species, such as Abeta oligomers. Examples are synaptic number reduction and membrane trafficking abnormalities, which can be measured by various methods including assays described herein. The normal phenotype can be, for example, normal membrane trafficking. In some embodiments, the normal phenotype is normal cognitive ability. The "normal" phenotype can be determined by comparing a subject's results with a sample of normal subjects. The sample may be as small as 1 subject or 1 sample or may be more than 10 samples or subjects and the norm is an average that is calculated based upon a plurality of subjects.

In some embodiments, a compound according to any embodiment described herein, generally inhibits the Abeta effect on neurons. In some embodiments, the compounds describe above have an $IC_{50}$ for inhibition of Abeta effect of less than about 100 µM, about 50 µM, about 20 µM, about 15 µM, about 10 µM, about 5 µM, about 1 µM, about 500 nM, about 100 nM, about 50 nM, or about 10 nM on neurons (such as neurons in the brain), amyloid assembly or disruption thereof, and amyloid (including amyloid oligomer) binding, and amyloid deposition. In some embodiments, a compound according to any embodiment described herein, may have an $IC_{50}$ for inhibition of the activity/effect of Abeta species such as oligomers of less than about 100 µM, about 50 µM, about 20 µM, about 15 µM, about 10 µM, about 5 µM, about 1 µM, about 500 nM, about 100 nM, about 50 nM, or about 10 nM on neurons (such as central nervous system neurons).

A compound according to any embodiment described herein, may inhibit the Abeta effect by specifically binding to a sigma-2 receptor. A compound can be said to be "specific" for a sigma-2 receptor when it binds with a binding affinity that is at least 10% greater than to the sigma-1 receptor, even though the compound is capable of binding both sigma-1 and sigma-2 receptor. The compounds of such embodiments may exhibit a specificity of at least 10%, 20%, 30%, 40%, 50%, 60%, 70%, 80%, 90%, 100%, 200%, 300%, 400%, 500%, or 1000% greater for sigma-2 receptor than sigma-1 receptor.

In some embodiments, percentage inhibition by a compound according to any embodiment described herein, of one or more of the effects of Abeta species such as oligomers on neurons (such as neurons in the brain), such as amyloid (including amyloid oligomer) binding to synapses, and abnormalities in membrane trafficking mediated by Abeta oligomer can be about 1% to about 20%, about 20% to about 50%, about 1% to about 50%, or about 1% to about 80% as measured at a concentration of from 10 nM to 10 µM. Inhibition can be assessed for example by quantifying synapse number of a neuron prior to and after exposure to an amyloid beta species or quantifying the number of synapses in the presence of both of the compound according to any embodiment described herein, and the Abeta species wherein the compound according to any embodiment described herein, is simultaneous with, or precedes or follows, Abeta species exposure. As another example, inhibition can be assessed by determining membrane trafficking and comparing one or more parameters that measure exocytosis rate and extent, endocytosis rate and extent, or other indicators of cell metabolism in the presence and absence of an Abeta species and in the presence and absence of a compound according to any embodiment described herein.

In some embodiments, the disclosure provides methods of measuring beta-amyloid-associated cognitive decline in an animal using a labeled compound according to any embodiment described herein. In some embodiments, the method comprises contacting the animal with a labeled compound according to any embodiment described herein, and measuring sigma-2 activity or expression. In some embodiments, the method comprises comparing the sigma-2 activity or expression in the animal with an animal known to have beta-amyloid induced cognitive decline. If the activity or expression is the same as the animal known to have beta-amyloid induced cognitive decline the animal is said to have the same level of cognitive decline. The animals can be ranked according the similarities in known activity or expression of various stages of beta amyloid induced cognitive decline. Any of the a compound according to any embodiment described herein, can be labeled so that the labeled compound can be used in vivo.

In some embodiments, an assay is used to determine if a compound according to any embodiment described herein, can bind to a sigma-2 receptor. In some embodiments, the method further comprises determining whether the compound that binds to a sigma-2 receptor acts as a functional antagonist at a sigma-2 receptor by inhibiting soluble Aβ oligomer induced neurotoxicity with respect to inhibiting soluble Aβ oligomer induced synapse loss, and inhibiting soluble Aβ oligomer induced deficits in a membrane trafficking assay.

Any form of amyloid β may be used in the practice of the screening methods and of the assays according to the disclosure, including amyloid β monomers, oligomers, fibrils, as well as amyloid β associated with proteins ("protein complexes") and more generally amyloid β assemblies. For example, screening methods can employ various forms of soluble amyloid β oligomers as disclosed, for example, in U.S. patent application Ser. No. 13/021,872; U.S. Patent Publication 2010/0240868; International Patent Application WO/2004/067561; International Patent Application WO/2010/011947; U.S. Patent Publication 20070098721; U.S. Patent Publication 20100209346; International Patent Application WO/2007/005359; U.S. Patent Publication 20080044356; U.S. Patent Publication 20070218491; WO/2007/126473; U.S. Patent Publication 20050074763; International Patent Application WO/2007/126473, International Patent Application WO/2009/048631, and U.S. Patent Publication 20080044406, U.S. Pat. Nos. 7,902,328 and 6,218,506, each of which is incorporated herein by reference.

Amyloid β forms, including monomers or oligomers of amyloid β may be obtained from any source. For example, in some embodiments, commercially available amyloid β monomers and/or amyloid β oligomers may be used in the aqueous solution, and in other embodiments, amyloid β monomers and/or amyloid β oligomers that are used in the aqueous protein solution can be isolated and purified by the skilled artisan using any number of known techniques. In general, the amyloid β monomers and/or amyloid β oligomers used in the preparation of the aqueous solution of proteins and amyloid β of various embodiments may be soluble in the aqueous solution. Therefore, both the proteins of the aqueous solution and the amyloid β may be soluble.

The amyloid β added may be of any isoform. For example, in some embodiments, the amyloid β monomers may be amyloid β 1-42, and in other embodiments the amyloid β monomers may be amyloid β 1-40. In still other embodiments, the amyloid β may be amyloid β 1-39 or amyloid β 1-41. Hence, the amyloid β of various embodiments may encompass any C-terminal isoform of amyloid β. Yet other embodiments include amyloid β in which the N-terminus has been frayed, and in some embodiments, the N-terminus of any of amyloid β C-terminal isomers described above may be amino acid 2, 3, 4, 5, or 6. For example, amyloid β 1-42 may encompass amyloid β 2-42, amyloid β 3-42, amyloid β 4-42, or amyloid β 5-42 and mixtures thereof, and similarly, amyloid β 1-40 may encompass amyloid β 2-40, amyloid β 3-40, amyloid β 4-40, or amyloid β 5-40.

The amyloid β forms used in various embodiments may be wild type, i.e. having an amino acid sequence that is identical to the amino acid sequence of amyloid β synthesized in vivo by the majority of the population, or in some embodiments, the amyloid β may be a mutant amyloid β. Embodiments are not limited to any particular variety of mutant amyloid β. For example, in some embodiments, the amyloid β introduced into the aqueous solution may include a known mutation, such as, for example, amyloid β having the "Dutch" (E22Q) mutation or the "Arctic" (E22G) mutation. Such mutated monomers may include naturally occurring mutations such as, for example, forms of amyloid β isolated from populations of individuals that are predisposed to, for example, Alzheimer's disease, familial forms of amyloid β. In other embodiments, mutant amyloid β monomers may be synthetically produced by using molecular techniques to produce an amyloid β mutant with a specific mutation. In still other embodiments, mutant amyloid β monomers may include previously unidentified mutations such as, for example, those mutants found in randomly generated amyloid β mutants. The term "amyloid β" as used herein, is meant to encompass both wild type forms of amyloid β as well as any of the mutant forms of amyloid β.

In some embodiments, the amyloid β in the aqueous protein solution may be of a single isoform. In other embodiments, various C-terminal isoforms of amyloid β and/or various N-terminal isoforms of amyloid β may be combined to form amyloid β mixtures that can be provided in the aqueous protein solution. In yet other embodiments, the amyloid β may be derived from amyloid precursor protein (APP) that is added to the protein containing aqueous solution and is cleaved in situ, and such embodiments, various isoforms of amyloid β may be contained within the solution. Fraying of the N-terminus and/or removal of C-terminal amino acids may occur within the aqueous solution after amyloid β has been added. Therefore, aqueous solutions prepared as described herein, may include a variety of amyloid β isoforms even when a single isoform is initially added to the solution.

The amyloid β monomers added to the aqueous solution may be isolated from a natural source such as living tissue, and in other embodiments, the amyloid β may be derived from a synthetic source such as transgenic mice or cultured cells. In some embodiments, the amyloid β forms, including monomers, oligomers, or combinations thereof are isolated from normal subjects and/or patients that have been diagnosed with cognitive decline or diseases associated therewith, such as, but not limited to, Alzheimer's disease. In some embodiments, the amyloid β monomers, oligomers, or combinations thereof are Abeta assemblies that have been isolated from normal subjects or diseased patients. In some embodiments, the Abeta assemblies are high molecular weight, e.g. greater than 100 KDa. In some embodiments, the Abeta assemblies are intermediate molecular weight, e.g. 10 to 100 KDa. In some embodiments, the Abeta assemblies are less than 10 kDa.

The amyloid β oligomers of some embodiments may be composed of any number of amyloid β monomers consistent with the commonly used definition of "oligomer." For example, in some embodiments, amyloid β oligomers may include from about 2 to about 300, about 2 to about 250, about 2 to about 200 amyloid β monomers, and in other embodiments, amyloid β oligomers may be composed from about 2 to about 150, about 2 to about 100, about 2 to about 50, or about 2 to about 25, amyloid β monomers. In some embodiments, the amyloid β oligomers may include 2 or more monomers. The amyloid β oligomers of various embodiments may be distinguished from amyloid β fibrils and amyloid β protofibrils based on the confirmation of the monomers. In particular, the amyloid β monomers of amyloid β oligomers are generally globular consisting of β-pleated sheets whereas secondary structure of the amyloid β monomers of fibrils and protofibrils is parallel β-sheets.

EXAMPLES

Examples 1 and 2 describe Abeta oligomer preparations that could be used for experiments described below. The particular preparations used in the membrane trafficking and oligomer bindin/synapse reduction assays as well as those used in the in vivo assays described below are each described in the example to which they pertain.

Example 1: Preparation of Amyloid β Oligomers

The conditions in which amyloid β may oligomerize in nervous tissue, a milieu of aqueous-soluble proteins with which it may associate, were re-created to identify the more disease-relevant structural state of amyloid β oligomers and fibrils. Aqueous soluble proteins were prepared from rat brain by ultracentrifugation. Specifically, 5 volumes of TBS buffer (20 mM Tris-HCL, pH 7.5, 34 mM NaCl and a complete protease inhibitor cocktail (Santa Cruz) per gram of brain tissue was added to the rat brain tissue on ice. Dounce homogenization was then carried out with a tight-fitting pestle. The homogenized brain tissues were then centrifuged at 150,000×g for 1 hour at 4° C. (40,000 rpm Ty65). The infranatant (between floating myelin and a half cm above the pellet) was then removed and aliquots were frozen at −75° C. The pellets were then resuspended in TBS to the original volume and frozen in aliquots at −75° C.

Synthetic, monomeric human amyloid β 1-42 was added to this mixture to provide a final concentration of 1.5 uM amyloid β, and the solution was incubated for 24 hours at 4° C. Centrifugation of the mixture at 5,800 g for 10 minutes was performed to remove fibrillar assemblies and then Immunoprecipitation was performed using 6E10 conjugated agarose spin columns (Pierce Chemical Company) for 24 hours at 4° C. The eluted amyloid β oligomers were then subject to MALDI-Tof mass spectroscopic analysis to identify the contents of the sample.

The amyloid β self-associated in the protein containing solution to form subunit assemblies of 22,599 Da, 5 subunit pentamers and 31,950 Da, 7 subunit, 7mers. Another peak at 49,291 Da may represent 12 subunit, 12mers, although this would not appear to be an accurate molecular weight for amyloid β 12mers. Notably, no peaks are observed at either 4518 Da or 9036 Da which would represent amyloid β monomers and dimers. However, peaks at 9,882 Da and 14,731 Da could represent amyloid β dimers associated with a 786 Da (or 2×393 Da) lipids or proteins and amyloid β trimers associated with 3×393 Da lipids or proteins, respectively. In addition, the presence of a peak at 19,686 Da is indicative of an assembly state possibly involving a trimer complex and a rat amyloid β fragment of 4954 Da. Accordingly these data may reflect the association of small lipids or proteins with dimers and trimers of amyloid β which may direct the assembly of conformational states unique to physiological systems.

Example 2 Preparation of Beta-Amyloid Oligomers

A solution of 1.5 uM monomeric human amyloid β 1-42 in a mixture of rat brain soluble proteins was incubated for 24 hours at 4° C. as described in Example 1. This solution was then treated with tri-fluoro ethanol (TFE) prior to taking the spectra. In TFE, assembled protein structures and non-covalently bound protein complexes dissociate into denatured proteins, and the peaks associated with assembled oligomers are expected to disappear. The majority of protein peaks observed in Example 1 disappeared including the 9822 Da, 14,731 Da, 31,950 Da, and 49,291 Da peaks identified above. However, an abundant peak is observed at 4518 Da which represents amyloid β monomer peak. A peak at 4954.7 is apparent which may represent a longer abeta fragment similar to amyloid β 1-46. An additional peak is observed at 7086 Da which was not present in the preparation described in Example 1, which may represent amyloid β monomers associated with a 2550 Da covalently bound protein.

Example 3: Isolation of Beta-Amyloid Oligomers from Human AD Brain Tissue

TBS soluble extracts: Samples of post-mortem brain tissue from human patients characterized via histopathological analysis as Braak Stage V/VI Alzheimer's disease (AD) were obtained from a hospital brain tissue bank. Age and gender matched AD and normal tissue specimens were diluted to 0.15 gm tissue/ml in 20 mM Tris-HCL, 137 mM NaCl, pH 7.6 containing ImM EDTA and 1 mg/ml complete protease inhibitor cocktail (Sigma P8340) and homogenized. Ultracentrifugation of the tissue homogenates was performed at 105,000 g for 1 hour in a Beckman Optima XL-80K Ultracentrifuge. The resulting TBS soluble fractions were immunodepleted using protein-A and protein-G agarose columns (Pierce Chemical) and then size fractionated with Amicon Ultra 3, 10 & 100 kDa NMWCO filters (Millipore Corporation).

Immunoprecipitation: Size fractionated and immunodepleted TBS soluble extracts were concentrated to approximately 200 ul in the appropriate NMWCO Amicon Ultra filters. The concentrated TBS soluble extracts were diluted up to 400 ul with TBS sample buffer (Pierce Chemical) and centrifuged for 10 minutes at 5,800 g to remove fibrils. The resulting supernatant was then immunoprecipitated with 6E10-conjugated agarose beads overnight at 4° C. followed by antigen elution using high osmotic strength Gentle elution buffers (Pierce Chemical) to isolate Abeta containing protein species.

MALDI-mass spectrometry: Immunoisolated beta amyloid was subjected to mass spectroscopic analysis using an Applied Biosystems (ABI) Voyager DE-Pro MALDI-Tof instrument. Samples were analyzed using various matrix types such as α-Cyano-4-hydroxycinnamic acid (CHCA), Sinapic acid (SA), or 6-Aza-2-thiothymine (ATT) depending on the target molecular weight range of the analysis. The instrument was run in a linear-positive ion mode along with a variable extraction delay. Non-accumulated spectra represented 100 shots of a "hot spot" per acquisition while accumulated spectra were represented by 12 separate areas of each spot with 200 laser shots per acquisition.

Data analysis: Data acquisition and analysis was performed using Voyager's Data Explorer software package. Standard processing of the mass spectra included smoothing of the spectrum and baseline subtraction functions in addition to variations in the signal to noise ratio.

ELISA for Ab quantification: Immunoprecipitated TBS soluble fractions were analyzed for both "total" Abeta and Abeta oligomer concentration using a modified sandwich ELISA technique. Briefly, 6E10 and 4G8 coated Nunc MaxiSorp 96-well plates were incubated with Abeta containing samples and then probed with a Biotinylated 4G8 detection antibody. Incubation with Streptavidin-HRP (Rockland) followed by development of a Tetramethyl benzidine (TMB) substrate allowed for colorimetric detection (OD 450) of abeta on a BioTEk Synergy HT plate reader. Monomeric Abeta 1-42 was used for generation of a standard curve and along with GEN 5 software allowed for quantification of Abeta levels in the immuno-precipitated samples.

Example 4: Receptor Binding Assays

Certain compounds were tested for interaction with several receptors by blocking the binding or action of their agonists or antagonists. Some compounds were tested to see whether they interact directly with known cellular receptor or signaling proteins. Compounds can be tested for the ability to displace binding of known agonists or antagonists of a given human receptor that was overexpressed in cell lines or isolated from tissue. Compounds can also be tested for the ability to block downstream signaling induced by agonists or antagonists of a given human receptor. Compounds can be tested for action at 100 known receptors, and it is desirable that specific activity will occur at only a small subset of CNS-relevant receptors.

Using the same protocol, some compounds for which membrane trafficking data are given in Table 1 were tested for recognition of sigma-2 receptor. Certain compounds preferentially bind to the sigma-2 receptor.

Competitive Radioligand Binding Assay 1

For Sigma-1 binding, various concentrations of test compounds from 100 μM to 1 nM were used to displace 8 nM [3H](+)pentazocine from endogenous receptors on Jurkat cell membranes (Ganapathy M E et al. 1991, J Pharmacol. Exp. Ther. 289:251-260). 10 μM Haloperidol was used to define non-specific binding. For Sigma-2 receptors various concentrations of test compounds from 100 μM to 1 nM were used to displace 5 nM [3H]1,3-Di-(2-tolyl)guanidine from endogenous receptors on membranes from rat cerebral cortex in the presence of 300 nM (+)pentazocine to mask Sigma-1 receptors. (Bowen W D, et al. 1993, Mol. Neuropharmcol 3:117-126). 10 μM Haloperidol was used to define non-specific binding. Reactions were terminated by rapid filtration through Whatman GF/C filters using a Brandel 12R cell harvester followed by two washes with ice-cold buffer. Radioactivity on the dried filter discs was measured using a liquid scintillation analyzer (Tri-Carb 2900TR; PerkinElmer Life and Analytical Sciences). The displacement curves were plotted and the Ki values of the test compounds for the receptor subtypes were determined using GraphPad Prism (GraphPad Software Inc., San Diego, Calif.). The percentage specific binding was determined by dividing the difference between total bound (disintegrations per minute) and nonspecific bound (disintegrations per minute) by the total bound (disintegrations per minute).

Affinities for Sigma-1 and Sigma-2 receptors are typically obtained from published studies using cerebral tissue homogenates with [3H](+)pentazocine to measure displacement from Sigma-1 receptors and [3H] 1,3-Di-(2-tolyl)guanidine in the presence of 300 nM (+)pentazocine to measure displacement from Sigma-2 receptors.

Competitive Radioligand Binding Assay 2

The affinity of test compounds at sigma-1 and sigma-2 receptors was also determined by displacement of different known labeled sigma-2 or sigma-1 ligands. Filtration assays were conducted according the previously published procedure (Xu, et al., 2005). Test compounds were dissolved in N,N-Dimethylformamide (DMF), dimethyl sulfoxide (DMSO) or ethanol and then diluted in 50 mM Tris-HCl pH 7.4 buffer containing 150 mM NaCl and 100 mM EDTA. Membrane homogenates were made from guinea pig brain for sigma-1 binding assay and rat liver for sigma-2 binding assay. Membrane homogenates were diluted with 50 mM Tris-HCl buffer, pH 8.0 and incubated at 25° C. in a total volume of 150 uL in 96 well plates with the radioligand and test compounds with concentrations ranging from 0.1 nM to 10 uM. After incubation was completed, the reactions were terminated by the addition of 150 uL of ice-cold wash buffer (10 mM Tris HCl, 150 mM NaCl, pH 7.4) using a 96 channel transfer pipette (Fisher Scientific, Pittsburgh, Pa.) and the samples harvested and filtered rapidly through 96 well fiber glass filter plate (Millipore, Billerica, Mass.) that had been presoaked with 100 uL of 50 mM Tris-HCl buffer. Each filter was washed four times with 200 uL of ice-cold wash buffer (10 mM Tris-HCl, 150 mM NaCl, pH 7.4). A Wallac 1450 MicroBeta liquid scintillation counter (Perkin Elmer, Boston, Mass.) was used to quantitate the bound radioactivity.

The sigma-1 receptor binding assays were conducted using guinea pig brain membrane homogenates (~300 ug protein) and ~5 nM [3H](+)-pentazocine (34.9 Ci/mmol, Perkin Elmer, Boston, Mass.), incubation time was 90 min at room temperature. Nonspecific binding was determined from samples that contained 10 μM of cold haloperidol.

The sigma-2 receptor binding assays were conducted using rat liver membrane homogenates (~300 ug protein) and ~2 nM sigma-2 highly selective radioligand [3H] RHM-1 only (no other blockers) (America Radiolabeled Chemicals Inc. St. Louis, Mo.), ~10 nM [3H]DTG (58.1 Ci/mmol, Perkin Elmer, Boston, Mass.) or ~10 nM [3H] Haloperidol (America Radiolabeled Chemicals Inc., St. Louis, Mo.) in the presence of 1 uM (+)-pentazocine to block sigma-1 sites, incubation times were 6 minutes for [3H]RHM-1, 120 min for [3H]DTG and [3H]haloperidol at room temperature. Nonspecific binding was determined from samples that contained 10 uM of cold haloperidol.

Data from the competitive inhibition experiments were modeled using nonlinear regression analysis to determine the concentration of inhibitor that inhibits 50% of the specific binding of the radioligand ($IC_{50}$ value). The binding affinity, Ki values was calculated using the method of Cheng and Prusoff. The Kd value used for [3H](+)-pentazocine in guinea pig brain was 7.89 nM, for [3H]RHM-1 and [3H] DTG in rat liver were 0.66 nM and 30.73 nM respectively. The standard compound haloperidol was used for quality assurance. Affinity data at the sigma-2 receptor for exemplary compounds are shown in Table 1.

In some embodiments, compounds according to according to any embodiment herein, or pharmaceutically acceptable salts thereof, exhibit sigma-2 receptor binding affinity Ki of not more than 1,000 nM, not more than 750 nM, not more than 500 nM, not more than 250 nM, not more than 100 nM, not more than 50 nM, not more than 25 nM, or not more than 10 nM, when tested according to a sigma-2 receptor binding assay protocol provided herein.

Example 5: Inhibition of Abeta Oligomer Effect on Neuronal Cells in Membrane Trafficking Assay Compounds according to any embodiment described herein, were tested for their ability to inhibit an amyloid beta effect on the cells. The compounds generally were able to inhibit the amyloid beta effect as measured by a membrane trafficking/exocytosis assay (MTT assay). The results are indicated in Table 1. The rationale for this assay was as follows:

Since synaptic and memory deficits, and not widespread cell death, predominate at the earliest stages of Alzheimer's disease, assays that measure these changes are particularly well suited to discovering small molecule inhibitors of oligomer activity. The MTT assay is frequently used as a measure of toxicity in cultures. Yellow tetrazolium salts are endocytosed by cells and reduced to insoluble purple formazan in the endosomal pathway. The level of purple formazan is a reflection of the number of actively metabolizing cells in culture, and reduction in the amount of formazan is taken as a measure of cell death or metabolic toxicity in culture. When observed through a microscope, the purple formazan is first visible in intracellular vesicles that fill the cell. Over time, the vesicles are exocytosed and the formazan precipitates as needle-shaped crystals on the outer surface of the plasma membrane as the insoluble formazan is exposed to the aqueous media environment. Liu and Schubert ('97) discovered that cells respond to sublethal levels of Abeta oligomers by selectively accelerating the exocytosis rate of reduced formazan, while leaving endocytosis rate unaffected. The inventors have replicated these observations in mature primary neurons in culture and quantified these morphological shifts via automated microscopy and image processing. Under these circumstances, there is no overall change in the total amount of reduced formazan, simply a shift in its morphology reflective of changes in rate of its formation and/or expulsion from the cell. The inventors have confirmed previous findings that this assay is sensitive to low levels of oligomers that do not cause cell death (Liu and Schubert '04, Hong et al., '07). Indeed, low amounts of oligomers that lead to inhibition of LTP do not lead to cell death (Tong et al., '04) and are not expected to change total amounts of formazan in culture (or in brain slices).

Evidence adduced by other investigators suggests that Abeta oligomer-mediated reduction in neuronal surface receptor expression mediated by membrane trafficking is the basis for oligomer inhibition of electrophysiological measures of synaptic plasticity (LTP) and thus learning and memory (Kamenetz et al., '03, Hseih et al., '06). Measuring membrane trafficking rate changes induced by oligomers via formazan morphological shifts has been used in cell lines to discover Abeta oligomer-blocking drugs (Maezawa et al., '06, Liu and Schubert '97, '04, '06, Rana et al., '09, Hong et al., '08) that lower Abeta brain levels in rodents in vivo (Hong et al., '09). Similar procedures for exocytosis assays/MTT assays can be found in the literature. See e.g., Liu Y, et. al., Detecting bioactive amyloid beta peptide species in Alzheimer's disease. J Neurochem. 2004 November; 91(3):648-56; Liu Y, and Schubert D. "Cytotoxic amyloid peptides inhibit cellular 3-(4,5-dimethylthiazol-2-yl)-2,5-diphenyltetrazolium bromide (MTT) reduction by enhancing MTT formazan exocytosis." J Neurochem. 1997 December; 69(6):2285-93; and Liu Y, and Schubert D. "Treating Alzheimer's disease by inactivating bioactive amyloid beta peptide" Curr. Alzheimer Res. 2006 April; 3(2):129-35. Therefore the approach is valid.

The present exocytosis assay was adapted for use with mature primary neuronal cultures grown for 3 weeks in vitro. See WO 2011/106785, which is incorporated herein by reference in its entirety. Abeta oligomers cause a dose-dependent decrease in the amount of intracellular vesicles (puncta) filled with reduced purple formazan as measured via image processing using a Cellomics VTI automated microscopy system. Photomicrographs for a cultured neuronal cell exposed to vehicle alone show vesicles filled with formazan; wherein a photomicrograph of a neuronal cell exposed to vehicle plus Abeta oligomer shows considerably fewer vesicles filled with formazan and instead shows exocytosed formazan which, when encountering the extracellular environment, precipitates into crystals. Increasing the amount of Abeta oligomers eventually results in overt toxicity. Thus, the concentration of neuroactive Abeta oligomers used in the assay is much lower than that causing cell death. The inventors confirmed that the assay is operative by showing that the effects of Abeta oligomer are blocked upon addition of anti-Abeta antibody but antibody alone has no effect on its own (data not shown). When configured in this manner, the assay is able to detect compounds that inhibit nonlethal effects of Abeta oligomer whether these compounds act via disruption of oligomers, inhibition of oligomer binding to neurons, or counteraction of signal transduction mechanisms of action initiated by oligomer binding.

The methods used to generate the results were as follows in the Membrane Trafficking/Exocytosis (MTT) assay.

Primary hippocampal neurons from E18 Sprague-Dawley rat embryos were plated at optimized concentrations in 384 well plates in NB media (Invitrogen). Neurons were maintained in cultures for 3 weeks, with twice weekly feeding of NB media with N2 supplement (Invitrogen). These neurons express the full complement of synaptic proteins characteristic of neurons in the mature brain, and exhibit a complex network of activity-dependent electrical signaling. Neurons and glia in such cultures have molecular signaling networks exhibiting excellent registration with intact brain circuitry, and for this reason have been used for over two decades as a model system for learning and memory (See e.g. Kaech S, Banker G. Culturing hippocampal neurons. Nat Protoc. 2006; 1(5):2406-15. Epub 2007 Jan. 11; See also Craig A M, Graf E R, Linhoff M W. How to build a central synapse: clues from cell culture. Trends Neurosci. 2006 January; 29(1):8-20. Epub 2005 Dec. 7. Review).

A test compound was added to cells at concentrations ranging from 100 uM to 0.001 nM followed by addition of vehicle or Abeta oligomer preparations (3 μM total Abeta protein concentration), and incubated for 1 to 24 hr at 37° C. in 5% $CO_2$. MTT reagent (3-(4,5-dimethylthizaol-2yl)-2,5diphenyl tetrazolium bromide) (Roche Molecular Biochemicals) was reconstituted in phosphate buffered saline to 5 mg/mL. 10 μL of MTT labeling reagent is added to each well and incubated at 37° C. for 1 h, then imaged. Exocytosis was assessed by automated microscopy and image processing to quantify the amount of endocytosed and exocytosed formazan.

Each assay plate was formatted so that compounds are tested with and without Abeta oligomer on each plate. This design eliminates toxic or metabolically active compounds early on in the screening cascade (at the level of the primary screen). Reduced formazan was first visible in intracellular vesicles. Eventual formazan exocytosis was accelerated via Abeta oligomers.

In the presence of an effective concentration of active test compound, the membrane traffic changes are blocked and the cell is indistinguishable from a vehicle-treated neuron. Furthermore, in some cases this effect of test compound appears to be independent of whether test compound is added before or after exposure of the cells to Abeta oligomer, which indicates a therapeutic as well as a prophylactic effect. Adequate concentration of active test compound blocks membrane trafficking effects of Abeta oligomer seen in this assay. Ascending doses of compounds according to any embodiment described herein, that are selective, high affinity agonists of the sigma-2 receptor, stop oligomer effects and make the cultures look more like vehicle-treated cultures.

Compounds according to any embodiment described herein, that are selective, high affinity agonists of the sigma-2 receptor that are effective for inhibiting Abeta oligomer toxicity are promising as therapeutic and prophylactic modalities for amyloid beta oligomer toxicity related cognitive decline such as that seen in Alzheimer's disease.

Synthetic Abeta oligomers were dosed in the membrane trafficking assay, where it exhibited an $EC_{50}$ of 820 nM. Each concentration of Abeta was tested against several concentrations of each test compound. Active compounds caused a rightward shift in the $EC_{50}$ by almost two orders of magnitude. When the data were fitted to classical linear and non linear models, the data were linear with a Schild analysis (Hill slope nH of 1), which indicates that the compounds exhibit true pharmacological competition between oligomers and compound for targets that mediate membrane trafficking.

Abeta oligomers derived from Alzheimer's patient's brains can be dosed against test compounds, and a rightward shift is also expected to be exhibited by compound exposure. Specifically, at effective doses, the active test compounds exhibit pharmacological competition with both synthetic and human Alzheimer's patient-derived oligomers.

Experimental Controls

Abeta 1-42 oligomers made according to published methods were used as positive controls. [See e.g. Dahlgren et al., "Oligomeric and fibrillar species of amyloid-beta peptides differentially affect neuronal viability" J Biol Chem. 2002 Aug. 30; 277(35):32046-53. Epub 2002 Jun. 10; LeVine H 3rd. "Alzheimer's beta-peptide oligomer formation at physiologic concentrations" Anal Biochem. 2004 Dec. 1; 335(1): 81-90; Shrestha et. al, "Amyloid beta peptide adversely affects spine number and motility in hippocampal neurons" Mol Cell Neurosci. 2006 November; 33(3):274-82. Epub 2006 Sep. 8; Puzzo et al., "Amyloid-beta peptide inhibits activation of the nitric oxide/cGMP/cAMP-responsive element-binding protein pathway during hippocampal synaptic plasticity" J Neurosci. 2005 Jul. 20; 25(29):6887-97; Barghorn et al., "Globular amyloid beta-peptide oligomer—a homogenous and stable neuropathological protein in Alzheimer's disease" J Neurochem. 2005 November; 95(3): 834-47. Epub 2005 Aug. 31; Johansson et al., Physiochemical characterization of the Alzheimer's disease-related peptides A beta 1-42 Arctic and A beta 1-42 wt. FEBS J. 2006 June; 2 73(12):2618-30] as well as brain-derived Abeta oligomers (See e.g. Walsh et al., Naturally secreted oligomers of amyloid beta protein potently inhibit hippocampal long-term potentiation in vivo. Nature (2002). 416, 535-539; Lesne et al., A specific amyloid-beta protein assembly in the brain impairs memory. Nature. 2006 Mar. 16; 440(7082): 352-7; Shankar et al, Amyloid-beta protein dimers isolated directly from Alzheimer's brains impair synaptic plasticity and memory. Nat Med. 2008 August; 14(8):837-42. Epub 2008 Jun. 22). It should be noted that any Abeta oligomer preparation can be used in this assay or as a control, including preparations described in the patent literature, cited above and incorporated by reference in their entirety.

Various different Abeta oligomer preparations were demonstrated to cause an Abeta effect in the membrane trafficking assay, including notably oligomer preparations isolated from the brain of Alzheimer's disease patients.

Oligomers were isolated from postmortem human hippocampus or prefrontal cortex without the use of detergents and inhibited membrane trafficking in a dose-dependent manner with a Kd of 6 pMolar. Human Alzheimer's disease patient-derived Abeta oligomers (137 pM) produce a statistically significant inhibition of membrane trafficking compared to vehicle. Compound 4-(3-(4-(trifluoromethyl)benzylamino)butyl)-2-methoxyphenol eliminates the membrane trafficking deficits induced by AD brain-derived Abeta oligomers, but does not affect trafficking when dosed in the absence of Abeta.

Although potencies of various Abeta oligomer preparations differ (for example native Alzheimer's isolates are more potent than any of the synthetic preparations tested-data not shown), the results are qualitatively the same: pathologies mediated by oligomers are countered by compounds according to any embodiment herein that act as sigma-2 functional antagonists.

Primary Neuronal Cultures

Optimal cell density is determined based on cellular response to Abeta oligomers using the exocytosis assay as a readout, and immunohistochemical analysis of the relative proportion of glia to neurons in the cultures. Cultures are monitored on a weekly basis with immunohistochemistry and image processing-based quantification to monitor the percentage of the cultures that are neurons vs. glia (Glial cells). Cultures containing more than 20% glia (positive for GFAP) vs. neurons (staining positively with (chicken polyclonal) antibodies (Millipore) directed against MAP2 at 1:5000 (concentration variable)) at the screening age of 21 days in vitro (21 DIV) are rejected.

Abeta Oligomer Preparations

Human amyloid peptide 1-42 was obtained from a number of commercial vendors such as California Peptide, with lot-choice contingent upon quality control analysis. Quality controls of oligomer preparations consist of Westerns to determine oligomer size ranges and relative concentrations, and the MTT assay to confirm exocytosis acceleration without toxicity. Toxicity was monitored in each image-based assay via quantification of nuclear morphology visualized with the DNA binding blue dye DAPI (Invitrogen). Nuclei that are fragmented are considered to be in late stage apoptosis (Majno and Joris '95) and the test would be rejected. Peptide lots producing unusual peptide size ranges or significant toxicity at a standard 1.5 µM concentration on neurons would also be rejected.

Plate-based controls—The assay optimization was considered complete when reformatted plates achieve a minimum of statistically significant two-fold separation between vehicle and Abeta oligomer-treated neurons (p<0.01, Student's t-test, unequal variance) on a routine basis, with no more than 10% CV between plates.

Statistical Software and Analysis

Data handling and analysis were accomplished by Cellomics VTI image analysis software and STORE automated database software. Because of the low dynamic range and neuronal well-to-well variability after three weeks in culture, statistical comparisons are made via pairwise Tukey-Kramer analysis to determine the significance of the separation between compound+Abeta oligomers from Abeta alone, and between compound alone from vehicle. The ability of mature primary neurons to more closely approximate the electrophysiologically mediated signal transduction network of the adult brain justifies this screening strategy. Power analysis was set for a number of replicate screening wells that minimized false negatives (e.g. N=4). Test compounds of the disclosure significantly reverse the effects of Abeta oligomers on membrane trafficking but do not affect neuronal metabolism themselves.

Selected compounds according to any embodiment described herein, were dosed in the MTT assay described herein, prior to Abeta oligomer addition and were shown to block the Abeta oligomer-induced membrane trafficking deficits with the indicated $EC_{50}$. Specifically, these results indicate that compounds block/abate the activity/effect of Abeta oligomer on membrane trafficking of neuron cells at micromolar concentrations. Certain compounds in Table 1 were shown to block the Abeta oligomer-induced acceleration of exocytosis with the indicated $EC_{50}$. Accordingly, the compounds in Table 1 significantly blocked Abeta oligomer-mediated changes in membrane trafficking. These results indicate that compounds block/abate the activity/effect of Abeta oligomer on neuron cells and that compounds according to any embodiment described herein, can be used to block the Abeta oligomer induced membrane trafficking abnormalities.

In some embodiments, compounds according to any embodiment described herein, inhibit Abeta oligomer-induced membrane trafficking deficits, with an $EC_{50}$ of not more than 20 uM, not more than 15 uM, not more than 10 uM, not more than 5 uM, not more than 1 uM, not more than 0.5 uM, when tested according to the membrane trafficking assay protocol provided herein.

Example 6: Pharmacokinetic and Metabolic Stability Studies

A first pharmacokinetic study was performed in microsomes of mice mouse liver microsomes, MLM). The studies were performed according to Obach, R. S et al. (1997) J. Pharmacol. Exp. Ther., 283: 46-58, which is incorporated herein by reference. The half-life ($t_{1/2}$) of the compounds in MLM assay is shown in Table 1.

In some embodiments, a compound according to any embodiment described herein, or pharmaceutically acceptable salts thereof, exhibits a half-life ($t\frac{1}{2}$) in a mouse liver microsome (MLM) assay, as provided herein, of at least 5 minutes, at least 10 minutes, at least 25 minutes, at least 50 minutes, at least 100 minutes, or at least 200 minutes.

The results indicate that several of the compounds tested had a substantially longer half-life in mouse liver microsomes. This result portends greater bioavalability after oral administration for these compounds. The same compounds have been tested by the membrane trafficking assay described above and their activity as referred to herein.

If the rate of intrinsic clearance of test compound was rapid, it is suggestive of substantial first pass metabolism. In order to improve pharmacokinetic properties, compounds were designed to enhance metabolic stability and improve drug-like properties. Microsomal stability experiments and plasma stability experiments were performed to determine metabolic and hepatic stability of candidate compounds. In some embodiments, in vitro microsomal stability was normalized to standard compound, 4-(3-(4-(trifluoromethyl) benzylamino)butyl)-2-methoxyphenol, an early lead compound that had a mouse liver microsome $t\frac{1}{2}$ (min) of 16. Compounds of the invention are superior to the this early lead compound.

A second PK study can be conducted in vivo and involves measuring plasma levels and brain levels for test compounds administered by various routes and in an acute or chronic manner, as follows:

HPLC-MS Optimization

A solution of each test compound is prepared and infused into the TSQ Quantum spectrometer (Fisher Thermo Scientific) source via syringe pump at a constant rate. Full scan MS (mass spectroscopy) analysis is conducted and total ion current chromatograms and corresponding mass spectra are generated for each test compound in both positive and negative ionization modes. The precursor ions for MS/MS are selected from either the positive or the negative mass spectrum, as a function of the respective ion abundance. In addition, product ion MS/MS analysis is performed in order to determine the appropriate selected fragmentation reaction for use in quantitative analysis. The final reaction monitoring parameters are chosen to maximize the ability to quantify the test compound when present within a complex mixture of components. Following identification of the specific SRM transition to be used for each test compound, the detection parameters are optimized using the automated protocol in the TSQ Quantum Compound Optimization workspace. Finally, the chromatographic conditions to be used for LC-MS analysis are identified by injection and separation of the analyte on a suitable LC column and adjustment of the gradient conditions is performed as necessary.

Formulation for IV Dosing:

The solubility of the test compound in phosphate-buffered saline, pH 7.4 (PBS) is first evaluated by visual inspection. PBS is used as the vehicle if the compound is soluble at the target concentration. (Other vehicles that are compatible with IV dosing may be evaluated if the compound is not completely soluble in PBS. Such vehicles include DMSO, polyethylene glycol (PEG 400), Solutol HS 15, and Cremophor EL among others.) In the experiments reported here a single bolus, 10 mg/kg, of test compound is administered IV.

Formulation for PO dosing: The solubility of the test compound in PBS is first evaluated. PBS is used as the vehicle if the compound is soluble at the target concentration. (DMSO/Solutol HS 15/PBS (5/5/90, v/v/v), or DMSO/ 1% methylcellulose (5/95, v/v) may be used if the test compound is not completely soluble in PBS at the respective concentration.)

Linearity in Plasma

Aliquots of plasma are spiked with the test compounds at the specified concentrations. The spiked samples are processed using acetonitrile precipitation and analyzed by HPLC-MS or HPLC-MS/MS. A calibration curve of peak area versus concentration is constructed. The reportable linear range of the assay is determined, along with the lower limit of quantitation (LLQ).

Quantitative Bioanalysis of Plasma Samples

The plasma samples are processed using acetonitrile precipitation and analyzed by HPLC-MS or HPLC-MS/MS. A plasma calibration curve was generated. Aliquots of drug-free plasma are spiked with the test compound at the specified concentration levels. The spiked plasma samples are processed together with the unknown plasma samples using the same procedure. The processed plasma samples (dried extracts) are typically stored frozen (−20° C.) until the HPLC-MS or HPLC-MS/MS analysis. The dried extracts are reconstituted into a suitable solvent and after centrifugation were analyzed by HPLC-MS or HPLC-MS/MS. Peak areas are recorded, and the concentrations of the test compound in the unknown plasma samples are determined using the respective calibration curve. The reportable linear range of the assay is determined, along with the lower limit of quantitation (LLQ).

Animals used in the study are typically male C57BL/6 mice weighing 20-30 g each or male Sprague-Dawley rats weighing 180-250 g. Three animals are treated for each administration condition and each time point, so that each animal is subjected to only one blood draw. Subcutaneous compound administration was accomplished by intraperitoneal injection. Per oral administration is accomplished by gastric gavage. Intravenous administration is accomplished via jugular catheter.

Following compound administration at various concentrations, plasma samples are collected at, e.g., 10, 30, 60, 120, 240, 360, 480 and 1440 min.

Plasma Sample Collection from Mice and Rats

Animals are sedated under general inhalant anesthesia (3% isoflurane) for blood collection by cardiac puncture (mice) or jugular catheter (rats). Blood aliquots (300-400 µL) are collected in tubes coated with lithium heparin, mixed gently, and are kept on ice and centrifuged at 2,500×g for 15 minutes at 4° C., within 1 hour of collection. The plasma is then harvested and kept frozen at −20° C. until further processing.

Animal Dosing Design—In Vivo PK—Non Cannulated, Nonfasted Animals

Group 1: SC, n=3 animals per time point (24 animals total) or

IV, n=3 animals per time point (24 animals total)

Group 2: PO, n=3 animals per time point (24 animals total)

Group 3: Control animals (for drug-free blood), n=5 mice

Each animal is subject to one blood draw and one brain collection.

Brain Sample Collection from Animals

Immediately after blood sampling, animals are decapitated and the whole brains are quickly removed, rinsed with cold saline (0.9% NaCl, g/mL), surface vasculature ruptured, blotted dry with gauze, weighted, kept on ice until further processing within one hour of collection. Each brain is homogenized in 1.5 mL cold phosphate buffered saline, pH 7.4 (mice=1.5 mL, rats=), for 10 seconds on ice using the Power Gen 125. The brain homogenate from each brain is then stored at −20° C. until further processing.

Linearity in Brain Samples

Aliquots of brain homogenate are spiked with the test compound at the specified concentrations. To each brain aliquot an equal volume of chilled 26% (g/mL) neutral Dextran (average molecular Weight 65,000-85,000 from Sigma, catalog number D-1390) solution is added to obtain a final Dextran concentration of 13%. The homogenate is centrifuged at 54000×g for 15 minutes at 4° C. The supernatants are subsequently processed using acetonitrile precipitation and analyzed by HPLC-MS/MS. A calibration curve of peak versus concentration i constructed. The reportable linear range of the assay is determined, along with the lower limit of quantitation (LLQ).

Quantitative Analysis of Brain Samples

To each brain homogenate aliquot an equal volume of chilled 26% (g/mL) neutral Dextran (average molecular Weight 65,000-85,000 from Sigma, catalog number D-1390) solution is added to obtain a final Dextran concentration of 13%. The homogenate is centrifuged at 54000×g for 15 minutes at 4° C. The supernatants are subsequently processed using acetonitrile precipitation and analyzed by HPLC-MS/MS. A brain calibration curve is generated. Aliquots of drug-free brain homogenate are spiked with the test compound at specified concentration levels. The spiked brain homogenate samples are processed together with the unknown brain homogenate samples using the same procedure. The processed brain samples are stored at −20° C. until the LC-MS/MS analysis, at which time peak areas were recorded, and the concentrations of test compound in the unknown brain samples were determined using the respective calibration curve. The reportable linear range of the assay was determined along with the lower limit of quantitation (LLQ).

Brain Penetratrability

The concentrations of test compound in brain (ng/g tissue) and in plasma (ng/mL) as well as the ratio of the brain concentration and the plasma concentration at each time point are determined by LC-MS/MS and reported as described above.

Pharmacokinetics

Plots of plasma concentration of compound versus time are constructed. The fundamental pharmacokinetic parameters of compound after oral and SC dosing (AUClast, AUCINF, T½, Tmax, and Cmax) are obtained from the non-compartmental analysis (NCA) of the plasma data using WinNonlin (Pharsight). Noncompartmental analysis does not require the assumption of a specific compartmental model for either drug or metabolite. NCA allows the application of the trapezoidal rule for measurements of the area under a plasma concentration-time curve (Gabrielsson, J. and Weiner, D. Pharmacokinetic and Pharmacodynamic Data Analysis: Concepts and Applications. Swedish Pharmaceutical Press. 1997).

Definitions of Terms Reported

Area Under the Curve (AUC)—Measure of the total amount of unchanged drug that reaches the systemic circulation. The area under the curve is a geometric measurement that was calculated by plotting concentration versus time and summing the incremental areas of each trapezoid.

WinNonlin has two computational methods for calculation of the area: the linear trapezoidal method and the linear-log trapezoidal method. Because the linear trapezoidal method may give biased results on the descending part of the concentration-time curve and overestimate the AUC, WinNonlin provides the linear-log option for calculation of AUC. By default, the log-linear trapezoidal method is used to measure the post-Tmax area for the remainder of the plasma concentration-time curve.

$AUC_{last}$: area under the curve from the time of dosing to the time of last observation that was greater than the limit of quantitation.

$AUC_{INF}$: Area under the curve from the time of dosing extrapolated to infinity.

$C_{max}$—Maximum plasma drug concentration obtained after oral or non-IV administration of a drug between the time of doing and the final observed time point.

$T_{max}$—Time at maximum observed plasma concentration (Cmax) noted in minutes after administration of drug.

$T_{1/2}$—Terminal elimination half-life from both IV and non-IV dosing.

where lambda Z (z) is the first order rate constant associated with the terminal (log-linear) portion of the plasma concentration-time curve. z is estimated by linear regression of time versus log concentration.

The results are expected to show that certain test compounds exhibit good bioavailability and good brain penetrability when administered at doses ranging from 0.1 to 0.5 mg/kg acutely or chronically (daily over 5 days). Selected test compounds are evaluated for oral bioavailability in this manner.

Example 8: In Vitro Testing for hERG Inhibition

In vitro testing for hERG inhibition was performed in a standard assay (See: Haverkamp W, Breithardt G, Carnm A J, Janse M J, Rosen M R, Antzelevitch C, Escande D, Franz M, Malik M, Moss A and Shah R. (2000) *Eur Heat J* 21 (15); 1216-31). Results for test compounds for hERG inhibition ($IC_{50}$, nM) is shown in Table 1. In some embodiments, compounds according to any embodiment described herein, or pharmaceutically acceptable salts thereof, exhibit minimal hERG inhibition, with an $IC_{50}$ of greater than 300 nM, greater than 500 nM, greater than 1,000 nM, greater than 3,000 nM, greater than 5,000 nM, greater than 10,000, or greater than 20,000 nM. In particular embodiments, compounds according to any embodiment described herein, or pharmaceutically acceptable salts thereof, exhibit minimal hERG inhibition, and exhibit an $IC_{50}$ of greater than 5,000 nM, greater than 10,000, or greater than 20,000 nM.

Combined Results for particular compounds described herein, with respect to log P, membrane trafficking (uM), sigma-2 receptor affinity, sigma-1 receptor affinity microsomal stability in mouse liver microsomes (MLM) ($t_{1/2}$, min), $t_{1/2}$ normalized to CT)10914 and in vitro toxicity potassium channel hERG ($IC_{50}$, nM) are provided in Table 1:

| Example Compound | MW g/mol | LC-MS [MH]+ | log P | EC$_{50}$ Abeta (uM) | S1 K$_i$ (nM) | S2 K$_i$ (nM) | MLM T$_{1/2}$ (min.) | T$_{1/2}$* | hERG IC$_{50}$ (nM) |
|---|---|---|---|---|---|---|---|---|---|
| 1 | 383.5 | 384.4 | 5.16 | | 0.7 | 0.2 | | | 740 |
| 2 | 357.5 | 358.5 | 4.67 | >15 | 0.9 | 0.6 | | | 9200 |
| 3 | 383.6 | 384.5 | 6.22 | 0.25 | | 0.76 | | | |
| 4 | 371.5 | 372.2 | 5.35 | | 0.5 | 0.8 | | | 2200 |
| 5 | 323.9 | 324.7 | 4.4 | >15 | | 0.8 | | | 75 |
| 6 | 343.4 | 344.4 | 4.49 | >15 | 0.3 | 1 | | | 750 |
| 7 | 343.4 | 344.6 | 4.31 | >15 | 0.7 | 1.5 | | | 1500 |
| 8 | 281.8 | 282.9 | 3.16 | 0.25 | 0.4 | 1.6 | | | 14000 |
| 9 | 437.6 | 438.5 | 6.58 | 0.5 | 13 | 1.8 | 114 | 166 | 1000 |
| 10 | 295.8 | 296.9 | 3.8 | 1.26 | 0.7 | 2.1 | | | 11000 |
| 11 | 404.0 | 405.2 | 6.31 | 3 | 14, 69 | 2.2 | 26, | 87 | 1500 |
| 12 | 343.4 | 344.1 | 4.13 | | 1 | 2.7 | | | 970 |
| 13 | 329.4 | 330.4 | 3.85 | | 1 | 2.9 | | | 2500 |
| 14 | 329.4 | 330.2 | 3.71 | | 1.9 | 3 | | | 18000 |
| 15 | 387.6 | 388.7 | 5.85 | 1.6 | 40 | 4.5 | 14 | 20 | 2200 |
| 16 | 309.9 | 310.9 | 4.03 | | 0.8 | 4.5 | | | 840 |
| 17 | 315.4 | 316.4 | 3.43 | 2.24 | 1.3 | 5.1 | | | 11000 |
| 18 | 293.4 | 294.4 | 2.72 | 0.25 | 2.6 | 5.6 | | | 29000 |
| 19 | 293.4 | 294.5 | 3.57 | <0.25 | 2.2 | 6 | | | 37000 |
| 20 | 295.8 | 296.9 | 3.57 | | 1 | 6.1 | | | 1700 |
| 21 | 359.5 | 360.4 | 5.26 | 20 | 8 | 6.2 | 11 | 37 | 830 |
| 22 | 309.9 | 310.8 | 3.85 | | 1 | 7 | | | 1700 |
| 23 | 392.0 | 393.2 | 6.49 | 0.95 | 140 | 9.2 | 8.2 | 25 | 2200 |
| 24 | 397.0 | 398.1 | 6.31 | 20 | | 10 | | | |
| 25 | 279.4 | 280.5 | 3.11 | | 2.3 | 10 | | | 4000 |
| 26 | 403.5 | 404.6 | 3.35 | 20 | | 11 | | | |
| 27 | 376.6 | 377.7 | 6.22 | 0.4 | | 15 | | | |
| 28 | 397.5 | 398.2 | 5.68 | 4 | 6.1 | 18 | 60 | 60 | 10200 |
| 29 | 392.6 | 393.7 | 5.55 | 20 | | 19 | | | |
| 30 | 381.5 | 382.7 | 6.97 | 2.2 | 4.1 | 19 | 83 | 78 | 6500 |
| 31 | 348.0 | 349.2 | 6.7 | 0.7 | 41 | 28 | 21 | 20 | 10900 |
| 32 | 474.1 | 475.3 | 6.37 | 6.9 | | 32 | | | |
| 33 | 341.6 | 342.6 | 7.04 | 1.92 | | 33 | | | |
| 34 | 423.6 | 424.7 | 6.15 | 20 | 5.3 | 39 | 60 | 60 | 23000 |
| 35 | 383.5 | 384.5 | 5.31 | 20 | 56 | 39 | 60 | 60 | 13400 |
| 36 | 373.5 | 374.6 | 5.41 | 20 | 12 | 40 | 25 | 129 | 10000 |
| 37 | 466.6 | 467.8 | 6.18 | 0.2 | 8.8 | 40 | 38 | 36 | 26200 |
| 38 | 369.5 | 370.5 | 4.85 | 4.5 | 190 | 42 | 84 | 79 | 16200 |
| 39 | 383.5 | 384.6 | 5.49 | 0.6 | 25 | 43 | | | 8200 |
| 40 | 455.6 | 456.9 | 6.28 | 0.83 | 170 | 44 | | | 9600 |
| 41 | 390.0 | 391.2 | 5.87 | 1.6 | 16 | 67 | 35 | 60 | 4000 |
| 42 | 349.9 | 350.7 | 5.04 | 20 | 150 | 71 | 88 | 83 | 6900 |
| 43 | 417.1 | 418.3 | 6.37 | 0.3 | 61 | 74 | 29 | 88 | 4900 |
| 44 | 411.5 | 412.3 | 6.27 | 1.4 | 260 | 79 | | | 9200 |
| 45 | 356.6 | 357.7 | 6.26 | 2.6 | | 85 | | | |
| 46 | 474.1 | 475.6 | 6.37 | 4.8 | | 86 | | | |
| 47 | 404.6 | 405.4 | 5.55 | | 1913 | 90 | | | 14000 |
| 48 | 349.9 | 350.7 | 5.3 | 1.8 | | 93 | | | |
| 49 | 404.6 | 405.7 | 5.74 | 575 | 94 | | | 2400 | |
| 50 | 313.5 | 314.7 | 6.31 | 1.7 | | 96 | | | |
| 51 | 440.6 | 441.4 | 4.55 | 20 | | 100 | | | |
| 52 | 327.5 | 328.6 | 6.9 | 4.8 | | 110 | | | |
| 53 | 364.0 | 365.2 | 5.41 | 20 | 74 | 110 | 28 | 26 | 13300 |
| 54 | 335.5 | 336.3 | 7.02 | 3.2 | | 120 | | | |
| 55 | 337.9 | 338.9 | 5.47 | 2.5 | 25 | 120 | 3.6 | 11 | 7200 |
| 56 | 362.5 | 362.8 | 4.49 | | 571 | 139 | | | 1900 |
| 57 | 329.5 | 330.4 | 5.21 | 0.73 | | 150 | | | |
| 58 | 347.5 | 348.6 | 4.94 | 0.5 | 64 | 160 | 39 | 79 | 14000 |
| 59 | 347.5 | 348.5 | 5.12 | 0.25 | 600 | 160 | | | 73000 |
| 60 | 376.6 | 377.8 | 6.91 | 1.0 | | 210 | | | |
| 61 | 353.5 | 354.2 | 6.38 | 4.7 | 160 | 230 | 53 | 77 | 7300 |
| 62 | 333.5 | 334.2 | 4.4 | 0.8 | 130 | 230 | 60 | 122 | 41000 |
| 63 | 466.1 | 467.2 | 7.42 | 1.5 | | 240 | | | |
| 64 | 318.4 | 319.6 | 3.52 | | 535 | 268 | | | 11000 |
| 65 | 335.5 | 336.7 | 4.13 | | 1200 | 270 | | | 2300 |
| 66 | 333.5 | 334.7 | 4.84 | 20 | 39 | 290 | 8.8 | 45 | 16000 |
| 67 | 482.1 | 483.2 | 6.8 | 13 | | 300 | | | |
| 68 | 303.5 | 304.4 | 5.65 | 20 | 500 | 300 | 11 | 57 | 27000 |
| 69 | 335.5 | 336.7 | 6.93 | 4.2 | | 320 | | | |
| 70 | 421.5 | 422.4 | 6.95 | 20 | 33 | 340 | 14 | 13 | 16300 |
| 71 | 396.5 | 397.8 | 4.61 | | 62 | 340 | | | 17000 |
| 72 | 355.4 | 356.6 | 5.32 | 20 | 770 | 400 | 2.1 | 11 | 80000 |
| 73 | 349.9 | 350.4 | 4.86 | 0.7 | 29 | 410 | 87 | 176 | 24000 |
| 74 | 345.5 | 346.5 | 4.54 | 12.9 | | 430 | | | |
| 75 | 362.9 | 363.8 | 4.33 | 0.25 | 690 | 690 | | | 15000 |
| 76 | 371.5 | 371.7 | 6.21 | 0.3 | 370 | 790 | 3.5 | 7 | 18000 |
| 77 | 335.9 | 336.8 | 4.58 | 20 | 540 | 800 | 44 | 41 | 15200 |

-continued

| Example Compound | MW g/mol | LC-MS [MH]⁺ | log P | EC$_{50}$ Abeta (uM) | S1 K$_i$ (nM) | S2 K$_i$ (nM) | MLM T$_{1/2}$ (min.) | T$_{1/2}$* | hERG IC$_{50}$ (nM) |
|---|---|---|---|---|---|---|---|---|---|
| 78 | 335.5 | 336.7 | 6.93 | 0.56 | | 940 | | | |
| 79 | 319.5 | 320.2 | 4.12 | 1.9 | 1200 | 940 | 74 | 150 | 29000 |
| 80 | 335.5 | 336.5 | 6.93 | 0.64 | | 1300 | | | |
| 81 | 346.5 | 347.6 | 3.87 | | 160 | 2500 | | | 32000 |
| 82 | 433.6 | 434.6 | 4.11 | 20 | 380 | 2800 | 60 | 60 | 100000 |
| 83 | 369.5 | 370.4 | 5.31 | 3.8 | 1000 | 1000 | | | 14000 |
| 84 | 309.9 | 310.5 | 4.67 | 0.25 | 1000 | 1000 | | | 3900 |
| 85 | 343.4 | 344.6 | 4.95 | 0.98 | 1000 | 1000 | | | 11000 |
| 86 | 357.6 | 358.6 | 6.37 | 0.22 | | | | | |
| 87 | 362.0 | 363.3 | 7.13 | 20 | | | | | |
| 88 | 393.6 | 394.5 | 3.54 | | | | | | |
| 89 | 405.6 | 406.6 | 5.37 | | | | | | |
| 90 | 440.1 | 441.3 | 7.02 | 20 | | | | | |
| 91 | 277.4 | 278.7 | 3.99 | 20 | | | | | |
| 92 | 275.4 | 276.4 | 5.06 | 20 | | | | | |
| 93 | 273.4 | 274.5 | 4.36 | 20 | | | 3.4 | 9 | |
| 94 | 271.4 | 272.6 | 5.43 | 20 | | | 1.8 | 5 | |
| 95 | 293.8 | 294.6 | 4.45 | 20 | | | 1.5 | 4 | |
| 96 | 291.9 | 292.3 | 5.52 | 1.6 | | | 6.2 | 16 | |
| 97 | 369.6 | 370.7 | 5.78 | 10 | | | 8.7 | 15 | |
| 98 | 385.6 | 386.4 | 5.11 | 20 | | | 1.7 | 4 | |
| 99 | 331.5 | 332.3 | 4.08 | 20 | | | 7.4 | 19 | |
| 100 | 315.5 | 316.9 | 4.75 | 13.6 | | | 4.5 | 12 | |
| 101 | 343.5 | 344.7 | 5.57 | 9.6 | | | 1.8 | 5 | |
| 102 | 359.5 | 360.5 | 4.9 | 20 | | | 1.5 | 4 | |
| 103 | 287.4 | 288.3 | 4.76 | 20 | | | 1.1 | 2 | |
| 104 | 289.4 | 290.4 | 3.69 | 20 | | | 1.3 | 2 | |
| 105 | 376.0 | 377.3 | 5.72 | 20 | | | 1.3 | 2 | |
| 106 | 373.6 | 374.7 | 5.35 | 20 | | | 3.9 | 7 | |
| 107 | 341.5 | 342.4 | 5.21 | 20 | | | 3.5 | 6 | |
| 108 | 345.5 | 344.5 | 4.46 | 20 | | | 7.3 | 12 | |
| 109 | 329.5 | 330.8 | 5.13 | 20 | | | 5.4 | 9 | |
| 110 | 387.6 | 388.5 | 5.73 | 20 | | | 2.6 | 4 | |
| 111 | 364.0 | 365.2 | 5.68 | 20 | | | 6.8 | 23 | |
| 112 | 343.5 | 344.4 | 5.59 | | | | 4.9 | 16 | |
| 113 | 359.5 | 360.7 | 4.92 | 20 | | | 8.2 | 27 | |
| 114 | 355.6 | 356.8 | 5.63 | | | | 1.8 | 6 | |
| 115 | 367.5 | 368.4 | 4.9 | 20 | | | | | |
| 116 | 337.5 | 338.7 | 5.71 | | | | | | |
| 117 | 341.9 | 342.6 | 6.47 | | | | | | |
| 118 | 339.5 | 340.9 | 4.64 | | | | | | |
| 119 | 426.0 | 427.0 | 6.67 | | | | | | |
| 120 | 343.9 | 344.6 | 5.4 | | | | | | |
| 121 | 371.9 | 372.9 | 5.66 | | | | | | |
| 122 | 421.6 | 422.4 | 5.91 | | | | | | |
| 123 | 387.9 | 388.8 | 6.67 | 0.3 | | | | | |
| 124 | 395.6 | 396.7 | 6.45 | 0.2 | | | | | |
| 125 | 372.6 | 373.4 | 5.23 | 0.25 | | | | | |
| 126 | 388.6 | 389.9 | 4.61 | 0.3 | | | | | 7400 |
| 127 | 436.6 | 437.7 | 6.41 | 0.3 | | | | | 3300 |
| 128 | 445.6 | 446.7 | 7.19 | 20 | | | | | |
| 129 | 383.5 | 384.4 | 5.13 | 1.3 | | | | | 24000 |
| 130 | 422.6 | 423.6 | 5.97 | 0.3 | | | | | |
| 131 | 331.5 | 332.8 | 6.24 | 20 | | | | | |
| 132 | 412.0 | 413.2 | 6.91 | 20 | | | | | |
| 133 | 386.6 | 387.6 | 5.68 | 2.2 | | | | | |
| 134 | 321.4 | 322.2 | 5.01 | 20 | | | | | |
| 135 | 389.0 | 390.2 | 5.69 | 20 | | | | | |
| 136 | 364.0 | 365.0 | 5.58 | 1.5 | | | | | 2100 |
| 137 | 438.6 | 439.8 | 5.34 | 0.15 | | | | | |
| 138 | 405.0 | 406.1 | 5.07 | 0.45 | | | | | |
| 139 | 375.6 | 376.9 | 6.03 | 20 | | | | | |
| 140 | 442.7 | 443.9 | 5.78 | 20 | | | | | |
| 141 | 371.5 | 372.5 | 5.74 | 1.6 | | | | | |
| 142 | 349.9 | 350.7 | 5.22 | 20 | | | | | |
| 143 | 438.6 | 439.6 | 5.96 | 20 | | | | | |
| 144 | 414.6 | 415.4 | 4.69 | 20 | | | | | |
| 145 | 333.5 | 334.9 | 4.76 | 20 | | | | | |
| 146 | 403.0 | 404.1 | 6.14 | 0.025 | | | | | |
| 147 | 440.7 | 441.8 | 5.16 | | | | | | |
| 148 | 400.6 | 401.7 | 4.14 | | | | | | |
| 149 | 454.7 | 455.8 | 5.59 | 20 | | | | | |
| 150 | 386.6 | 387.8 | 3.86 | 20 | | | | | |
| 151 | 372.5 | 373.3 | 4.65 | 20 | | | | | |
| 152 | 389.0 | 390.2 | 5.11 | 0.26 | | | | | |

-continued

| Example Compound | MW g/mol | LC-MS [MH]+ | log P | EC$_{50}$ Abeta (uM) | S1 K$_i$ (nM) | S2 K$_i$ (nM) | MLM T$_{1/2}$ (min.) | T$_{1/2}$* | hERG IC$_{50}$ (nM) |
|---|---|---|---|---|---|---|---|---|---|
| 153 | 408.6 | 409.7 | 5.73 | 0.5 | | | | | |
| 154 | 382.5 | 383.2 | 3.37 | | | | | | |
| 155 | 458.6 | 459.6 | 6.46 | | | | | | |
| 156 | 399.0 | 400.0 | 3.83 | 0.34 | | | | | |
| 157 | 425.0 | 426.3 | 6.19 | | | | | | |
| 158 | 378.0 | 379.1 | 5.99 | 2.88 | | | | | |
| 159 | 389.6 | 390.4 | 6.36 | 10 | | | | | |
| 160 | 406.0 | 407.2 | 6.82 | 15 | | | | | |
| 161 | 432.5 | 433.5 | 4.1 | 0.27 | | | | | |
| 162 | 422.0 | 423.2 | 6 | 15 | | | | | |
| 163 | 405.6 | 406.3 | 5.54 | 15 | | | | | |
| 164 | 439.6 | 440.3 | 7.1 | | | | | | |
| 165 | 351.9 | 352.9 | 4.6 | | | | | | |
| 166 | 317.5 | 318.7 | 3.99 | | | | | | |
| 167 | 321.9 | 322.9 | 5.1 | | | | | | |
| 168 | 427.7 | 428.8 | 6.17 | | | | | | |
| 169 | 387.6 | 388.3 | 5.15 | | | | | | |
| 170 | 373.6 | 374.3 | 4.87 | | | | | | |
| 171 | 415.7 | 416.5 | 6.5 | | | | | | |
| 172 | 277.4 | 278.4 | 3.52 | | | | | | |
| 173 | 275.4 | 276.4 | 4.81 | | | | | | |
| 174 | 295.4 | 296.3 | 3.67 | | | | | | |
| 175 | 311.8 | 312.8 | 4.13 | | | | | | |
| 176 | 293.4 | 294.2 | 4.96 | | | | | | |
| 177 | 309.9 | 310.7 | 5.42 | | | | | | |
| 178 | 359.5 | 360.5 | 4.59 | | | | | | |
| 179 | 417.6 | 418.6 | 5.49 | | 430 | | | | 4000 |
| 180 | 373.6 | 374.2 | 4.87 | | | | | | 20000 |
| 181 | 434.1 | 435.6 | 5.95 | | | | | | 1800 |
| 182 | 467.6 | 468.6 | 6.22 | | 160 | | | | 2600 |
| 183 | 429.7 | 430.7 | 6.79 | | | | | | 2100 |
| 184 | 275.4 | 276.2 | 2.57 | | 220 | | | | 62000 |
| 185 | 407.6 | 408.4 | 6.16 | | | | | | 3000 |
| 186 | 309.8 | 310.9 | 3.18 | | 42 | | | | 2300 |
| 187 | 424.0 | 425.2 | 6.62 | | | | | | 1000 |
| 188 | 337.9 | 338.9 | 4 | | | | | | 400 |
| 189 | 457.6 | 458.5 | 6.89 | | 37 | | | | 5700 |
| 190 | 349.5 | 350.6 | 4.63 | | | | | | |
| 191 | 329.4 | 330.2 | 4.07 | | | | | | |
| 192 | 295.8 | 296.8 | 3.44 | | | | | | 19000 |
| 193 | 349.9 | 350.7 | 4.89 | | | | | | |
| 194 | 421.0 | 422.1 | 6.01 | | | | | | |
| 195 | 411.6 | 412.7 | 3.36 | | | | | | |
| 196 | 376.5 | 377.4 | 4.85 | | | | | | |
| 197 | 378.9 | 379.7 | 4.95 | | | | | | |
| 198 | 421.0 | 422.0 | 6.2 | | | | | | 4800 |
| 199 | 309.9 | 310.8 | 4.22 | | | | | | 1200 |
| 200 | 454.6 | 455.4 | 6.28 | | | | | | 83000 |
| 201 | 301.5 | 302.5 | 3.97 | 15 | | | | | 15000 |
| 202 | 315.5 | 316.6 | 4.62 | | | | | | |
| 203 | 332.5 | 333.6 | 3.75 | | | | | | |
| 204 | 369.6 | 370.5 | 5.7 | | | | | | |
| 205 | 445.6 | 446.7 | 6.5 | 0.59 | | | | | 3900 |
| 206 | 368.4 | 369.5 | 4.26 | | | | | | |
| 207 | 461.6 | 462.7 | 4.09 | | | | | | |
| 208 | 426.5 | 427.3 | 5.58 | | | | | | |
| 209 | 454.6 | 455.8 | 6.47 | | | | | | |
| 210 | 427.5 | 428.6 | 4.79 | 0.42 | | | | | 4400 |
| 211 | 412.0 | 413.0 | 6.23 | | | | | | |
| 212 | 425.6 | 426.8 | 6.54 | 1.8 | | | | | 27000 |
| 213 | 315.5 | 316.7 | 4.25 | 6.6 | | | | | 6400 |
| 214 | 392.0 | 393.1 | 6.27 | | | | | | |
| 215 | 418.6 | 419.6 | 5.5 | | | | | | |
| 216 | 510.7 | 511.9 | 7.65 | | | | | | |
| 217 | 394.0 | 395.0 | 4.51 | 4.6 | | | | | 7700 |
| 218 | 377.5 | 378.7 | 4.05 | | | | | | 13000 |
| 219 | 359.5 | 360.3 | 3.91 | | | | | | |
| 220 | 377.6 | 378.2 | 5.62 | | | | | | |
| 221 | 395.6 | 396.7 | 5.76 | | | | | | |
| 222 | 375.6 | 376.5 | 5.81 | | | | | | |
| 223 | 357.6 | 357.9 | 5.67 | | | | | | |
| 224 | 334.9 | 335.6 | 3.98 | | | | | | |
| 225 | 477.1 | 478.1 | 7.37 | | | | | | |
| 226 | 460.7 | 461.6 | 6.91 | 1.25 | | | | | |
| 227 | 300.4 | 301.3 | 3.38 | | | | | | |

-continued

| Example Compound | MW g/mol | LC-MS [MH]+ | log P | EC$_{50}$ Abeta (uM) | S1 K$_i$ (nM) | S2 K$_i$ (nM) | MLM T$_{1/2}$ (min.) | T$_{1/2}$* | hERG IC$_{50}$ (nM) |
|---|---|---|---|---|---|---|---|---|---|
| 228 | 468.6 | 469.8 | 6.24 | | | | | | |
| 229 | 295.8 | 296.8 | 4.03 | 15 | | | | | 21000 |
| 230 | 321.9 | 323.0 | 4.52 | 10 | | | | | 16000 |
| 231 | 295.8 | 296.6 | 4.03 | | | | | | 11000 |
| 232 | 355.4 | 356.4 | 4.79 | 15 | | | | | 29000 |
| 233 | 315.4 | 316.9 | 3.79 | 0.26 | | | | | 24000 |
| 234 | 349.9 | 350.7 | 5.68 | | | | | | |
| 235 | 349.9 | 350.9 | 5.68 | | | | | | |
| 236 | 369.5 | 370.5 | 5.31 | 15 | | | | | 20000 |
| 237 | 335.9 | 336.7 | 5.04 | | | | | | |
| 238 | 309.9 | 310.7 | 4.67 | 15 | | | | | 13000 |
| 239 | 335.9 | 336.5 | 5.04 | | | | | | 4600 |
| 240 | 335.9 | 336.9 | 5.04 | | | | | | |
| 241 | 319.5 | 320.7 | 4.57 | | | | | | |
| 242 | 319.5 | 320.3 | 4.57 | | | | | | 14000 |
| 243 | 369.5 | 370.7 | 5.31 | | | | | | |
| 244 | 333.5 | 334.6 | 5.22 | 8.5 | | | | | 4800 |
| 245 | 333.5 | 334.5 | 5.22 | >15 | | | | | 14000 |
| 246 | 349.9 | 350.9 | 5.68 | | | | | | |
| 247 | 383.5 | 384.3 | 5.95 | | | | | | |
| 248 | 392.0 | 393.0 | 5.84 | | | | | | |
| 249 | 315.5 | 316.7 | 5.07 | 15 | | | | | 9400 |
| 250 | 281.8 | 282.3 | 3.51 | 15 | | | | | 28000 |
| 251 | 333.5 | 334.6 | 5.22 | | | | | | |
| 252 | 315.5 | 316.7 | 5.07 | 15 | | | | | 7000 |
| 253 | 309.9 | 310.9 | 4.67 | 0.25 | | | | | |
| 254 | 343.4 | 344.4 | 4.95 | | | | | | 5000 |
| 255 | 281.8 | 282.9 | 3.51 | 15 | | | | | |
| 256 | 543.7 | 544.3 | 5.01 | 15 | | | | | |
| 257 | 507.6 | 508.7 | 4.08 | | | | | | |
| 258 | 508.7 | 509.6 | 2.62 | | | | | | |
| 259 | 570.7 | 571.5 | 4.03 | | | | | | |
| 260 | 520.7 | 521.7 | 2.46 | | | | | | |
| 261 | 437.6 | 438.9 | 6.58 | 0.73 | | | | | |
| 262 | 437.6 | 438.7 | 6.58 | 1.85 | | | | | |
| 263 | 455.6 | 456.9 | 6.28 | | | | | | |
| 264 | 455.6 | 456.4 | 6.28 | | | | | | |
| 265 | 383.5 | 384.7 | 5.13 | | | | | | |
| 266 | 383.5 | 384.6 | 5.13 | | | | | | |
| 267 | 375.5 | 376.5 | 5.37 | | | | | | |
| 268 | 351.9 | 352.9 | 4.83 | | | | | | |
| 269 | 494.6 | 495.4 | 2.2 | | | | | | |
| 270 | 480.6 | 481.5 | 1.81 | | | | | | |
| 271 | 598.8 | 599.7 | 4.85 | | | | | | |
| 272 | 481.6 | 482.6 | 3.35 | | | | | | |
| 273 | 522.7 | 523.7 | 3.19 | | | | | | |
| 274 | 534.7 | 535.9 | 3.24 | | | | | | |
| 275 | 383.5 | 384.1 | 5.95 | | | | | | |
| 276 | 343.4 | 344.6 | 4.95 | | | | | | |
| 277 | 385.5 | 386.5 | 5.11 | | | | | | |
| 278 | 357.5 | 358.5 | 5.23 | | | | | | |
| 279 | 522.6 | 523.6 | 1.63 | | | | | | |
| 280 | 612.8 | 613.9 | 3.85 | | | | | | |
| 281 | 495.6 | 496.4 | 2.48 | | | | | | |
| 282 | 562.7 | 563.9 | 2.47 | | | | | | |
| 283 | 295.8 | 296.4 | 3.62 | | | | | | |
| 284 | 309.9 | 310.7 | 3.98 | | | | | | |
| 285 | 357.9 | 358.9 | 4.81 | | | | | | |
| 286 | 425.5 | 426.5 | 6.11 | | | | | | |
| 287 | 337.9 | 338.7 | 4.41 | | | | | | |
| 288 | 267.8 | 267.9 | 3.1 | | | | | | |
| 289 | 295.8 | 296.8 | 4.26 | | | | | | |
| 290 | 309.8 | 310.6 | 4.08 | | | | | | |
| 291 | 323.9 | 324.9 | 4.06 | | | | | | |
| 292 | 392.0 | 393.2 | 6.49 | 1.6 | | | | | |
| 293 | 275.4 | 276.5 | 3.48 | | | | | | |
| 294 | 275.4 | 276.7 | 3.48 | | | | | | |
| 295 | 289.4 | 290.5 | 3.45 | | | | | | |
| 296 | 261.4 | 262.7 | 2.83 | | | | | | |
| 297 | 321.5 | 322.4 | 5.81 | | | | | | |
| 298 | 295.8 | 296.8 | 4.26 | | | | | | |
| 299 | 303.4 | 304.4 | 3.81 | | | | | | |
| 300 | 261.4 | 262.7 | 3.65 | | | | | | |
| 301 | 233.3 | 234.5 | 2.49 | | | | | | |
| 302 | 261.4 | 262.4 | 3.65 | | | | | | |

-continued
| Example Compound | MW g/mol | LC-MS [MH]+ | log P | EC$_{50}$ Abeta (uM) | S1 K$_i$ (nM) | S2 K$_i$ (nM) | MLM T$_{1/2}$ (min.) | T$_{1/2}$* | hERG IC$_{50}$ (nM) |
|---|---|---|---|---|---|---|---|---|---|
| 303 | 368.0 | 369.0 | 4.58 | | | | | | |
| 304 | 275.4 | 276.5 | 3.38 | | | | | | |
| 305 | 553.6 | 554.6 | 3.1 | | | | | | |
| 306 | 329.4 | 330.3 | 3.89 | | | | | | |
| 307 | 391.5 | 392.6 | 5.08 | | | | | | |
| 308 | 261.4 | 262.4 | 3.01 | | | | | | |
| 309 | 579.6 | 579.6 | 3.96 | | | | | | |
| 310 | 261.4 | 262.5 | 3.2 | | | | | | |
| 311 | 371.4 | 372.3 | 4.69 | | | | | | |
| 312 | 329.4 | 330.5 | 4.53 | | | | | | |
| 313 | 315.5 | 316.4 | 4.28 | | | | | | |
| 314 | 401.5 | 402.7 | 4.85 | | | | | | |
| 315 | 301.3 | 302.3 | 3.37 | | | | | | |
| 316 | 341.5 | 342.5 | 4.34 | | | | | | |
| 317 | 329.4 | 330.6 | 4.53 | | | | | | |
| 318 | 279.4 | 280.3 | 3.8 | | | | | | |
| 319 | 279.4 | 280.6 | 3.8 | | | | | | |
| 320 | 293.4 | 294.4 | 3.62 | | | | | | |
| 321 | 321.5 | 322.7 | 4.61 | | | | | | |
| 322 | 321.4 | 322.4 | 3.95 | | | | | | |
| 323 | 249.4 | 250.4 | 4.15 | | | | | | |
| 324 | 337.9 | 338.7 | 5.07 | | | | | | |
| 325 | 303.5 | 304.6 | 4.47 | | | | | | |
| 326 | 307.4 | 308.4 | 3.6 | | | | | | |
*normalized to 4-(3-(4-(trifluoromethyl)benzylamino)butyl)-2-methoxyphenol
SYNTHETIC EXAMPLES
Example Syn 1: Preparation of Example Compound 9
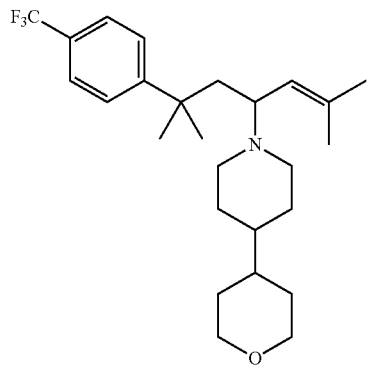 [SMILES: CC(C)=CC(CC(C)(C)c1ccc(C(F)(F)F)cc1)N1CCC(C2CCOCC2)CC1]
Example 9
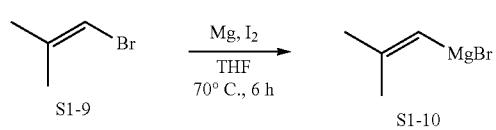
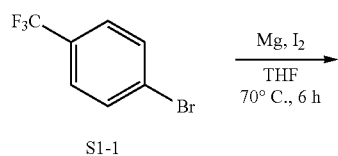
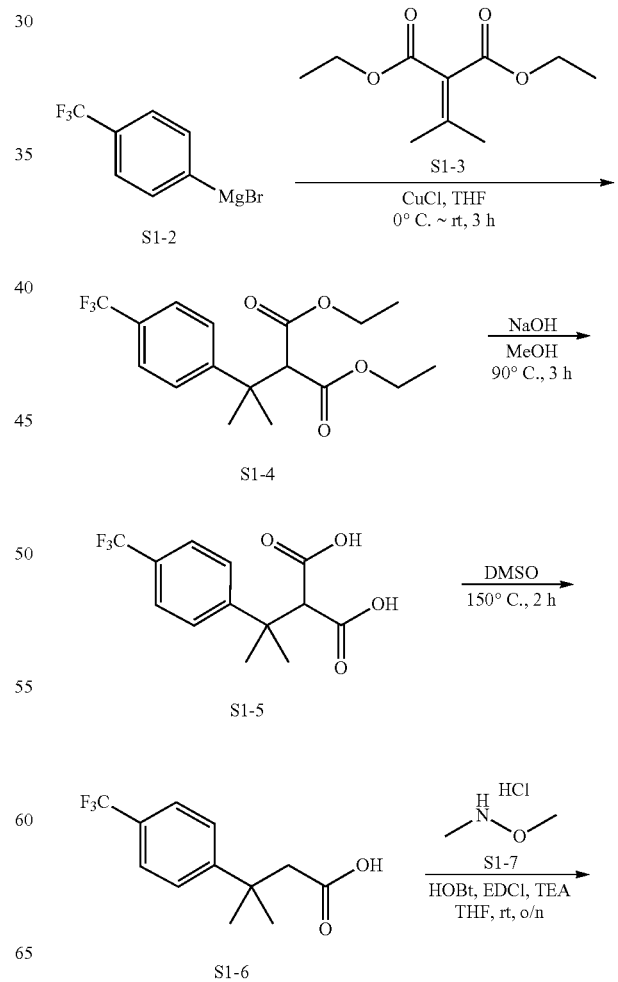

-continued

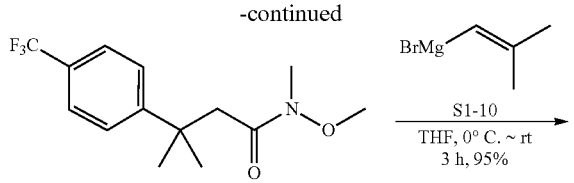

S1-8

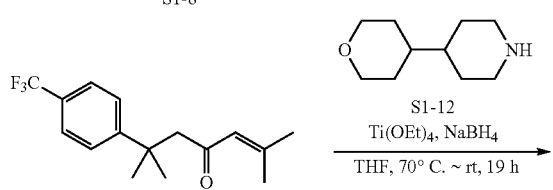

S1-11

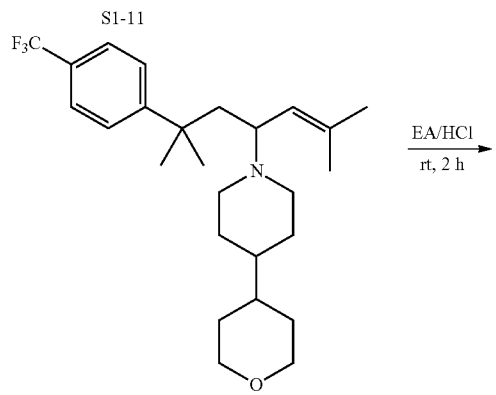

Example 9

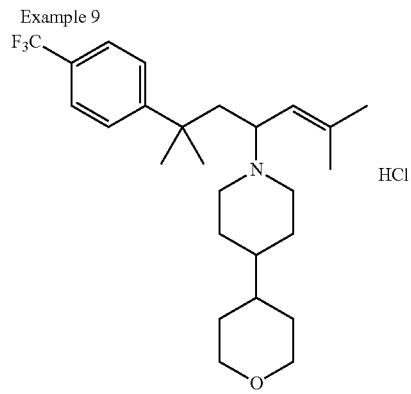

Example 9 HCl

General Procedure for the Preparation of Compound S1-2

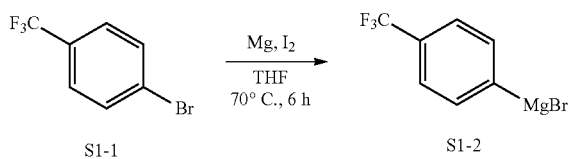

In three-neck flask, was placed magnesium (9.39 g, 391.09 mmol, 1.1 eq) and a grain of iodine. Then 15 percent volume of compound S1-1 (80 g, 355.54 mmol, 1.0 eq) in THF (800 mL) was added into the mixture under nitrogen atmosphere, and the stirred mixture was heated to 70° C. until yellow brown disappeared and then stirred at that temperature for another 6 h, to give a solution of compound S1-2 (0.44 M) in THF, which was used directly in next step.

General Procedure for the Preparation of Compound S1-4

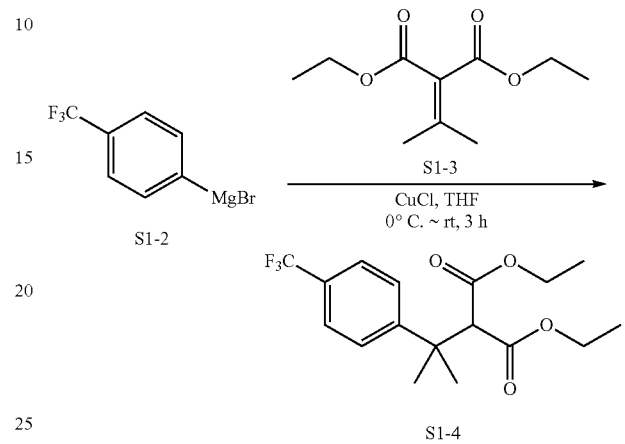

To a solution of compound S1-2 (320 mmol, 1.0 eq) in THF (500 mL) was added CuCl (3.17 g, 32 mmol, 0.1 eq). When the solution was cooled to 0° C. the compound S1-3 (64 g, 320 mmol, 1.0 eq) was added dropwise. The reaction mixture was stirred at rt for 3 h, quenched with saturated NH$_4$Cl solution, extracted with ethyl acetate. The organic layer was dried over Na$_2$SO$_4$, concentrated under vacuum. The residue was purified by column chromatography (PE/EA, 50:1-10:1) to afford the title compound S1-4 (51 g, 46%). $^1$H NMR (400 MHz, CDCl$_3$) δ 7.57-7.49 (m, 4H), 4.08-4.03 (m, 4H), 3.80 (d, J=2.4 Hz, 1H), 1.62-1.58 (m, 6H), 1.13-1.09 (m, 6H)

TLC: PE/EA=10:1, UV 254 nm

R$_f$ (Compound S1-4)=0.5

General Procedure for the Preparation of Compound S1-5

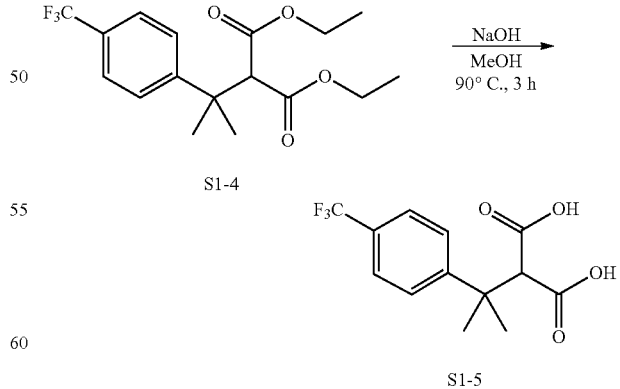

To a solution of compound S1-4 (51 g, 147.25 mmol, 1.0 eq) in MeOH (300 mL) was added 1N aqueous solution of NaOH (736 mL, 736.25 mmol, 5.0 eq). The reaction mixture was stirred at 90° C. for 3 h, and then cooled to rt. The mixture was acidified with 1N HCl solution until pH 4-5 and extracted with ethyl acetate. The organic layer was dried over Na$_2$SO$_4$ and concentrated under vacuum to give a compound S1-5 (40 g, 94%), which was used directly in next step without further purification. $^1$H NMR (400 MHz, CDCl$_3$) δ 7.57-7.55 (m, 2H), 7.50-7.48 (m, 2H), 3.86 (s, 1H), 1.59 (s, 6H);

TLC: DCM/MeOH=10:1, UV 254 nm
R$_f$ (Compound S1-5)=0.5

General Procedure for the Preparation of Compound S1-6

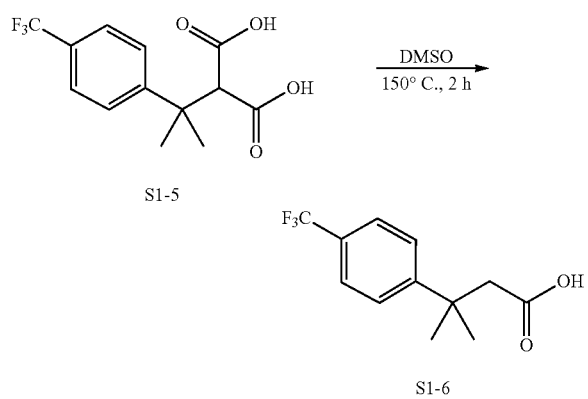

A solution of compound S1-5 (40 g, 137.82 mmol, 1.0 eq) in DMSO (200 mL) was stirred at 150° C. for 2 h, diluted with ethyl acetate, washed with water, brine. Then the organic phase was dried over Na$_2$SO$_4$ and concentrated under vacuum to afford the title compound S1-6 (30 g, 88%), which was used directly without further purification. $^1$H NMR (400 MHz, CDCl$_3$) δ 7.57-7.55 (m, 2H), 7.48-7.45 (m, 2H), 2.67 (s, 2H), 1.49-1.46 (m, 6H);

TLC: DCM/MeOH=10:1, UV 254 nm
R$_f$ (Compound S1-5)=0.4
R$_f$ (Compound S1-6)=0.8

General Procedure for the Preparation of Compound S1-8

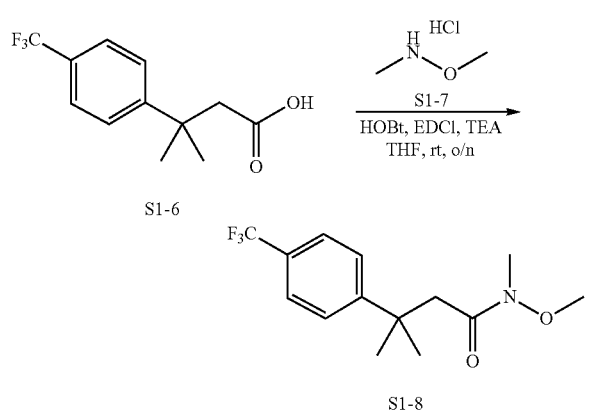

To a solution of compound S1-6 (30 g, 121.84 mmol, 1.0 eq) in THF (500 mL) was added HOBt (19.8 g, 146.2 mmol, 1.2 eq), EDCI (28 g, 146.21 mmol, 1.2 eq), TEA (37 g, 365.52 mmol, 3.0 eq) and compound S1-7 (23.77 g, 243.68 mmol, 2.0 eq). The reaction was stirred at rt overnight and then quenched with water, extracted with ethyl acetate. The organic layer was dried over Na$_2$SO$_4$ and concentrated to give the crude product, which was purified by column chromatography on a silica gel (PE/EA, 10:1~3:1) to give compound S1-8 (31 g, 88%). $^1$H NMR (400 MHz, CDCl$_3$) δ 7.56-7.54 (m, 2H), 7.50-7.47 (m, 2H), 3.59 (s, 3H), 3.06 (s, 3H), 2.78 (s, 2H), 1.49 (s, 6H);

TLC: PE/EA=3:1, UV 254 nm
R$_f$ (Compound S1-6)=0.4
R$_f$ (Compound S1-8)=0.8

General Procedure for the Preparation of Compound S1-10

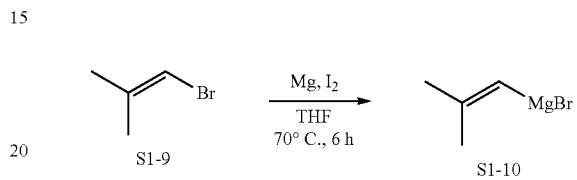

In three-neck flask, was placed magnesium (8.0 g, 331.39 mmol, 1.1 eq) and a grain of iodine. Then 15 percent volume of compound S1-9 (40.67 g, 301.26 mmol, 1.0 eq) in THF(300 mL) was added into the mixture under nitrogen atmosphere, and the stirred mixture was heated to 70° C. until yellow brown disappeared and then the solution was stirred at that temperature for another 6 h, to give a solution of compound S1-10 (1.0 M) in THF, which was used directly in next step.

General Procedure for the Preparation of Compound S-11

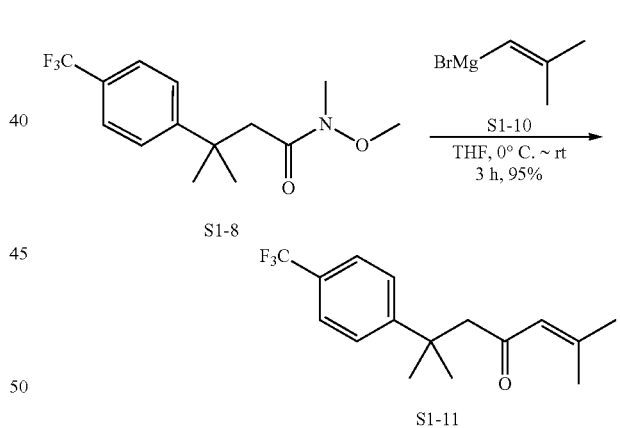

To a solution of compound S1-8 (31 g, 107.16 mmol, 1.0 eq) in THF (200 mL) was added compound S1-10 (1.0 M, 215 mL, 214.32 mmol, 2.0 eq) at 0° C. The reaction was stirred at rt for 3 h. Then the mixture was quenched with saturated NH$_4$Cl solution, extracted with ether, and the organic layer was dried over Na$_2$SO$_4$, concentrated in vacuum to give crude product, which was purified by column chromatography on a silica gel (PE) to give crude compound S-11 (28.9 g, 95%). $^1$H NMR (400 MHz, CDCl$_3$) δ 7.56-7.54 (m, 2H), 7.47-7.45 (m, 2H), 7.75 (m, 1H), 2.75 (s, 2H), 2.01-1.99 (m, 3H), 1.74-1.73 (m, 3H), 1.44-1.42 (m, 6H);

TLC: PE/EA=10:1, UV 254 nm
R$_f$ (Compound S1-8)=0.5
R$_f$ (Compound S1-11)=0.9

General Procedure for the Preparation of Example 9

Example Syn 2: Preparation of Example Compound 262

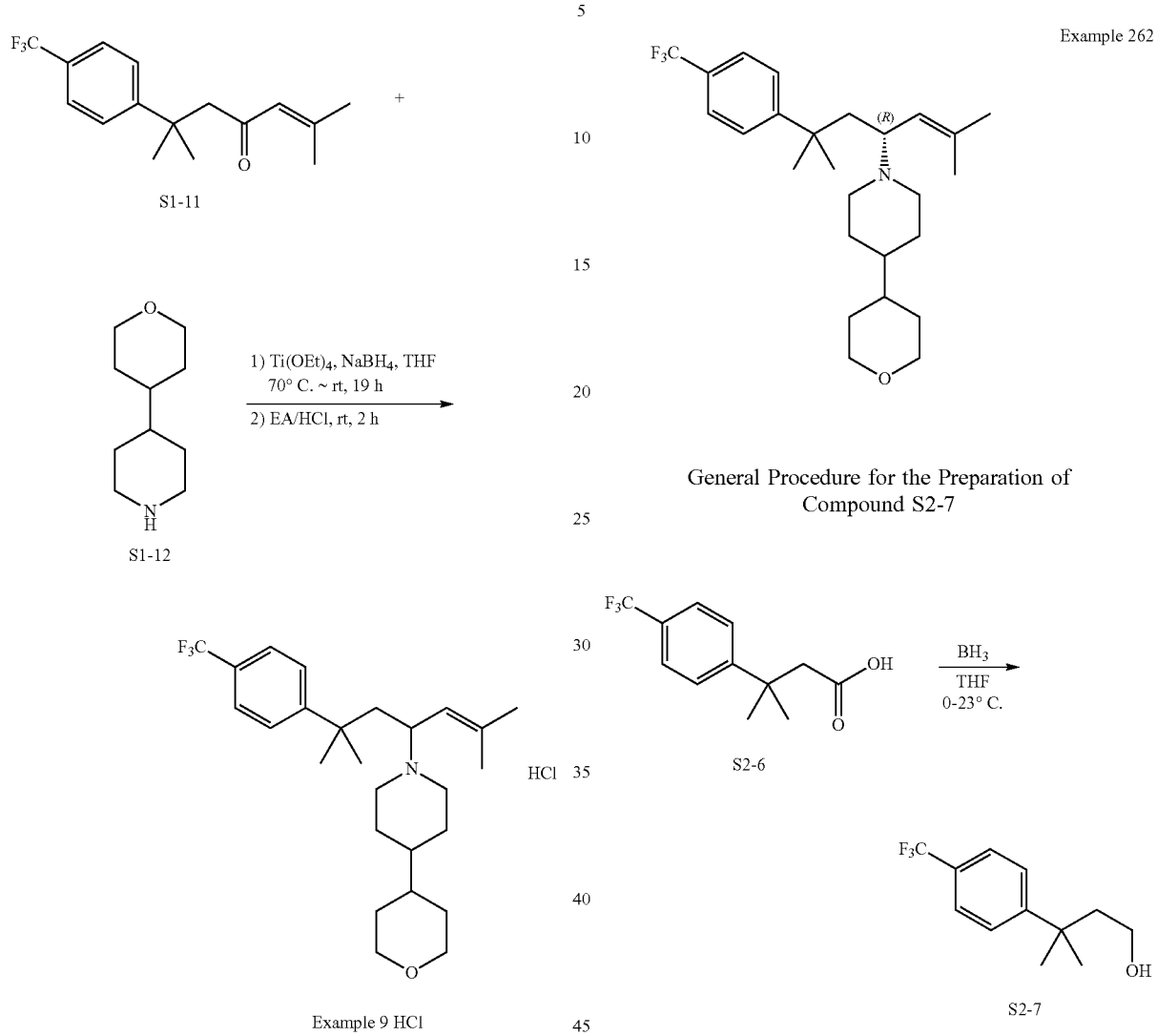

A mixture of compound S1-11 (2.4 g, 8.44 mmol, 1.0 eq), compound S1-12 (1.43 g, 8.44 mmol, 1.0 eq) and Ti(EtO)$_4$ (7.7 g, 33.76 mmol, 4.0 eq) in THF (100 mL) was stirred at 70° C. overnight under nitrogen atmosphere. Then the mixture was allowed to cool to rt, NaBH$_4$ (1.23 g, 33.76 mmol, 4.0 eq) was added. After complete addition, the mixture was stirred at rt for 3 h. Then water was added and extracted with ethyl acetate, filtered. The organic phase was dried over Na$_2$SO$_4$, concentrated in vacuum. The residue was purified by column chromatography on a silica gel (PE/EA, 10:1~1:1) to give compound Example 9, which was dissolved in HCl/EA (2.0 M, 10 mL). The mixture was stirred at rt for 2 h, concentrated to give Example 9 HCl (600 mg, 15%) as oil. $^1$H NMR (400 MHz, CD$_3$OD) δ 7.60-7.52 (m, 4H), 4.70-4.67 (m, 1H), 3.95-3.92 (m, 2H), 3.79-3.73 (m, 1H), 3.61-3.59 (m, 1H), 2.81-2.73 (m, 2H), 2.38-2.22 (m, 2H), 1.98 (s, 6H), 1.64-1.61 (m, 2H), 1.46-1.43 (m, 12H), 1.31-1.28 (m, 6H);

MS: [M+H]+=438.5

To a solution of compound S2-6 (450 g, 1.83 mol, 1.0 eq) in anhydrous THF (4.5 L) cooled to 0° C., a solution of 1 M BH$_3$ (2.75 L, 2.745 mol, 1.5 eq) was added dropwise. The mixture was stirred at rt for 16 h. The reaction was monitored by TLC. The colorless homogeneous reaction mixture was cooled to 0° C., and MeOH (2 L) was carefully added followed by water (1 L). MeOH and THF were then removed under vacuum. The mixture was extracted with DCM (3×1 L), the combined organic extracts were washed with brine (1 L), dried over MgSO4, filtered, and concentrated to dryness under reduced pressure to give crude compound S2-7 (340 g, 80%) as a colorless oil. $^1$H NMR (400 MHz, CDCl$_3$): δ 7.57 (d, J=8.0 Hz, 2H), 7.47 (d, J=8.4 Hz, 2H), 3.47 (t, J=7.2 Hz, 2H), 1.98 (t, J=7.2 Hz, 2H), 1.29 (s, 6H).

General Procedure for the Preparation of Compound S2-9

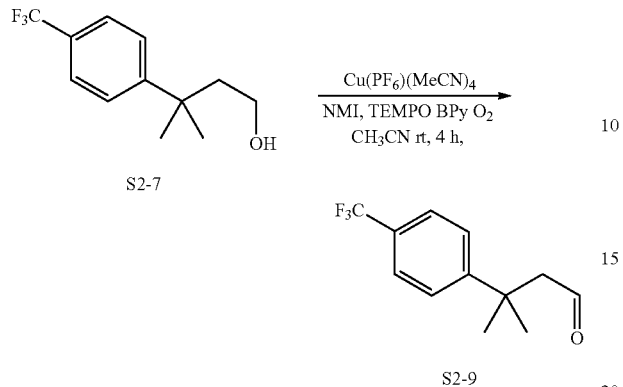

A solution of compound S2-7 (296 g, 1.27 mol, 1.0 eq) was dissolved in CH$_3$CN (3.6 L), NMI (10.3 g, 127 mmol, 0.1 eq), TEMPO (9.8 g, 63 mmol, 0.05 eq) and BPy (9.7 g, 63 mmol, 0.05 eq) were added, then Cu(PF$_6$)(MeCN)$_4$ (23.5 g, 63 mmol, 0.05 eq) was added. The mixture was stirred under oxygen atmosphere for 4 h. The reaction was monitored by TLC. The mixture was poured into water (2 L), extracted with DCM (3×2 L). The combined extracts were washed with water, dried over Na$_2$SO$_4$ and concentrated to give compound S2-9 (281 g, 96%) as a dark green oil. $^1$HNMR (400 MHz, CDCl$_3$): δ 9.54 (s, 1H), 7.61 (d, J=7.6 Hz, 2H), 7.51 (d, J=7.6 Hz, 2H), 2.66 (s, 2H), 1.49 (s, 6H).

TLC: PE/EA=20:1, UV 254 nm
R$_f$ (compound S2-7)=0.1
R$_f$(S2-9)=0.8

General Procedure for the Preparation of Compound S2-11R

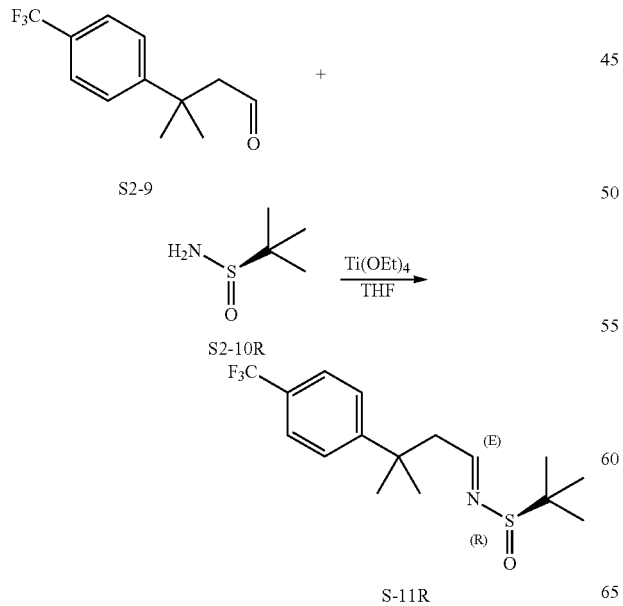

To a solution of compound S2-9 (150 g, 652.5 mmol, 1.0 eq) in THF (750 mL), compound S2-10R (118.96 g, 978.77 mmol, 1.5 eq) and Ti(OEt)$_4$ (74.4 g, 326.2 mmol, 0.5 eq) were added. The mixture was stirred at rt overnight, and then quenched with water (24 g, 1.3 mol), filtered by celite pad and diluted with ethyl acetate, washed with brine, water. The organic layer was dried over Na$_2$SO$_4$ and concentrated to give crude product, which was purified by column chromatography on a silica gel (PE/EA, 5:1) to give compound S2-11R (165 g, 75.9%).

TLC: PE/EA=3:1, UV 254 nm
R$_f$ (Compound S2-9)=0.6
R$_f$ (Compound S2-11R)=0.5

General Procedure for the Preparation of Compound S2-12

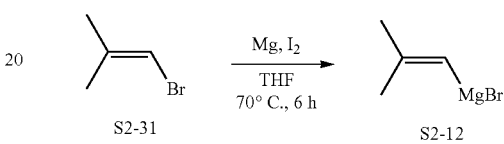

In three-neck flask, was placed magnesium (31.9 g, 1.3 mol, 1.1 eq) and a grain of iodine. Then 15 percent volume of compound S2-31 (149 g, 1.2 mol, 1.0 eq) in THF (1.5 L) was added into the mixture under nitrogen atmosphere, and the stirred mixture was heated to 70° C. until yellow brown disappeared. Then the remaining solution was added dropwise and stirred for another 6 h to give a solution of compound S2-12 (1.0 M) in THF, which was used directly in next step.

General Procedure for the Preparation of Compound S2-13R

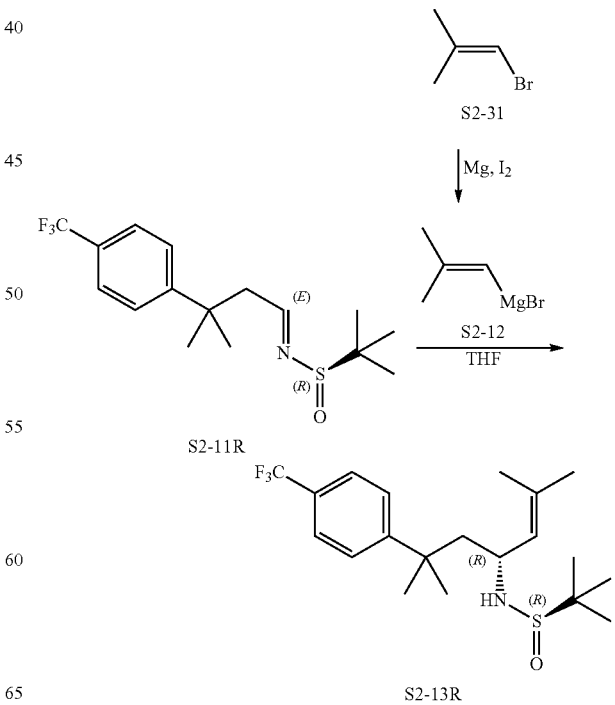

To a solution of compound S2-11R (120 g, 359.9 mmol, 1.0 eq) in THF (80 mL) was added the compound S2-12 (1080 mL, 539.9 mmol, 1.50 eq, 0.5 M) at 0-5° C. After stirring at rt for overnight, the reaction was quenched by NH$_4$Cl, extracted with ethyl acetate. The organic layer was dried over Na$_2$SO$_4$ and concentrated to give crude product, which was purified by column chromatography on a silica gel (PE/EA, 10:1~3:1) to give compound S2-13R (69.1 g, 49.3%).

The compound S2-13R (69.1 g) was recrystallized with ether/hexane (1/1) (30 mL) at 4-8° C. for up to two days, to give white solid (25.6 g, 37%), which was used to produce Example 262 in 99% ee. The mother liquor was recrystallized with ether/hexane (1/1) (20 mL) to give white solid (15.1 g).

TLC: PE/EA=3:1, UV 254 nm
R$_f$ (Compound S2-11R)=0.5
R$_f$ (Compound S2-13R)=0.3

General Procedure for the Preparation of Compound S2-14R

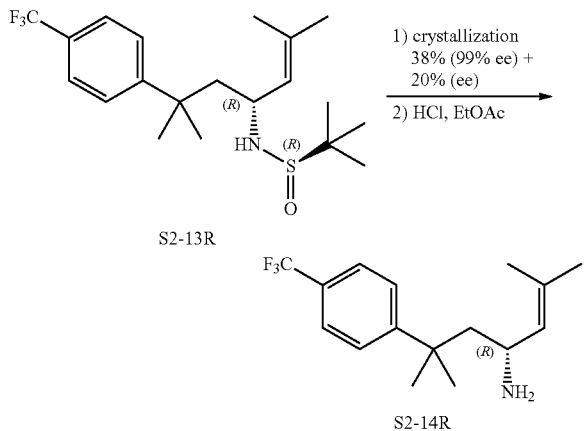

Compound S2-13R (34.6 g, 88.8 mmol, 1.0 eq) was added in the round bottom flask. HCl in EtOAc (90 mL, 2N, 2 eq) was then added. After stirring for two hours, about 80 mL of solvent was removed under vacuous. The mixture diluted with ether (20 mL), the white solid was filtered out as compound S2-14R hydrochloride. The hydrochloride was dissolved in H$_2$O (30 mL), alkalinized with saturated aqueous of Na$_2$CO$_3$ to pH 10. Then extracted with ether (30 mL×3), dried over (Na$_2$SO$_4$), concentrate to give colorless oil (20.2 g 79.7%).

TLC: PE/EA=3:1, UV 254 nm
R$_f$ (Compound S2-13R)=0.3
R$_f$ (Compound S2-14R)=0.1

General Procedure for the Preparation of Example Compound 262

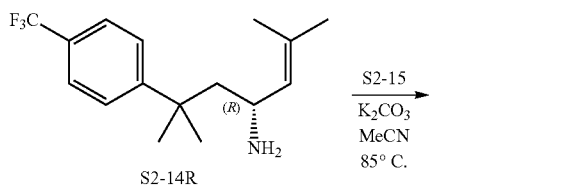

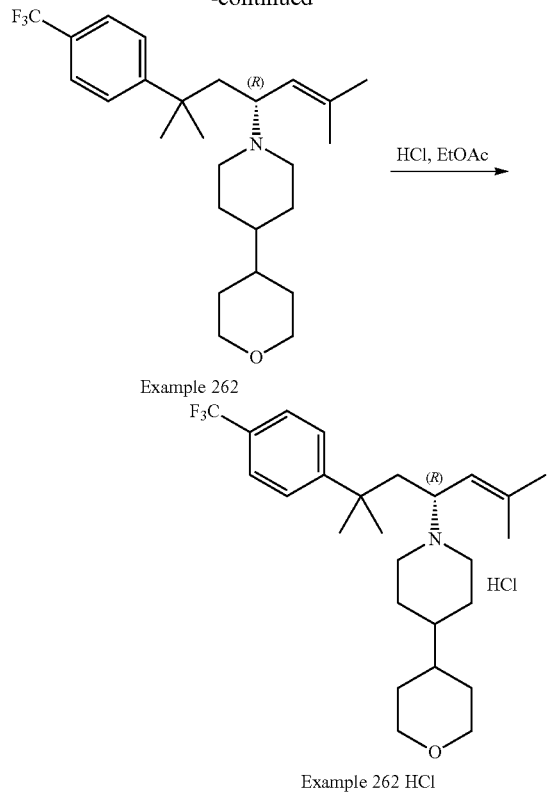

To a solution of compound S2-14R (4.8 g, 16.8 mmol, 1.0 eq) in ACN (48 mL) was added the compound S2-15 (8.35 g, 16.8 mmol, 1.0 eq) and K$_2$CO$_3$ (4.46 g, 33.6 mmol, 2.0 eq). After stirring at 85° C. overnight, the reaction was quenched by H$_2$O (50 mL) and extracted with ethyl acetate (40 mL×3). The organic layer was dried over Na$_2$SO$_4$ and concentrated to give crude product, which was purified by column chromatography on a silica gel (PE/EA, 10:1~3:1) to give compound Example 262 (5.1 g 69%) as the free base. The ee % was determined to be 99% on chiral HPLC. The free base was dissolved in HCl/EA (1.3 M, 50 mL). The mixture was stirred at rt for 2 h, concentrated to give Example 262 HCl (5.5 g, 69%) as a white solid. $^1$H NMR (400 MHz, CD$_3$OD) δ 7.60-7.52 (m, 4H), 4.70-4.67 (m, 1H), 3.95-3.92 (m, 2H), 3.79-3.73 (m, 1H), 3.61-3.59 (m, 1H), 2.81-2.73 (m, 2H), 2.38-2.22 (m, 2H), 1.98 (s, 6H), 1.64-1.61 (m, 2H), 1.46-1.43 (m, 12H), 1.31-1.28 (m, 6H);
MS: [M+H]+=438.5

General Procedure for the Preparation of Compound 2-15

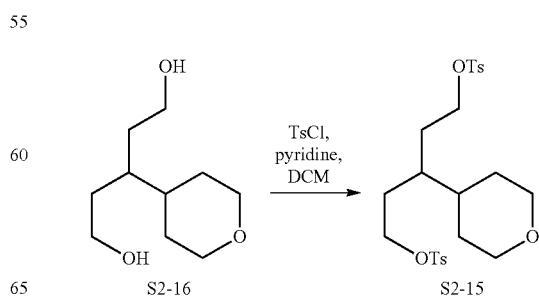

To a solution of compound S2-16 (5.0 g, 26.6 mmol, 1.0 eq) in DCM (50 mL) was added the compound TsCl (20.2 g, 106.2 mmol, 4.0 eq) and pyridine (8.4 g, 106.2 mmol, 4.0 eq). After stirring at rt overnight, the reaction was quenched by H$_2$O (100 mL) and extracted with ethyl acetate (40 mL×3). The organic layer was dried over Na$_2$SO$_4$ and concentrated to give crude product, which was purified by column chromatography on a silica gel (PE/EA, 10:1~3:1) to give compound S2-15 (5.4 g 40.9%).

Example Syn 3: Preparation of Example Compound 14

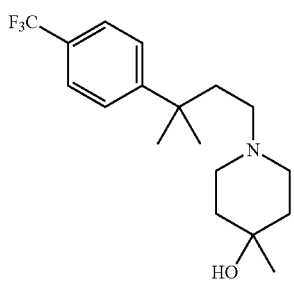 [SMILES: CC1(O)CCN(CCC(C)(C)c2ccc(C(F)(F)F)cc2)CC1]

Example 14

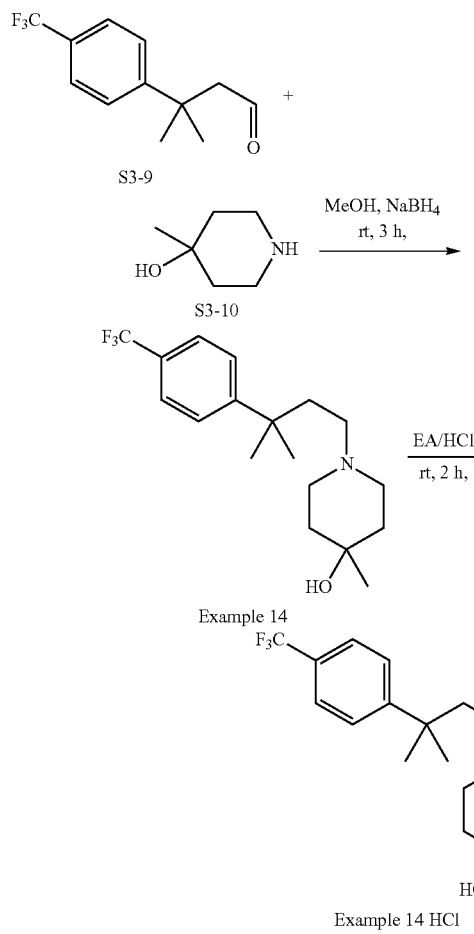

-continued

General Procedure for the Preparation of Example Compound 14

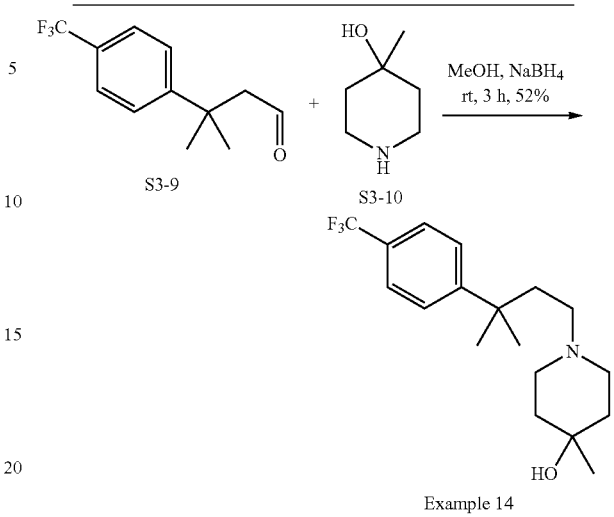

To a mixture of compound S3-9 (60.0 g, 0.26 mol, 1.0 eq) and compound S3-10 (30.0 g, 0.26 mol, 1.0 eq) in MeOH (600 mL) was added NaBH$_4$ (39.6 g, 1.04 mol, 4.0 eq). The mixture was stirred at rt for 3 h under nitrogen atmosphere. Then brine was added and the solution was extracted with ethyl acetate. The organic phase was combined, dried over Na$_2$SO$_4$, concentrated in vacuum. The residue was purified by column chromatography to give compound Example 14 (45.1 g, 52%).

TLC: DCM:MeOH=10:1

R$_f$ (Example 14)=0.2

General Procedure for the Preparation of Example Compound 14 HCl

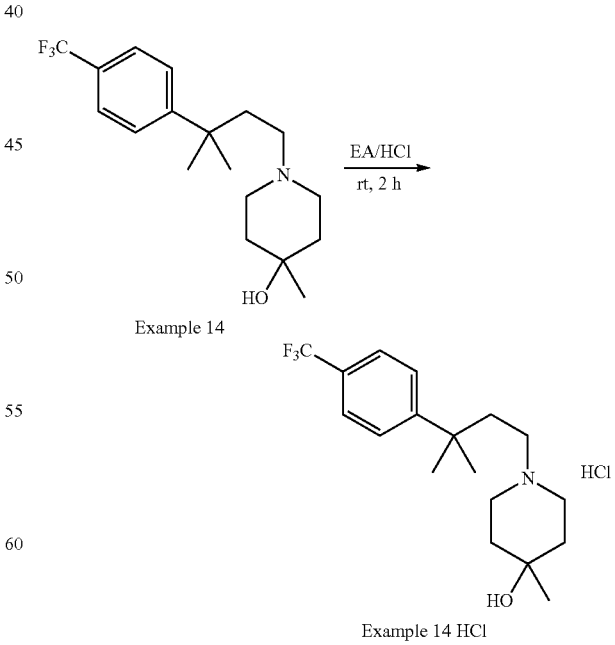

A mixture of Example 14 (65 g, 0.2 mol) in HCl/EA (2.5 M, 160 mL). was stirred at rt for 2 h. The cloudy mixture was concentrated to give Example 14 HCl (68 g, 94%) as white solid. $^1$H NMR (400 MHz, CD$_3$OD): δ ppm 7.67-7.61 (m, 4H), 3.31-3.3 (m, 3H), 3.15-3.11 (m, 2H), 2.85-2.79 (m, 2H), 2.17-2.12 (m, 2H), 1.82-1.76 (m, 2H), 1.43 (s, 6H), 1.27 (s, 3H).

MS: [M+H]+=330.20

Example Syn 4: Preparation of Example Compound 17

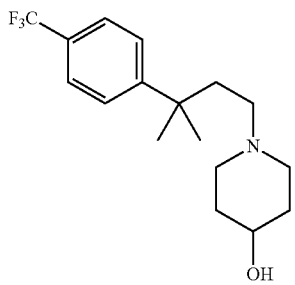 [SMILES: CC(C)(CCN1CCC(O)CC1)c1ccc(C(F)(F)F)cc1]

Example 17

4.07-4.03 (m, 1H), 3.63-3.57 (m, 1H), 3.34-3.30 (m, 6H), 3.16-3.09 (m, 2H), 2.87-2.83 (m, 2H), 2.19-2.14 (m, 2H), 1.43 (s, 6H);

MS: [M+H]+=316.4

Example Syn 5: Preparation of Example Compound 307

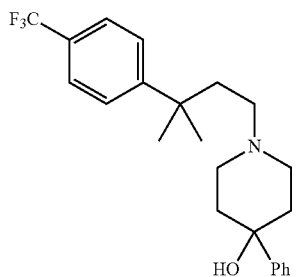 [SMILES: CC(C)(CCN1CCC(O)(c2ccccc2)CC1)c1ccc(C(F)(F)F)cc1]

Example 307

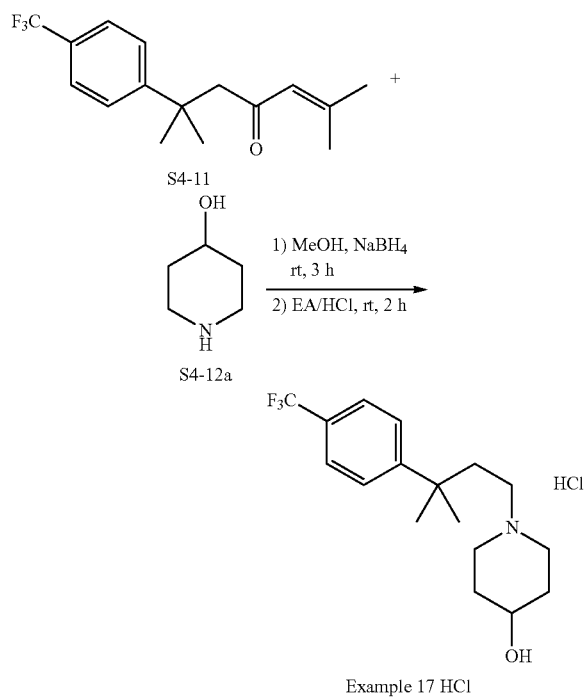

A mixture of compound S4-11 (300 mg, 1.3 mmol, 1.0 eq), compound S4-12 (150 mg, 1.3 mmol, 1.0 eq) and NaBH$_4$ (197 mg, 5.2 mmol, 4.0 eq) in MeOH (10 mL) was stirred at rt for 3 h under nitrogen atmosphere. Then aq. NaCl was added and extracted with ethyl acetate, filtered. The organic phase was dried over Na$_2$SO$_4$, concentrated in vacuum. The residue was purified by pre-TLC to give compound Example 17, which was dissolved in HCl/EA (1.3 M, 10 mL). The mixture was stirred at rt for 2 h, concentrated to give Example 17 HCl (144.1 mg, 31.4%) as white solid. $^1$H NMR (400 MHz, CD$_3$OD): δ7.75-7.60 (m, 4H), To a solution of compound S5-9 (3.54 g, 15.38 mmol, 1.0 eq) in MeOH (60 mL) was added compound S5-10 (3.0 g, 16.9 mmol, 1.1 eq) and 2 drops of AcOH. The reaction mixture was stirred at rt for 2 h. NaBH$_4$ (2.33 g, 61.55 mmol, 4.0 eq) was added and then the reaction mixture was stirred at rt for 2 h. The reaction was quenched with H$_2$O (20 mL), filtered, extracted with EA (20 mL×3) and concentrated to get a residue, which was purified by column chromatography (PE:EA=1:1) to give compound Example 307 (1.3 g, 21.6%).

TLC: DCM:EA:MeOH=1:1:0.1

R$_f$ (compound S5-9)=0.9

R$_f$ (compound Example 307)=0.3

General Procedure for the Preparation of Example 307 HCl

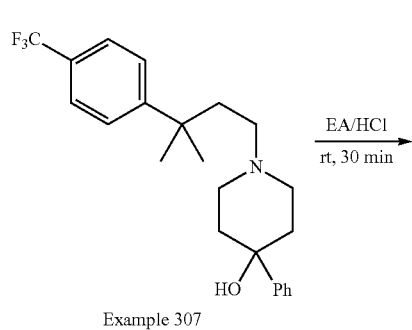

Example 307

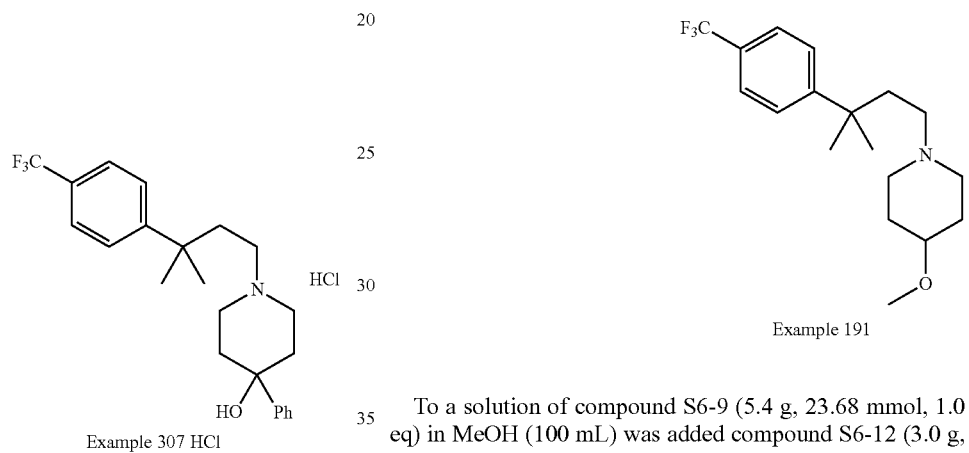

Example 307 HCl

To a solution of compound Example 307 (1.9 g, 4.85 mmol, 1.0 eq) in EA (5 mL) was added EA/HCl (2.5 M, 6 mL, 3.0 eq). The reaction mixture was stirred at rt for 30 min. The reaction mixture was concentrated to give Example 307 HCl (2.1 g, 100%). $^1$H NMR (400 MHz, CDCl$_3$) δ 7.62-7.60 (m, 2H), 7.50-7.47 (m, 4H), 7.46-7.31 (m, 2H), 7.28 (m, 2H), 3.32 (m, 2H), 3.13 (m, 2H), 2.64 (m, 2H), 2.32 (m, 2H), 1.67 (m, 3H), 1.39 (m, 6H);

MS: [M+H]+=392.6

Example Syn 6: Preparation of Example Compound 191

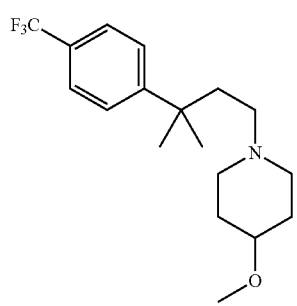 [SMILES: COC1CCN(CCC(C)(C)c2ccc(C(F)(F)F)cc2)CC1]

Example 191

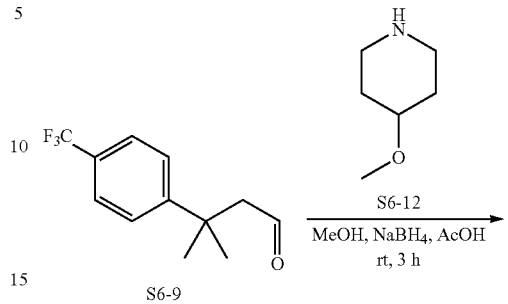

Example 191

To a solution of compound S6-9 (5.4 g, 23.68 mmol, 1.0 eq) in MeOH (100 mL) was added compound S6-12 (3.0 g, 26 mmol, 1.1 eq) and 2 drops of AcOH. The reaction mixture was stirred at rt for 2 h. NaBH$_4$ (3.58 g, 94.71 mmol, 4.0 eq) was added and then the reaction mixture was stirred at rt for 2 h. The reaction was quenched with H$_2$O (30 mL), filtered, extracted with EA (30 mL×3) and concentrated to get a residue, which was purified by column chromatography (PE:EA=1:1) to give Example 191 (3.4 g, 44%).

TLC: DCM:EA:MeOH=1:1:0.1

R$_f$ (compound S6-9)=0.9

R$_f$ (Example 191)=0.3

General Procedure for the Preparation of Example 191 HCl

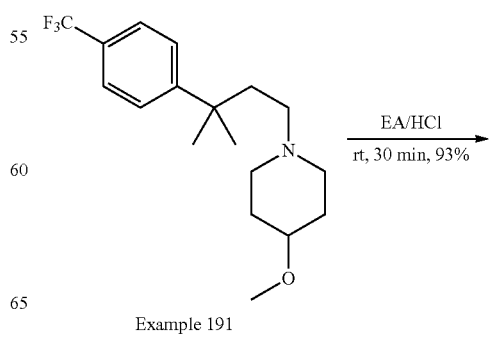

Example 191

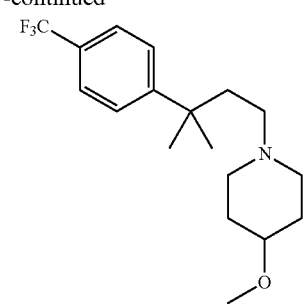

Example 191 HCl

To a solution of Example 191 (3.4 g, 10.33 mmol, 1.0 eq) in EA (10 mL) was added EA/HCl (2.5 M, 8.9 mL, 2.0 eq). The reaction mixture was stirred at rt for 30 min. The reaction mixture was concentrated to give Example 191 HCl (3.5 g, 93%). $^1$H NMR (400 MHz, CDCl$_3$) δ 7.60-7.58 (m, 2H), 7.49-7.47 (m, 2H), 3.56 (s, 1H), 3.25 (s, 3H), 3.19 (m, 2H), 2.80 (m, 2H), 2.59 (m, 2H), 2.39 (m, 2H), 2.30 (m, 2H), 1.93 (m, 2H), 1.37 (s, 6H);

MS: [M+H]+=330.2

Example Syn 7: Preparation of Example Compound 317

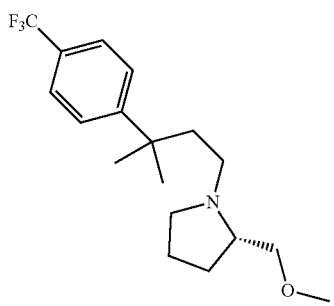 [SMILES: COC[C@@H]1CCCN1CCC(C)(C)c1ccc(C(F)(F)F)cc1]

Example 317

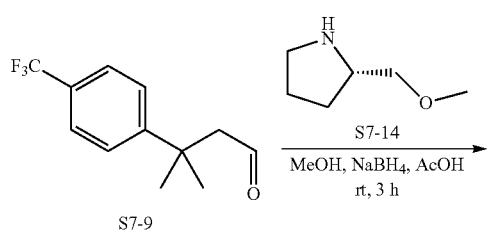

To a solution of compound S7-9 (5.46 g, 23.7 mmol, 1.0 eq) in MeOH (100 mL) was added compound S7-14 (3.0 g, 26 mmol, 1.1 eq) and 2 drops of AcOH. The reaction mixture was stirred at rt for 2 h. NaBH$_4$ (3.58 g, 94.63 mmol, 4.0 eq) was added and then the reaction mixture was stirred at rt for 2 h. The reaction was quenched with H$_2$O (30 mL), filtered, extracted with EA (30 mL×3) and concentrated to get a residue, which was purified by column chromatography (PE:EA=1:1) to give Example 317 (2.1 g, 27%).

TLC: DCM:EA:MeOH=1:1:0.1

R$_f$ (compound S7-9)=0.9

R$_f$ (Example 317)=0.3

General Procedure for the Preparation of Example 317 HCl

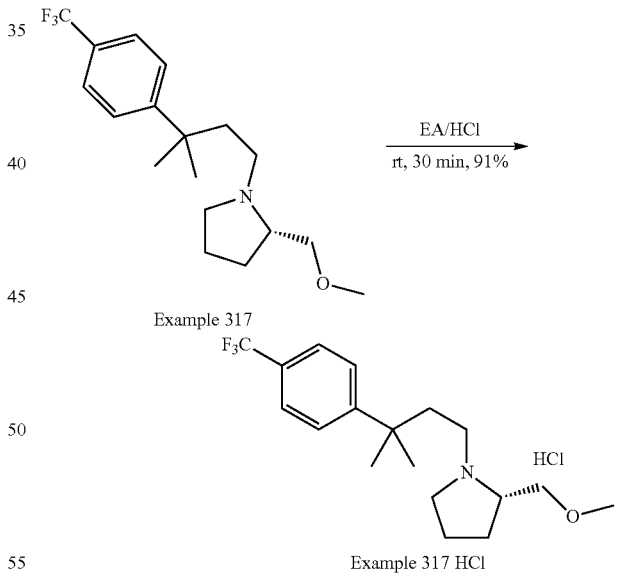

To a solution of Example 317 (2.1 g, 6.37 mmol, 1.0 eq) in EA (10 mL) was added EA/HCl (2.5 M, 6 mL, 2.0 eq). The reaction mixture was stirred at rt for 30 min. The reaction mixture was concentrated to give Example 317 HCl (2.1 g, 91%). $^1$H NMR (400 MHz, CDCl$_3$) δ 12.17 (m, 1H), 7.61-7.59 (m, 2H), 7.50-7.48 (m, 2H), 4.16-4.13 (m, 1H), 3.90-3.86 (m, 1H), 3.55-3.53 (m, 1H), 3.33 (m, 1H), 3.23 (s, 3H), 2.63-2.59 (m, 2H), 2.51 (m, 1H), 2.23 (m, 1H), 2.19-1.90 (m, 4H), 1.39-1.37 (m, 6H);

MS: [M+H]+=330.6

Example Syn 8: Preparation of Example Compound 306

General Procedure for the Preparation of Example 306 HCl

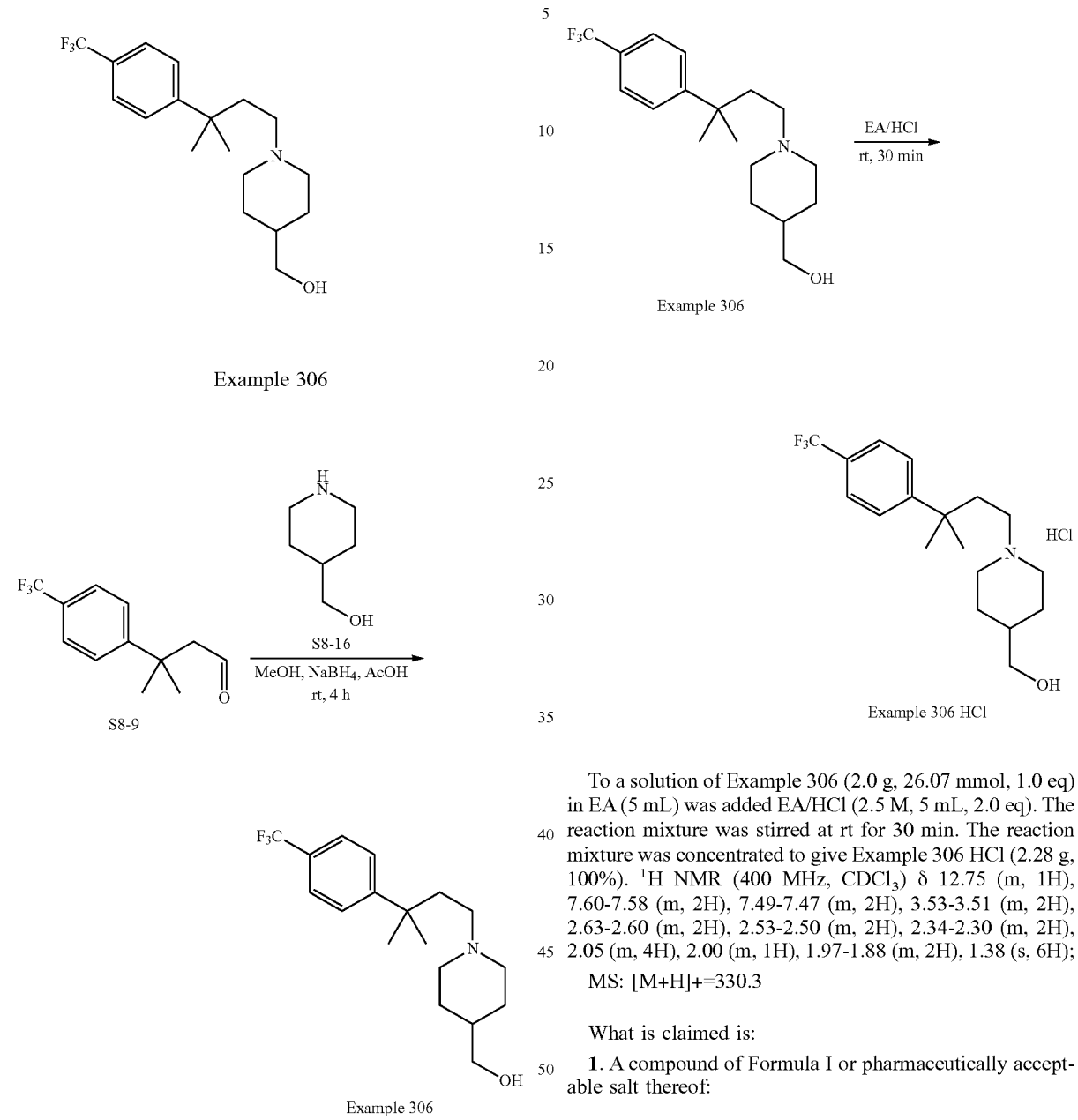

To a solution of compound S8-9 (3.08 g, 13.3 mmol, 1.0 eq) in MeOH (80 mL) was added compound S8-16 (2.0 g, 17.36 mmol, 1.1 eq) and 2 drops of AcOH. The reaction mixture was stirred at rt for 2 h. NaBH$_4$ (2.02 g, 53.4 mmol, 4.0 eq) was added and then the reaction mixture was stirred at rt for 2 h. The reaction was quenched with H$_2$O (30 mL), filtered, extracted with EA (30 mL×3) and concentrated to get a residue, which was purified by column chromatography (PE:EA=1:1) to give Example 306 (1.2 g, 27%).

TLC: DCM:EA:MeOH=1:1:0.1

R$_f$ (compound S8-9)=0.9

R$_f$ (Example 306)=0.3

To a solution of Example 306 (2.0 g, 26.07 mmol, 1.0 eq) in EA (5 mL) was added EA/HCl (2.5 M, 5 mL, 2.0 eq). The reaction mixture was stirred at rt for 30 min. The reaction mixture was concentrated to give Example 306 HCl (2.28 g, 100%). $^1$H NMR (400 MHz, CDCl$_3$) δ 12.75 (m, 1H), 7.60-7.58 (m, 2H), 7.49-7.47 (m, 2H), 3.53-3.51 (m, 2H), 2.63-2.60 (m, 2H), 2.53-2.50 (m, 2H), 2.34-2.30 (m, 2H), 2.05 (m, 4H), 2.00 (m, 1H), 1.97-1.88 (m, 2H), 1.38 (s, 6H);

MS: [M+H]+=330.3

What is claimed is:

1. A compound of Formula I or pharmaceutically acceptable salt thereof:

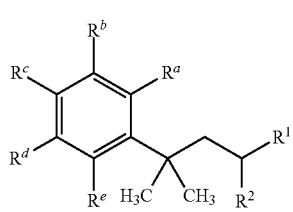

I wherein:

each of R$^a$, R$^b$, R$^c$, R$^d$ and R$^e$ is independently selected from the group consisting of, H, hydroxyl, halo, alkyl, alkoxy, CF$_3$, SO$_2$CH$_3$, and morpholino;

$R^1$ is selected from the group consisting of hydrogen, alkyl, phenyl, or —CH=C(CH$_3$)$_2$; and
$R^2$ is an optionally substituted cyclic amino group; selected from the groups consisting of:
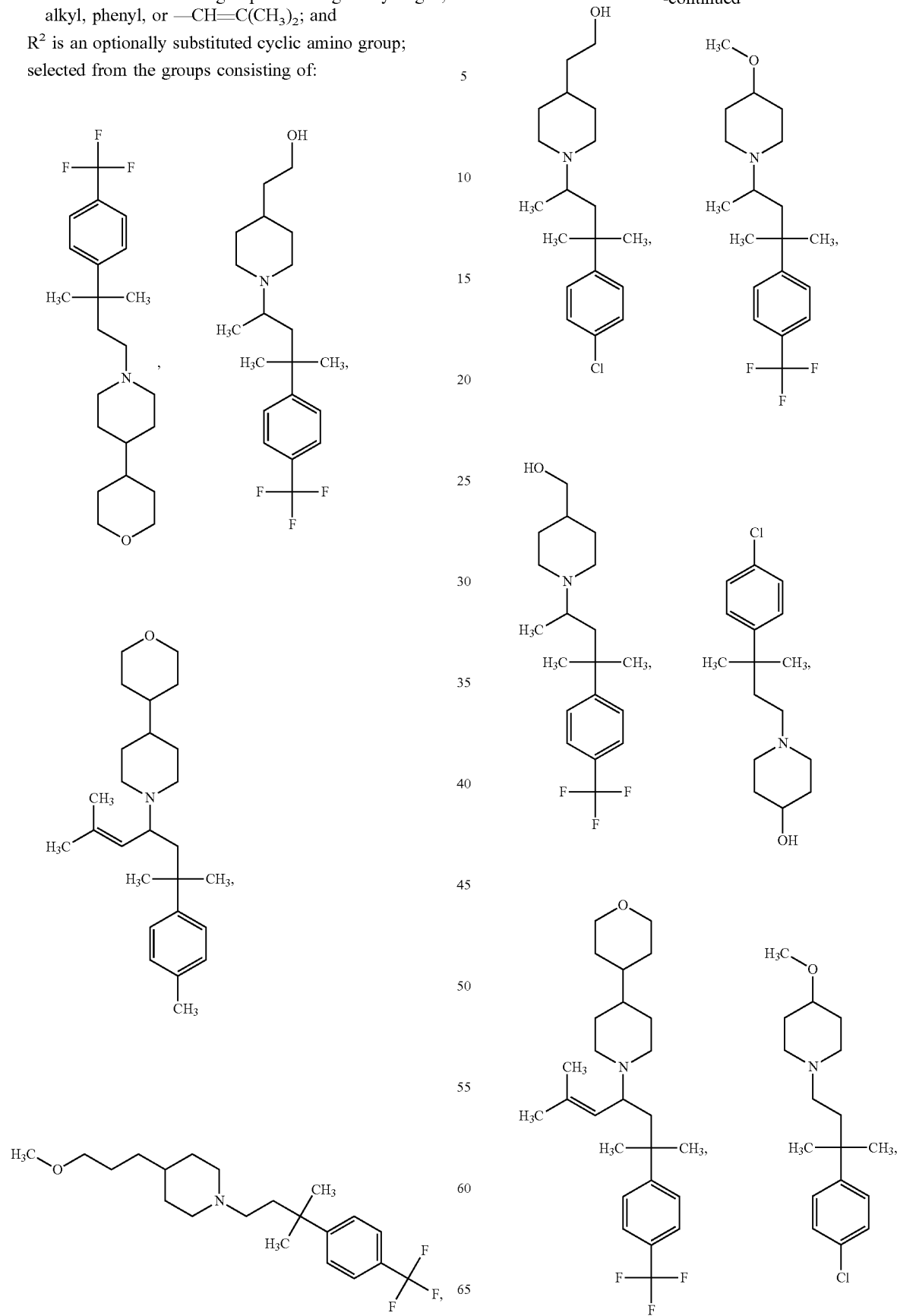

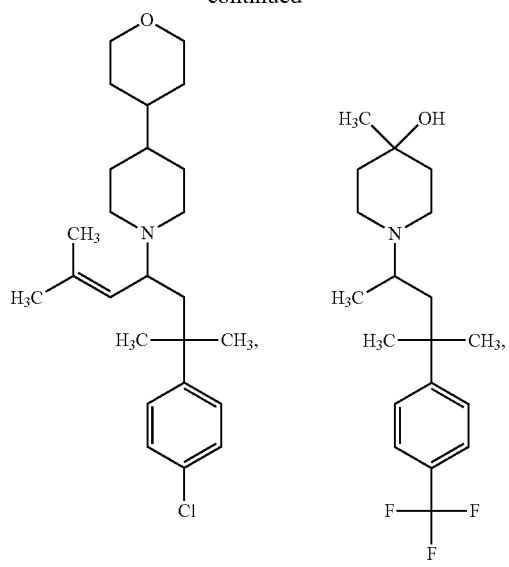
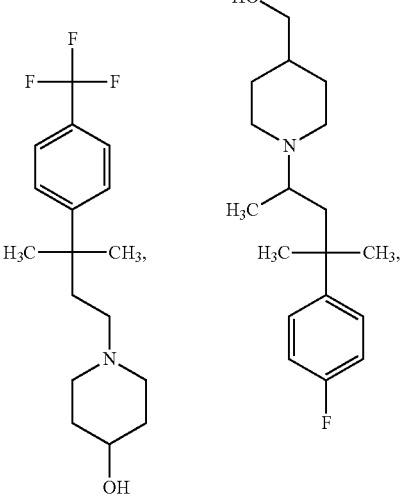
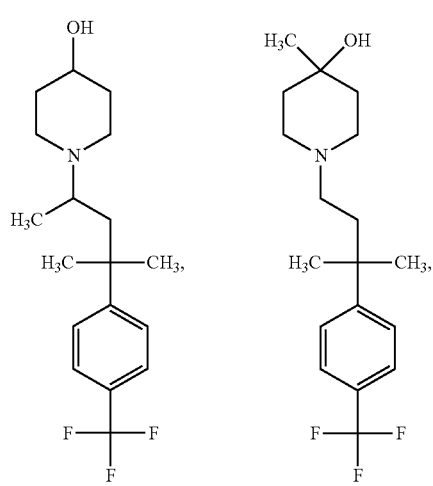
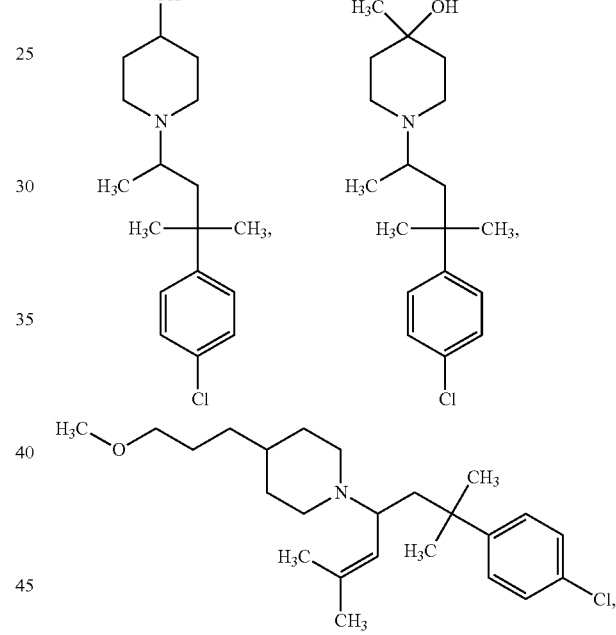
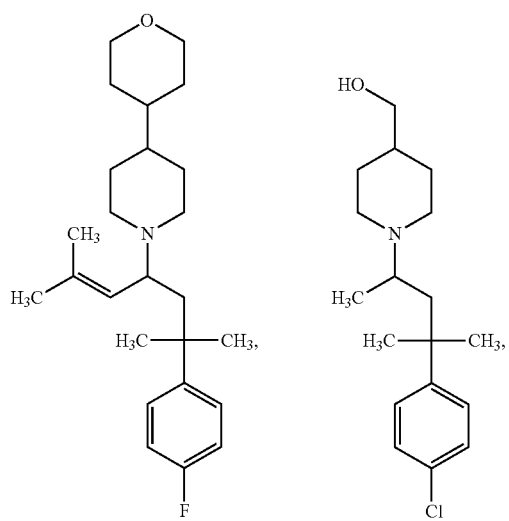
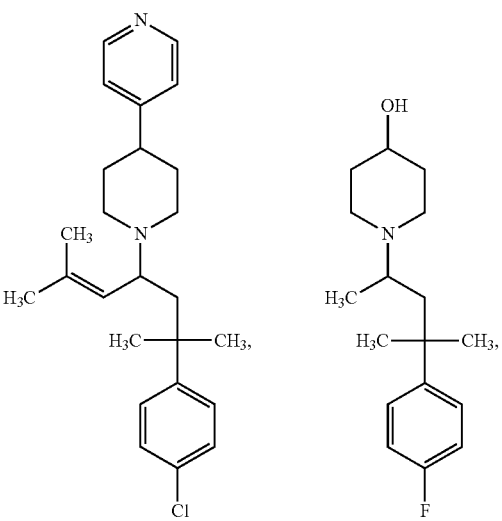

209
-continued
210
-continued
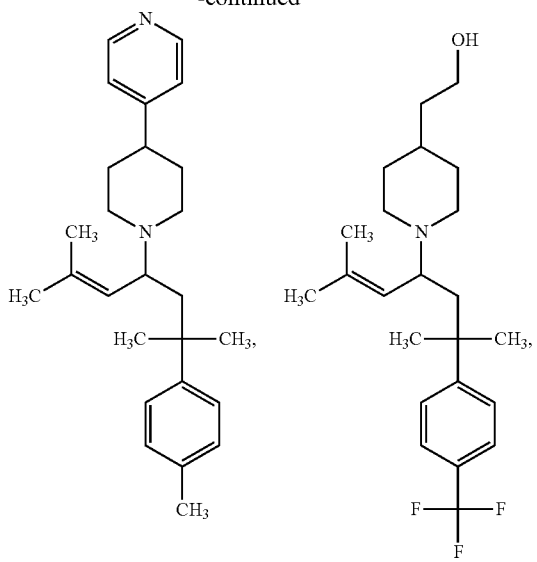
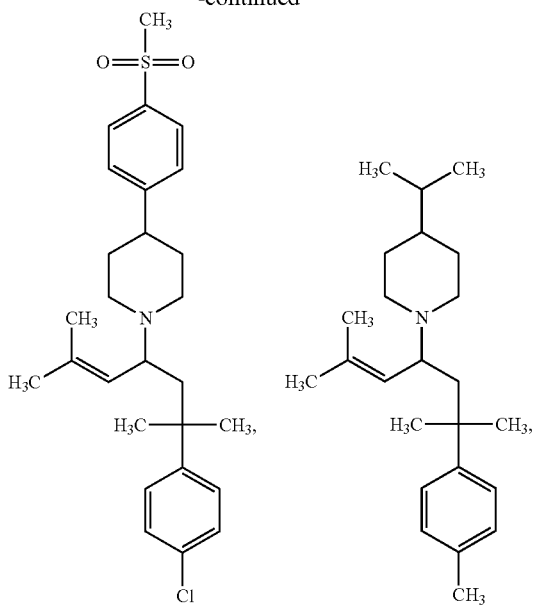
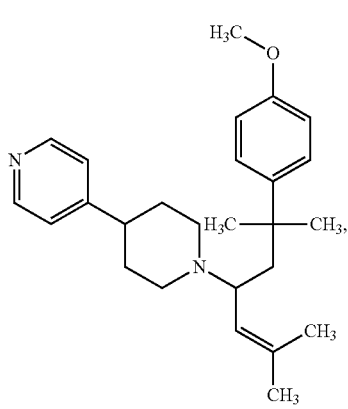
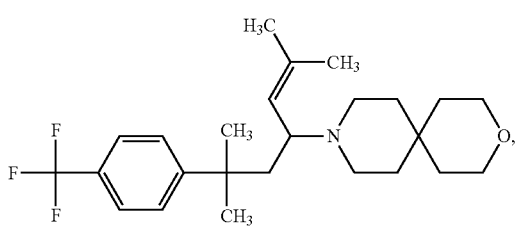
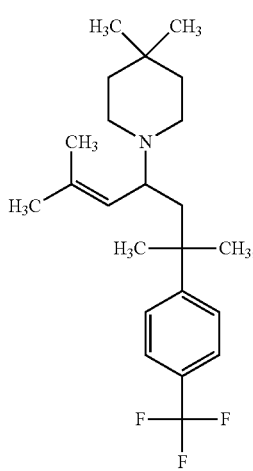 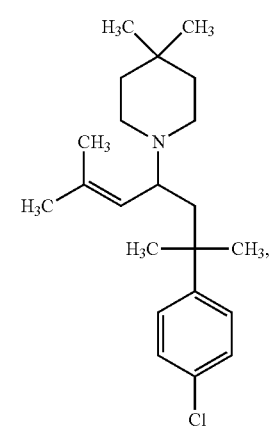
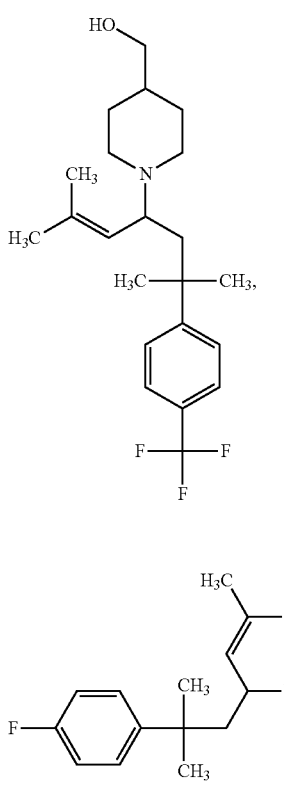

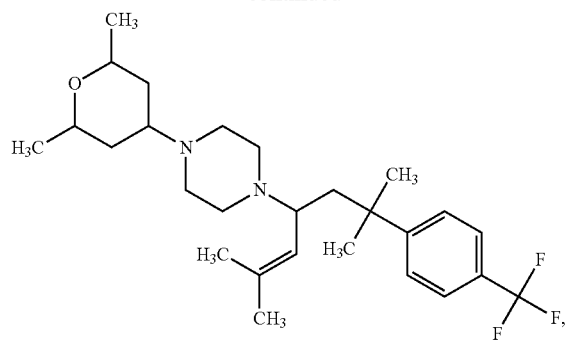
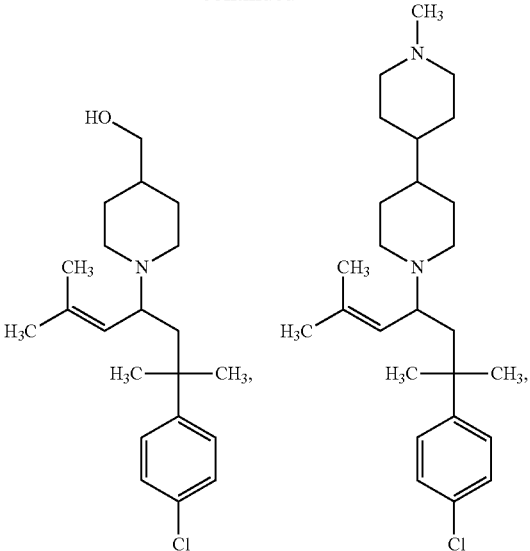
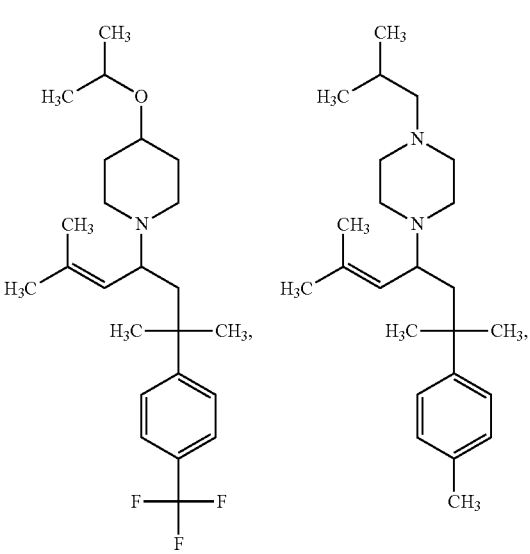
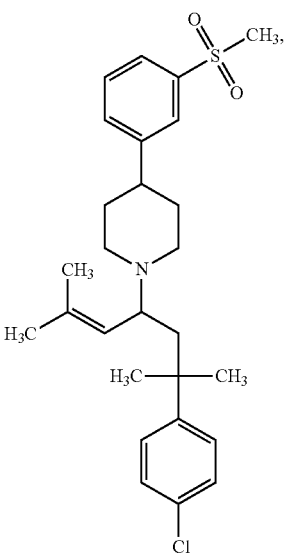

213
-continued
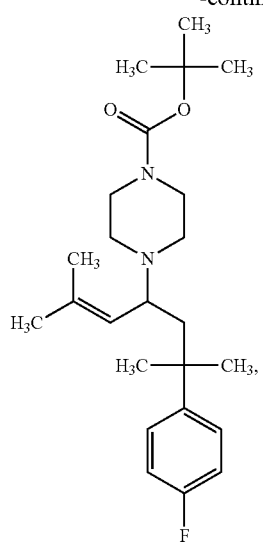
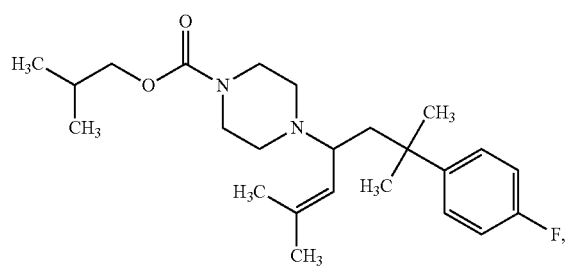
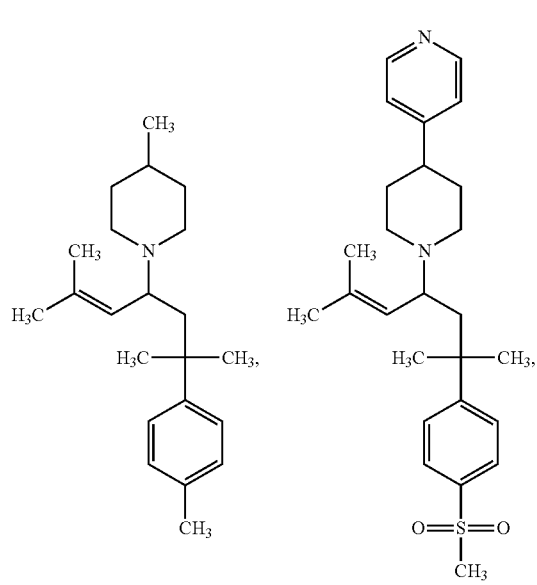
214
-continued
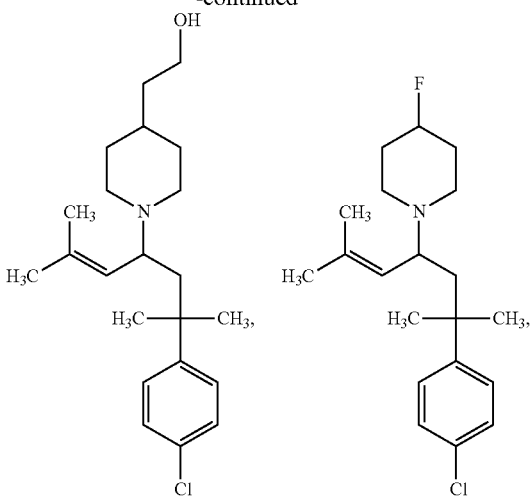
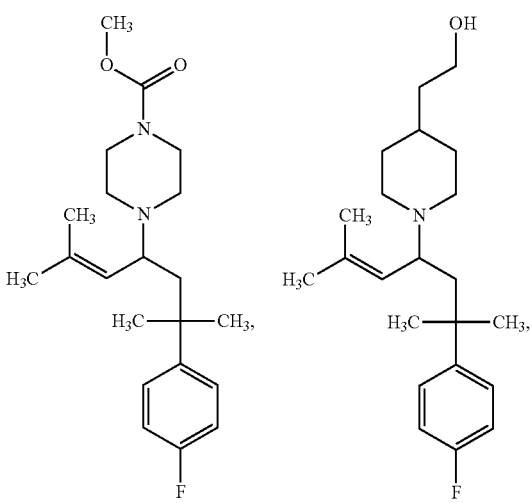
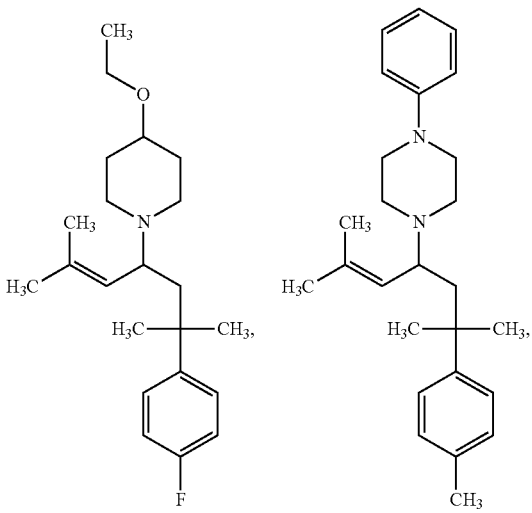

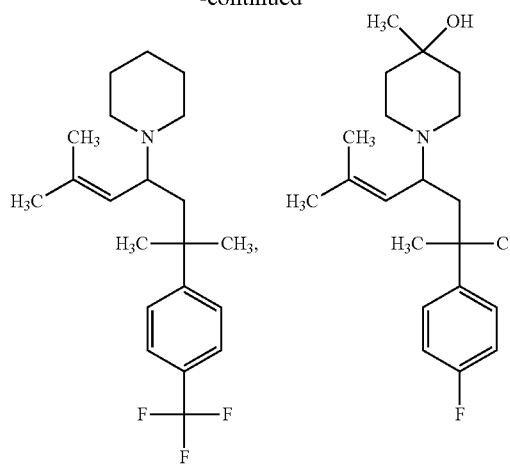
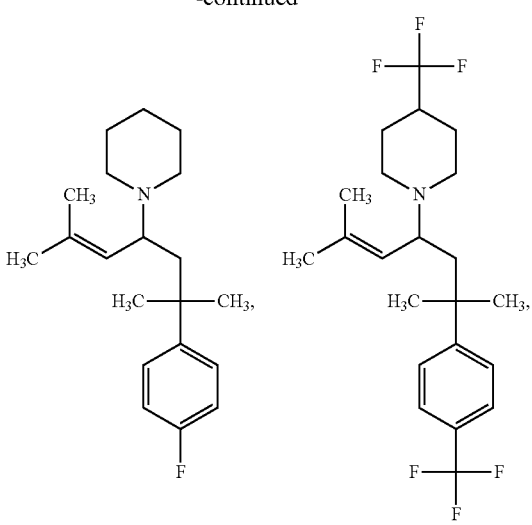
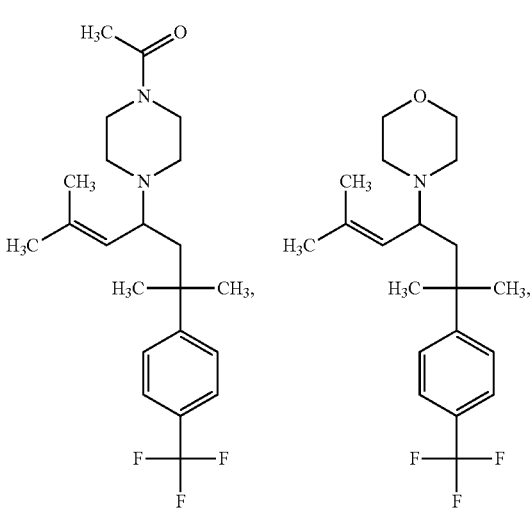
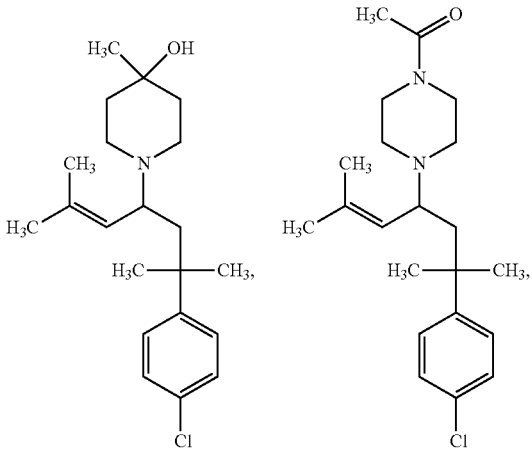

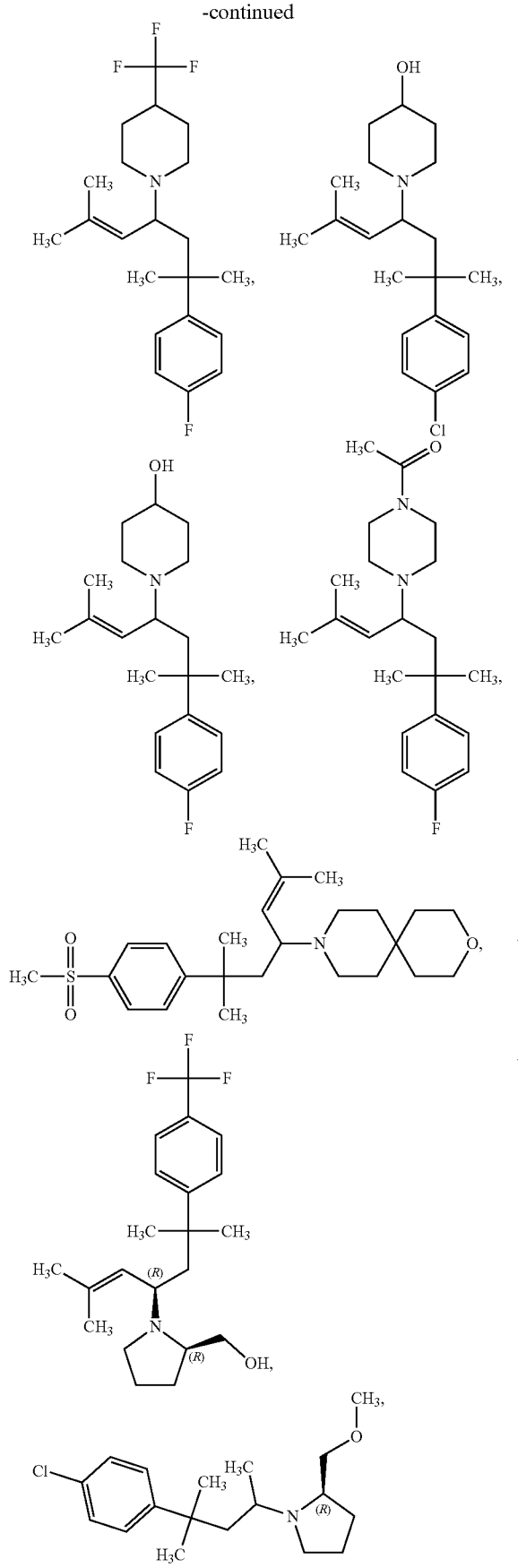
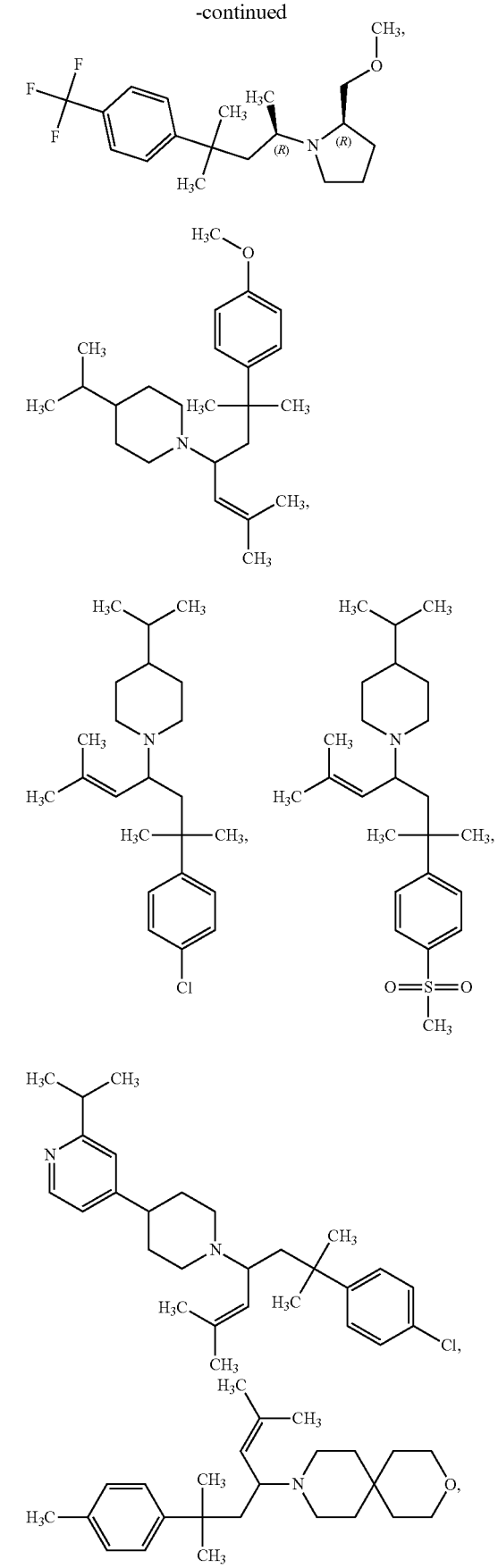

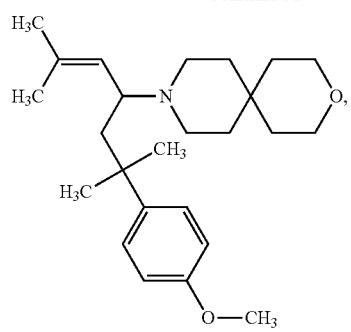
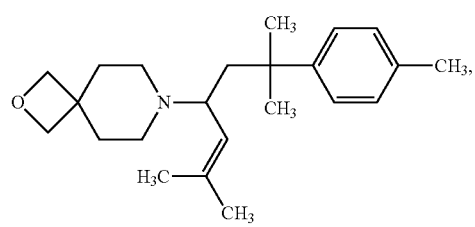
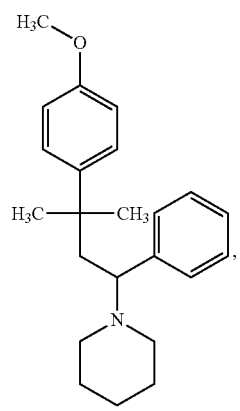
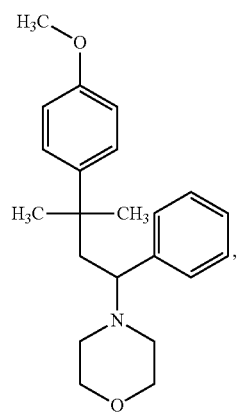
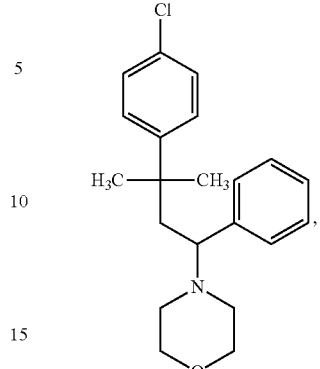
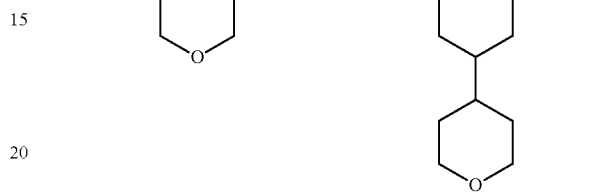
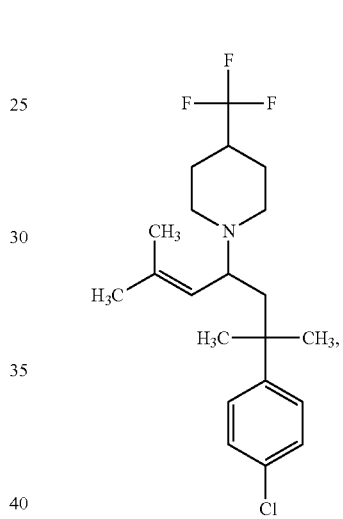
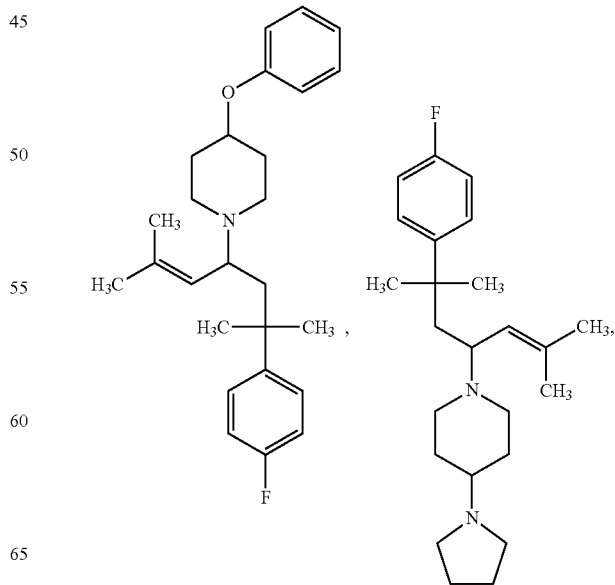

221
-continued
222
-continued
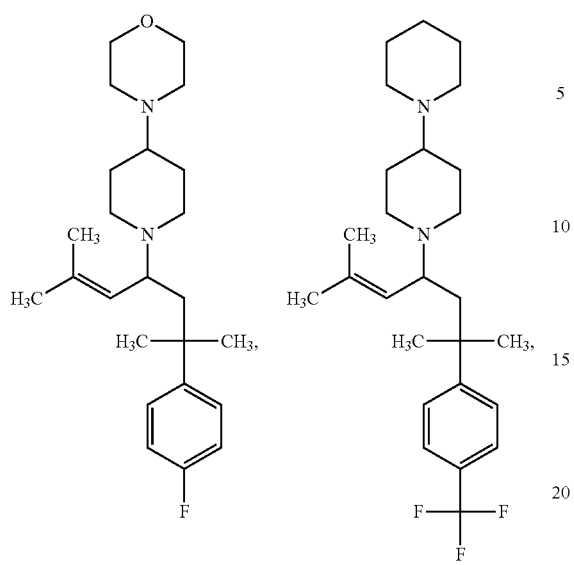
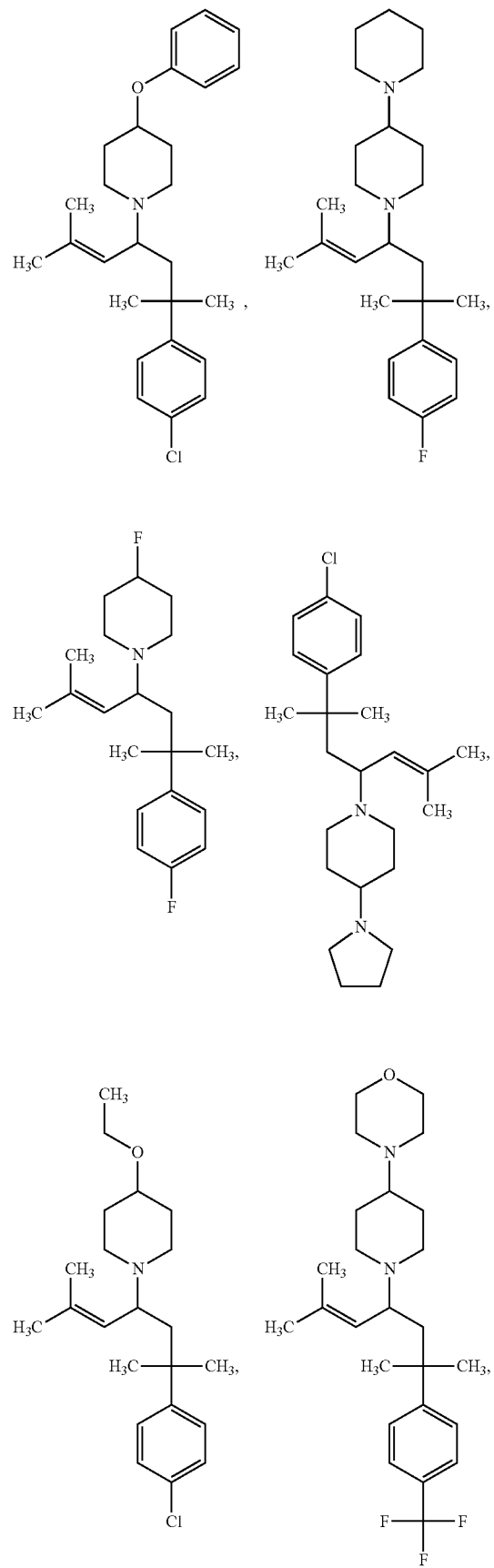

-continued
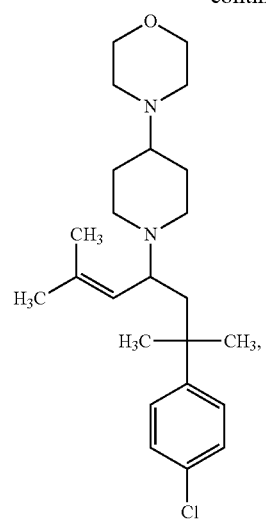
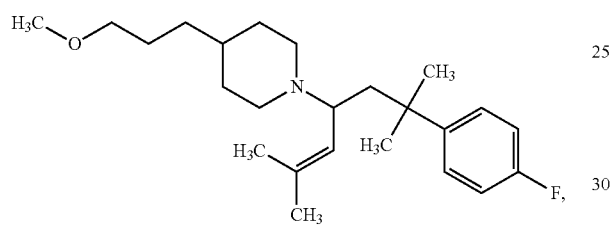
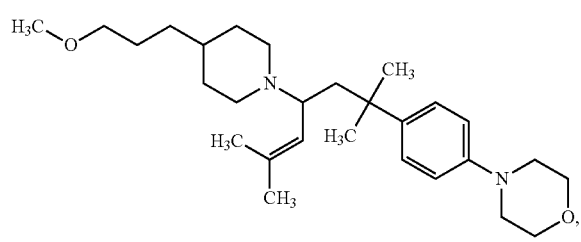
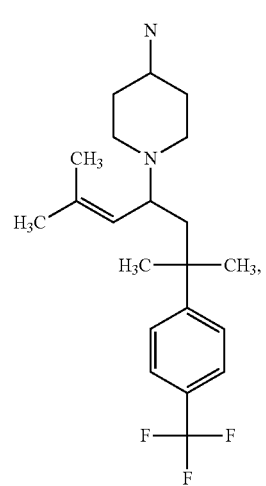 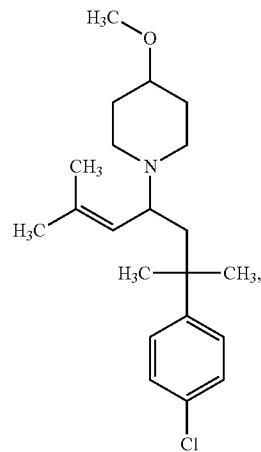
-continued
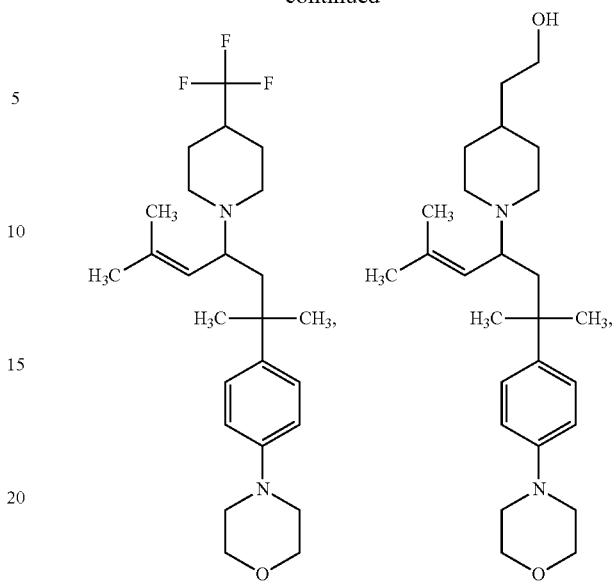
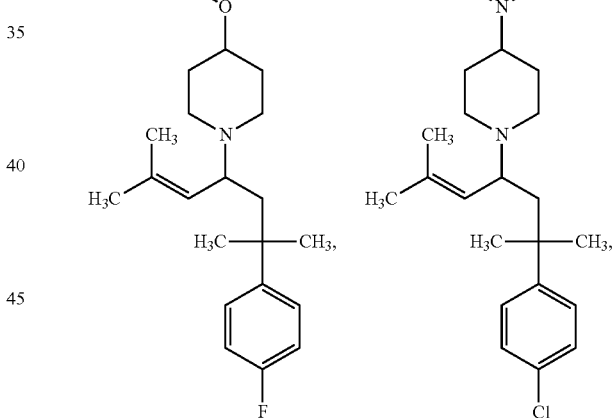
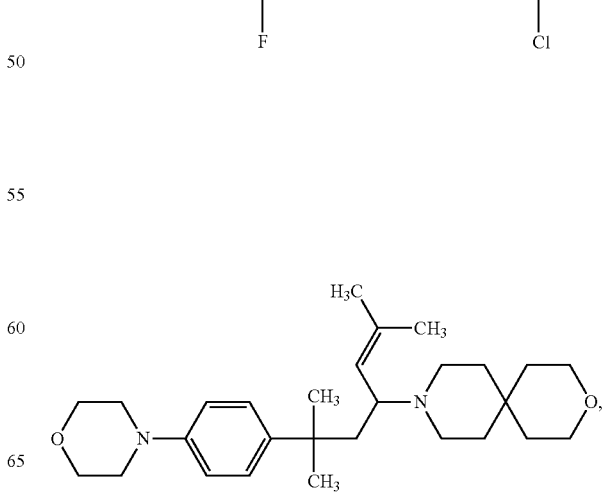

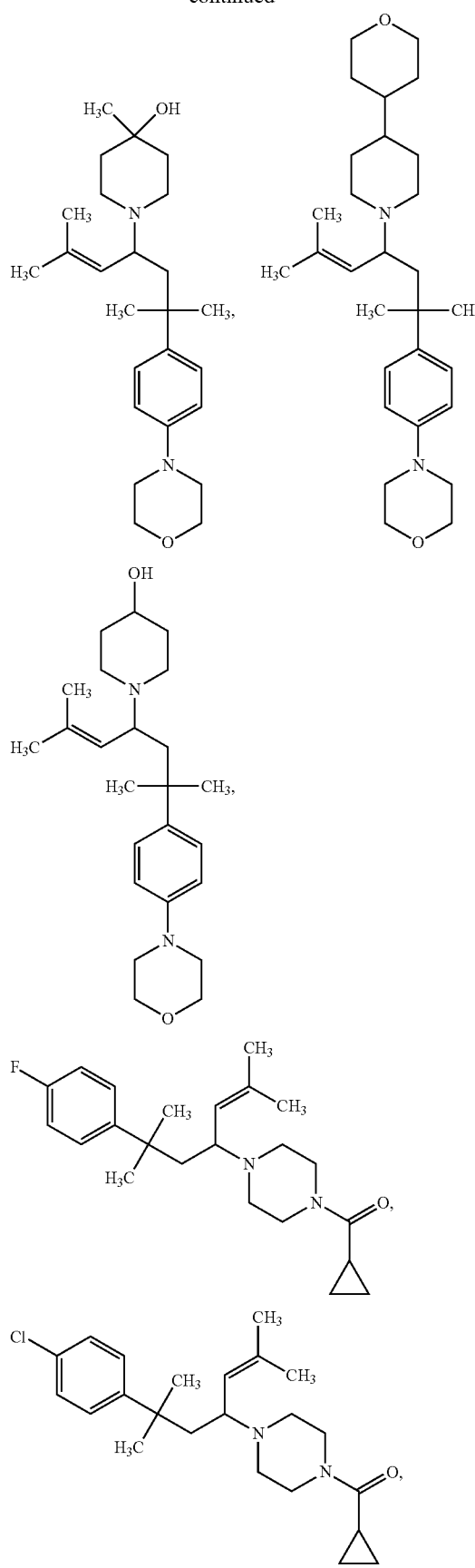
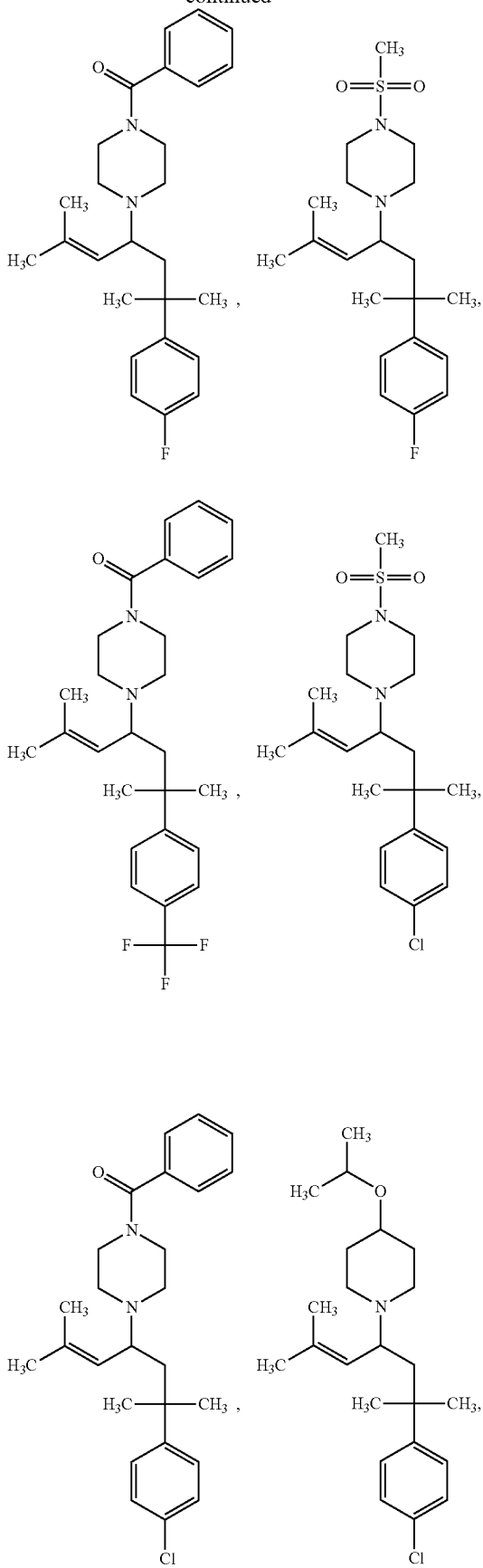

227
-continued
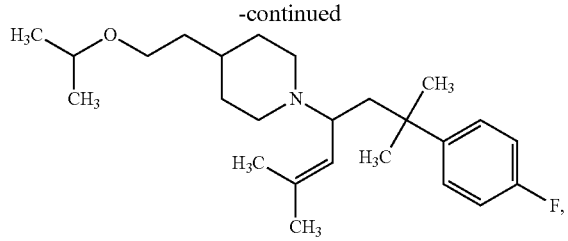
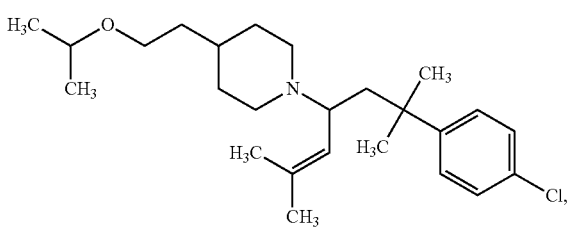
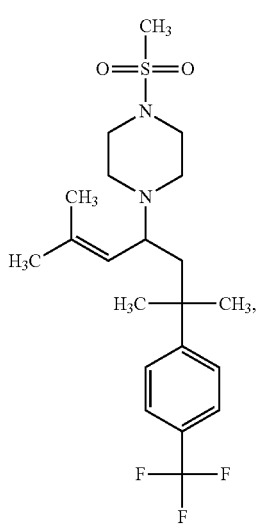
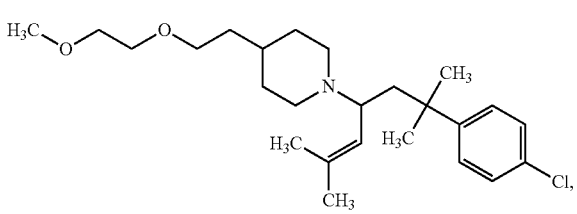
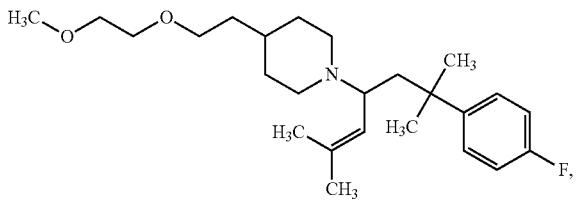
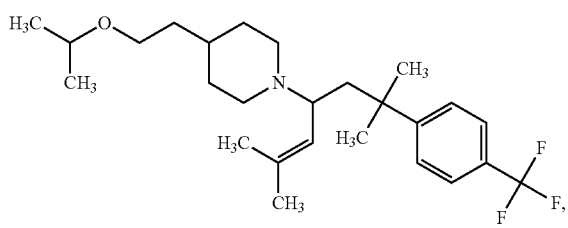
228
-continued
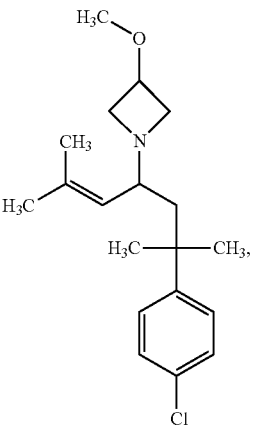
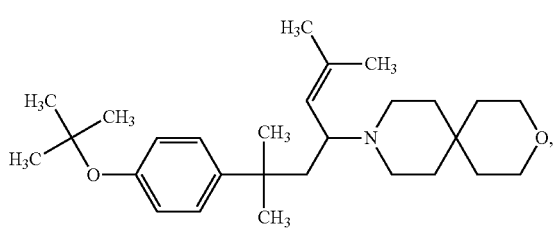
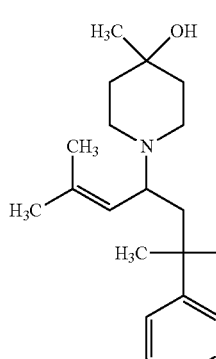
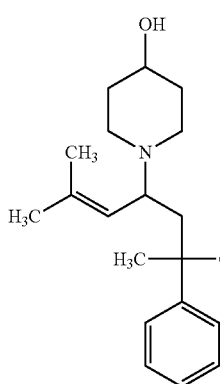
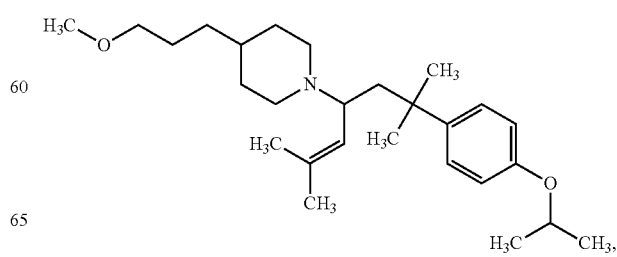

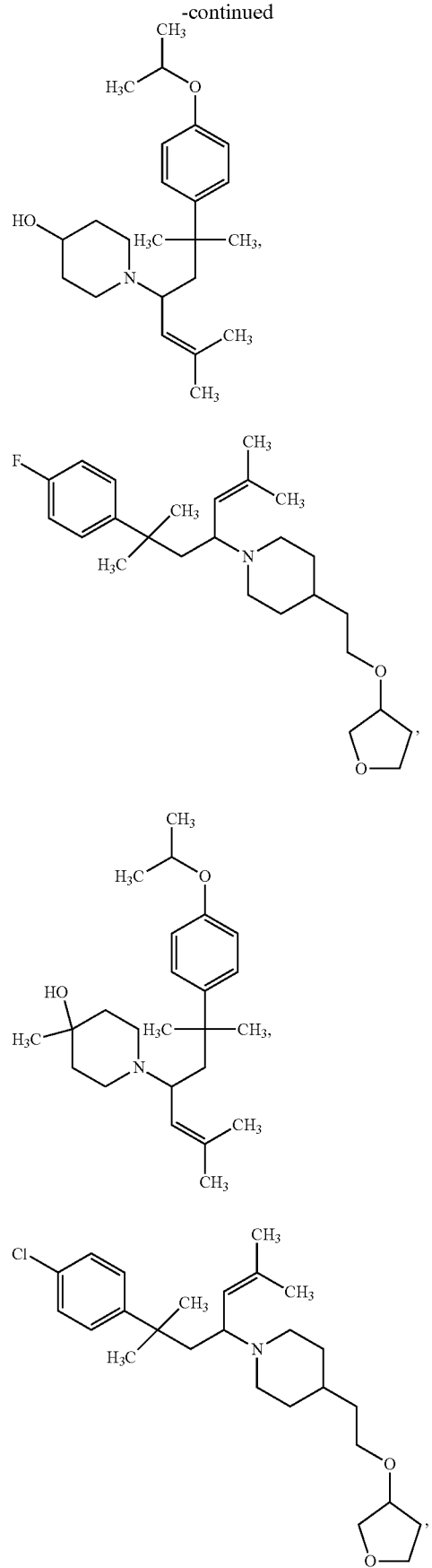
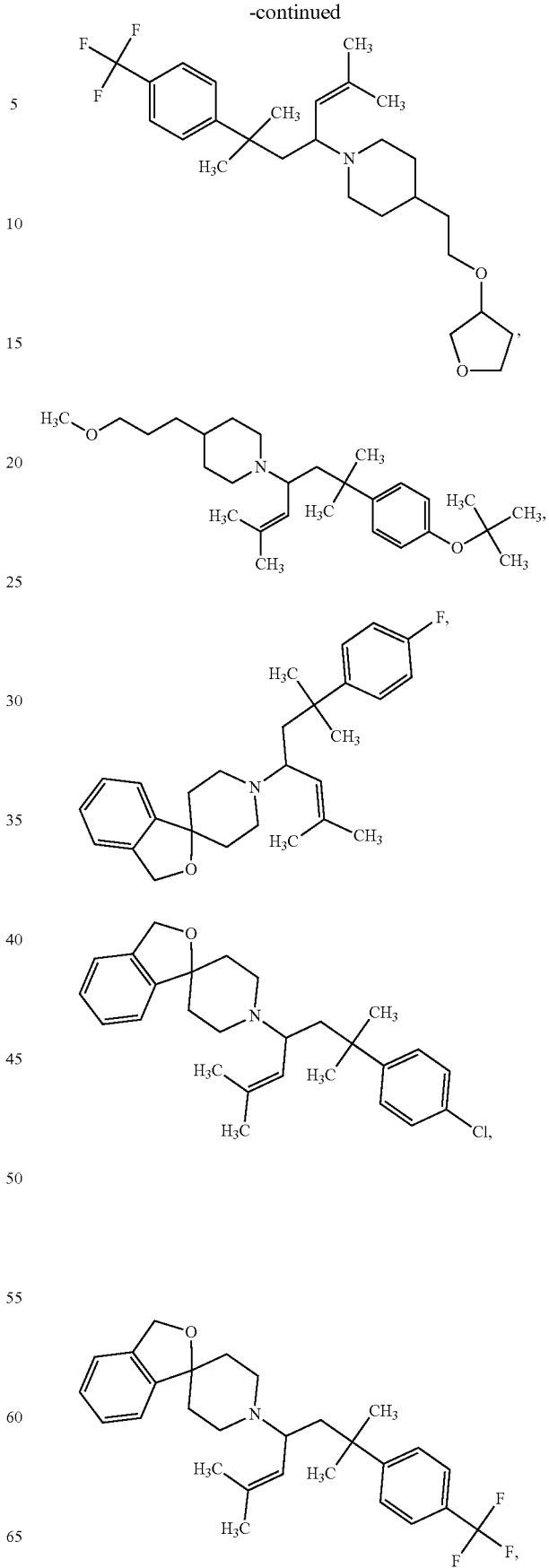

231
-continued
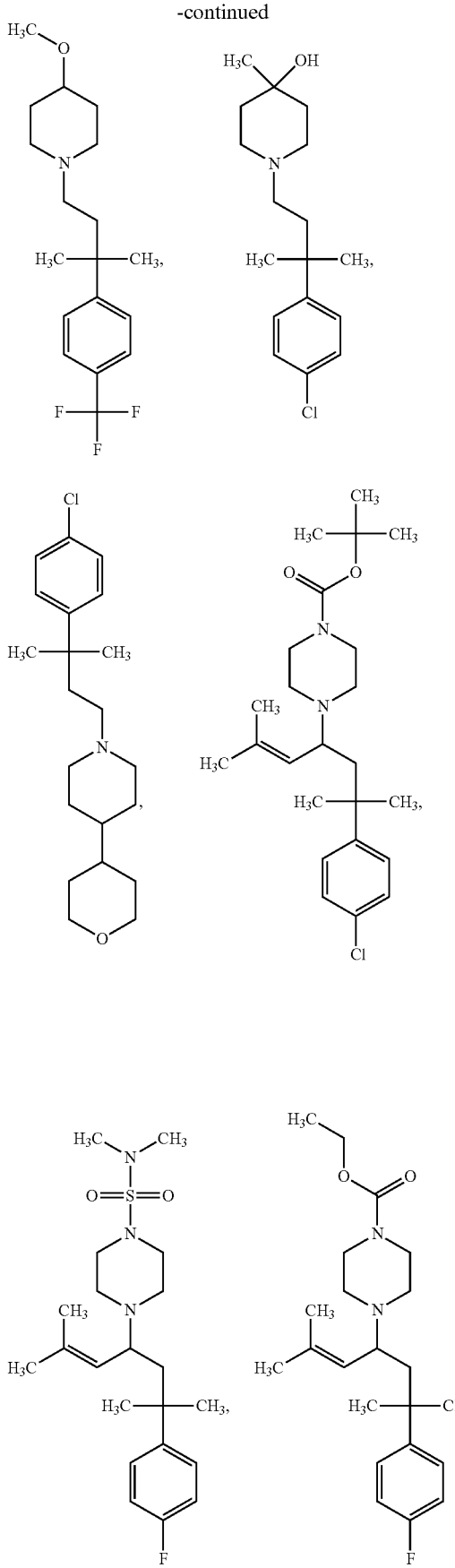
232
-continued
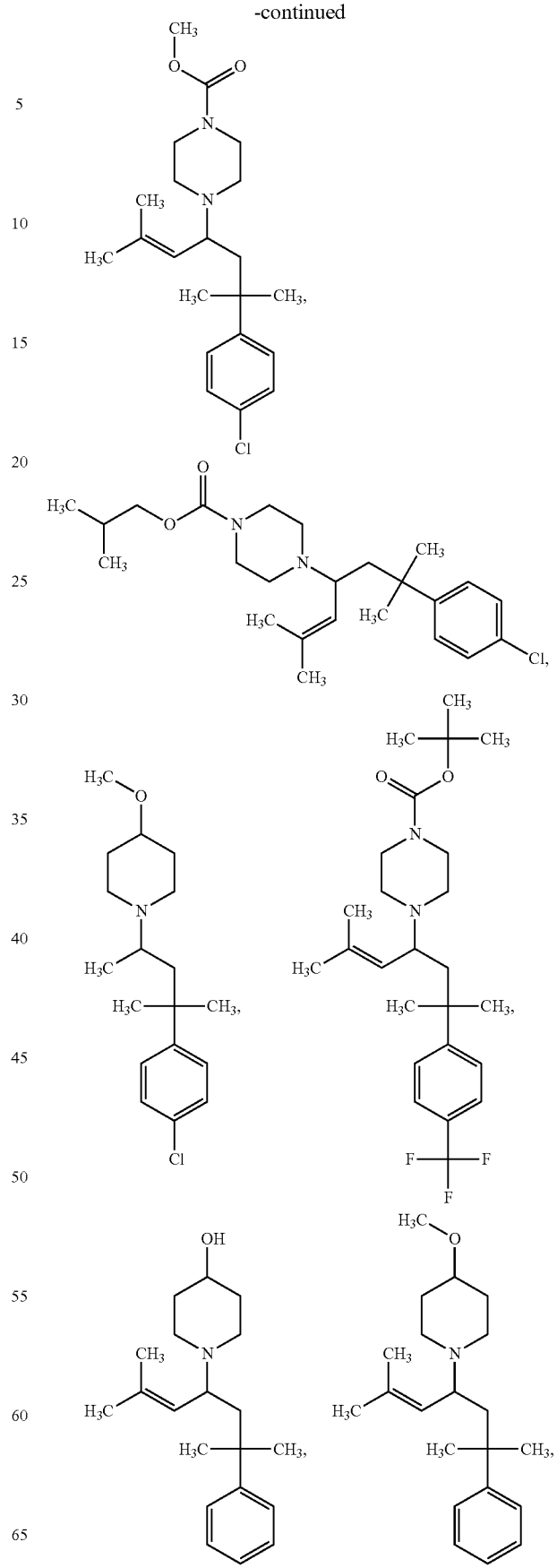

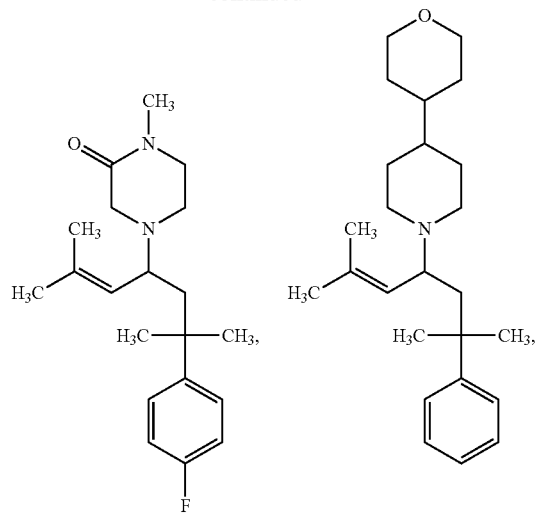
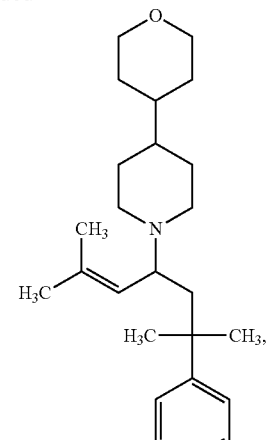
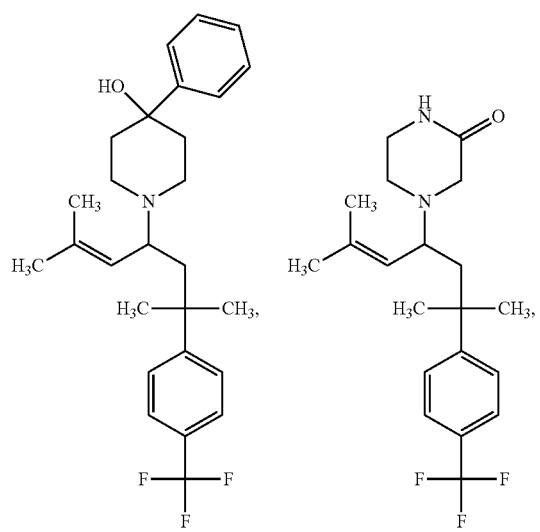
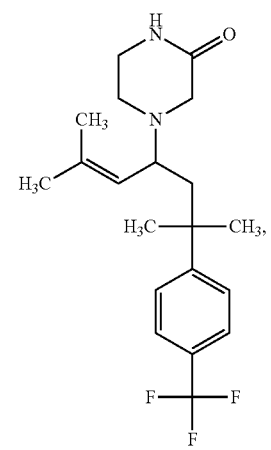
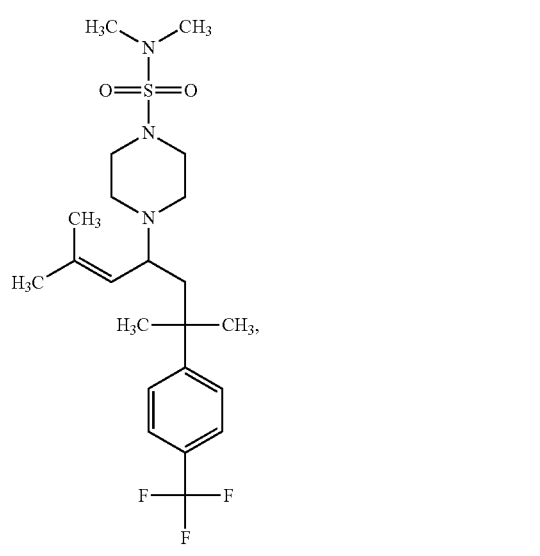 [SMILES: CC(C)=CC(CC(C)(C)c1ccc(C(F)(F)F)cc1)N1CCN(S(=O)(=O)N(C)C)CC1]
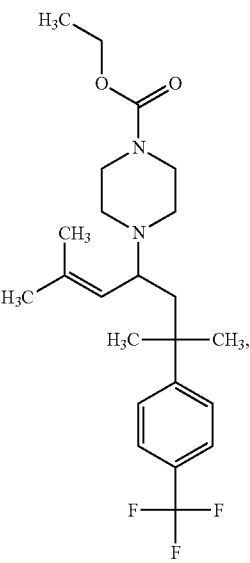
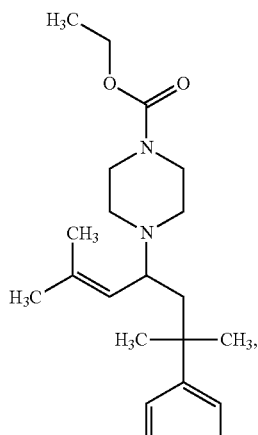
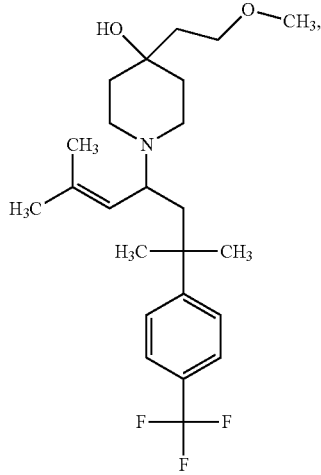

235
-continued
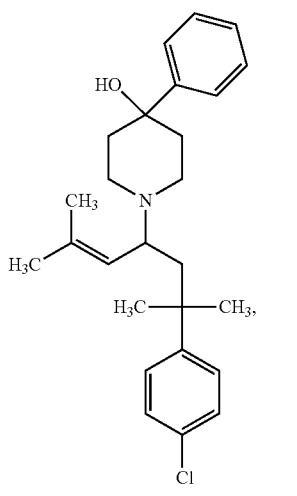
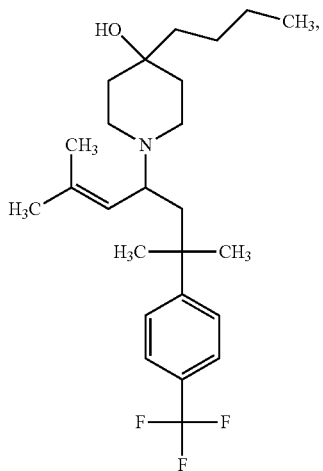
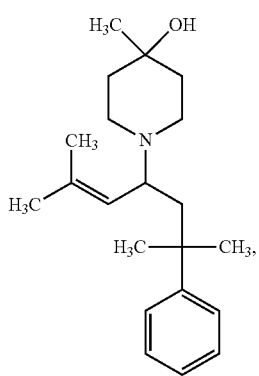
236
-continued
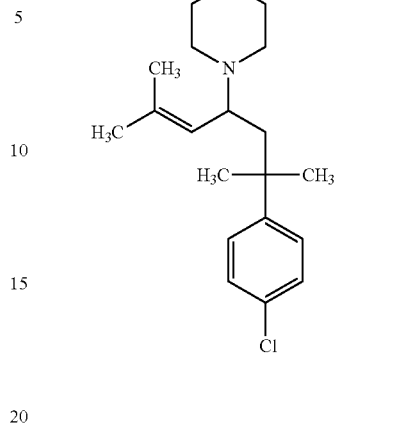
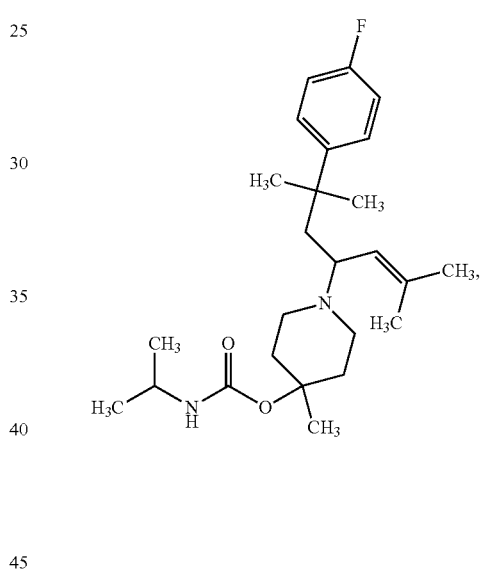
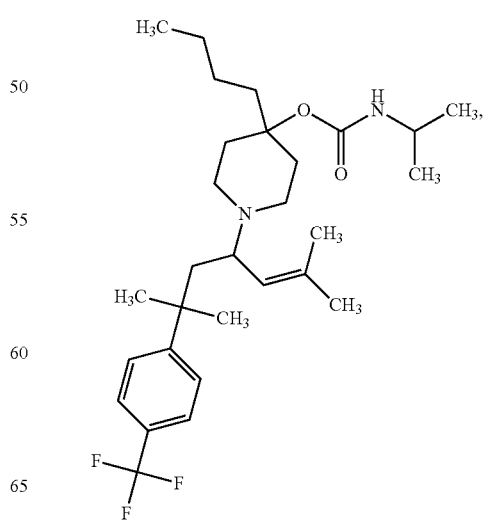

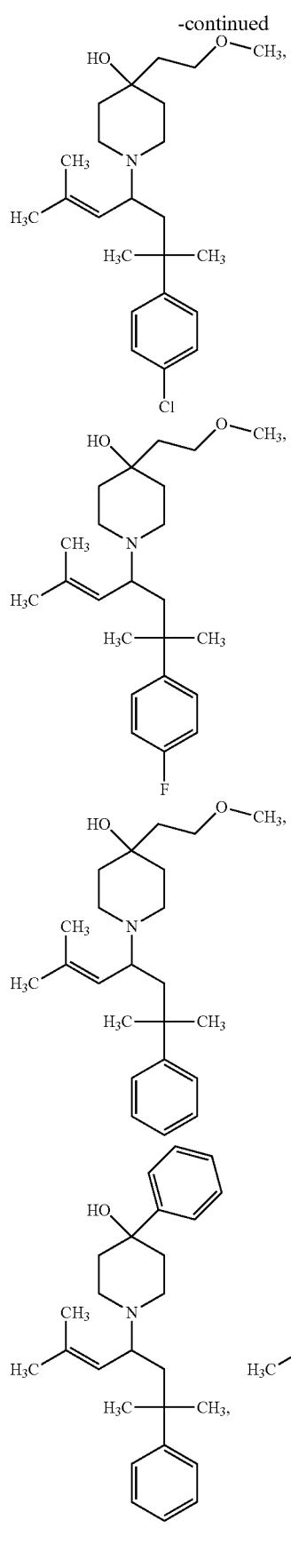
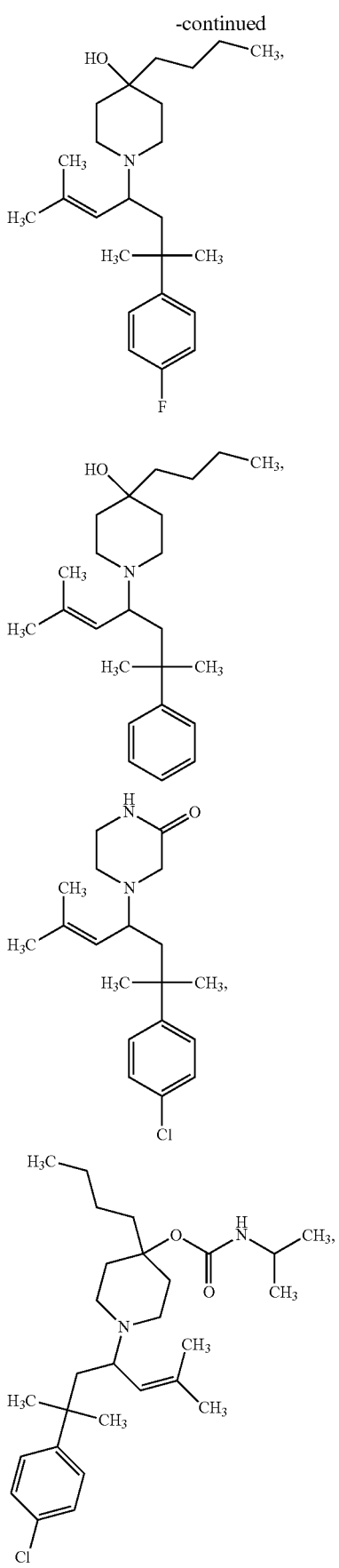

-continued
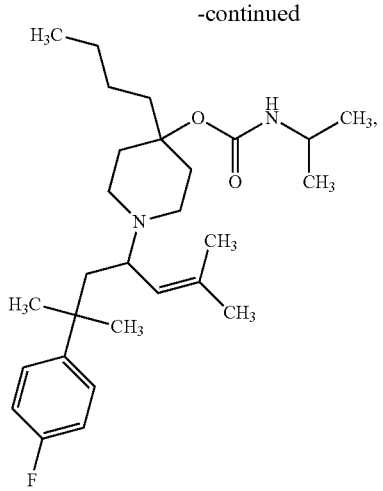
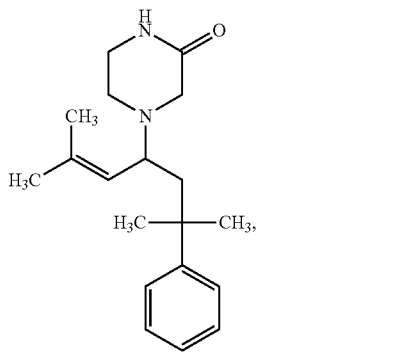
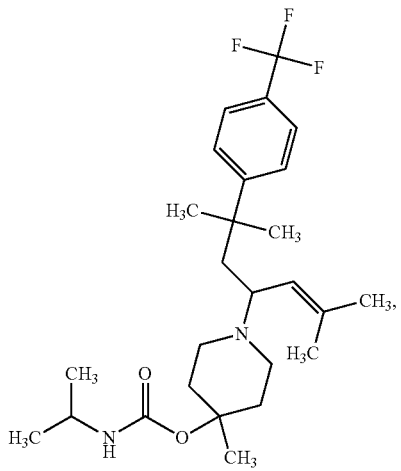
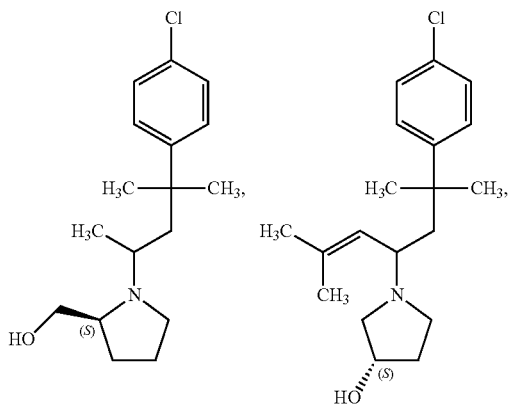
-continued
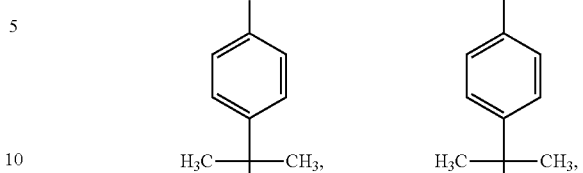
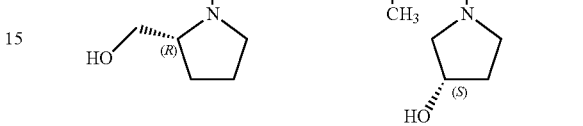
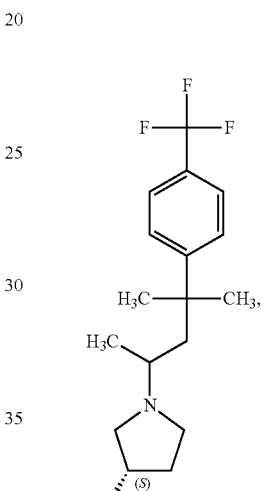
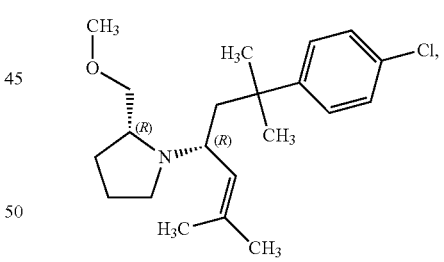
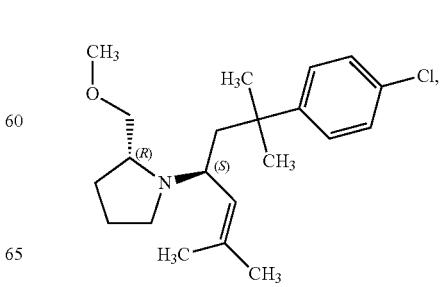

241
-continued
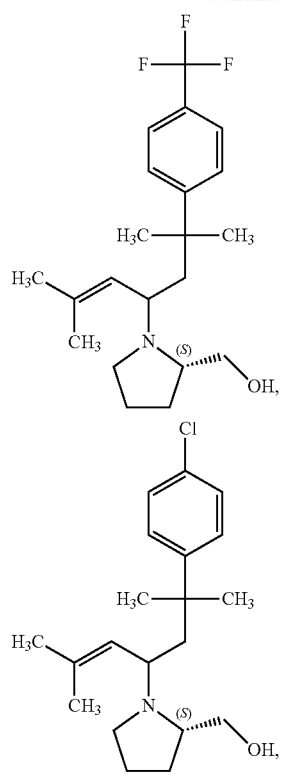
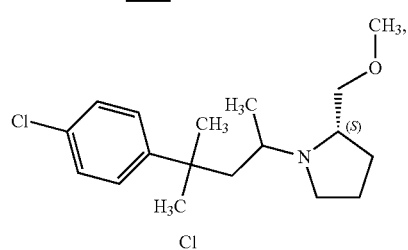
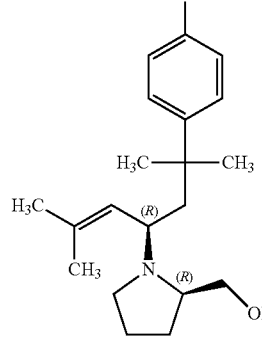
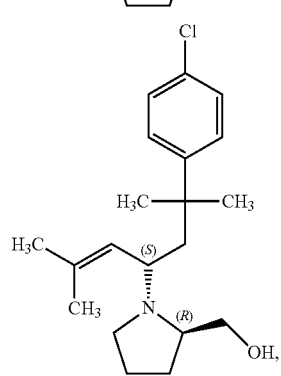
242
-continued
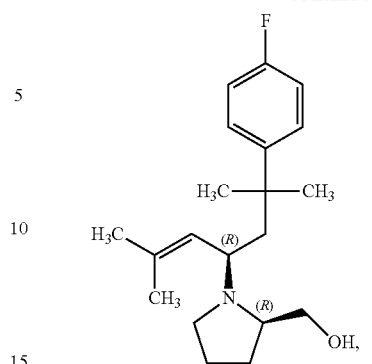
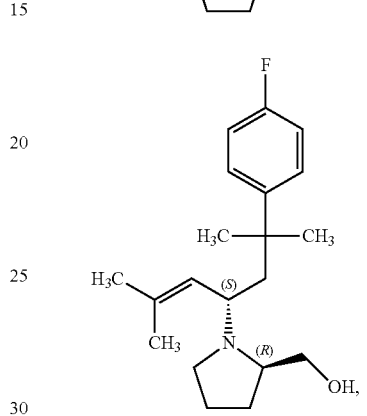
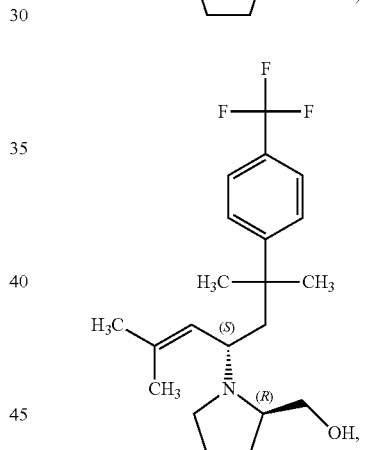
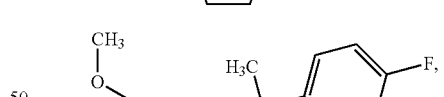
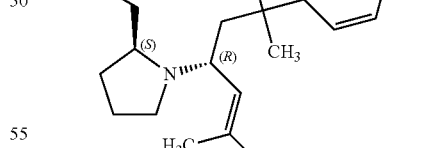
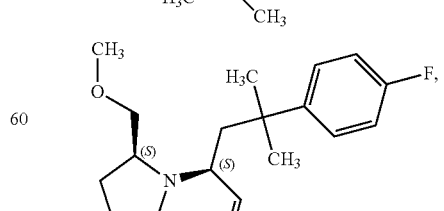
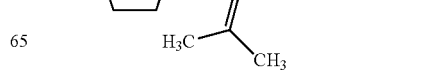

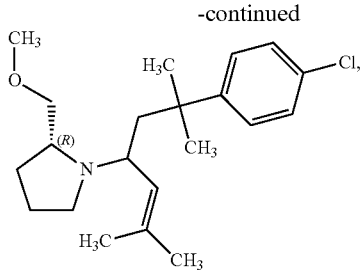
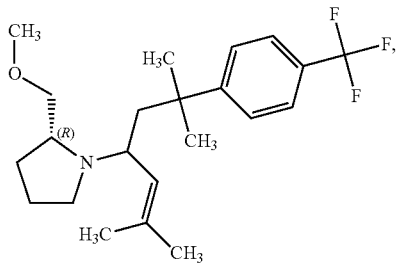
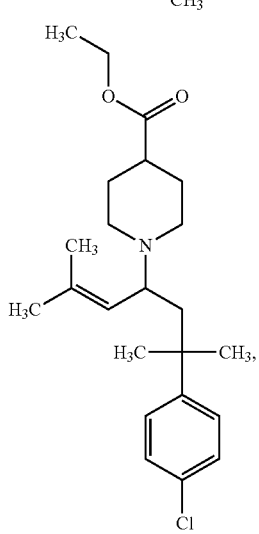
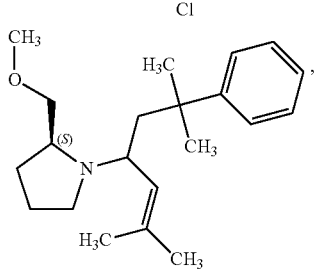
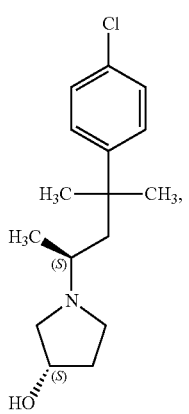
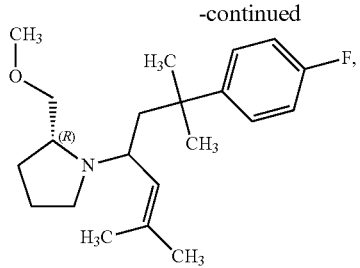
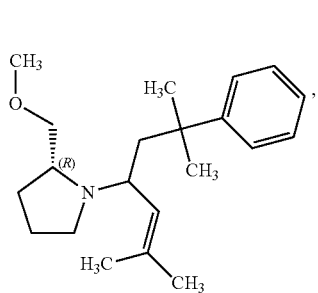
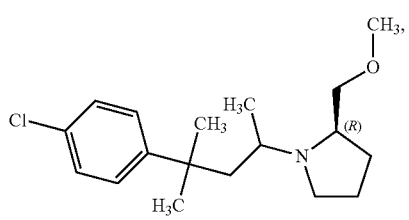
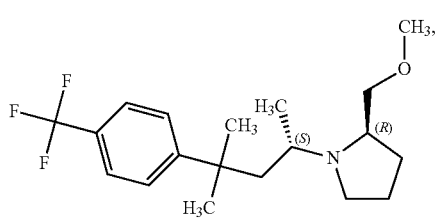
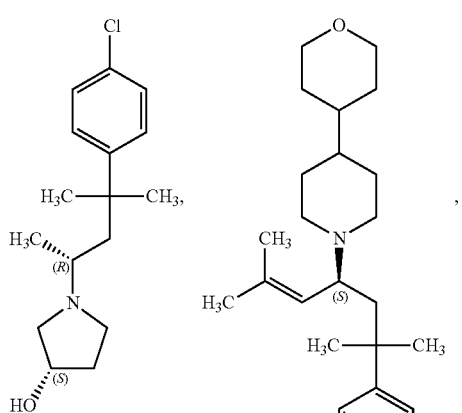

245
-continued
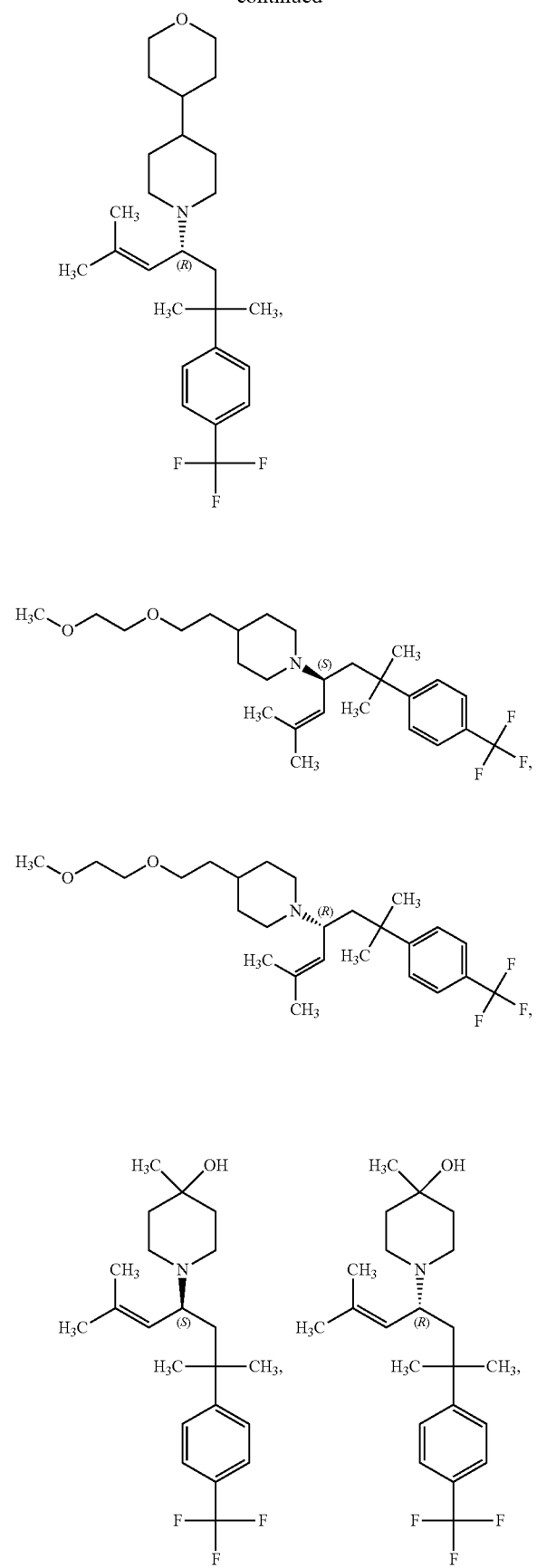
246
-continued
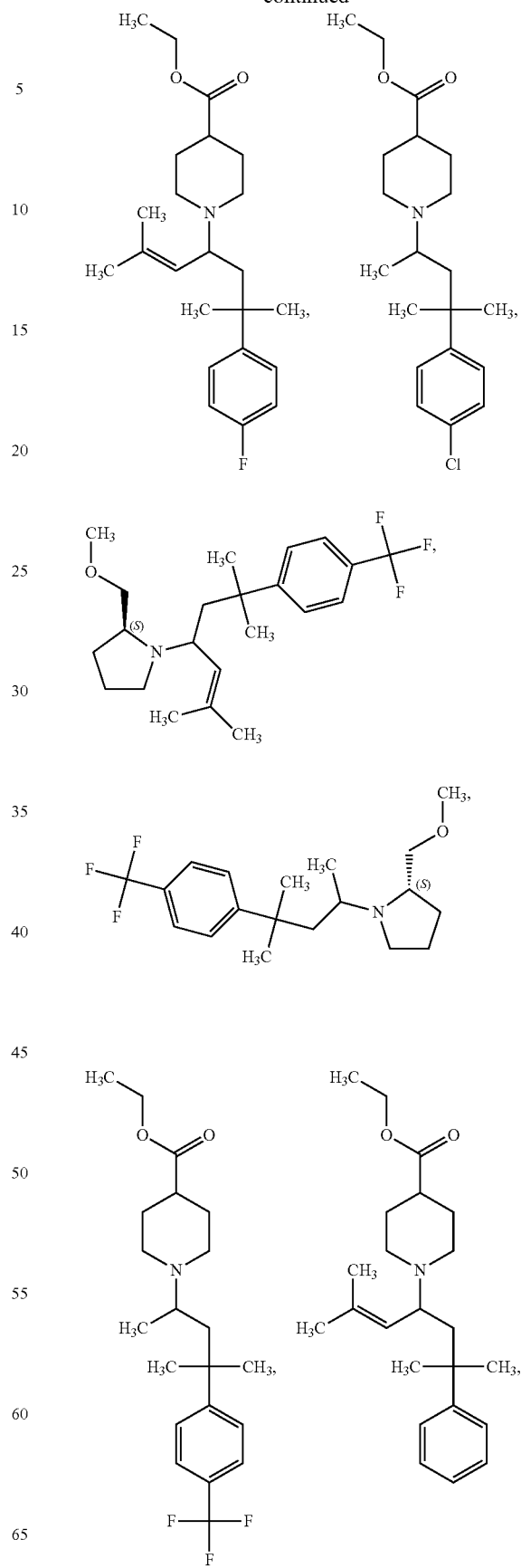

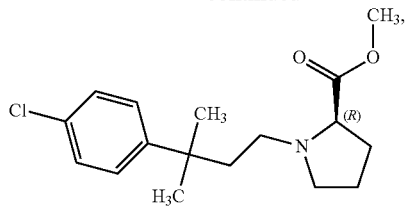
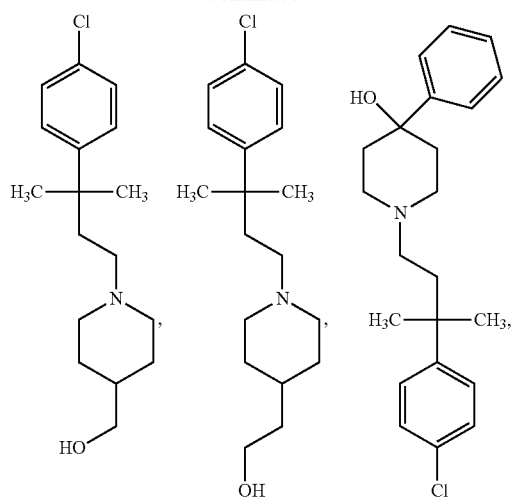
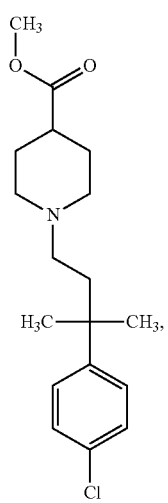
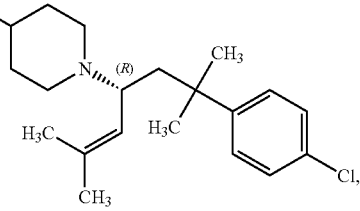
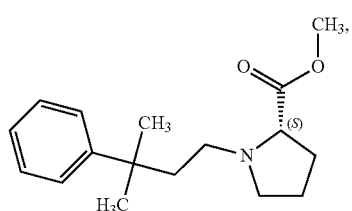
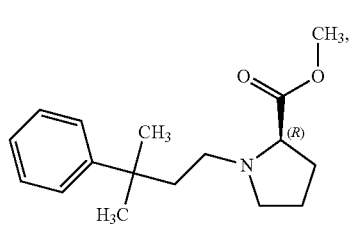

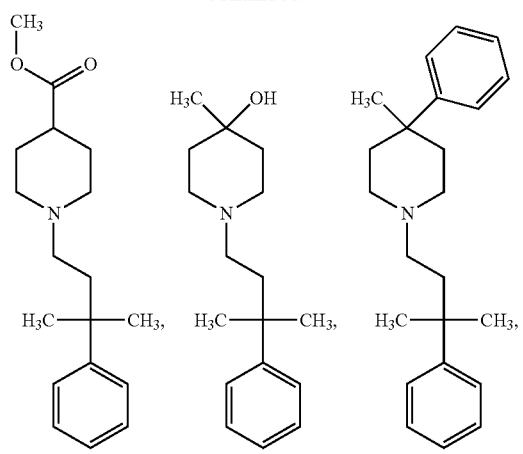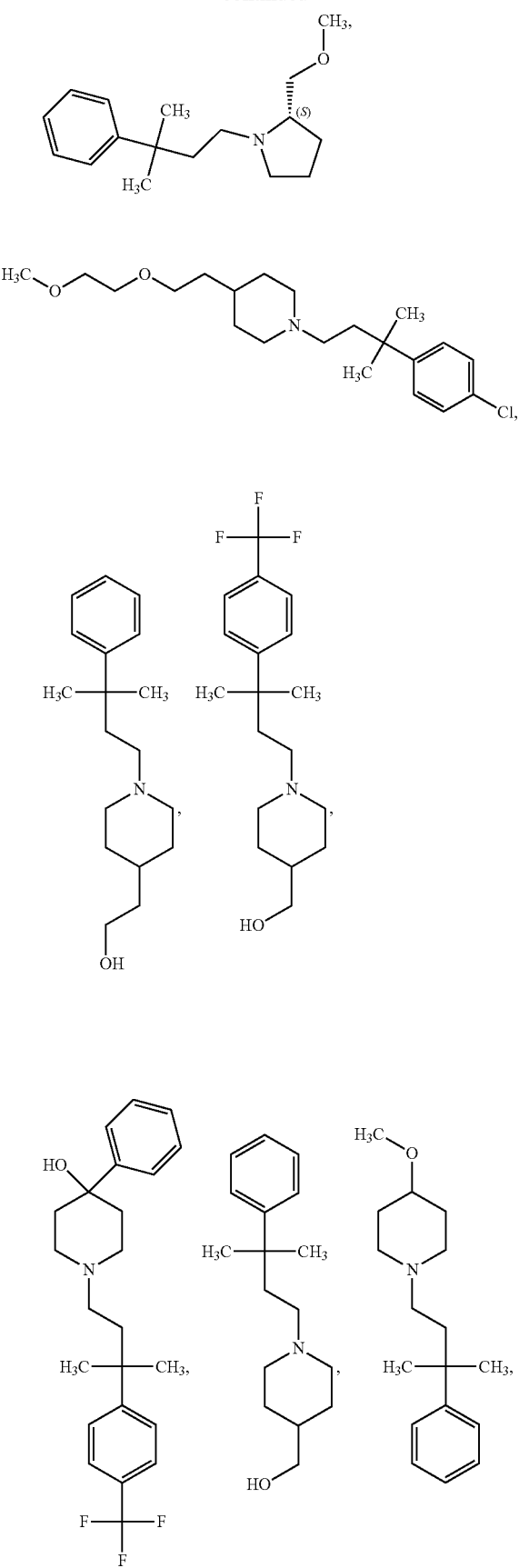

251
-continued
252
-continued
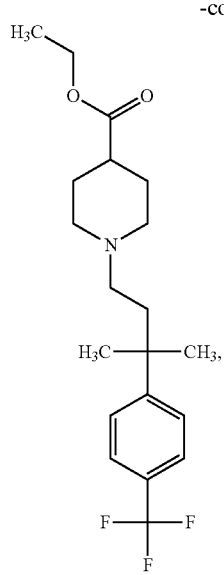
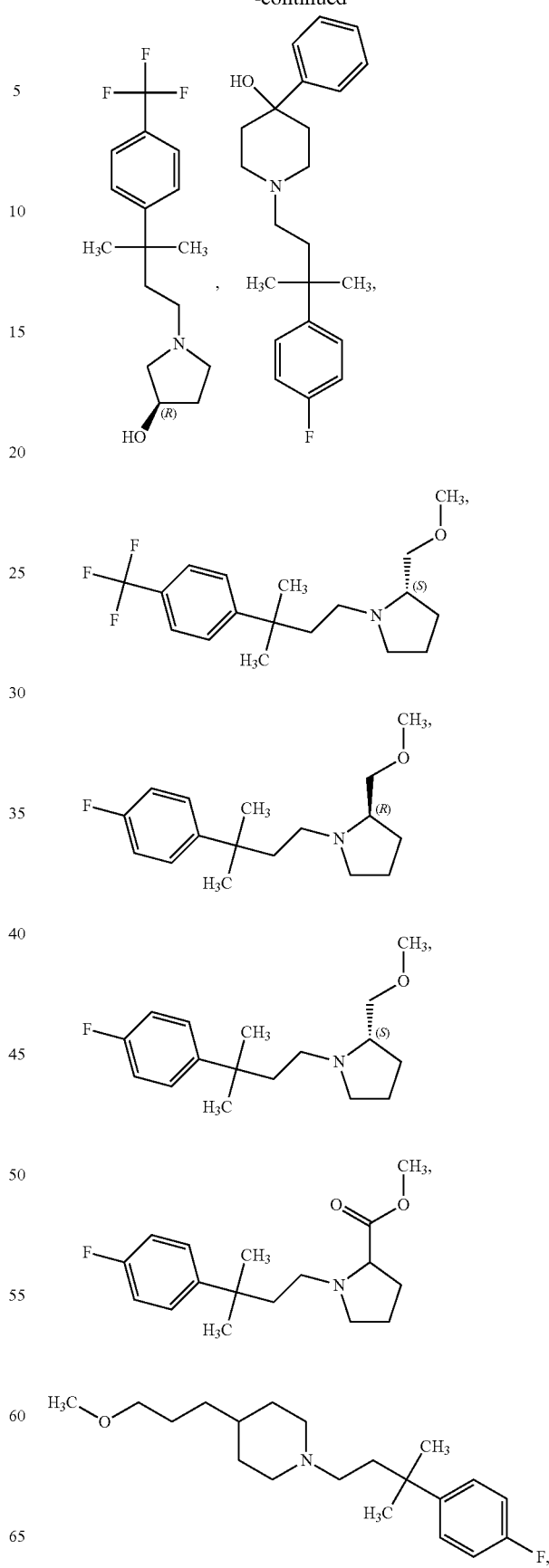

-continued
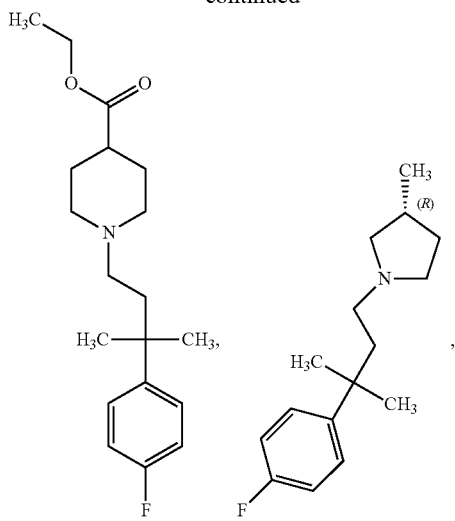
2. The compound of claim 1, selected from the group consisting of
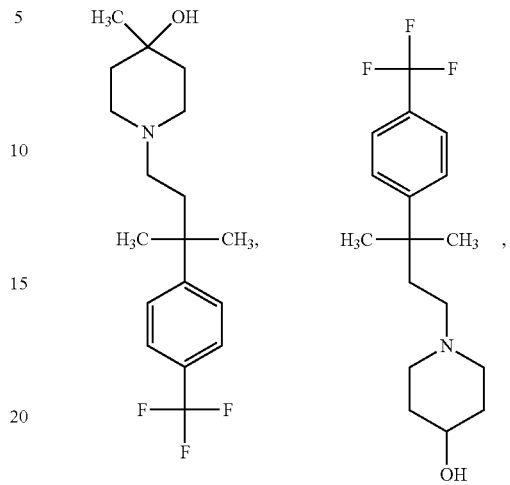
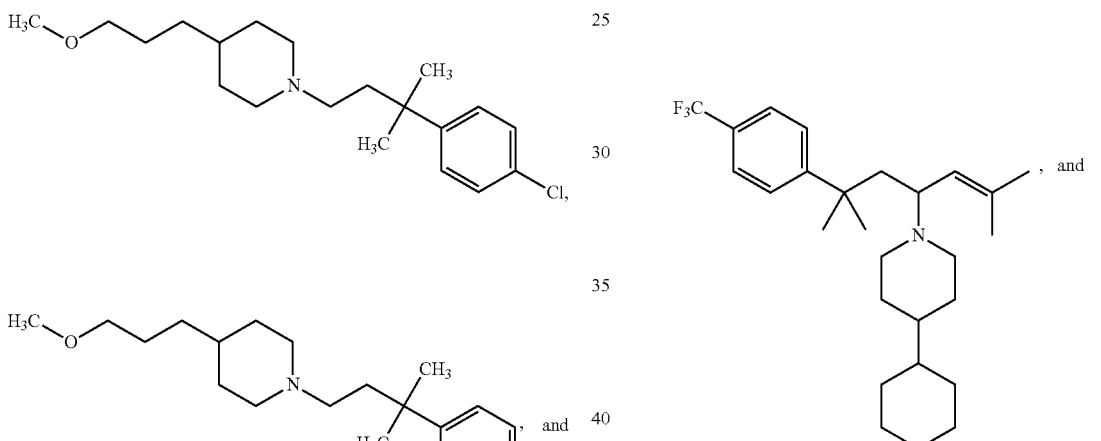
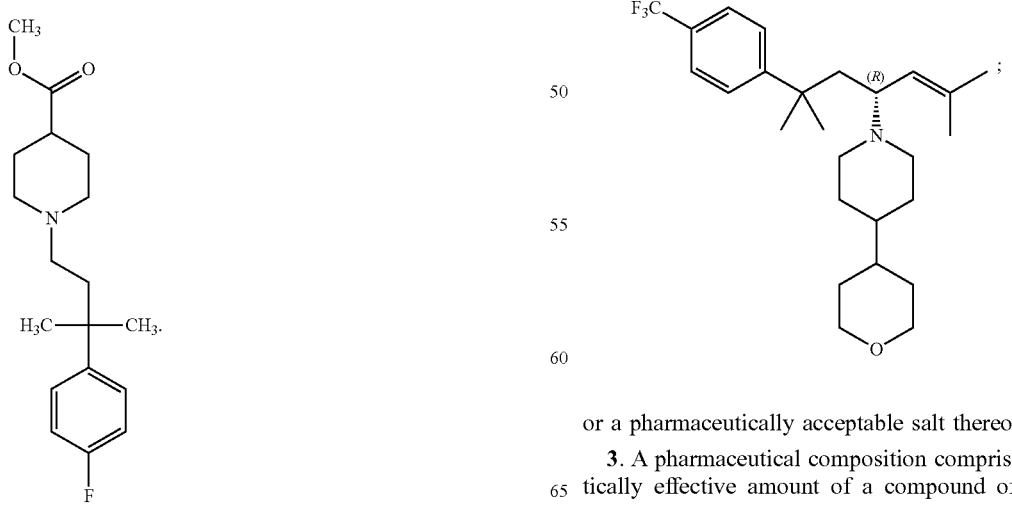
or a pharmaceutically acceptable salt thereof.
3. A pharmaceutical composition comprising a therapeutically effective amount of a compound of claim 1 or a pharmaceutically acceptable salt thereof, and a pharmaceutically acceptable carrier or diluent.

4. The pharmaceutical composition of claim 3 wherein the compound is selected from the group consisting of

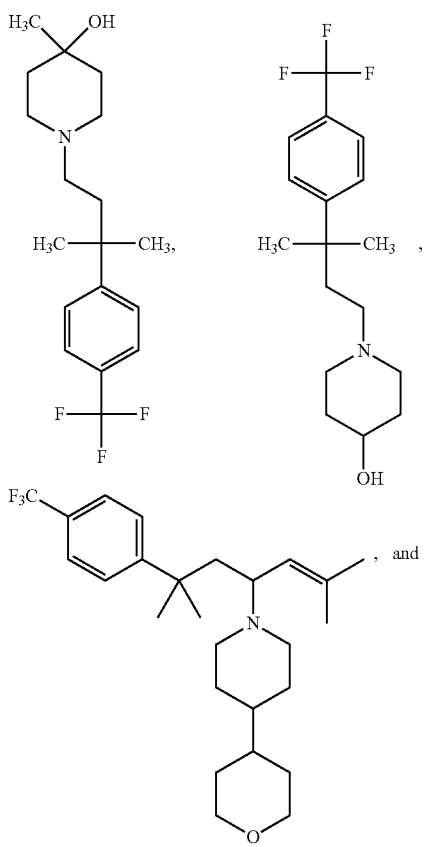

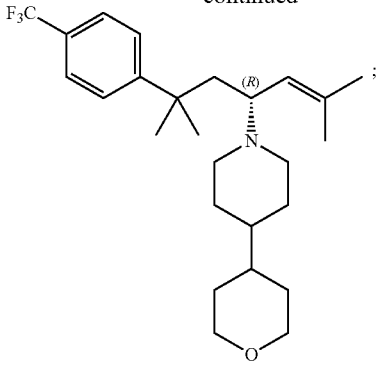

or a pharmaceutically acceptable salt thereof.

5. A method of treating Alzheimer's disease comprising administering to a subject in need thereof, a therapeutically effective amount of a pharmaceutical composition according to claim 3.

6. A method for inhibiting cognitive decline in a subject exhibiting, or at risk of exhibiting, cognitive decline, comprising administering a therapeutically effective amount of a pharmaceutical composition according to claim 3.

7. A method of inhibiting amyloid beta effect on a neuronal cell comprising administering to a subject in need thereof, a therapeutically effective amount of a pharmaceutical composition according to claim 3.

8. A method of treating mild cognitive impairment in Alzheimer's disease in a subject in need thereof, comprising administering to the subject a therapeutically effective amount of a pharmaceutical composition according to claim 3.

* * * * *